US010562917B2

(12) United States Patent
Chan et al.

(10) Patent No.: US 10,562,917 B2
(45) Date of Patent: *Feb. 18, 2020

(54) CHIMERIC COMPOUNDS TARGETING PROTEINS, COMPOSITIONS, METHODS, AND USES THEREOF

(71) Applicant: BioTheryX, Inc., Chappaqua, NY (US)

(72) Inventors: Kyle W. H. Chan, San Diego, CA (US); Leah Fung, San Diego, CA (US); Robert Sullivan, Vista, CA (US); Paul E. Erdman, San Diego, CA (US); Frank Mercurio, Rancho Santa Fe, CA (US); Eduardo Torres, San Diego, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,267

(22) Filed: Feb. 8, 2018

(65) Prior Publication Data

US 2018/0230167 A1    Aug. 16, 2018

Related U.S. Application Data

(63) Continuation of application No. 15/599,401, filed on May 18, 2017, now Pat. No. 9,938,302.

(Continued)

(51) Int. Cl.
| | | |
|---|---|---|
| C07D 513/16 | (2006.01) | |
| C07D 401/14 | (2006.01) | |
| C07D 413/14 | (2006.01) | |
| C07D 403/04 | (2006.01) | |
| C07D 403/14 | (2006.01) | |
| C07D 417/14 | (2006.01) | |
| C07D 471/14 | (2006.01) | |
| C07D 513/14 | (2006.01) | |
| A61K 47/55 | (2017.01) | |
| A61K 9/00 | (2006.01) | |
| A61K 9/06 | (2006.01) | |
| A61K 9/08 | (2006.01) | |
| A61K 9/20 | (2006.01) | |
| A61K 9/48 | (2006.01) | |
| A61K 9/70 | (2006.01) |

(Continued)

(52) U.S. Cl.
CPC ............ *C07D 513/16* (2013.01); *A61K 9/006* (2013.01); *A61K 9/007* (2013.01); *A61K 9/0014* (2013.01); *A61K 9/0019* (2013.01); *A61K 9/0043* (2013.01); *A61K 9/0048* (2013.01); *A61K 9/0053* (2013.01); *A61K 9/0078* (2013.01); *A61K 9/06* (2013.01); *A61K 9/08* (2013.01); *A61K 9/20* (2013.01); *A61K 9/48* (2013.01); *A61K 9/7023* (2013.01); *A61K 31/40* (2013.01); *A61K 31/437* (2013.01); *A61K 31/55* (2013.01); *A61K 38/00* (2013.01); *A61K 47/55* (2017.08); *C07C 223/02* (2013.01); *C07D 207/04* (2013.01); *C07D 209/00* (2013.01); *C07D 221/00* (2013.01); *C07D 225/02* (2013.01); *C07D 247/02* (2013.01); *C07D 401/14* (2013.01); *C07D 403/04* (2013.01); *C07D 403/14* (2013.01); *C07D 409/14* (2013.01); *C07D 413/14* (2013.01); *C07D 417/14* (2013.01); *C07D 471/14* (2013.01); *C07D 487/00* (2013.01); *C07D 513/14* (2013.01); *A61K 2039/505* (2013.01); *A61K 2121/00* (2013.01)

(58) Field of Classification Search
CPC ..................................................... C07D 513/16
See application file for complete search history.

(56) References Cited

U.S. PATENT DOCUMENTS

| | | |
|---|---|---|
| 5,552,397 A | 9/1996 | Karanewsky et al. |
| 7,968,708 B2 | 6/2011 | Hangauer et al. |

(Continued)

FOREIGN PATENT DOCUMENTS

| | | |
|---|---|---|
| CN | 104004122 | 8/2014 |
| JP | 2001-503384 | 3/2001 |

(Continued)

OTHER PUBLICATIONS

STN Registry No. 131926-36-8 (1991).*

(Continued)

*Primary Examiner* — Paul V Ward
(74) *Attorney, Agent, or Firm* — Knobbe, Martens, Olson & Bear, LLP

(57) ABSTRACT

The present invention provides chimeric compounds that modulate protein function, to restore protein homeostasis, including cytokine, aiolos, and/or ikaros activity, TNF-alpha activity, CK1-alpha activity and cell-cell adhesion. The invention provides methods of modulating protein-mediated diseases, such as cytokine-mediated diseases, disorders, conditions, or responses. Compositions, including in combination with other cytokine and inflammatory mediators, are provided. Methods of treatment, amelioration, or prevention of protein-mediated diseases, disorders, and conditions, such as cytokine-mediated diseases, disorders, and conditions, including inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, organ transplant rejection, and cancer, are provided.

22 Claims, 21 Drawing Sheets

Related U.S. Application Data

(60) Provisional application No. 62/338,303, filed on May 18, 2016.

(51) Int. Cl.

| | | |
|---|---|---|
| *A61K 31/40* | (2006.01) | |
| *A61K 31/55* | (2006.01) | |
| *A61K 31/437* | (2006.01) | |
| *A61K 38/00* | (2006.01) | |
| *C07C 223/02* | (2006.01) | |
| *C07D 207/04* | (2006.01) | |
| *C07D 209/00* | (2006.01) | |
| *C07D 221/00* | (2006.01) | |
| *C07D 225/02* | (2006.01) | |
| *C07D 247/02* | (2006.01) | |
| *C07D 409/14* | (2006.01) | |
| *C07D 487/00* | (2006.01) | |
| *A61K 39/00* | (2006.01) | |

(56) References Cited

U.S. PATENT DOCUMENTS

| | | |
|---|---|---|
| 9,822,098 B2 | 11/2017 | Chan et al. |
| 9,938,302 B2 * | 4/2018 | Chan .................. A61K 47/55 |
| 2017/0333443 A1 | 11/2017 | Chan et al. |
| 2018/0065952 A1 | 3/2018 | Chan et al. |

FOREIGN PATENT DOCUMENTS

| | | | |
|---|---|---|---|
| JP | 2002-506861 | | 3/2002 |
| WO | WO 97/38705 | | 10/1997 |
| WO | WO 98/03502 | | 1/1998 |
| WO | WO 99/47512 | | 9/1999 |
| WO | WO 08/070161 | | 6/2008 |
| WO | WO2008070161 | * | 6/2008 |
| WO | WO 14/089495 | | 6/2014 |
| WO | WO 16/191178 | | 12/2016 |
| WO | WO 17/197055 | | 11/2017 |
| WO | WO 17/197056 | | 11/2017 |

OTHER PUBLICATIONS

STN Registiry No. 131926-37-9 (1991).*
Audit, 1994, Thalidomide-induced polymine acylation: a new insight into the acylation mechanism, Biogenic Amines, 10(6):543-554.
Bell et al., 2015, Sustained in vivo signaling by long-lived IL-2 induces prolonged increases of regulatory T cells, Journal of Autoimmunity, 56:66-80.
Belyaev et al., 1992, A novel synthetic route to L-α-aminoadipic acid, Izsvestiya Akademi Nauk, Seriya Khimicheskaya, 7:1692-1693.
Belyaev et al., May 1991, A novel synthetic route to $N^6$-methyl-L-lysine and $N^5$-methyl-L-ornithine via $N^3$-protected (S)-3-aminolactams, Synthesis, 417-419.
Belyaev, Jan. 16, 1995, A novel synthetic route to enantiomers of epsilon-hydroxynorleucine and epsilon-chloronorleucine from L- and D,L-lysine, Tetrahedron Letters, 36(3):439-440.
Billot et al., Feb. 10, 2011, Deregulation of aiolos expression in chronic lymphocytic leukemia is associated with epigenetic modifications, Blood, 117(6):1917-1927.
Cary, 1992, 8.15 Sulfonate esters as substrates in nucleophilic substitution reactions, in Organic Chemistry Second Edition, McGraw-Hill, Inc., New York, pp. 328-331.
Desagher et al., Sep. 2001, Phosphorylation of bid by casein kinases I and II regulates its cleavage by caspase 8, Molecular Cell, 8:601-611.

Eger et al., 1990, Synthesis, central nervous system activity and teratogenicity of a homothalidomide, Arzneimittel-Forschung, 40(10)1073-1075.
Greene et al., eds., Protective Groups in Organic Synthesis, John Wiley & Sons, Inc., New York, 1999.
IUPAC-IUB Commission on Biochemical Nomenclature, Abbreviated Nomenclature of Synthetic {olypeptides (Polymerized Amino Acids) Revised Recommendations (1971), Biochemistry, 11(5):942-944, 1972.
Kikuchi et al., 2009, Lacking of aiolos accelerates pre-mature B cell apoptosis mediated by BCR signaling through elevation in cytochrome c release, Biochimica et Biophysica Acta, 1793:1304-1314.
Knippschild et al., 2005, The casein kinase 1 family: participation in multiple cellular processes in eukaryotes, Cellular Signalling 17:675-689.
Lee et al., Jun. 2011, Assessing chiral self-recognition using chiral stationary phases, Tetrahedron, 67:7143-7147.
Li et al., May 12, 2014, Aiolos promotes anchorage independence by silencing $p66^{Sch}$ transcription in cancer cells, Cancer Cell, 25:575-589.
McMurray, 2000, Organic Chemistry Fifth Edition, Brooks/Cole, Pacific Grove, CA, pp. 398, 408.
McOmie ed., Protective Groups in Organic Chemistry, Plenum Press, London and New York, 1973.
Ouellet et al., 2013, Regulation of host gene expression by HIV-1 TAR microRNAs, Retrovirology, 10:86.
Robl et al., 1994, A synthetic route for the generation of C-7 substituted azepinones, Tetrahedron Letters, 35(9):1393-1396.
Robl et al., 1994, Peptidomimetic synthesis: a novel, highly stereoselective route to substituted Freidinger lactams, J. Am. Chem. Soc., 116(6):2348-2355.
Robl et al., 1996, Dual metalloprotease inhibitors. 6. Incorporation of bicyclic and substituted monocyclic azepinones as dipeptide surrogates in angiotensin-converting enzyme/netural endopeptidase inhibitors, J. Med. Chem. 39:494-502.
Rosenberg et al., Apr. 3, 2015, Adoptive cell transfer as personalized immunotherapy for human cancer, 348(6230):62-68.
Skrombolas et al., Feb. 2014, Challenges and developing solutions for increasing the benefits of IL-2 treatment in tumor therapy, Expert Rev Clin Immunol., 19(2):207-217.
Streitwieser et al., 1981, 8.10 Leaving Groups, in Introduction to Organic Chemistry Second Edition, Macmillan Publishing Co., Inc., New York, pp. 169-171.
CAS RN 131926-36-8, STN entry date Feb. 9, 1991, 1H-Isoindole-1,3(2H)-dione, 2-(hexahydro-2,7-dioxo-1H-azepin-3-yl)-, (S)-.
CAS RN 131926-37-9, STN entry date Feb. 9, 1991, 1H-Isoindole-1,3(2H)-dione, 2-(hexahydro-2,7-dioxo-1H-azepin-3-yl)-, (R)-.
Chang et al., 2013, Mechanism of immunomodulatory drugs' action in the treatment of multiple myeloma, Acta Biochim Biophys Sin, 46(3):240-253.
Lai et al., 2016, Modular PROTEC design for the degradation of oncogenic BCR-ABL, Angewandte Chemie International Edition, 55(2):807-810.
Ruchelman et al., 2013, Isosteric analogs of lenalidomide and pomlidomide: synthesis and biological activity, Bioorganic & Medicinal Chemistry Letters, 23(1):360-365.
Winter et al., 2015, Selective target protein degradation via phthalimide conjugation, Science, 348(6241):1376.
Kobayashi, 2014, How the anti-tumor effect of Lenalidomide, thalidomide derivative, is expressed, Farumashia, 2014, 50(11):1145.
Torigoe et al., 2016, Pomalidomide (Pomalyst capsule 1 mg/2 mg/3 mg/4 mg): pharmacokinetics, pharmacodynamics and clinical study outcome, Japanese Journal of Pharmacology, 148(3):154-161.
International Search Report and Written Opinion dated Aug. 4, 2016 in PCT/US2016/033133.
International Search Report and Written Opinion dated Jul. 28, 2017 in PCT/US2017/032936.

* cited by examiner

FIGURE 16

| Compoud No. | IL-1β | IL-6 | TNFa | Anti CD3 IL-2 Induction |
|---|---|---|---|---|
| 37 | 78 | 30 | 82 | 4.3 (72 h) |
| 38 | 73 | 25 | 83 | 8 (72 h) |
| 39 | -- | -- | -- | 20 (72 h) |
| 40 | 76 | 31 | 79 | 2.2 (24h) |
| 41 | 74 | 37 | 85 | 1.9 (24h) |
| 42 | 0.83 | 0.4 | 0.88 | 1.2 (24 h) |
| 43 | 58 | 8 | 66 | 1 (24 h) |
| 44 | 42 | 2 | 29 | 0.9 (24 h) |
| 45 | 0.2 | 0.05 | 0.21 | 0.3 (24 h) |
| 46 | 76 | 30 | 73 | 2 (72 h) |
| 47 | 0.65 | 0.17 | 0.66 | 1 (24 h) |
| 48 | 0.4 | 0.07 | 0.37 | 2 (24 h) |
| 49 | 0.34 | 0 | 0.12 | 1.1 (24 h) |
| 50 | 0.25 | 0 | 0 | 1.4 (24 h) |
| 51 | 0.47 | 0.32 | 0.48 | 1.5 (24 h) |
| 52 | 12 | 0 | 11 | 0.7 (24 h) |
| 53 | 0.42 | 0.2 | 0.48 | 0.6 (24 h) |
| 54 | 0.81 | 0.24 | 0.62 | 1 (24 h) |
| 55 | 0.22 | 0 | 0.41 | 0.3 (24 h) |
| 56 | 22 | 4 | 2 | 0.2 (24h) |
| 57 | 0.82 | 0.75 | 0.76 | 0.9 (24 h) |

CHIMERIC COMPOUNDS TARGETING PROTEINS, COMPOSITIONS, METHODS, AND USES THEREOF

BACKGROUND OF THE INVENTION

Field of the Invention

Compounds, methods of making such compounds, pharmaceutical compositions and medicaments comprising such compounds, and methods of using such compounds to treat, prevent or diagnose diseases, disorders, or conditions associated with protein malfunction are provided.

Description of the Related Technology

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis ($R_A$), Crohn's disease, inflammatory bowel disease, multiple sclerosis, endotoxin shock, osteoporosis, Alzheimer's disease, congestive heart failure, and psoriasis among others.

TNF-alpha is produced by variety of activated immune cells, particularly monocytes and macrophages. Elevated levels of TNF-alpha have been implicated in several pathological conditions including inflammation, infection, autoimmune disease, cancer development and several other disorders. Indeed, virtually all of the players in the human immune system have been report to have some level of functional relationship with TNF-alpha. See, e.g., Wallach, Cytokine, Vol. 63, 225-9 (2013). TNF is able to induce fever, apoptotic cell death, cachexia, inflammation, and to inhibit tumorigenesis and viral replication.

IL-1α and IL-1β are proinflammatory cytokines that activate cells by binding the IL-1 receptor type I (IL-1RI). These proteins are the most powerful endogenous pyrogens known. IL-1α is constitutively expressed as a precursor in cells forming biological barriers, such as epithelial cells, keratinocytes, and mucosal and endothelial cells, as well as other organ cells. IL-1α does not require processing for activation and is released from damaged or dying cells. In contrast, IL-1β must be proteolytically cleaved into its active form. Active IL-1β is primarily generated in a subset of blood monocytes, dendritic cells, and tissue macrophages, where its activation and release are tightly regulated, although studies systematically assessing other cells capable of producing IL-1β are limited. See, e.g., Nold, et al., Blood, Vol. 113, 2324-35 (2009).

Recent data from clinical trials support the use of protein antagonists of cytokines, for example soluble TNF-alpha receptor fusion protein (etanercept) or the monoclonal TNF-alpha antibody (infliximab), for the treatment of rheumatoid arthritis, Crohn's disease, juvenile chronic arthritis and psoriatic arthritis. Thus, the reduction of pro-inflammatory cytokines such as TNF-alpha and interleukin-1 (IL-I) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the zinc-finger transcription factor Aiolos. Aiolos is a transcription factor whose expression is restricted to lymphoid lineages. Aiolos binds to the Bcl-2 promoter, and also interacts with the Bcl-2 and Bcl-XL proteins to promote cell survival. Upregulation of Aiolos expression, for example, can reduce apoptosis of HIV-1 infected cells.

Likewise, expression of Aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Thus, down-regulation of Aiolos may reduce or eliminate metastasis.

Similarly, the casein kinase 1 family of proteins plays a role in the mitotic spindle formation, in DNA repair, and in RNA metabolism. See, e.g., Knippschild, et al., Cell Signal, Vol 17, pp. 675-689 (2005). There are six isoforms in humans: α, γ1, γ2, γ3, δ and ε. CK1α has been shown to have an anti-apoptotic function; its inhibition increased Fas-induced apoptosis, whereas the overexpression of CK1α delayed BID-mediated cell death. See, e.g., Desagher, et al., Mol Cell., Vol. 8, pp. 601-611 (2001). In addition, CK1α inhibits TRAIL induced apoptosis by modification of the TNF receptor or FADD at the death-inducing signaling complex (DISC). Thus, downregulation of CK1α leads to enhancement of TRAIL-induced cell death. CK1α also promotes cell survival by interacting with the retinoid X receptor (RXR). Downregulation of CK1α enhances the apoptotic effect of RXR agonists. Likewise, the ikaros family of proteins are tumor suppressors that play a role in leukemia.

One mechanism to disrupt protein drivers of disease is to decrease the cellular concentration of these proteins. For example, proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY OF THE INVENTION

The compounds disclosed in the present application have been discovered to exert surprising and unexpected biological effects. The compounds disclosed in the present application have been discovered to exert surprising and unexpected biological effects. In particular, the compounds disclosed in the present application modulate protein levels to restore protein homeostasis. Some embodiments provide chimeric compounds comprising a targeting group, a linker group, and an E1-binding group. Some embodiments provide chimeric compounds comprising a targeting group, a linker group, and an E2-binding group. Some embodiments provide chimeric compounds comprising a targeting group, a linker group, and an E3-binding group. Some embodiments provide chimeric compounds comprising a targeting group, a linker group, and a combination of one or more E1-, E2-, or E-3-binding groups.

Some embodiments provide a compound of Formula (I):

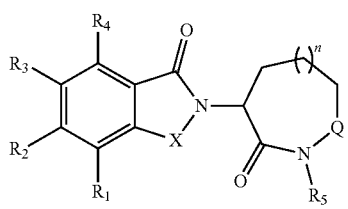

(I)

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H.

In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O. In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is present in a form of a racemic mixture. In some embodiments, the compound of Formula (I) has an S-configuration. In some embodiments, the compound of Formula (I) has an R-configuration.

Some embodiments provide a pharmaceutical composition comprising a compound of Formula (I):

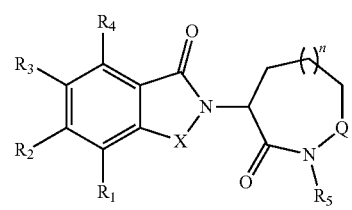

(I)

or a pharmaceutically acceptable salt or solvate thereof, and at least one pharmaceutically acceptable carrier.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O. In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, —$CH_2F$, —$CF_2H$, —$CF_3$, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the pharmaceutical composition of Formula (I) is in a form of a racemic mixture. In some embodiments, the pharmaceutical composition of Formula (I) has an S-configuration. In some embodiments, the pharmaceutical composition of Formula (I) has an R-configuration.

In some embodiments, the composition is formulated for oral, parenteral, topical, ophthalmic, inhalation, nasal, or intravenous administration.

In some embodiments, the pharmaceutical composition further comprises a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

Some embodiments provide methods of treating, ameliorating, or preventing a disease, disorder, or condition associated with cytokines, comprising administering a therapeutically effective amount of a compound of Formula (I):

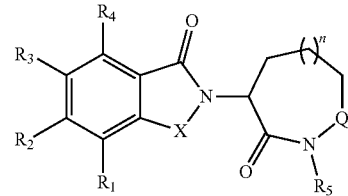

or a pharmaceutically acceptable salt or solvate thereof, to a subject in need thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, organ transplant rejection, and cancer.

In some embodiments, the compound of Formula (I) is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, —$CH_2F$, —$CF_2H$, —$CF_3$, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is in a form of a racemic mixture. In some embodiments, the compound of Formula (I) has an S-configuration. In some embodiments, the compound of Formula (I) has an R-configuration.

Some embodiments provide methods of inhibiting cytokine activity, comprising contacting a cell with a compound of Formula (I):

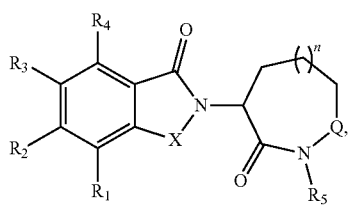

(I)

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, —$CH_2F$, —$CF_2H$, —$CF_3$, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is in a form of a racemic mixture. In some embodiments, the compound of Formula (I) has an S-configuration. In some embodiments, the compound of Formula (I) has an R-configuration.

In some embodiments, the compound of Formula (I) is provided in combination with a second agent. In some embodiments, the second agent is selected from the group consisting of anti-inflammatory agents, anti-cancer agents, immunostimulatory agents, and immunosuppressive agents. In some embodiments, the second agent is an anti-cancer agent.

Some embodiments provide methods of inducing cytokine activity, comprising contacting a cell with a compound of Formula (I):

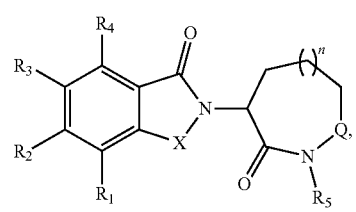

(I)

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, —$CH_2F$, —$CF_2H$, —$CF_3$, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is in a form of a racemic mixture. In some embodiments, the compound of Formula (I) has an S-configuration. In some embodiments, the compound of Formula (I) has an R-configuration.

In some embodiments, the compound of Formula (I) is provided in combination with a second agent. In some embodiments, the second agent is selected from the group consisting of anti-inflammatory agents, anti-cancer agents, immunostimulatory agents, and immunosuppressive agents. In some embodiments, the second agent is an anti-cancer agent.

Some embodiments provide methods of inhibiting TNF-alpha activity, comprising contacting a cell with a compound of Formula (I):

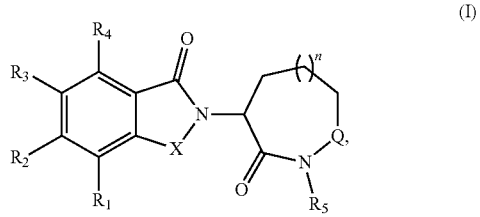

(I)

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, —$CH_2F$, —$CF_2H$, —$CF_3$, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is in a form of a racemic mixture. In some embodiments, the compound of Formula (I) has an S-configuration. In some embodiments, the compound of Formula (I) has an R-configuration.

In some embodiments, the compound of Formula (I) is provided in combination with a second agent. In some embodiments, the second agent is selected from the group consisting of anti-inflammatory agents, anti-cancer agents, immunostimulatory agents, and immunosuppressive agents. In some embodiments, the second agent is an anti-cancer agent.

Some embodiments provide methods of inhibiting organ transplant rejection, comprising administering a therapeutically effective amount of a compound of Formula (I):

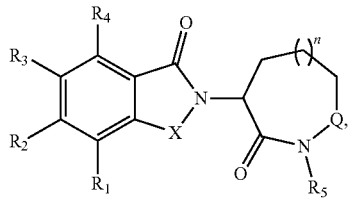

(I)

or a pharmaceutically acceptable salt or solvate thereof, to a subject in need thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, —$CH_2F$, —$CF_2H$, —$CF_3$, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is in a form of a racemic mixture. In some embodiments, the compound of Formula (I) has an S-configuration. In some embodiments, the compound of Formula (I) has an R-configuration.

In some embodiments, the compound of Formula (I) is provided in combination with a second agent. In some embodiments, the second agent is selected from the group consisting of anti-inflammatory agents, anti-cancer agents, and immunosuppressive agents. In some embodiments, the second agent is an anti-inflammatory agent.

In some embodiments, the subject in need thereof is a liver transplant recipient, a kidney transplant recipient, a heart transplant recipient, a skin transplant recipient, or a lung transplant recipient.

Some embodiments provide a compound of Formula (II):

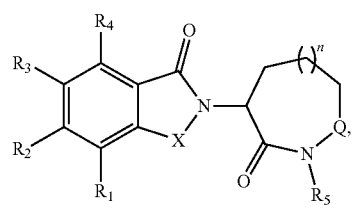

(II)

or a pharmaceutically acceptable salt or solvate thereof.

In some embodiments, $R_1$, $R_2$, $R_3$, and $R_4$, are each independently H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, optionally substituted $C_6$ to $C_{10}$ heteroaryl, or L-Y. In some embodiments, $R_1$, $R_2$, $R_3$, and $R_4$, cannot all be H. In some embodiments, one of $R_1$ or $R_2$ must by L-Y.

In some embodiments, each $R_5$ is independently H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_6$ to $C_{10}$ heteroaryl.

In some embodiments, X is $C(R_5)_2$, $CH(R_5)$, $CH_2$, C=O, or C=S.

In some embodiments, Q is $C(R_5)_2$, $CH(R_5)$, $CH_2$, C=O, C=S; S=O, or $SO_2$.

In some embodiments, n is 1 or 2.

In some embodiments, L is —$Z_1$—$(R_6$—O—$R_6)_t$—$Z_2$—; —$Z_1$—$(R_6$—NH—$R_6)_t$—$Z_2$—; —$Z_1$—$(R_6$—S—$R_6)_t$—$Z_2$—; —$Z_1$—$(R_6$—(CO)—$R_6)_t$—$Z_2$—; —$Z_1$—$(R_6$—(CO$_2$)—$R_6)_t$—$Z_2$—; —$Z_1$—$(R_6$—(NHCO)—$R_6)_t$—$Z_2$—; —$Z_1$—

$-(R_6-(CONH)-R_6)_t-Z_2-$; $-Z_1-(R_6-S-R_6)_t-Z_2-$; $-Z_1-(R_6-(SO)-R_6)_t-Z_2-$; $-Z_1-(R_6-(SO_2)-R_6)_t-Z_2-$; $-Z_1-(R_6-(NHSO_2)-R_6)_t-Z_2-$; $-Z_1-(R_6-(SO_2NH)-R_6)_t-Z_2-$; or $-Z_1-(R_6-R_7-R_6)_t-Z_2-$.

In some embodiments, t is 1, 2, 3, 4, 5, 6, 7, or 8.

In some embodiments, $Z_1$ and $Z_2$ are independently $-CH_2-$; $-O-$; $-S-$; $S=O$; $-SO_2-$; $C=O$; $-CO_2-$; $-NH-$; $-NH(CO)-$; $-(CO)NH-$; $-NH-SO_2-$; $-SO_2-NH-$; $-R_6CH_2-$; $-R_6O-$; $-R_6S-$; $R_6-S=O$; $-R_6SO_2-$; $R_6-C=O$; $-R_6CO_2-$; $-R_6NH-$; $-R_6NH(CO)-$; $-R_6(CO)NH-$; $-R_6NH-SO_2-$; $-R_6SO_2-NH-$; $-CH_2R_6-$; $-OR_6-$; $-SR_6-$; $S=O-R_6$; $-SO_2R_6-$; $C=O-R_6$; $-CO_2R_6-$; $-NHR_6-$; $-NH(CO)R_6-$; $-(CO)NHR_6-$; $-NH-SO_2R_6-$; or $-SO_2-NHR_6-$.

In some embodiments, each $R_6$ is absent, or independently $C_1$ to $C_6$ alkyl, $C_2$ to $C_6$ alkenyl, $C_2$ to $C_6$ alkynyl, $C_6$ to $C_{10}$ aryl, $C_3$ to $C_8$ heterocyclyl, or $C_6$ to $C_{10}$ heteroaryl.

In some embodiments, $R_7$ is optionally substituted $C_1$ to $C_6$ alkyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_6$ to $C_{10}$ heteroaryl.

In some embodiments, Y is

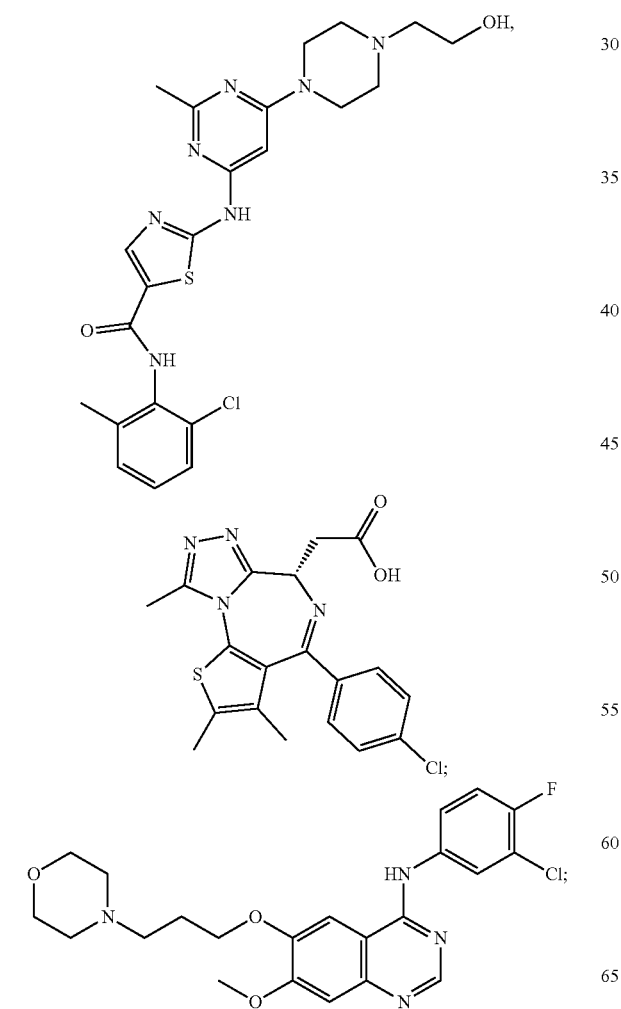

-continued

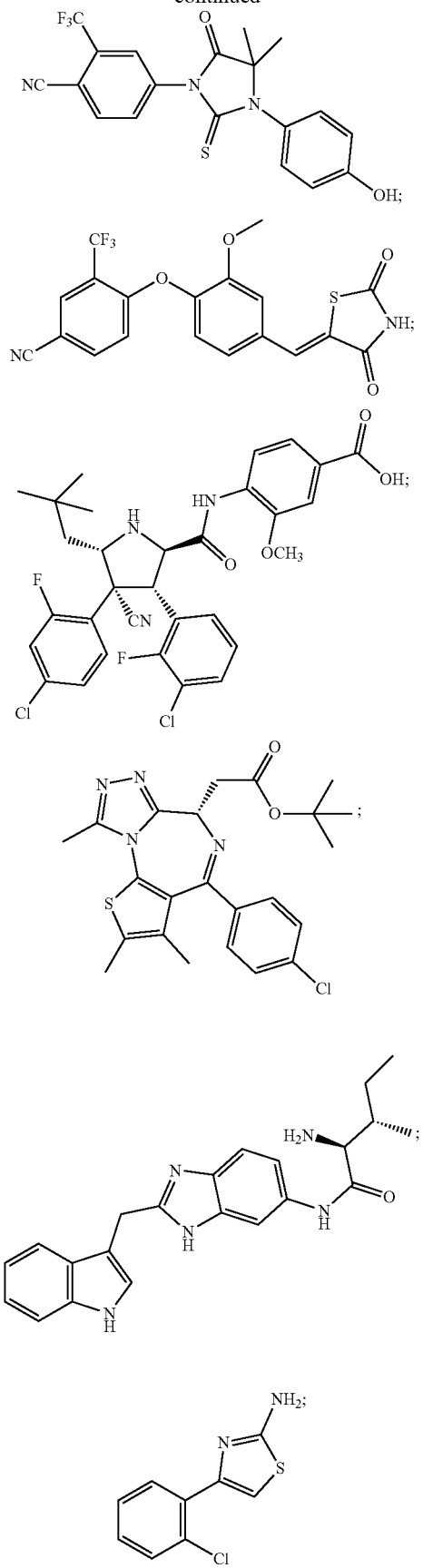

-continued

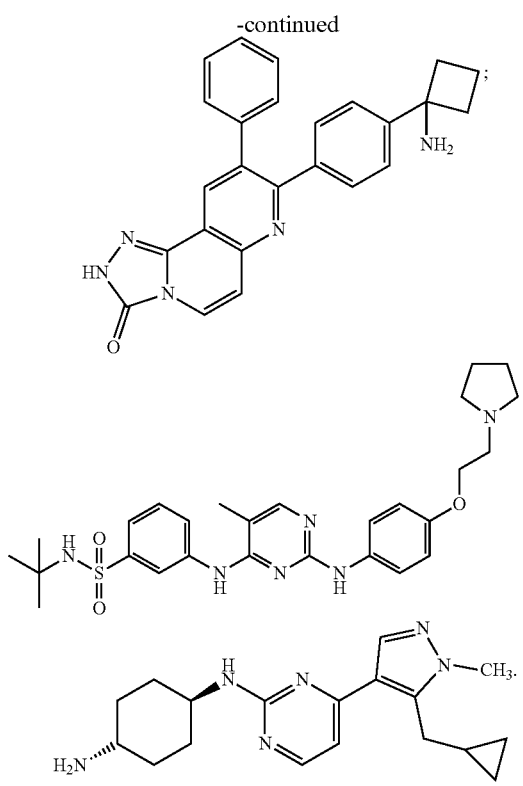

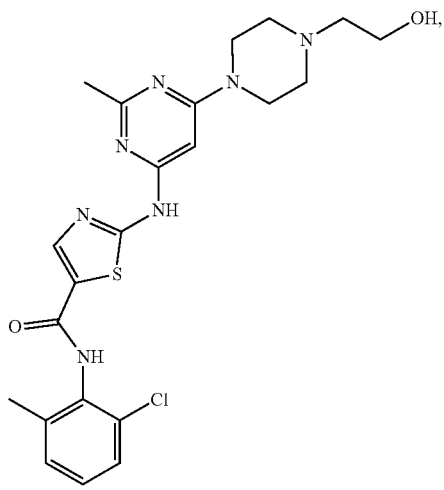 [SMILES: Cc1nc(Nc2ncc(C(=O)Nc3c(C)cccc3Cl)s2)cc(N2CCN(CCO)CC2)n1]

In some embodiments, at least one of $R_1$, $R_2$, $R_3$, and $R_4$ is L-Y.

In some embodiments, Q is selected from the group consisting of $CH_2$ and C=O. In some embodiments, Q is $CH_2$. In some embodiments, Q is C=O. In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H. In some embodiments, X is $CH_2$. In some embodiments, X is C=O. In some embodiments, $R_1$ is L-Y.

In some embodiments, Y is

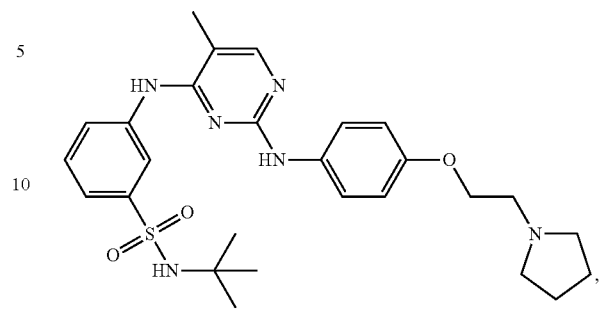

derivatized to attach to L. In some embodiments, Y is

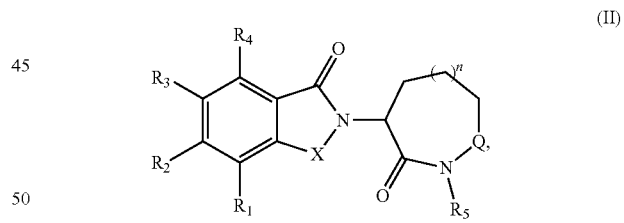

derivatized to attach to L.

In some embodiments, $R_2$ is $NH_2$. In some embodiments, $R_2$ is $NO_2$. In some embodiments, $R_1$ is hydroxyl. In some embodiments, $R_1$, $R_2$, $R_3$, and $R_4$ are independently selected from H, fluoro, chloro, methyl, $-CH_2F$, $-CF_2H$, $-CF_3$, ethyl, n-propyl, isopropyl, sec-butyl, isobutyl, tert-butyl, cyclopropyl, cyclobutyl, cyclopentyl, and aminomethyl ($-CH_2-NH_2$).

In some embodiments, the compound of Formula (II) is present in a form of a racemic mixture. In some embodiments, the compound of Formula (II) has an S-configuration. In some embodiments, the compound of Formula (II) has an R-configuration.

In some embodiments, L is $-Z_1-(R_6-O-R_6)_t-Z_2-$; $-Z_1(R_6-NH-R_6)_t-Z_2-$; $-Z_1-(R_6-(NHCO)-R_6)_t-Z_2-$; $-Z_1-(R_6-(CONH)-R_6)_t-Z_2-$. In some embodiments, t is 1, 2, 3, or 4. In some embodiments, $Z_1$ and $Z_2$ are independently $-CH_2-$; $-O-$; $-NH-$; $-NH(CO)-$; or $-(CO)NH$.

Some embodiments provide a method of treating a disease, disorder, or condition associated with an interleukin, aiolos, ikaros, TNF-alpha, CK1-alpha, or a combination of any of the foregoing comprising administering a therapeutically effective amount of a compound of Formula (II):

![Formula II structure]

(II)

or a pharmaceutically acceptable salt or solvate thereof.

In some embodiments, $R_1$, $R_2$, $R_3$, and $R_4$, are each independently H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, optionally substituted $C_6$ to $C_{10}$ heteroaryl, or L-Y. In some embodiments, $R_1$, $R_2$, $R_3$, and $R_4$, cannot all be H. In some embodiments, one of $R_1$ or $R_2$ must by L-Y.

In some embodiments, each $R_5$ is independently H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_6$ to $C_{10}$ heteroaryl.

In some embodiments, X is $C(R_5)_2$, $CH(R_5)$, $CH_2$, C=O, or C=S.

In some embodiments, Q is $C(R_5)_2$, $CH(R_5)$, $CH_2$, C=O, C=S; S=O; or $SO_2$.

In some embodiments, n is 1 or 2.

In some embodiments, L is $-Z_1-(R_6-O-R_6)_t-Z_2-$; $-Z_1(R_6-NH-R_6)_t-Z_2-$; $-Z_1-(R_6-S-R_6)_t-Z_2-$; $-Z_1-(R_6-(CO)-R_6)_t-Z_2-$; $-Z_1-(R_6-(CO_2)-R_6)_t-Z_2-$; $-Z_1-(R_6-(NHCO)-R_6)_t-Z_2-$; $-Z_1-(R_6-(CONH)-R_6)_t-Z_2-$; $-Z_1-(R_6-S-R_6)_t-Z_2-$; $-Z_1-(R_6-(SO)-R_6)_t-Z_2-$; $-Z_1-(R_6-(SO_2)-R_6)_t-Z_2-$; $-Z_1-(R_6-(NHSO_2)-R_6)_t-Z_2-$; $-Z_1-(R_6-(SO_2NH)-R_6)_t-Z_2-$; or $-Z_1-(R_6-R_7-R_6)_t-Z_2-$.

In some embodiments, t is 1, 2, 3, 4, 5, 6, 7, or 8.

In some embodiments, $Z_1$ and $Z_2$ are independently $-CH_2-$; $-O-$; $-S-$; S=O; $-SO_2-$; C=O; $-CO_2-$; $-NH-$; $-NH(CO)-$; $-(CO)NH-$; $-NH-SO_2-$; $-SO_2-NH-$; $-R_6CH_2-$; $-R_6O-$; $-R_6S-$; $R_6-S=O$; $-R_6SO_2-$; $R_6-C=O$; $-R_6CO_2-$; $-R_6NH-$; $-R_6NH(CO)-$; $-R_6(CO)NH-$; $-R_6NH-SO_2-$; $-R_6SO_2-NH-$; $-CH_2R_6-$; $-OR_6-$; $-SR_6-$; S=O$-R_6$; $-SO_2R_6-$; C=O$-R_6$; $-CO_2R_6-$; $-NHR_6-$; $-NH(CO)R_6-$; $-(CO)NHR_6-$; $-NH-SO_2R_6-$; or $-SO_2-NHR_6-$.

In some embodiments, each $R_6$ is absent, or independently $C_1$ to $C_6$ alkyl, $C_2$ to $C_6$ alkenyl, $C_2$ to $C_6$ alkynyl, $C_6$ to $C_{10}$ aryl, $C_3$ to $C_8$ heterocyclyl, or $C_6$ to $C_{10}$ heteroaryl.

In some embodiments, $R_7$ is optionally substituted $C_1$ to $C_6$ alkyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_6$ to $C_{10}$ heteroaryl.

In some embodiments, Y is

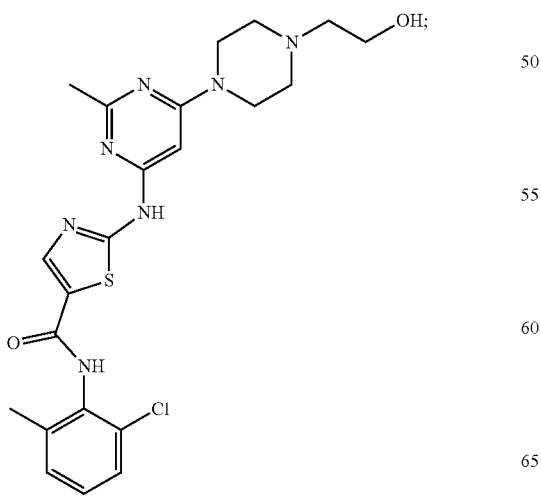

-continued

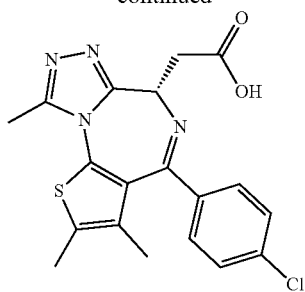

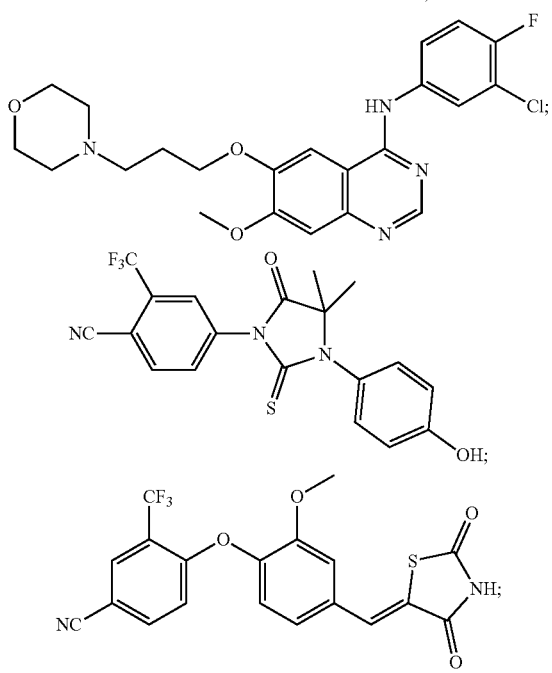

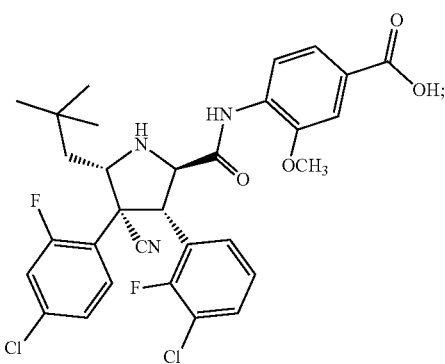

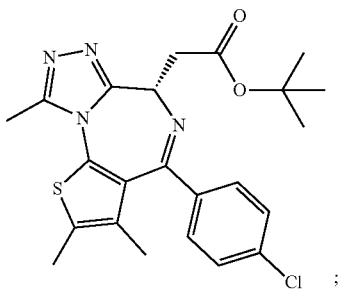

-continued

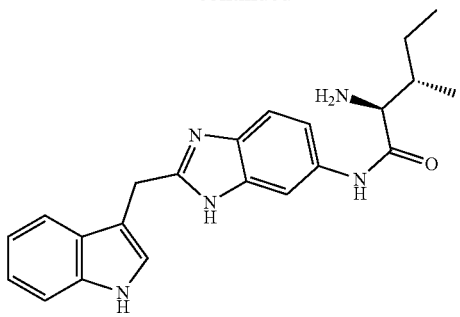

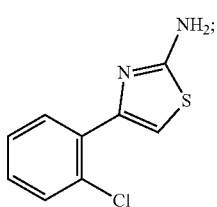

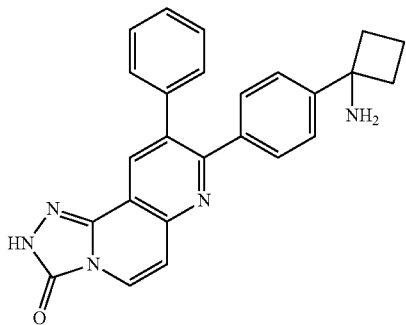

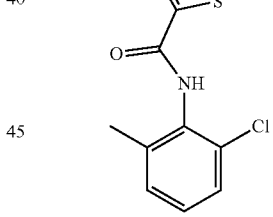

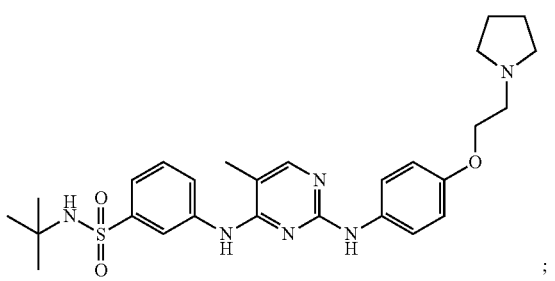

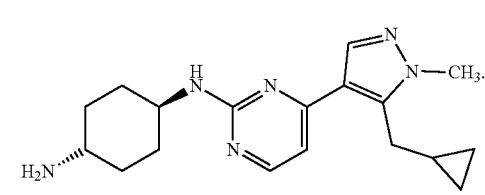

In some embodiments, at least one of $R_1$, $R_2$, $R_3$, and $R_4$ is L-Y. In some embodiments, Y is

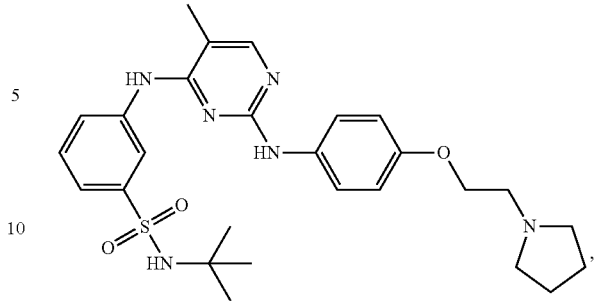

derivatized to attach to L

In some embodiments, Q is selected from the group consisting of $CH_2$ and C=O. In some embodiments, Q is $CH_2$. In some embodiments, Q is C=O. In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H. In some embodiments, X is $CH_2$. In some embodiments, X is C=O. In some embodiments, $R_1$ is L-Y.

In some embodiments, Y is

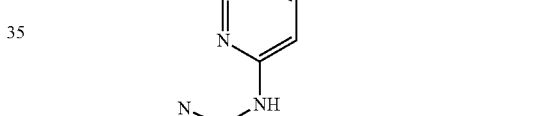

derivatized to attach to L. In some embodiments, Y is

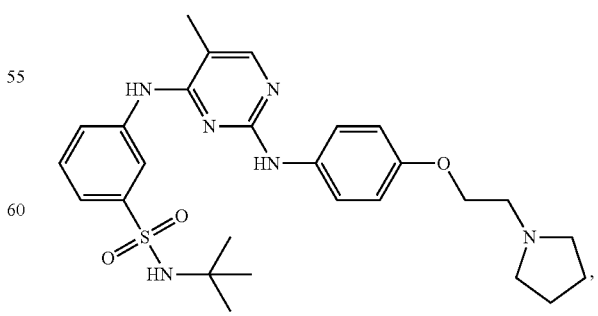

derivatized to attach to L In some embodiments, $R_2$ is $NH_2$. In some embodiments, $R_2$ is $NO_2$. In some embodiments, $R_1$ is hydroxyl. In some embodiments, $R_1$, $R_2$, $R_3$, and $R_4$ are independently selected from H, fluoro, chloro, methyl, $—CH_2F$, $—CF_2H$, $—CF_3$, ethyl, n-propyl, isopropyl, sec-butyl, isobutyl, tert-butyl, cyclopropyl, cyclobutyl, cyclopentyl, and aminomethyl ($—CH_2—NH_2$).

In some embodiments, the compound of Formula (II) is present in a form of a racemic mixture. In some embodiments, the compound of Formula (II) has an S-configuration. In some embodiments, the compound of Formula (II) has an R-configuration.

In some embodiments, L is $—Z_1—(R_6—O—R_6)_t—Z_2—$; $—Z_1(R_6—NH—R_6)_t—Z_2—$; $—Z_1—(R_6—(NHCO)—R_6)_t—Z_2—$; $—Z_1—(R_6—(CONH)—R_6)_t—Z_2—$. In some embodiments, t is 1, 2, 3, or 4. In some embodiments, $Z_1$ and $Z_2$ are independently $—CH_2—$; $—O—$; $—NH—$; $—NH(CO)—$; or $—(CO)NH$.

In some embodiments, at least one of $R_1$, $R_2$, $R_3$, and $R_4$ is L-Y.

In some embodiments, Q is selected from the group consisting of $CH_2$ and $C=O$. In some embodiments, Q is $CH_2$. In some embodiments, Q is $C=O$. In some embodiments, n is 1. In some embodiments, n is 2.

In some embodiments, each $R_5$ is independently H. In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H. In some embodiments, X is $CH_2$. In some embodiments, X is $C=O$. In some embodiments, $R_1$ is L-Y.

In some embodiments, Y is

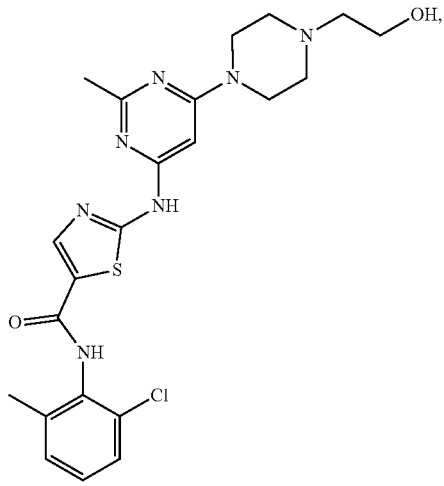 [SMILES: Cc1nc(Nc2ncc(C(=O)Nc3c(C)cccc3Cl)s2)cc(N2CCN(CCO)CC2)n1]

derivatized to attach to L. In some embodiments, Y is

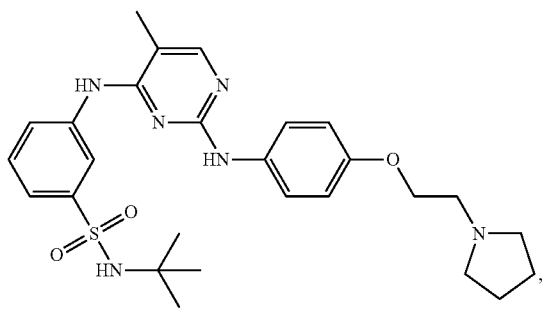 [SMILES: Cc1cnc(Nc2ccc(OCCN3CCCC3)cc2)nc1Nc1cccc(S(=O)(=O)NC(C)(C)C)c1]

derivatized to attach to L. In some embodiments, $R_2$ is $NH_2$. In some embodiments, $R_2$ is $NO_2$. In some embodiments, $R_1$ is hydroxyl. In some embodiments, $R_1$, $R_2$, $R_3$, and $R_4$ are independently selected from H, fluoro, chloro, methyl, $—CH_2F$, $—CF_2H$, $—CF_3$, ethyl, n-propyl, isopropyl, sec-butyl, isobutyl, tert-butyl, cyclopropyl, cyclobutyl, cyclopentyl, and aminomethyl ($—CH_2—NH_2$).

In some embodiments, the compound of Formula (II) is present in a form of a racemic mixture. In some embodiments, the compound of Formula (II) has an S-configuration. In some embodiments, the compound of Formula (II) has an R-configuration.

In some embodiments, L is $—Z_1—(R_6—O—R_6)_t—Z_2—$; $—Z_1(R_6—NH—R_6)_t—Z_2—$; $—Z_1—(R_6—(NHCO)—R_6)_t—Z_2—$; $—Z_1—(R_6—(CONH)—R_6)_t—Z_2—$. In some embodiments, t is 1, 2, 3, or 4. In some embodiments, $Z_1$ and $Z_2$ are independently $—CH_2—$; $—O—$; $—NH—$; $—NH(CO)—$; or $—(CO)NH$.

In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, organ transplant rejection, and cancer.

In some embodiments, the compound of Formula (II) is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

Some embodiments provide a compound of Formula (III):

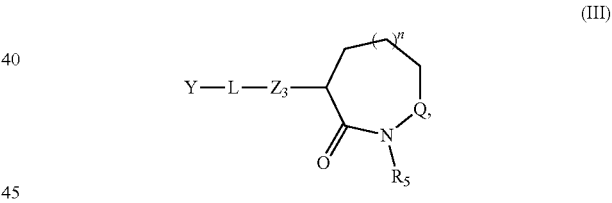

(III)

or a pharmaceutically acceptable salt or solvate thereof.

In some embodiments, Q is $C(R_5)_2$, $CH(R_5)$, $CH_2$, $C=O$, $C=S$; $S=O$, or $SO_2$. In some embodiments, Q is $CH_2$ or $C=O$.

In some embodiments, n is 1 or 2.

In some embodiments, each $R_5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_6$ to $C_{10}$ heteroaryl.

In some embodiments, $Z_3$ is $—CH_2—$; $—O—$; $—S—$; $S=O$; $—SO_2—$; $C=O$; $—CO_2—$; $—NH—$; $—NH(CO)—$; $—(CO)NH—$; $—NH—SO_2—$; $—SO_2—NH—$; $—R_6O—$; $—R_6S—$; $R_6S=O$; $—R_6SO_2—$; $R_6C=O$; $—R_6CO_2—$; $—R_6NH—$; $—R_6NH(CO)—$; $—R_6(CO)NH—$; $—R_6NH—SO_2—$; or $—R_6SO_2—NH—$. In some embodiments, $Z_3$ is $—CH_2—$; $—O—$; $—S—$; $S=O$; $—SO_2—$; $C=O$; $—CO_2—$; $—NH—$; $—NH(CO)—$; $—(CO)NH—$; $—NH—SO_2—$; or $—SO_2—NH—$.

In some embodiments, L is —(R$_6$—O—R$_6$)$_t$—; —(R$_6$—NH—R$_6$)$_t$—; —(R$_6$—S—R$_6$)$_t$—; —(R$_6$—(CO)—R$_6$)$_t$—; —(R$_6$—(CO$_2$)—R$_6$)$_t$—; —(R$_6$—(NHCO)—R$_6$)$_t$—; —(R$_6$—(CONH)—R$_6$)$_t$—; —(R$_6$—S—R$_6$)$_t$—; —(R$_6$—(SO)—R$_6$)$_t$—; —(R$_6$—(SO$_2$)—R$_6$)$_t$—; —(R$_6$—(NHSO$_2$)—R$_6$)$_t$—; —(R$_6$—(SO$_2$NH)—R$_6$)$_t$—; or —(R$_6$—R$_7$—R$_6$)$_t$—.

In some embodiments, t is 1, 2, 3, 4, 5, 6, 7, or 8.

In some embodiments, each R$_6$ is absent or independently C$_1$ to C$_6$ alkyl, C$_2$ to C$_6$ alkenyl, C$_2$ to C$_6$ alkynyl, C$_6$ to C$_{10}$ aryl, C$_3$ to C$_8$ heterocyclyl, or C$_6$ to C$_{10}$ heteroaryl.

In some embodiments, R$_7$ is optionally substituted C$_1$ to C$_6$ alkyl, optionally substituted C$_3$ to C$_8$ carbocyclyl, optionally substituted C$_6$ to C$_{10}$ aryl, optionally substituted C$_3$ to C$_8$ heterocyclyl, or optionally substituted C$_6$ to C$_{10}$ heteroaryl.

Some embodiments provide a compound of Formula (III):

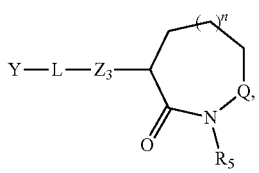

(III)

or a pharmaceutically acceptable salt or solvate thereof. In some embodiments of this paragraph, Q is CH$_2$ or C=O. In some embodiments of this paragraph, n is 1 or 2. In some embodiments of this paragraph, R$_5$ is H or optionally substituted C$_1$ to C$_6$ alkyl. In some embodiments of this paragraph, Z$_3$ is —CH$_2$—; —O—; —S—; S=O; —SO$_2$—; C=O; —CO$_2$—; —NH—; —NH(CO)—; —(CO)NH—; —NH—SO$_2$—; or —SO$_2$—NH—. In some embodiments of this paragraph, L is —(R$_6$—O—R$_6$)$_t$—; —(R$_6$—NH—R$_6$)$_t$—; —(R$_6$—S—R$_6$)$_t$—; —(R$_6$—(CO)—R$_6$)$_t$—; —(R$_6$—(CO$_2$)—R$_6$)$_t$—; —(R$_6$—(NHCO)—R$_6$)$_t$—; or —(R$_6$—(CONH)—R$_6$)$_t$—. In some embodiments of this paragraph, t is 1, 2, 3, or 4. In some embodiments of this paragraph, each R$_6$ is absent. In some embodiments of this paragraph, each R$_6$ is unsubstituted C$_1$ to C$_6$ alkyl. In some embodiments of this paragraph, R$_7$ is optionally substituted C$_1$ to C$_6$ alkyl, optionally substituted C$_3$ to C$_8$ carbocyclyl, optionally substituted C$_6$ to C$_{10}$ aryl, optionally substituted C$_3$ to C$_8$ heterocyclyl, or optionally substituted C$_6$ to C$_{10}$ heteroaryl.

In some embodiments, Y, as used with respect to Formulae (II) and (III) herein, is

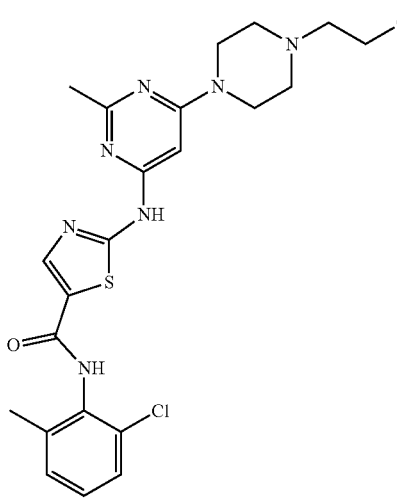

-continued

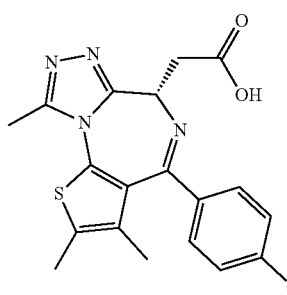

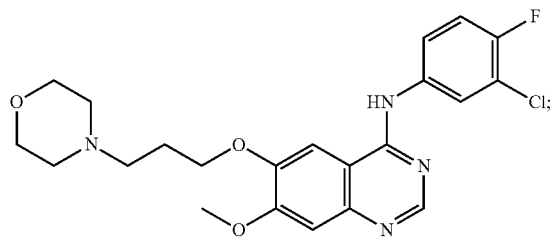

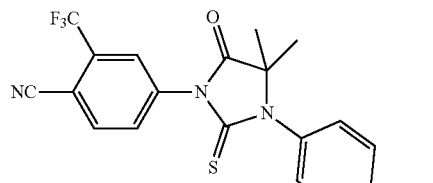

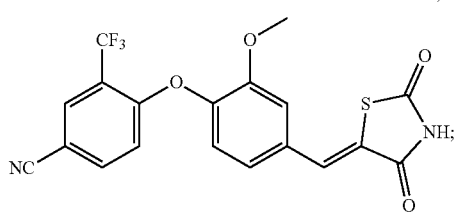

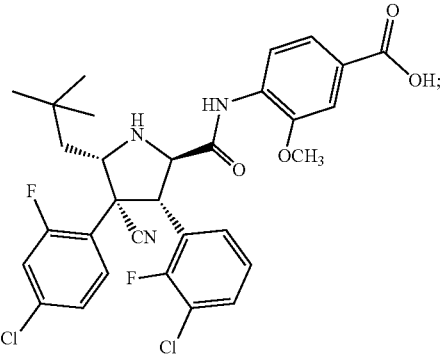

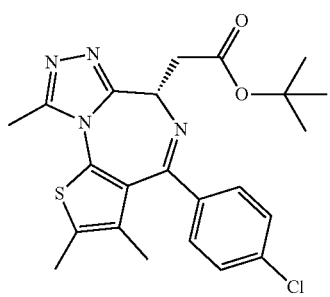

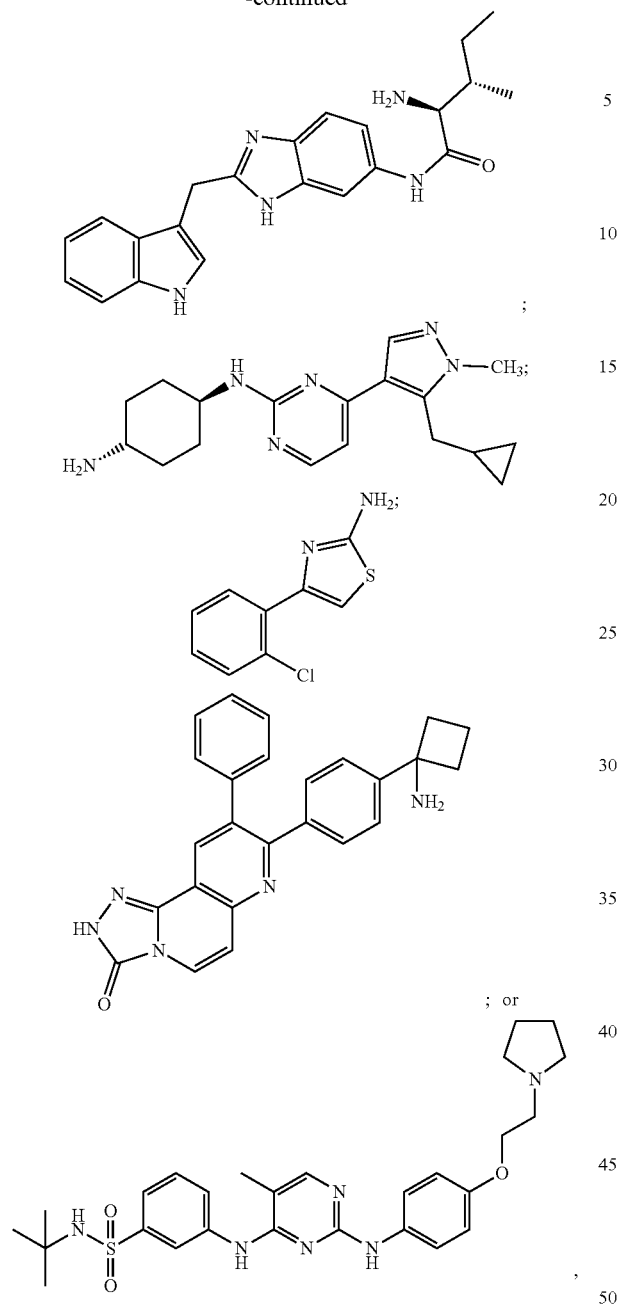

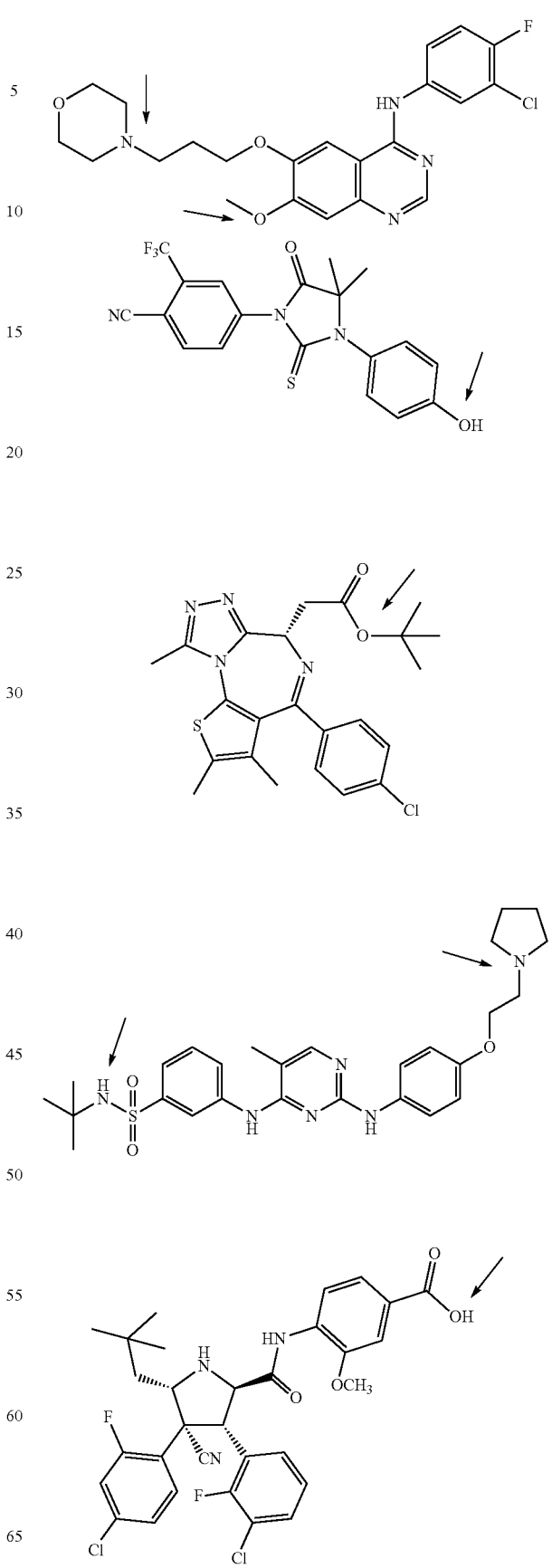

derivatized to connect with L. As used herein, "derivatized" to connect with L refers to the Y moiety forming a new bond (or a new functional group) with the linker moiety L. This new bond can be, but is not limited to, a C-amide, a N-amide, a C-carboxy, an O-carboxy, an ether, an substituted amine, a sulfinyl, a sulfenyl, a sulfonyl, a N-sulfonamido, a S-sulfonamido, a carbon-carbon bond (i.e., an alkyl, alkenyl, or alkynyl), an O-carbamyl, a N-carbamyl, a thiocarbonyl, a carbonyl, an O-thiocarbamyl, and a N-thiocarbamyl. Exemplary point of derivitization include, but are not limited to those shown below with an arrow. In some embodiments, derivatization can include removing a functional group to expose (for example) an amino, hydroxy, or carboxy group. The necessary derivitization to the groups shown below is within the ability of one skilled in the art.

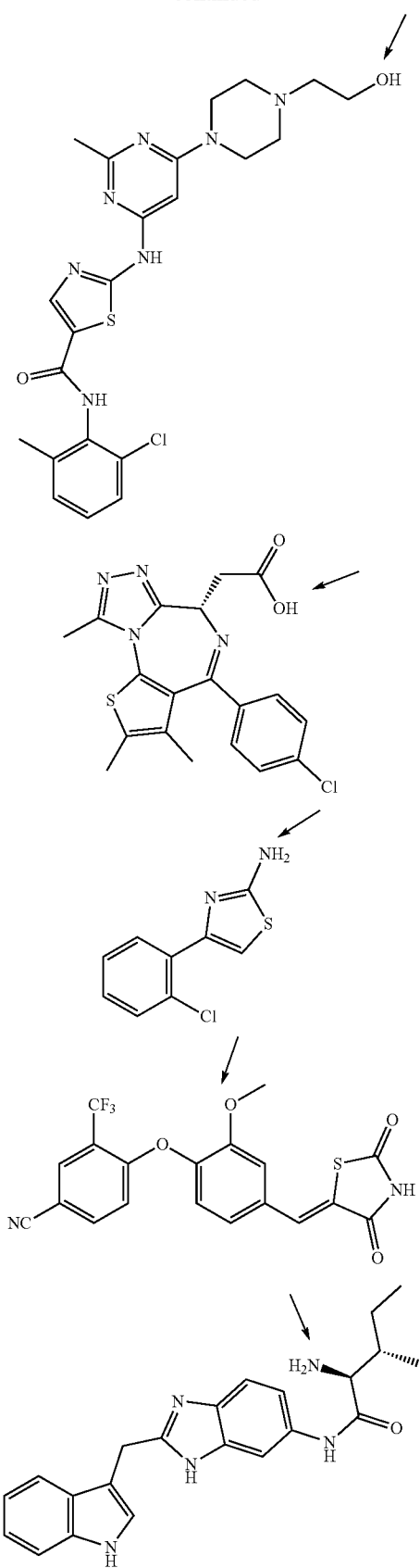

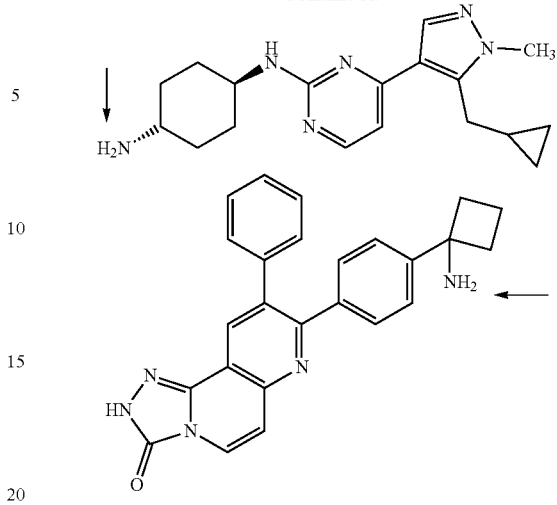

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

BRIEF DESCRIPTION OF THE DRAWINGS

FIG. 16 represents percent inhibition values for IL1-beta, IL6, and TNF-alpha compared to a DMSO-LPS treated control (control exhibits 0% inhibition). The IL2 values represent the fold change in IL2 activity related to DMSO-aCD3 treated cells (control exhibits an activity of 1.0).

DETAILED DESCRIPTION

Figure 1:
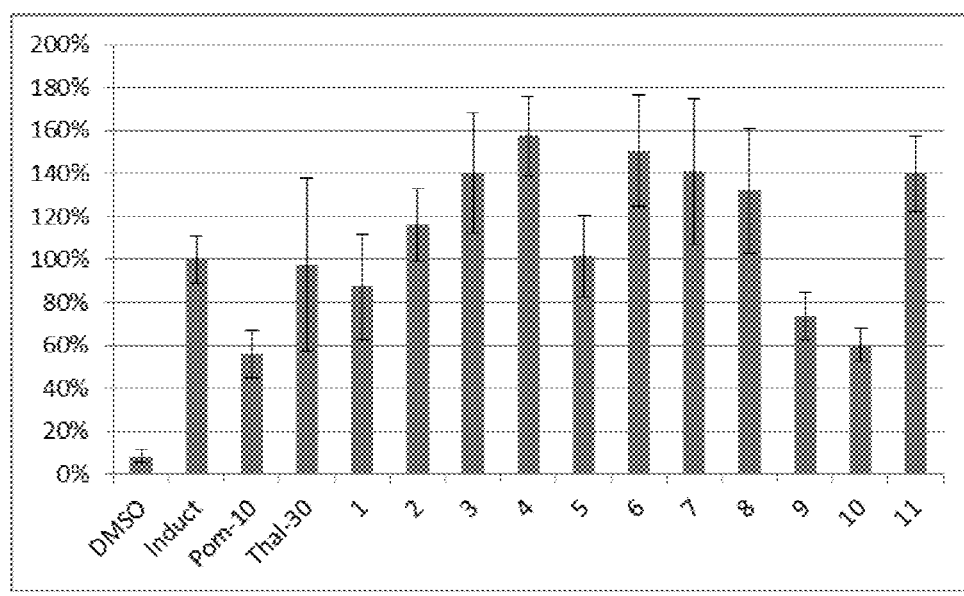
FIG. 1 represents the activity against IL-1-beta in CD14 macrophages, plated in 96 well plates and treated with 100 ng/mL macrophage colony-stimulating factor (M-CSF) for up to 1 week to differentiate cells into macrophages. Cells were pretreated with compounds for 1 hr and then induced with either 200 ng/ml LPS or 20 ng/ml of TNF-alpha for 18-24 hrs. Cytokines in the media were measured according to MesoScale protocol. Pom-10 is 10 uM pomalidomide; Thal-30 is 30 uM thalidomide. The negative control wells were treated with DMSO. Cells were treated with the indicated compound (20 uM). Compound activity is measured as a percentage of LPS-induced activity.

Some embodiments provide a compound of Formula (I):

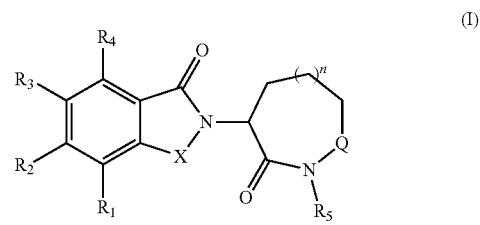

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, $R_1$, $R_2$, $R_3$, and $R_4$, are each independently selected from the group consisting of H, deuterium, hydroxyl, halogen, cyano, optionally substituted amino, optionally substituted C-amido, optionally substituted N-amido, optionally substituted ester, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, and optionally substituted $C_3$ to $C_8$ carbocyclyl.

In some embodiments, $R_1$, $R_2$, $R_3$, and $R_4$, are each independently selected from the group consisting of H, deuterium, hydroxyl, halogen, cyano, optionally substituted amino, optionally substituted C-amido, optionally substituted N-amido, unsubstituted $C_1$ to $C_6$ alkoxy, unsubstituted $C_1$ to $C_6$ alkyl, and unsubstituted $C_3$ to $C_8$ carbocyclyl.

In some embodiments, each $R_5$ is independently selected from the group consisting of H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S. In some embodiments, X is $CH_2$ or C=O.

In some embodiments, Q is selected from the group consisting of $C(R_5)_2$, $CH(R_5)$, $CH_2$, C=O, C=S; S=O, and $SO_2$. In some embodiments, Q is $C(R_5)_2$, $CH(R_5)$, $CH_2$, or C=O. In some embodiments, Q is $CH_2$ or C=O.

In some embodiments, n is 1 or 2. In some embodiments n is 1. In some embodiments, n is 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, each $R_5$ is independently H.

In some embodiments, each $R_5$ is independently optionally substituted $C_1$ to $C_6$ alkyl. In some embodiments, each $R_5$ is independently optionally substituted $C_6$ to $C_{10}$ aryl. In some embodiments, one $R_5$ is optionally substituted $C_6$ to $C_{10}$ aryl and the other $R_5$ are H.

In some embodiments, X is $CH_2$. In some embodiments, X is C=O. In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy. In some embodiments, $R_1$ is hydroxyl. In some embodiments, $R_1$, $R_2$, $R_3$, and $R_4$ are independently selected from H, fluoro, chloro, methyl, ethyl, n-propyl, isopropyl, sec-butyl, isobutyl, tert-butyl, cyclopropyl, cyclobutyl, cyclopentyl, and aminomethyl (—$CH_2$—$NH_2$).

In some embodiments, the compound of Formula (I) is present in a form of a racemic mixture. In some embodiments, the compound of Formula (I) has an S-configuration. In some embodiments, the compound of Formula (I) has an R-configuration.

In some embodiments, the compound of Formula (I) is selected from:

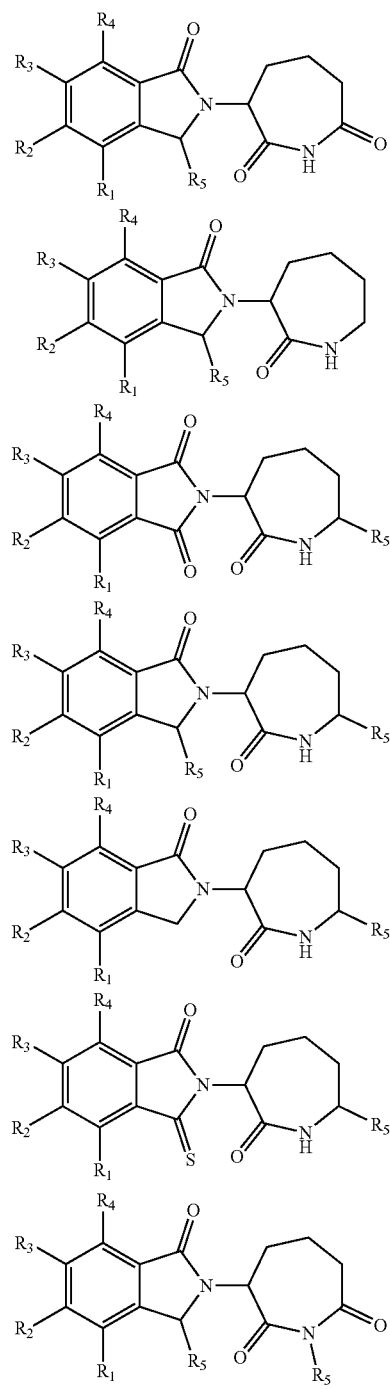

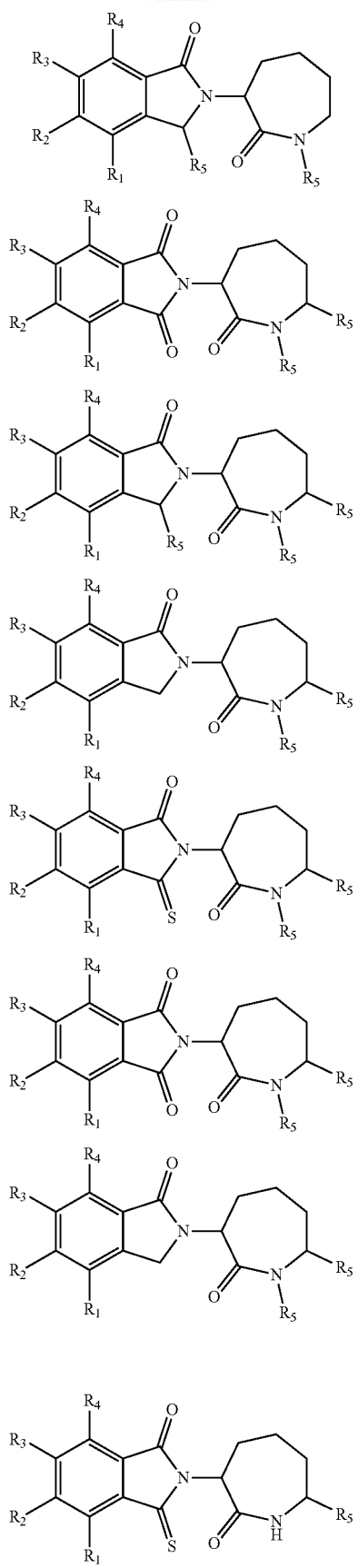
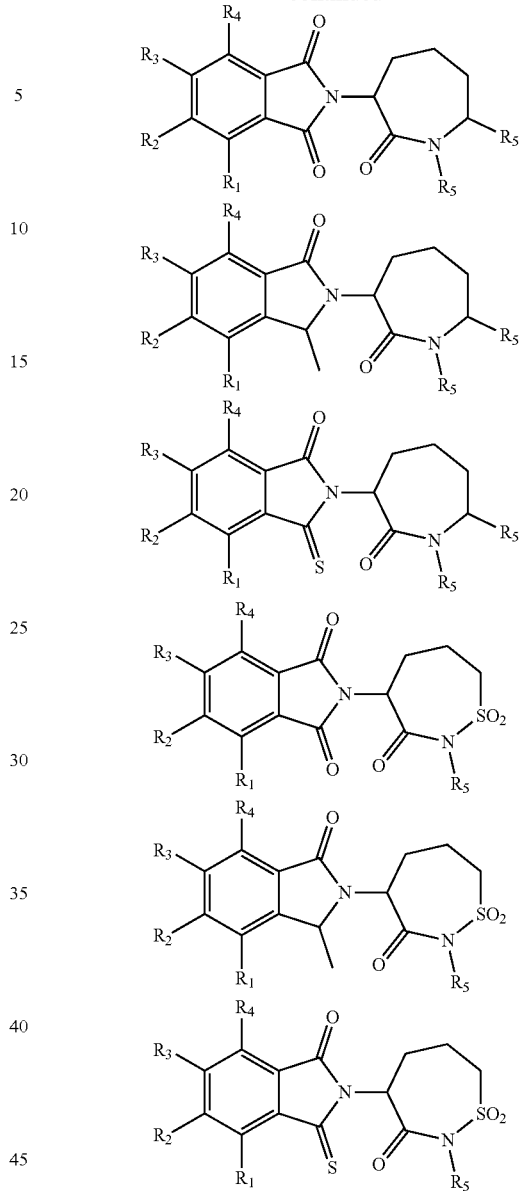

In some embodiments of this paragraph, $R_1$, $R_2$, $R_3$, and $R_4$ are selected from H, deuterium, $NH_2$, $NHCH_3$, $N(CH_3)_2$, $NO_2$, hydroxyl, halogen (for example, fluoro or chloro), optionally substituted $C_1$ to $C_6$ alkyl (for example, optionally substituted methyl, ethyl, n-propyl, isopropyl, sec-butyl, isobutyl, or tert-butyl, such as aminomethyl ($-CH_2-NH_2$), $-CF_2H$, or benzyl), unsubstituted $C_1$ to $C_6$ alkyl (for example, unsubstituted methyl, ethyl, n-propyl, isopropyl, sec-butyl, isobutyl, or tert-butyl), optionally substituted $C_3$ to $C_6$ cycloalkyl (for example, optionally substituted cyclopropyl, cyclobutyl, or cyclopentyl), and unsubstituted $C_3$ to $C_6$ cycloalkyl (unsubstituted cyclopropyl, cyclobutyl, or cyclopentyl). In some embodiments of this paragraph, each $R_5$ is independently H, an optionally substituted $C_1$ to $C_6$ alkyl or an unsubstituted $C_1$ to $C_6$ alkyl. In some embodiments of this paragraph, one $R_5$ is an optionally substituted $C_1$ to $C_6$ alkyl and the other $R_5$ is H. In some embodiments of this paragraph, $R_1$ and $R_2$ are selected from H, deuterium, $NH_2$, $NHCH_3$, $N(CH_3)_2$, $NO_2$, hydroxyl, halogen, optionally substituted $C_1$ to $C_6$ alkyl, unsubstituted $C_1$ to $C_6$ alkyl, optionally substituted $C_3$ to $C_6$ cycloalkyl, and unsubstituted $C_3$ to $C_6$ cycloalkyl, and $R_3$ and $R_4$ are both H. In some embodiments of this paragraph, $R_1$ and $R_3$ are selected from H, deuterium, $NH_2$, $NHCH_3$, $N(CH_3)_2$, $NO_2$, hydroxyl, halogen, optionally substituted $C_1$ to $C_6$ alkyl, unsubstituted $C_1$ to $C_6$ alkyl, optionally substituted $C_3$ to $C_6$ cycloalkyl, and unsubstituted $C_3$ to $C_6$ cycloalkyl, and $R_2$ and $R_4$ are both H. In some embodiments of this paragraph, $R_1$ and $R_4$ are selected from H, deuterium, $NH_2$, $NHCH_3$, $N(CH_3)_2$, $NO_2$, hydroxyl, halogen, optionally substituted $C_1$ to $C_6$ alkyl, unsubstituted $C_1$ to $C_6$ alkyl, optionally substituted $C_3$ to $C_6$ cycloalkyl, and unsubstituted $C_3$ to $C_6$ cycloalkyl, and $R_2$ and $R_3$ are both H. In some embodiments of this paragraph, $R_2$ and $R_3$ are selected from H, deuterium, $NH_2$, $NHCH_3$, $N(CH_3)_2$, $NO_2$, hydroxyl, halogen, optionally substituted $C_1$ to $C_6$ alkyl, unsubstituted $C_1$ to $C_6$ alkyl, optionally substituted $C_3$ to $C_6$ cycloalkyl, and unsubstituted $C_3$ to $C_6$ cycloalkyl, and $R_1$ and $R_4$ are both H. In some embodiments of this paragraph, $R_2$ and $R_4$ are selected from H, deuterium, $NH_2$, $NHCH_3$, $N(CH_3)_2$, $NO_2$, hydroxyl, halogen, optionally substituted $C_1$ to $C_6$ alkyl, unsubstituted $C_1$ to $C_6$ alkyl, optionally substituted $C_3$ to $C_6$ cycloalkyl, and unsubstituted $C_3$ to $C_6$ cycloalkyl, and $R_1$ and $R_3$ are both H. In some embodiments of this paragraph, only one of $R_1$, $R_2$, $R_3$, and $R_4$ is H. In some embodiments of this paragraph, two of $R_1$, $R_2$, $R_3$, and $R_4$ is H. In some embodiments of this paragraph, three of $R_1$, $R_2$, $R_3$, and $R_4$ is H.

Some embodiments provide a compound of Formula (II):

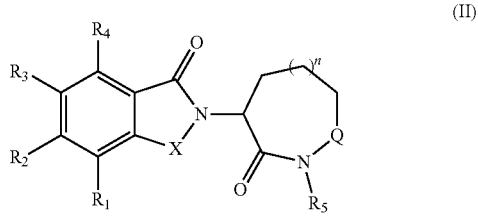

(II)

Some embodiments provide a pharmaceutically acceptable salt or solvate of a compound of Formula (I).

$R_1$, $R_2$, $R_3$, and $R_4$, are each independently selected from L-Y, H, deuterium, hydroxyl, halogen, cyano, nitro, optionally substituted amino, optionally substituted amido, optionally substituted ester, optionally substituted sulfonyl, optionally substituted S-sulfonamido, optionally substituted N-sulfonamido, optionally substituted sulfonate, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl. In some embodiments, $R_1$, $R_2$, $R_3$, and $R_4$, cannot all be H.

In some embodiments, at least one of $R_1$, $R_2$, $R_3$, and $R_4$ is L-Y. In some embodiments, one of $R_1$ or $R_2$ must by L-Y. In some embodiments, $R_1$ is L-Y. In some embodiments, $R_2$ is L-Y. In some embodiments, $R_3$ is L-Y. In some embodiments, $R_4$ is L-Y.

In some embodiments, $R_2$, $R_3$, and $R_4$, are each H. In some embodiments, $R_1$, $R_3$, and $R_4$, are each H. In some embodiments, $R_1$, $R_2$, and $R_4$, are each H. In some embodiments, $R_1$, $R_2$, and $R_3$, are each H. In some embodiments, none of $R_1$, $R_2$, $R_3$, and $R_4$, are H.

In some embodiments, $R_2$, $R_3$, and $R_4$, are each deuterium. In some embodiments, $R_1$, $R_3$, and $R_4$, are each deuterium. In some embodiments, $R_1$, $R_2$, and $R_4$, are each deuterium. In some embodiments, $R_1$, $R_2$, and $R_3$, are each deuterium. In some embodiments, none of $R_1$, $R_2$, $R_3$, and $R_4$, are deuterium.

In some embodiments, $R_2$, $R_3$, and $R_4$, are each halogen. In some embodiments, $R_1$, $R_3$, and $R_4$, are each halogen. In some embodiments, $R_1$, $R_2$, and $R_4$, are each halogen. In some embodiments, $R_1$, $R_2$, and $R_3$, are each halogen. In some embodiments, none of $R_1$, $R_2$, $R_3$, and $R_4$, are halogen.

In some embodiments, $R_1$ is optionally substituted amino. In some embodiments, $R_1$ is unsubstituted amino. In some embodiments, $R_1$ is nitro. In some embodiments, $R_1$ is optionally substituted $C_1$ to $C_6$ alkoxy. In some embodiments, $R_1$ is unsubstituted $C_1$ to $C_6$ alkoxy.

In some embodiments, $R_1$ is halogen. In some embodiments, $R_1$ is cyano. In some embodiments, $R_1$ is optionally substituted amido. In some embodiments, $R_1$ is optionally substituted ester. In some embodiments, $R_1$ is optionally substituted sulfonyl. In some embodiments, $R_1$ is optionally substituted S-sulfonamido. In some embodiments, $R_1$ is optionally substituted N-sulfonamido. In some embodiments, $R_1$ is optionally substituted sulfonate.

In some embodiments, $R_1$ is optionally substituted $C_1$ to $C_6$ alkyl. In some embodiments, $R_1$ is optionally substituted $C_2$ to $C_6$ alkenyl. In some embodiments, $R_1$ is optionally substituted $C_2$ to $C_6$ alkynyl. In some embodiments, $R_1$ is optionally substituted $C_3$ to $C_8$ carbocyclyl. In some embodiments, $R_1$ is optionally substituted $C_6$ to $C_{10}$ aryl. In some embodiments, $R_1$ is optionally substituted $C_3$ to $C_8$ heterocyclyl. In some embodiments, $R_1$ is optionally substituted $C_6$ to $C_{10}$ heteroaryl.

In some embodiments, $R_1$ is unsubstituted amido. In some embodiments, $R_1$ is unsubstituted ester. In some embodiments, $R_1$ is unsubstituted sulfonyl. In some embodiments, $R_1$ is unsubstituted S-sulfonamido. In some embodiments, $R_1$ is unsubstituted N-sulfonamido. In some embodiments, $R_1$ is unsubstituted sulfonate.

In some embodiments, $R_1$ is unsubstituted $C_1$ to $C_6$ alkoxy. In some embodiments, $R_1$ is unsubstituted $C_1$ to $C_6$ alkyl. In some embodiments, $R_1$ is unsubstituted $C_2$ to $C_6$ alkenyl. In some embodiments, $R_1$ is hydroxyl.

In some embodiments, $R_1$ is unsubstituted $C_2$ to $C_6$ alkynyl. In some embodiments, $R_1$ is unsubstituted $C_3$ to $C_8$ carbocyclyl. In some embodiments, $R_1$ is unsubstituted $C_6$ to $C_{10}$ aryl. In some embodiments, $R_1$ is unsubstituted $C_3$ to $C_8$ heterocyclyl. In some embodiments, $R_1$ is unsubstituted $C_6$ to $C_{10}$ heteroaryl.

In some embodiments, $R_2$ is optionally substituted amino. In some embodiments, $R_2$ is unsubstituted amino. In some embodiments, $R_2$ is nitro. In some embodiments, $R_2$ is optionally substituted $C_1$ to $C_6$ alkoxy. In some embodiments, $R_2$ is unsubstituted $C_1$ to $C_6$ alkoxy.

In some embodiments, $R_2$ is halogen. In some embodiments, $R_2$ is cyano. In some embodiments, $R_2$ is optionally substituted amido. In some embodiments, $R_2$ is optionally substituted ester. In some embodiments, $R_2$ is optionally substituted sulfonyl. In some embodiments, $R_2$ is optionally substituted S-sulfonamido. In some embodiments, $R_2$ is optionally substituted N-sulfonamido. In some embodiments, $R_2$ is optionally substituted sulfonate.

In some embodiments, $R_2$ is optionally substituted $C_1$ to $C_6$ alkyl. In some embodiments, $R_2$ is optionally substituted $C_2$ to $C_6$ alkenyl. In some embodiments, $R_2$ is optionally substituted $C_2$ to $C_6$ alkynyl. In some embodiments, $R_2$ is optionally substituted $C_3$ to $C_8$ carbocyclyl. In some embodiments, $R_2$ is optionally substituted $C_6$ to $C_{10}$ aryl. In some embodiments, $R_2$ is optionally substituted $C_3$ to $C_8$ heterocyclyl. In some embodiments, $R_2$ is optionally substituted $C_6$ to $C_{10}$ heteroaryl.

In some embodiments, $R_2$ is unsubstituted amido. In some embodiments, $R_2$ is unsubstituted ester. In some embodiments, $R_2$ is unsubstituted sulfonyl. In some embodiments, $R_2$ is unsubstituted S-sulfonamido. In some embodiments, $R_2$ is unsubstituted N-sulfonamido. In some embodiments, $R_2$ is unsubstituted sulfonate. In some embodiments, $R_2$ is unsubstituted $C_1$ to $C_6$ alkoxy.

In some embodiments, $R_2$ is unsubstituted $C_1$ to $C_6$ alkyl. In some embodiments, $R_2$ is unsubstituted $C_2$ to $C_6$ alkenyl. In some embodiments, $R_2$ is unsubstituted $C_2$ to $C_6$ alkynyl. In some embodiments, $R_2$ is unsubstituted $C_3$ to $C_8$ carbocyclyl. In some embodiments, $R_2$ is unsubstituted $C_6$ to $C_{10}$ aryl. In some embodiments, $R_2$ is unsubstituted $C_3$ to $C_8$ heterocyclyl. In some embodiments, $R_2$ is unsubstituted $C_6$ to $C_{10}$ heteroaryl.

In some embodiments, $R_3$ is optionally substituted amino. In some embodiments, $R_3$ is unsubstituted amino. In some embodiments, $R_3$ is nitro. In some embodiments, $R_3$ is optionally substituted $C_1$ to $C_6$ alkoxy. In some embodiments, $R_3$ is unsubstituted $C_1$ to $C_6$ alkoxy. In some embodiments, $R_3$ is halogen. In some embodiments, $R_3$ is cyano.

In some embodiments, $R_3$ is optionally substituted amido. In some embodiments, $R_3$ is optionally substituted ester. In some embodiments, $R_3$ is optionally substituted sulfonyl. In some embodiments, $R_3$ is optionally substituted S-sulfonamido. In some embodiments, $R_3$ is optionally substituted N-sulfonamido. In some embodiments, $R_3$ is optionally substituted sulfonate.

In some embodiments, $R_3$ is optionally substituted $C_1$ to $C_6$ alkyl. In some embodiments, $R_3$ is optionally substituted $C_2$ to $C_6$ alkenyl. In some embodiments, $R_3$ is optionally substituted $C_2$ to $C_6$ alkynyl. In some embodiments, $R_3$ is optionally substituted $C_3$ to $C_8$ carbocyclyl. In some embodiments, $R_3$ is optionally substituted $C_6$ to $C_{10}$ aryl. In some embodiments, $R_3$ is optionally substituted $C_3$ to $C_8$ heterocyclyl. In some embodiments, $R_3$ is optionally substituted $C_6$ to $C_{10}$ heteroaryl.

In some embodiments, $R_3$ is unsubstituted amido. In some embodiments, $R_3$ is unsubstituted ester. In some embodiments, $R_3$ is unsubstituted sulfonyl. In some embodiments, $R_3$ is unsubstituted S-sulfonamido. In some embodiments, $R_3$ is unsubstituted N-sulfonamido. In some embodiments, $R_3$ is unsubstituted sulfonate.

In some embodiments, $R_3$ is unsubstituted $C_1$ to $C_6$ alkoxy. In some embodiments, $R_3$ is unsubstituted $C_1$ to $C_6$ alkyl. In some embodiments, $R_3$ is unsubstituted $C_2$ to $C_6$ alkenyl. In some embodiments, $R_3$ is unsubstituted $C_2$ to $C_6$ alkynyl. In some embodiments, $R_3$ is unsubstituted $C_3$ to $C_8$ carbocyclyl. In some embodiments, $R_3$ is unsubstituted $C_6$ to $C_{10}$ aryl. In some embodiments, $R_3$ is unsubstituted $C_3$ to $C_8$ heterocyclyl. In some embodiments, $R_3$ is unsubstituted $C_6$ to $C_{10}$ heteroaryl.

In some embodiments, $R_4$ is optionally substituted amino. In some embodiments, $R_4$ is unsubstituted amino. In some embodiments, $R_4$ is nitro. In some embodiments, $R_4$ is optionally substituted $C_1$ to $C_6$ alkoxy. In some embodiments, $R_4$ is unsubstituted $C_1$ to $C_6$ alkoxy. In some embodiments, $R_4$ is halogen. In some embodiments, $R_4$ is cyano.

In some embodiments, $R_4$ is optionally substituted amido. In some embodiments, $R_4$ is optionally substituted ester. In some embodiments, $R_4$ is optionally substituted sulfonyl. In some embodiments, $R_4$ is optionally substituted S-sulfonamido. In some embodiments, $R_4$ is optionally substituted N-sulfonamido. In some embodiments, $R_4$ is optionally substituted sulfonate.

In some embodiments, $R_4$ is optionally substituted $C_1$ to $C_6$ alkyl. In some embodiments, $R_4$ is optionally substituted $C_2$ to $C_6$ alkenyl. In some embodiments, $R_4$ is optionally substituted $C_2$ to $C_6$ alkynyl. In some embodiments, $R_4$ is optionally substituted $C_2$ to $C_6$ alkynyl. In some embodiments, $R_4$ is optionally substituted $C_3$ to $C_8$ carbocyclyl. In some embodiments, $R_4$ is optionally substituted $C_6$ to $C_{10}$ aryl. In some embodiments, $R_4$ is optionally substituted $C_3$ to $C_8$ heterocyclyl. In some embodiments, $R_4$ is optionally substituted $C_6$ to $C_{10}$ heteroaryl. In some embodiments, $R_4$ is halogen.

In some embodiments, $R_4$ is unsubstituted amido. In some embodiments, $R_4$ is unsubstituted ester. In some embodiments, $R_4$ is unsubstituted sulfonyl. In some embodiments, $R_4$ is unsubstituted S-sulfonamido. In some embodiments, $R_4$ is unsubstituted N-sulfonamido. In some embodiments, $R_4$ is unsubstituted sulfonate.

In some embodiments, $R_4$ is unsubstituted $C_1$ to $C_6$ alkoxy. In some embodiments, $R_4$ is unsubstituted $C_1$ to $C_6$ alkyl. In some embodiments, $R_4$ is unsubstituted $C_2$ to $C_6$ alkenyl. In some embodiments, $R_4$ is unsubstituted $C_2$ to $C_6$ alkynyl. In some embodiments, $R_4$ is unsubstituted $C_3$ to $C_8$ carbocyclyl. In some embodiments, $R_4$ is unsubstituted $C_6$ to $C_{10}$ aryl. In some embodiments, $R_4$ is unsubstituted $C_3$ to $C_8$ heterocyclyl. In some embodiments, $R_4$ is unsubstituted $C_1$ to $C_6$ heteroaryl.

In some embodiments, each $R_5$ is independently selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, $R_5$ is H. In some embodiments, $R_5$ is optionally substituted $C_1$ to $C_6$ alkyl. In some embodiments, $R_5$ is unsubstituted $C_1$ to $C_6$ alkyl. In some embodiments, $R_5$ is optionally substituted $C_2$ to $C_6$ alkenyl. In some embodiments, $R_5$ is unsubstituted $C_2$ to $C_6$ alkenyl. In some embodiments, $R_5$ is optionally substituted $C_2$ to $C_6$ alkynyl. In some embodiments, $R_5$ is unsubstituted $C_2$ to $C_6$ alkynyl. In some embodiments, $R_5$ is optionally substituted $C_3$ to $C_8$ carbocyclyl. In some embodiments, $R_5$ is unsubstituted $C_3$ to $C_8$ carbocyclyl. In some embodiments, $R_5$ is optionally substituted $C_6$ to $C_{10}$ aryl. In some embodiments, $R_5$ is unsubstituted $C_6$ to $C_{10}$ aryl. In some embodiments, $R_5$ is optionally substituted $C_3$ to $C_8$ heterocyclyl. In some embodiments, $R_5$ is unsubstituted $C_3$ to $C_8$ heterocyclyl. In some embodiments, $R_5$ is optionally substituted $C_6$ to $C_{10}$ heteroaryl. In some embodiments, $R_5$ is unsubstituted $C_6$ to $C_{10}$ heteroaryl.

In some embodiments, each $R_5$ is H. In some embodiments, each $R_5$ is optionally substituted $C_1$ to $C_6$ alkyl. In some embodiments, one $R_5$ is optionally substituted $C_1$ to $C_6$ alkyl and the other $R_5$ are H. In some embodiments, one $R_5$ is unsubstituted $C_1$ to $C_6$ alkyl. In some embodiments, one $R_5$ is optionally substituted $C_2$ to $C_6$ alkenyl and the other $R_5$ are H. In some embodiments, one $R_5$ is unsubstituted $C_2$ to $C_6$ alkenyl and the other $R_5$ are H. In some embodiments, one $R_5$ is optionally substituted $C_2$ to $C_6$ alkynyl and the other $R_5$ are H. In some embodiments, one $R_5$ is unsubstituted $C_2$ to $C_6$ alkynyl and the other $R_5$ are H. In some embodiments, one $R_5$ is optionally substituted $C_3$ to $C_8$ carbocyclyl and the other $R_5$ are H. In some embodiments, one $R_5$ is unsubstituted $C_3$ to $C_8$ carbocyclyl and the other $R_5$ are H. In some embodiments, one $R_5$ is optionally substituted $C_6$ to $C_{10}$ aryl and the other $R_5$ are H. In some embodiments, one $R_5$ is unsubstituted $C_6$ to $C_{10}$ aryl and the other $R_5$ are H. In some embodiments, one $R_5$ is optionally substituted $C_3$ to $C_8$ heterocyclyl and the other $R_5$ are H. In some embodiments, one $R_5$ is unsubstituted $C_3$ to $C_8$ heterocyclyl and the other $R_5$ are H. In some embodiments, one $R_5$ is optionally substituted $C_6$ to $C_{10}$ heteroaryl and the other $R_5$ are H. In some embodiments, one $R_5$ is unsubstituted $C_6$ to $C_{10}$ heteroaryl and the other $R_5$ are H.

In some embodiments, X is selected from $C(R_5)_2$, $CH(R_5)$, $CH_2$, C=O, and C=S. In some embodiments, X is $C(R_5)_2$. In some embodiments, X is $CH(R_5)$. In some embodiments, X is $CH_2$. In some embodiments, X is C=O. In some embodiments, X is C=S.

In some embodiments, Q is selected from $C(R_5)_2$, $CH(R_5)$, $CH_2$, C=O, C=S; S=O, and $SO_2$. In some embodiments, Q is selected from $CH_2$ and C=O. In some embodiments, Q is $C(R_5)_2$. In some embodiments, Q is $CH(R_5)$. In some embodiments, Q is $CH_2$. In some embodiments, Q is C=O. In some embodiments, Q is C=S. In some embodiments, Q is S=O. In some embodiments, Q is and $SO_2$.

In some embodiments, n is 1 or 2. In some embodiments, n is 1. In some embodiments, n is 2.

In some embodiments, L is a linker group. In some embodiments, L is an alkyl linker. In some embodiments, L is a polyethylene glycol (PEG)-based linker. L is connected to Y such that Y maintains binding affinity for its target(s), as discussed herein.

In some embodiments, L is —$Z_1$—($R_6$—O—$R_6$)$_t$—$Z_2$—; —$Z_1$($R_6$—NH—$R_6$)$_t$—$Z_2$—; —$Z_1$—($R_6$—S—$R_6$)$_t$—$Z_2$—; —$Z_1$—($R_6$—(CO)—$R_6$)$_t$—$Z_2$—; —$Z_1$—($R_6$—(CO$_2$)—$R_6$)$_t$—$Z_2$—; —$Z_1$—($R_6$—(NHCO)—$R_6$)$_t$—$Z_2$—; —$Z_1$—($R_6$—(CONH)—$R_6$)$_t$—$Z_2$—; —$Z_1$—($R_6$—S—$R_6$)$_t$—$Z_2$—; —$Z_1$—($R_6$—(SO)—$R_6$)$_t$—$Z_2$—; —$Z_1$—($R_6$—(SO$_2$)—$R_6$)$_t$—$Z_2$—; —$Z_1$—($R_6$—(NHSO$_2$)—$R_6$)$_t$—$Z_2$—; —$Z_1$—($R_6$—(SO$_2$NH)—$R_6$)$_t$—$Z_2$—; or —$Z_1$—($R_6$—$R_7$—$R_6$)$_t$—$Z_2$—.

In some embodiments, t is 1, 2, 3, 4, 5, 6, 7, or 8.

In some embodiments, $Z_1$ and $Z_2$ are independently —$CH_2$—; —O—; —S—; S=O; —$SO_2$—; C=O; —$CO_2$—; —NH—; —NH(CO)—; —(CO)NH—; —NH—$SO_2$—; —$SO_2$—NH—; —$R_6CH_2$—; —$R_6O$—; —$R_6S$—; $R_6$—S=O; —$R_6SO_2$—; $R_6$—C=O; —$R_6CO_2$—; —$R_6NH$—; —$R_6NH(CO)$—; —$R_6$(CO)NH—; —$R_6NH$—$SO_2$—; —$R_6SO_2$—NH—; —$CH_2R_6$—; —$OR_6$—; —$SR_6$—; S=O—$R_6$; —$SO_2R_6$—; C=O—$R_6$; —$CO_2R_6$—; —$NHR_6$—; —NH(CO)$R_6$—; —(CO)$NHR_6$—; —NH—$SO_2R_6$—; or —$SO_2$—$NHR_6$—.

In some embodiments, each $R_6$ is absent, or independently $C_1$ to $C_6$ alkyl, $C_2$ to $C_6$ alkenyl, $C_2$ to $C_6$ alkynyl, $C_6$ to $C_{10}$ aryl, $C_3$ to $C_8$ heterocyclyl, or $C_6$ to $C_{10}$ heteroaryl.

In some embodiments, $R_7$ is optionally substituted $C_1$ to $C_6$ alkyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_6$ to $C_{10}$ heteroaryl.

In some embodiments, Y is

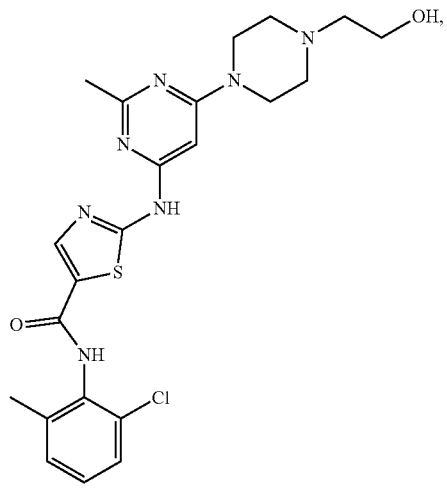

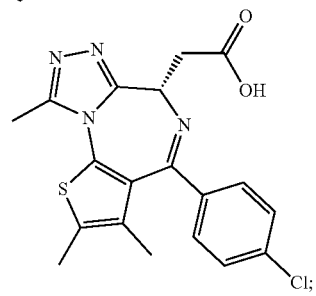

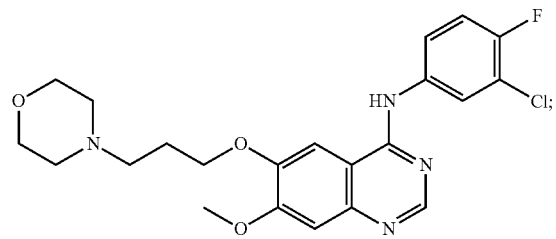

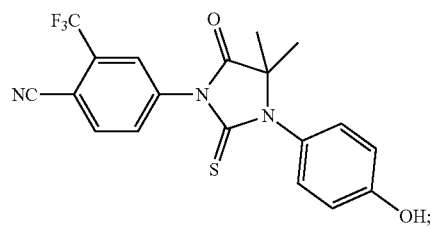

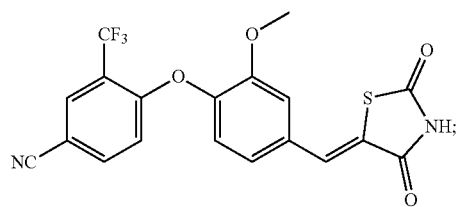

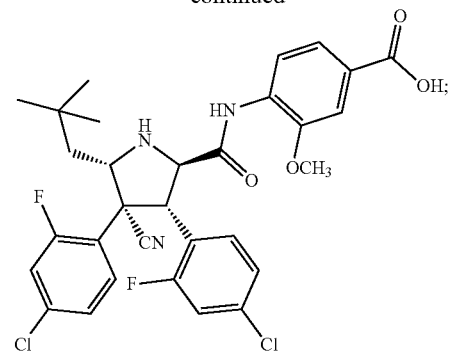
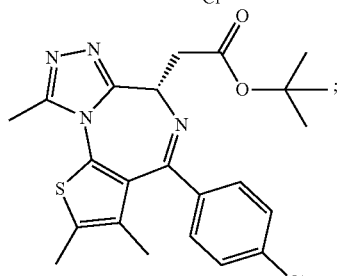
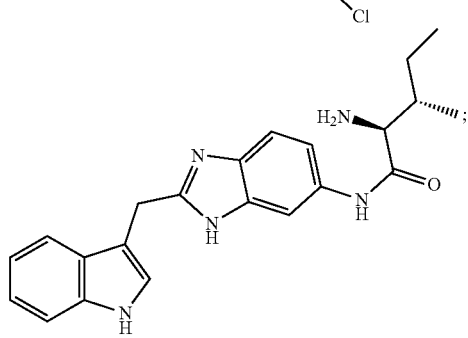
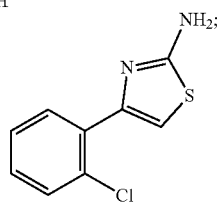
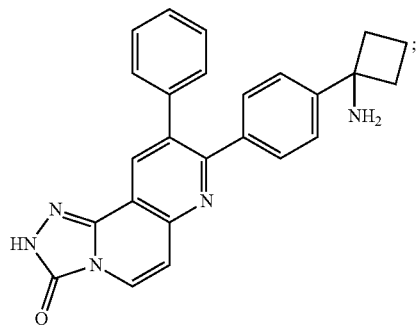
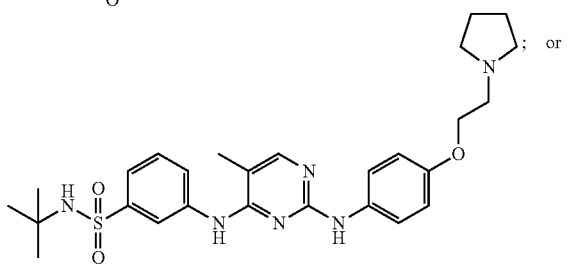
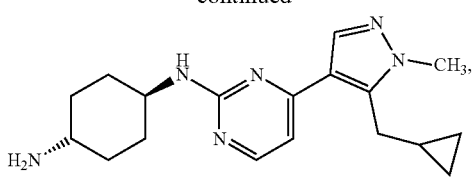
wherein Y is derivatized to attach to L.
In some embodiments, the compound of Formula (II) is selected from:
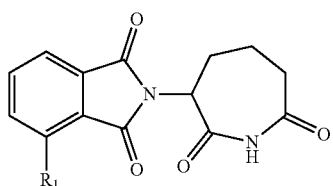
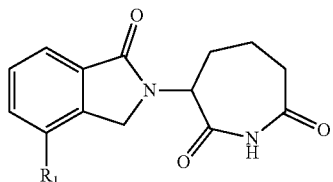
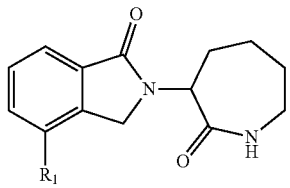
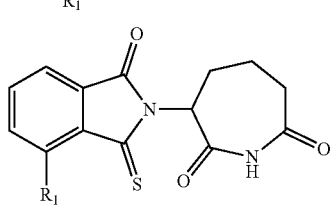
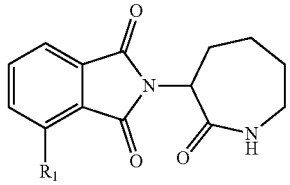
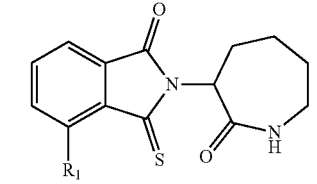
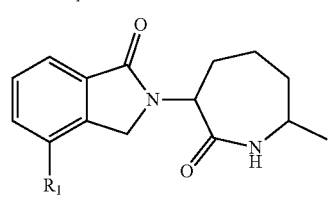

-continued

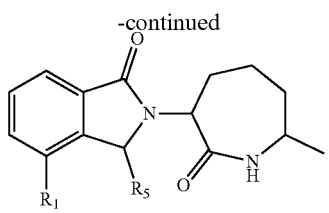

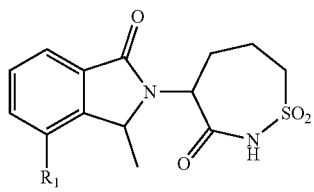

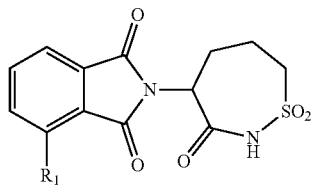

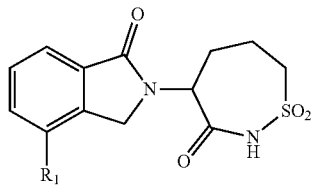

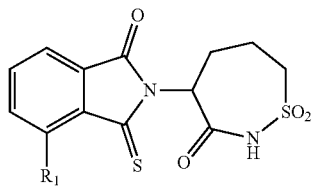

In some embodiments of this paragraph, R₁ is halogen. In some embodiments of this paragraph, R₁ is cyano. In some embodiments of this paragraph, R₁ is an optionally substituted amino. In some embodiments of this paragraph, R₁ is an optionally substituted $C_1$ to $C_6$ alkoxy. In some embodiments of this paragraph, R₁ is optionally substituted $C_1$ to $C_6$ alkyl. In some embodiments of this paragraph, R₁ is an optionally substituted $C_3$ to $C_8$ carbocyclyl. In some embodiments of this paragraph, R₁ is L-Y. In some embodiments of this paragraph, L is —$Z_1$—$(R_6$—O—$R_6)_t$—$Z_2$—; —$Z_1$—$(R_6$—NH—$R_6)_t$—$Z_2$—; —$Z_1$—$(R_6$—(NHCO)—$R_6)_t$—$Z_2$—; —$Z_1$—$(R_6$—(CONH)—$R_6)_t$—$Z_2$—; t is 1, 2, 3, or 4; and $Z_1$ and $Z_2$ are independently —$CH_2$—; —O—; —NH—; —NH(CO)—; or —(CO)NH. In some embodiments of this paragraph, Y is In some embodiments of this paragraph, Y is selected from

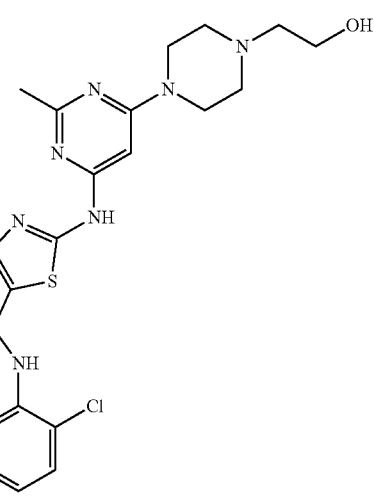

(connected to $Z_2$ through the hydroxyl group);

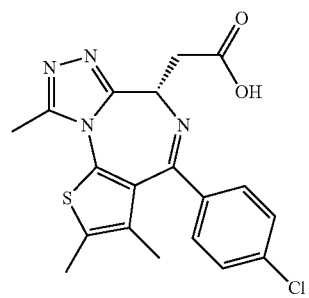 [SMILES: Cc1sc2c(c1C)C(c1ccc(Cl)cc1)=N[C@@H](CC(=O)O)c1nnc(C)n1-2]

(connected to $Z_2$ through the carboxy group);

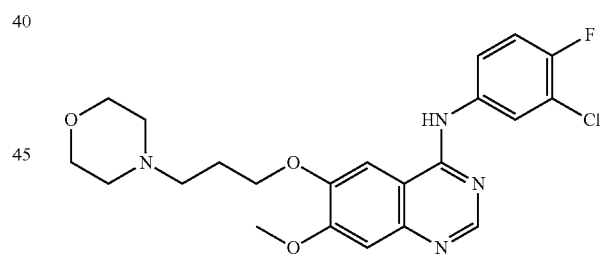

(connected to $Z_2$ through the hydroxyl group exposed upon removal of the N-propylmorpholino group, or after removing the methyl group from the methoxy group);

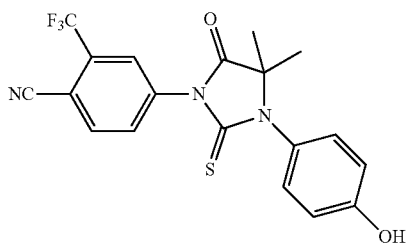 [SMILES: CC1(C)C(=O)N(c2ccc(C#N)c(C(F)(F)F)c2)C(=S)N1c1ccc(O)cc1]

(connected to $Z_2$ through the hydroxyl group);

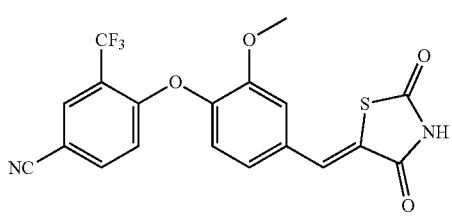 [SMILES: COc1cc(/C=C2\SC(=O)NC2=O)ccc1Oc1ccc(C#N)cc1C(F)(F)F]

(connected to $Z_2$ through hydroxyl group exposed upon removal of the methyl group from the methoxy group);

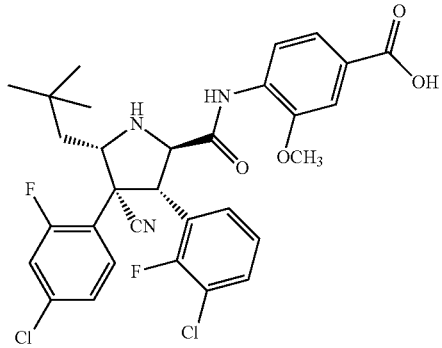 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

(connected to $Z_2$ through the carboxy group);

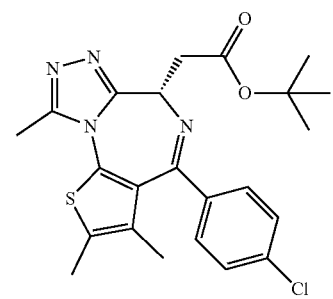 [SMILES: Cc1sc2c(c1C)C(c1ccc(Cl)cc1)=N[C@@H](CC(=O)OC(C)(C)C)c1nnc(C)n1-2]

(connected to $Z_2$ through the carboxy group exposed upon hydrolysis of the t-butyl ester group);

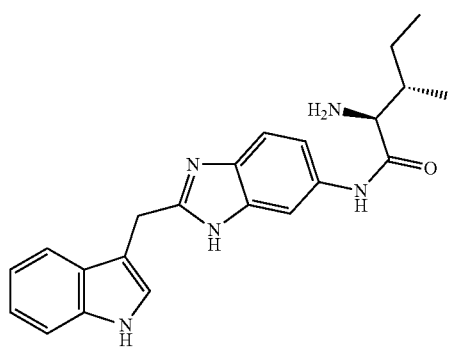 [SMILES: CC[C@H](C)[C@H](N)C(=O)Nc1ccc2nc(Cc3c[nH]c4ccccc34)[nH]c2c1]

(connected to $Z_2$ through the primary amino group);

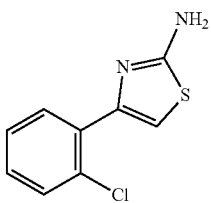 [SMILES: Nc1nc(-c2ccccc2Cl)cs1]

(connected to $Z_2$ through the primary amino group);

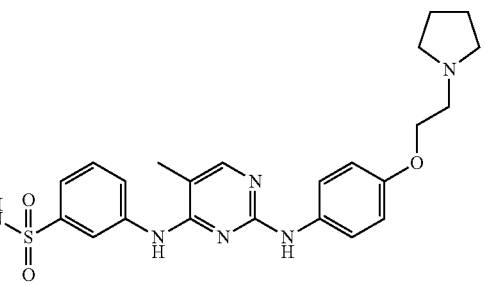

(connected to $Z_2$ through the primary amino group);

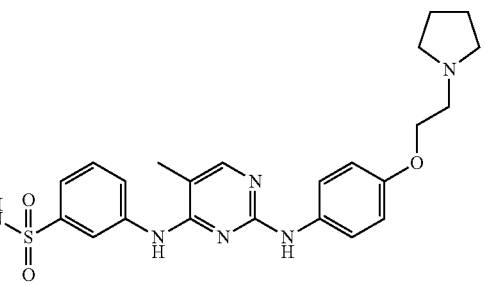

(connected to $Z_2$ through the hydroxyl group exposed upon removal of the N-ethylpyrrolidine, or through the sulfonamide exposed upon removal of the N-tertiary butyl group); or

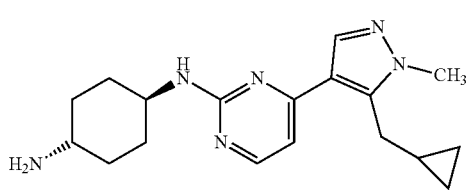

(connected to $Z_2$ through the primary amino group).

In some embodiments, the compound of Formula (II) is selected from:

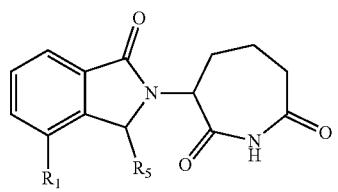
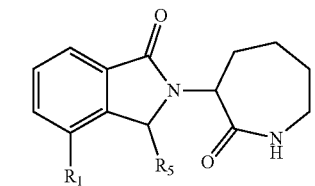
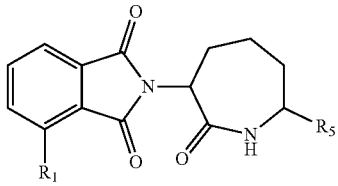
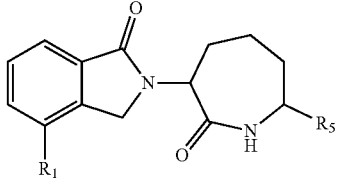
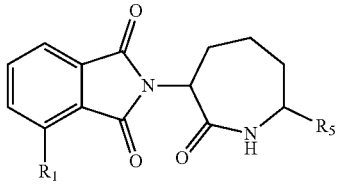
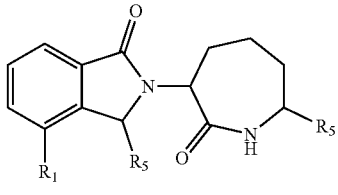
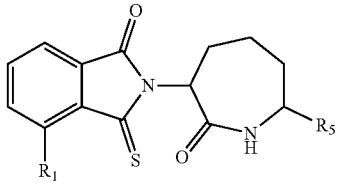
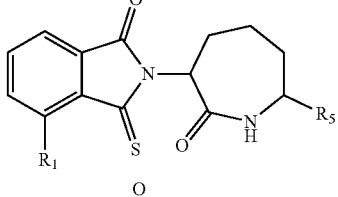
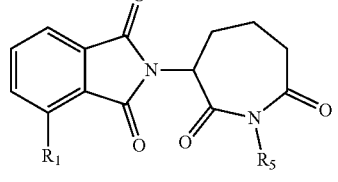
-continued
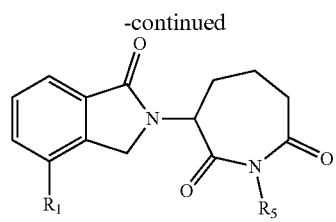
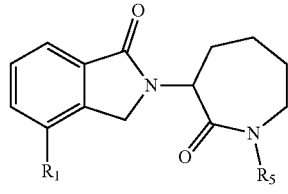
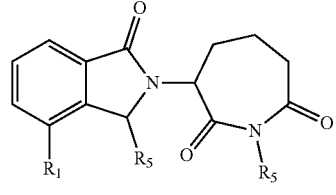
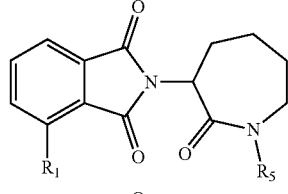
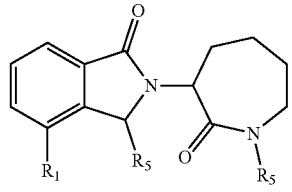
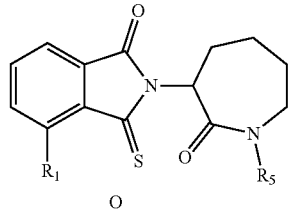
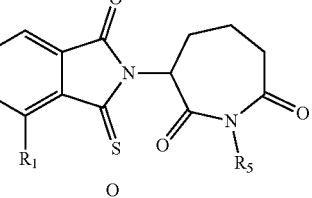
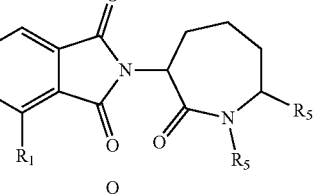
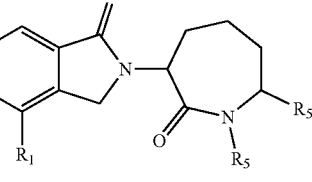

-continued

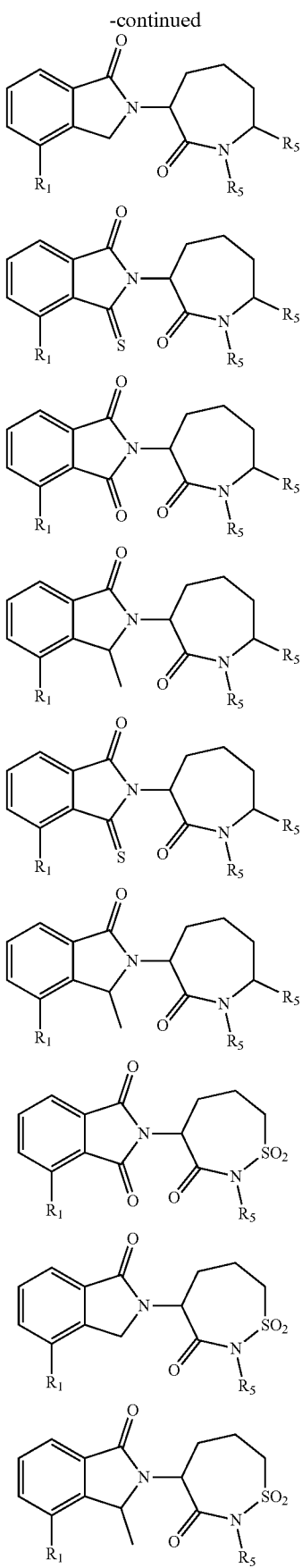

-continued

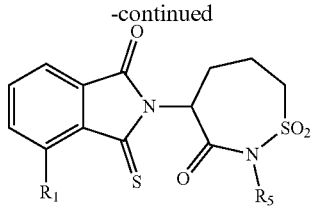

In some embodiments of this paragraph, each $R_5$ is independently an optionally substituted $C_1$ to $C_6$ alkyl or an optionally substituted $C_3$ to $C_6$ cycloalkyl. In some embodiments of this paragraph, each $R_5$ is independently an unsubstituted $C_1$ to $C_6$ alkyl or an unsubstituted $C_3$ to $C_6$ cycloalkyl. In some embodiments of this paragraph, one $R_5$ is an optionally substituted $C_1$ to $C_6$ alkyl and the other $R_5$ is an optionally substituted $C_3$ to $C_6$ cycloalkyl. In some embodiments of this paragraph, one $R_5$ is an unsubstituted $C_1$ to $C_6$ alkyl and the other $R_5$ is an unsubstituted $C_3$ to $C_6$ cycloalkyl. In some embodiments of this paragraph, $R_1$ is halogen. In some embodiments of this paragraph, $R_1$ is cyano. In some embodiments of this paragraph, $R_1$ is an optionally substituted amino. In some embodiments of this paragraph, $R_1$ is an optionally substituted $C_1$ to $C_6$ alkoxy. In some embodiments of this paragraph, $R_1$ is optionally substituted $C_1$ to $C_6$ alkyl. In some embodiments of this paragraph, $R_1$ is an optionally substituted $C_3$ to $C_8$ carbocyclyl. In some embodiments of this paragraph, $R_1$ is L-Y. In some embodiments of this paragraph, L is —$Z_1$—($R_6$—O—$R_6$)$_t$—$Z_2$—; —$Z_1$($R_6$—NH—$R_6$)$_t$—$Z_2$—; —$Z_1$—($R_6$—(NHCO)—$R_6$)$_t$—$Z_2$—; —$Z_1$—($R_6$—(CONH)—$R_6$)$_t$—$Z_2$—; t is 1, 2, 3, or 4; and $Z_1$ and $Z_2$ are independently —$CH_2$—; —O—; —NH—; —NH(CO)—; or —(CO)NH. In some embodiments of this paragraph, Y is In some embodiments of this paragraph, Y is selected from

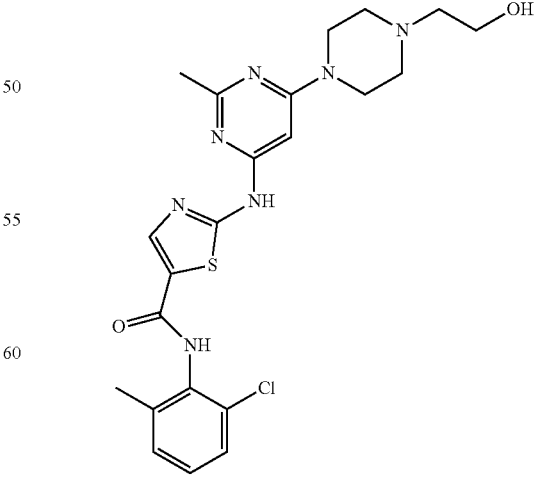

(connected to $Z_2$ through the hydroxyl group);

51

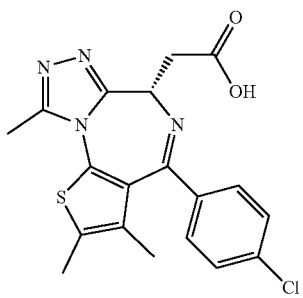 [SMILES: Cc1sc2c(c1C)C(c1ccc(Cl)cc1)=N[C@@H](CC(=O)O)c1nnc(C)n1-2]

(connected to $Z_2$ through the carboxy group);

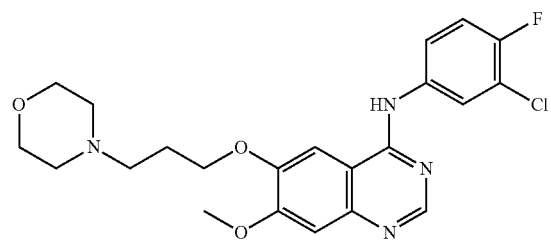 [SMILES: COc1cc2ncnc(Nc3ccc(F)c(Cl)c3)c2cc1OCCCN1CCOCC1]

(connected to $Z_2$ through the hydroxyl group exposed upon removal of the N-propylmorpholino group, or after removing the methyl group from the methoxy group);

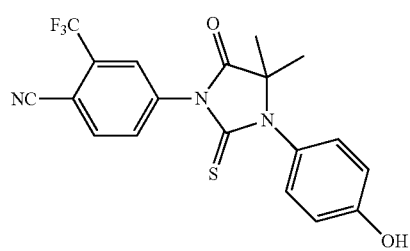 [SMILES: CC1(C)C(=O)N(c2ccc(C#N)c(C(F)(F)F)c2)C(=S)N1c1ccc(O)cc1]

(connected to $Z_2$ through the hydroxyl group);

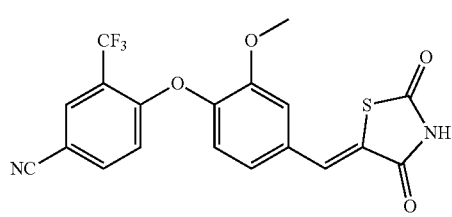 [SMILES: COc1cc(/C=C2\SC(=O)NC2=O)ccc1Oc1ccc(C#N)cc1C(F)(F)F]

(connected to $Z_2$ through hydroxyl group exposed upon removal of the methyl group from the methoxy group);

52

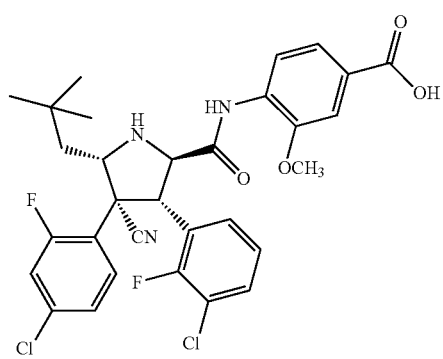 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

(connected to $Z_2$ through the carboxy group);

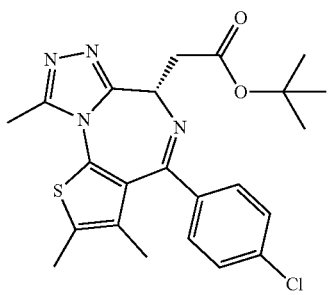 [SMILES: Cc1sc2c(c1C)C(c1ccc(Cl)cc1)=N[C@@H](CC(=O)OC(C)(C)C)c1nnc(C)n1-2]

(connected to $Z_2$ through the carboxy group exposed upon hydrolysis of the t-butyl ester group);

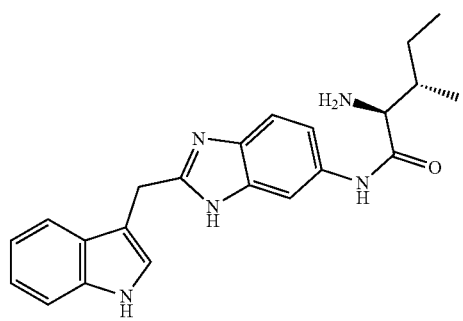 [SMILES: CC[C@H](C)[C@H](N)C(=O)Nc1ccc2nc(Cc3c[nH]c4ccccc34)[nH]c2c1]

(connected to $Z_2$ through the primary amino group);

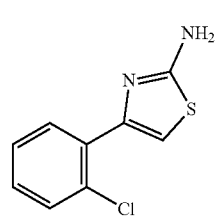 [SMILES: Nc1nc(-c2ccccc2Cl)cs1]

(connected to $Z_2$ through the primary amino group);

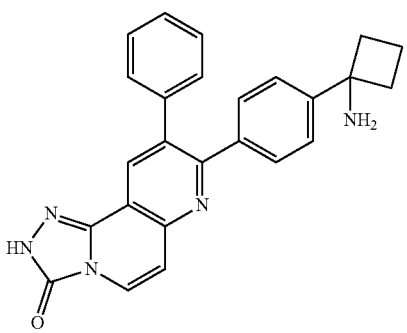 [SMILES: NC1(c2ccc(-c3nc4ccn5c(=O)[nH]nc5c4cc3-c3ccccc3)cc2)CCC1]
(connected to $Z_2$ through the primary amino group);
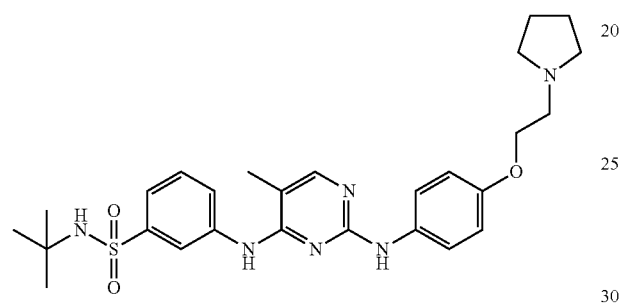
(connected to $Z_2$ through the hydroxyl group exposed upon removal of the N-ethylpyrrolidine, or through the sulfonamide exposed upon removal of the N-tertiary butyl group); or
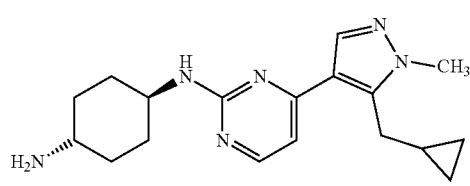
(connected to $Z_2$ through the primary amino group).
In some embodiments, the compound of Formula (II) is selected from:
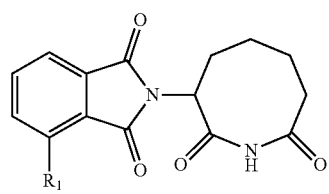
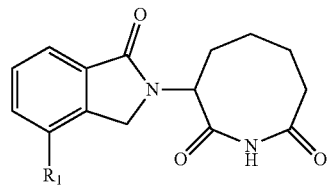
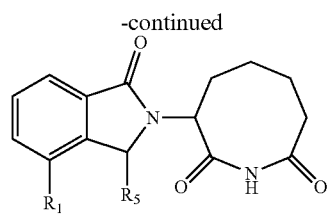
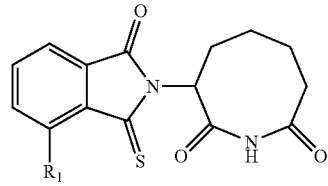
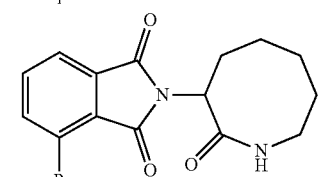
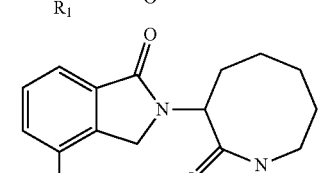
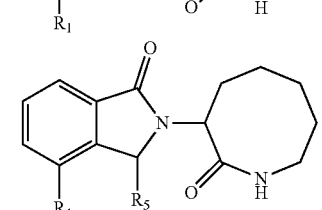
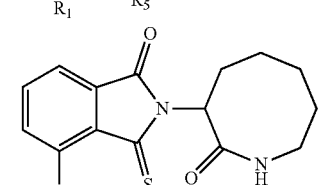
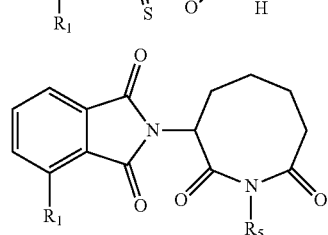
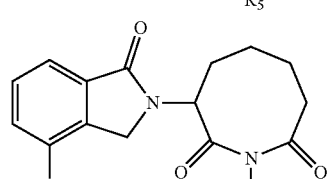
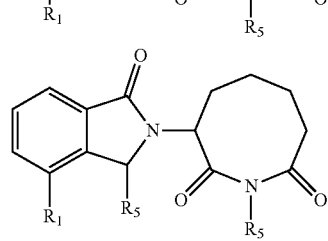

-continued

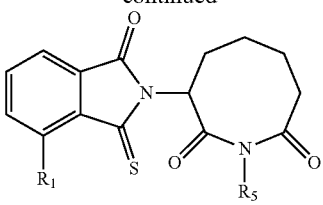
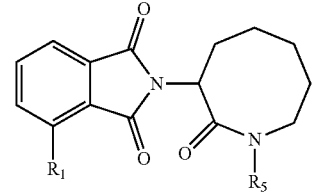
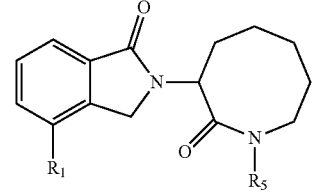
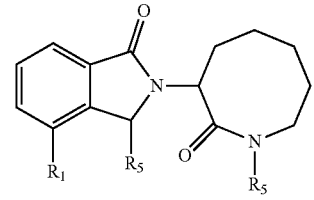
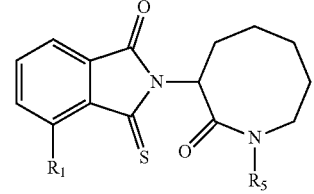
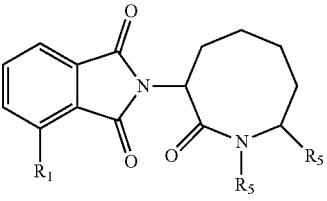
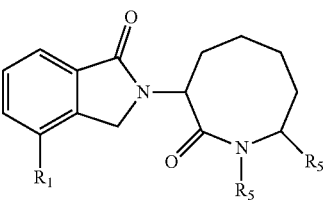
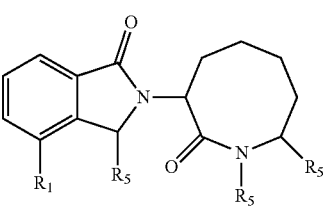

-continued

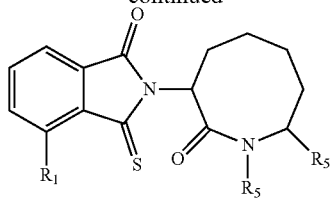

In some embodiments of this paragraph, each $R_5$ is independently an optionally substituted $C_1$ to $C_6$ alkyl or an optionally substituted $C_3$ to $C_6$ cycloalkyl. In some embodiments of this paragraph, each $R_5$ is independently an unsubstituted $C_1$ to $C_6$ alkyl or an unsubstituted $C_3$ to $C_6$ cycloalkyl. In some embodiments of this paragraph, one $R_5$ is an optionally substituted $C_1$ to $C_6$ alkyl and the other $R_5$ is an optionally substituted $C_3$ to $C_6$ cycloalkyl. In some embodiments of this paragraph, one $R_5$ is an unsubstituted $C_1$ to $C_6$ alkyl and the other $R_5$ is an unsubstituted $C_3$ to $C_6$ cycloalkyl. In some embodiments of this paragraph, $R_1$ is halogen. In some embodiments of this paragraph, $R_1$ is cyano. In some embodiments of this paragraph, $R_1$ is an optionally substituted amino. In some embodiments of this paragraph, $R_1$ is an optionally substituted $C_1$ to $C_6$ alkoxy. In some embodiments of this paragraph, $R_1$ is optionally substituted $C_1$ to $C_6$ alkyl. In some embodiments of this paragraph, $R_1$ is an optionally substituted $C_3$ to $C_8$ carbocyclyl. In some embodiments of this paragraph, $R_1$ is L-Y. In some embodiments of this paragraph, L is —$Z_1$—($R_6$—O—$R_6$)$_t$—$Z_2$—; —$Z_1$—($R_6$—NH—$R_6$)$_t$—$Z_2$—; —$Z_1$—($R_6$—(NHCO)—$R_6$)$_t$—$Z_2$—; —$Z_1$—($R_6$—(CONH)—$R_6$)$_t$—$Z_2$—; t is 1, 2, 3, or 4; and $Z_1$ and $Z_2$ are independently —$CH_2$—; —O—; —NH—; —NH(CO)—; or —(CO)NH. In some embodiments of this paragraph, Y is In some embodiments of this paragraph, Y is selected from

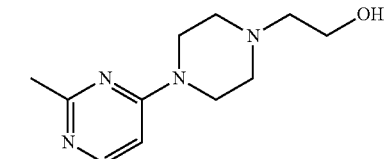
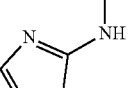
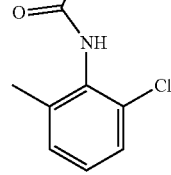

(connected to $Z_2$ through the hydroxyl group);

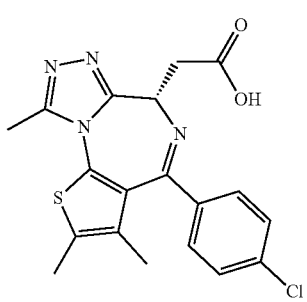 [SMILES: Cc1sc2c(c1C)C(c1ccc(Cl)cc1)=N[C@@H](CC(=O)O)c1nnc(C)n1-2]

(connected to $Z_2$ through the carboxy group);

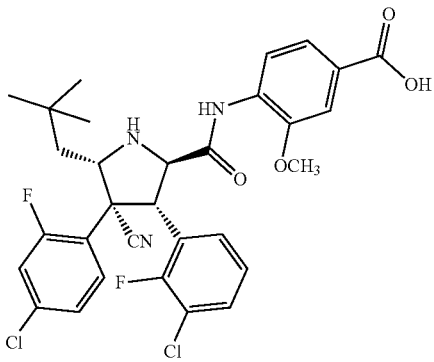

(connected to $Z_2$ through the carboxy group);

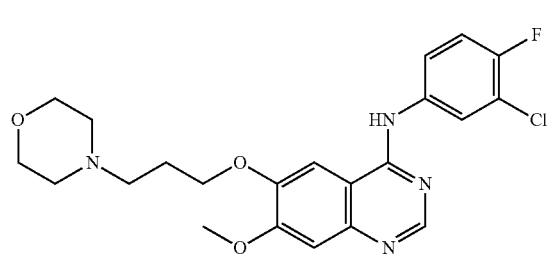 [SMILES: COc1cc2ncnc(Nc3ccc(F)c(Cl)c3)c2cc1OCCCN1CCOCC1]

(connected to $Z_2$ through the hydroxyl group exposed upon removal of the N-propylmorpholino group, or after removing the methyl group from the methoxy group);

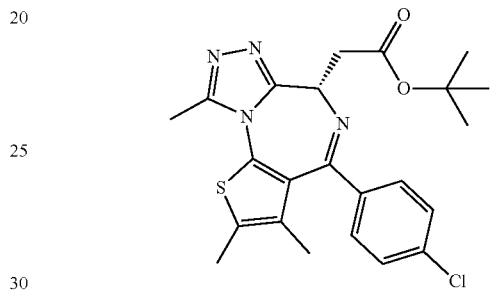

(connected to $Z_2$ through the carboxy group exposed upon hydrolysis of the t-butyl ester group);

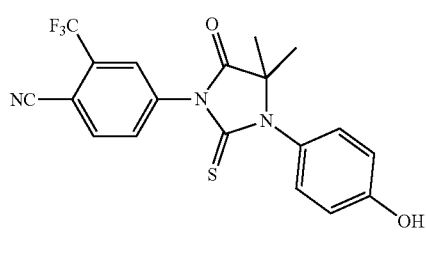 [SMILES: CC1(C)C(=O)N(c2ccc(C#N)c(C(F)(F)F)c2)C(=S)N1c1ccc(O)cc1]

(connected to $Z_2$ through the hydroxyl group);

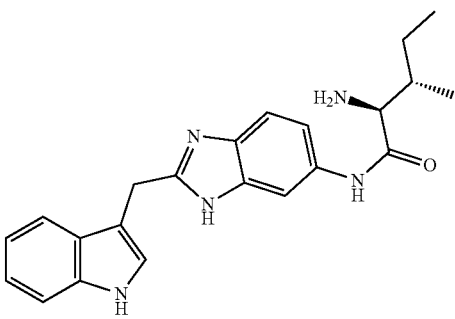

(connected to $Z_2$ through the primary amino group);

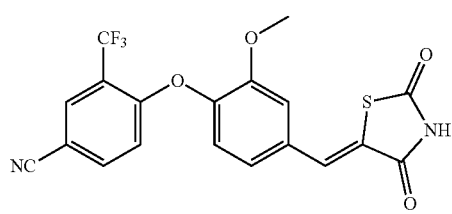 [SMILES: COc1cc(/C=C2\SC(=O)NC2=O)ccc1Oc1ccc(C#N)cc1C(F)(F)F]

(connected to $Z_2$ through hydroxyl group exposed upon removal of the methyl group from the methoxy group);

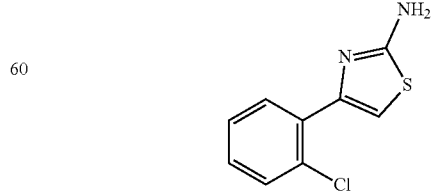

(connected to $Z_2$ through the primary amino group);

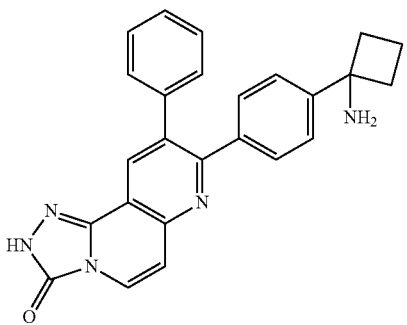 [SMILES: NC1(c2ccc(-c3nc4ccn5c(=O)[nH]nc5c4cc3-c3ccccc3)cc2)CCC1]

(connected to $Z_2$ through the primary amino group);

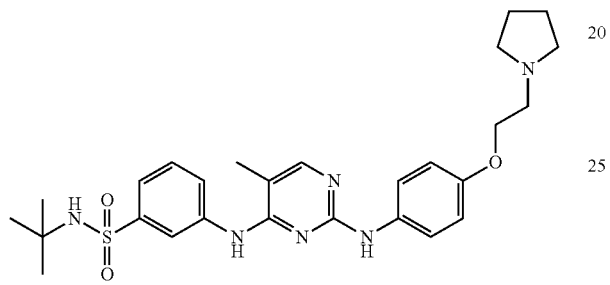

(connected to $Z_2$ through the hydroxyl group exposed upon removal of the N-ethylpyrrolidine, or through the sulfonamide exposed upon removal of the N-tertiary butyl group); or

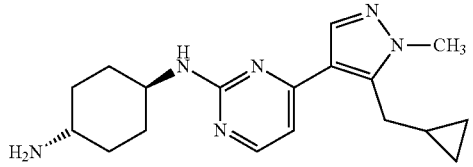

(connected to $Z_2$ through the primary amino group).

In some embodiments, the compound of Formula (II) is selected from:

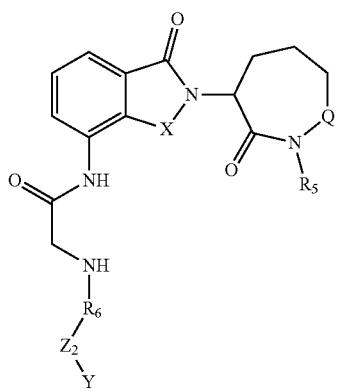

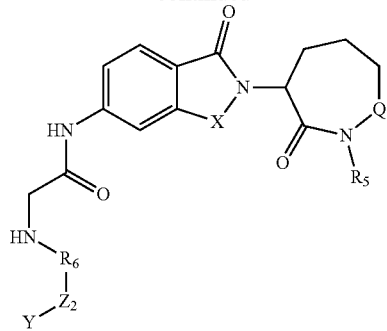

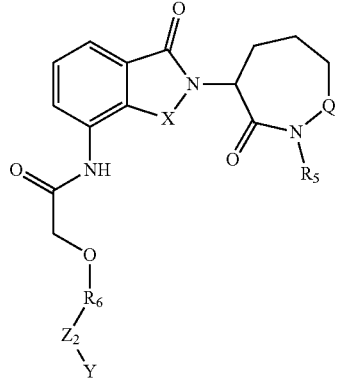

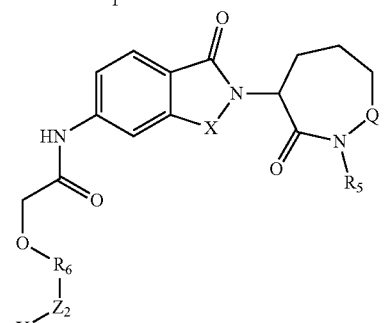

In some embodiments of this paragraph, each $R_5$ is independently an optionally substituted $C_1$ to $C_6$ alkyl or an optionally substituted $C_3$ to $C_6$ cycloalkyl. In some embodiments of this paragraph, each $R_5$ is independently an unsubstituted $C_1$ to $C_6$ alkyl or an unsubstituted $C_3$ to $C_6$ cycloalkyl. In some embodiments of this paragraph, one $R_5$ is an optionally substituted $C_1$ to $C_6$ alkyl and the other $R_5$ is an optionally substituted $C_3$ to $C_6$ cycloalkyl. In some embodiments of this paragraph, one $R_5$ is an unsubstituted $C_1$ to $C_6$ alkyl and the other $R_5$ is an unsubstituted $C_3$ to $C_6$ cycloalkyl. In some embodiments of this paragraph, Q and X are both C=O. In some embodiments of this paragraph, Q and X are both $CH_2$. In some embodiments of this paragraph, Q is C=O and X is $CH_2$. In some embodiments of this paragraph, X is C=O and Q is $CH_2$. In some embodiments of this paragraph, $R_6$ is absent. In some embodiments of this paragraph, $R_6$ is an unsubstituted $C_1$ to $C_6$ alkyl.

In some embodiments of this paragraph, $Z_2$ is —$CH_2$—; —O—; —S—; S=O; —$SO_2$—; C=O; —$CO_2$—; —NH—; —NH(CO)—; —(CO)NH—; —NH—$SO_2$—; or —$SO_2$—NH—.

In some embodiments of this paragraph, Y is selected from

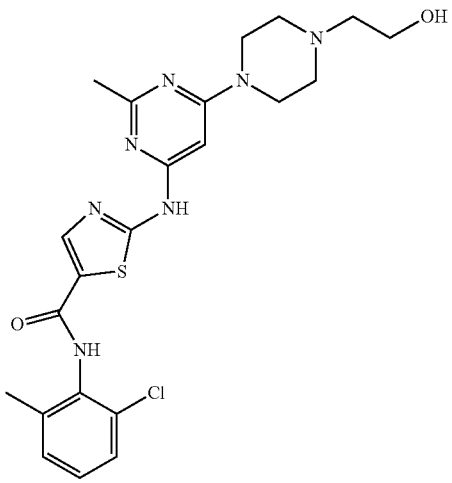 [SMILES: Cc1nc(Nc2ncc(C(=O)Nc3c(C)cccc3Cl)s2)cc(N2CCN(CCO)CC2)n1]

(connected to $Z_2$ through the hydroxyl group);

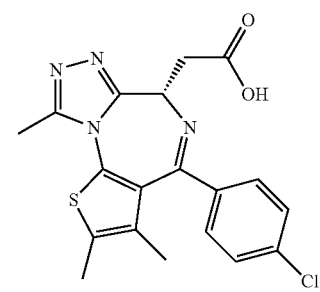 [SMILES: Cc1sc2c(c1C)C(c1ccc(Cl)cc1)=N[C@@H](CC(=O)O)c1nnc(C)n1-2]

connected to $Z_2$ through the carboxy group);

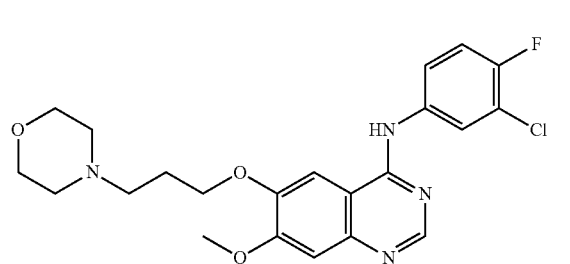 [SMILES: COc1cc2ncnc(Nc3ccc(F)c(Cl)c3)c2cc1OCCCN1CCOCC1]

(connected to $Z_2$ through the hydroxyl group exposed upon removal of the N-propylmorpholino group, or after removing the methyl group from the methoxy group);

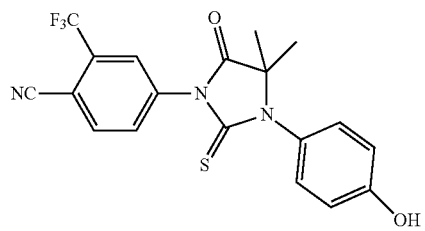 [SMILES: CC1(C)C(=O)N(c2ccc(C#N)c(C(F)(F)F)c2)C(=S)N1c1ccc(O)cc1]

(connected to $Z_2$ through the hydroxyl group);

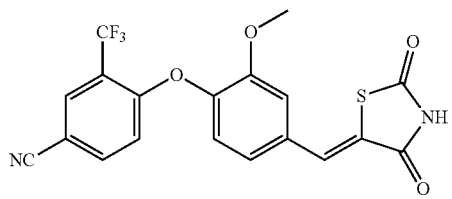 [SMILES: COc1cc(/C=C2\SC(=O)NC2=O)ccc1Oc1ccc(C#N)cc1C(F)(F)F]

(connected to $Z_2$ through hydroxyl group exposed upon removal of the methyl group from the methoxy group);

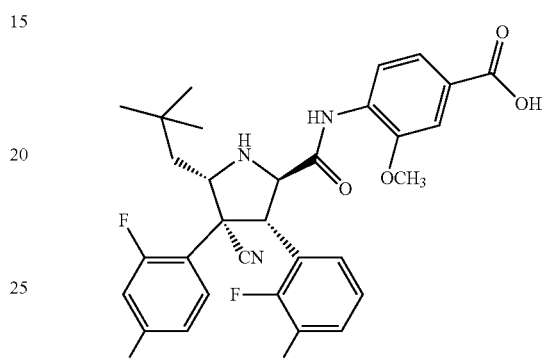

(connected to $Z_2$ through the carboxy group);

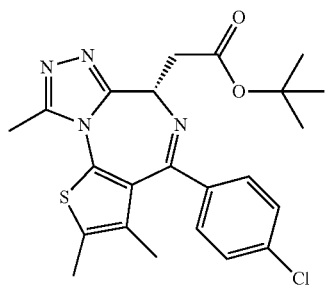 [SMILES: Cc1sc2c(c1C)C(c1ccc(Cl)cc1)=N[C@@H](CC(=O)OC(C)(C)C)c1nnc(C)n1-2]

(connected to $Z_2$ through the carboxy group exposed upon hydrolysis of the t-butyl ester group);

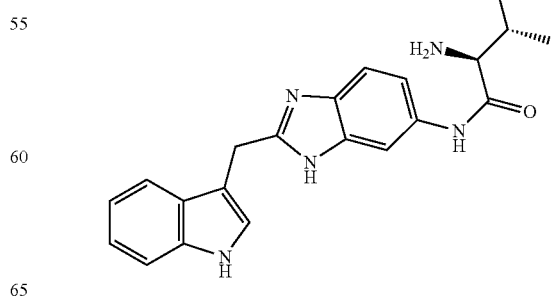

(connected to $Z_2$ through the primary amino group);

63

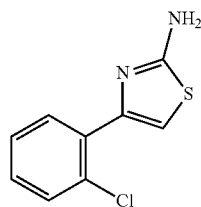 [SMILES: Nc1nc(-c2ccccc2Cl)cs1]

(connected to $Z_2$ through the primary amino group);

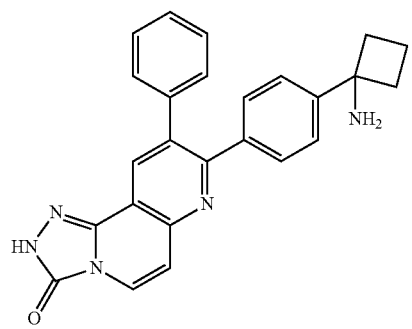 [SMILES: NC1(c2ccc(-c3nc4ccn5c(=O)[nH]nc5c4cc3-c3ccccc3)cc2)CCC1]

(connected to $Z_2$ through the primary amino group);

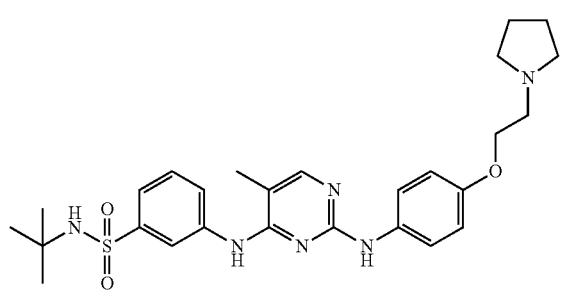 [SMILES: Cc1cnc(Nc2ccc(OCCN3CCCC3)cc2)nc1Nc1cccc(S(=O)(=O)NC(C)(C)C)c1]

(connected to $Z_2$ through the hydroxyl group exposed upon removal of the N-ethylpyrrolidine, or through the sulfonamide exposed upon removal of the N-tertiary butyl group); or

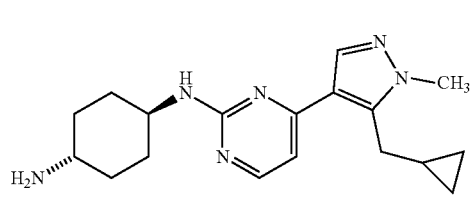 [SMILES: Cn1ncc(-c2ccnc(N[C@H]3CC[C@H](N)CC3)n2)c1CC1CC1]

(connected to $Z_2$ through the primary amino group).

In some embodiments, the compound of Formula (II) is selected from:

64

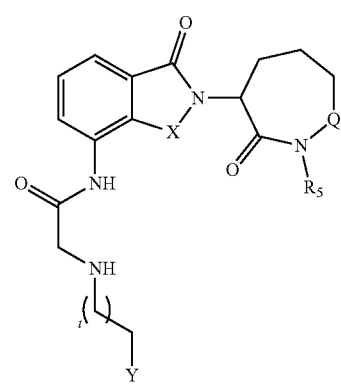

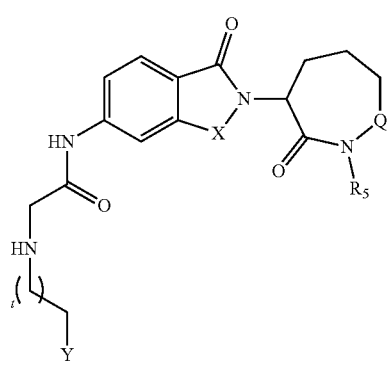

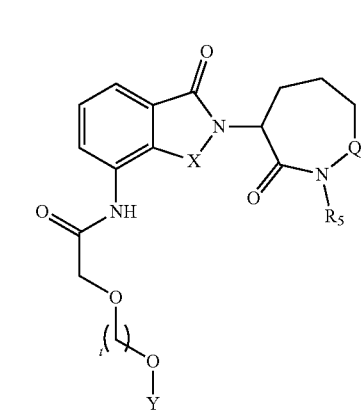

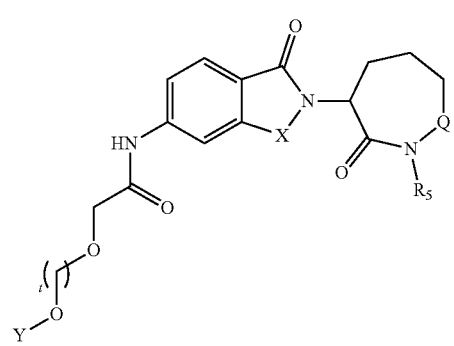

65
-continued
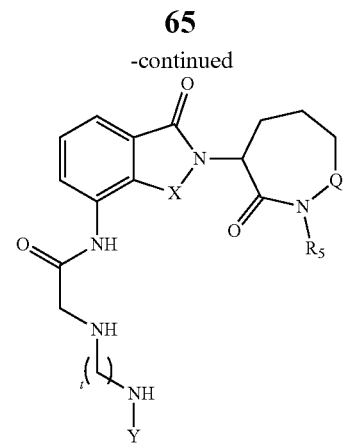
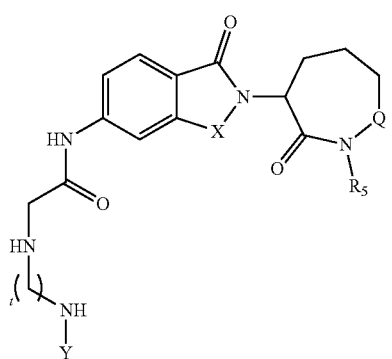
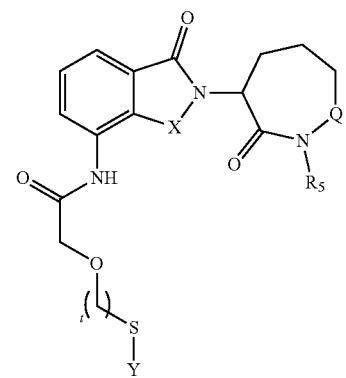
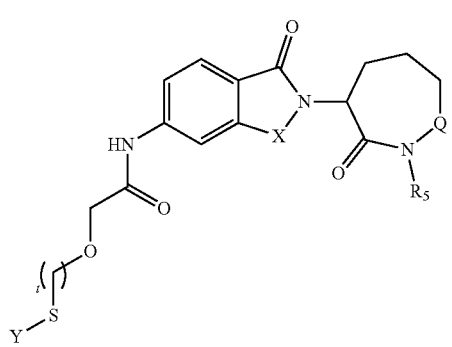
66
-continued
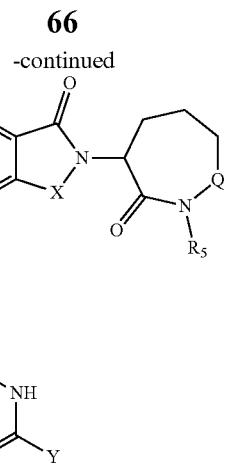
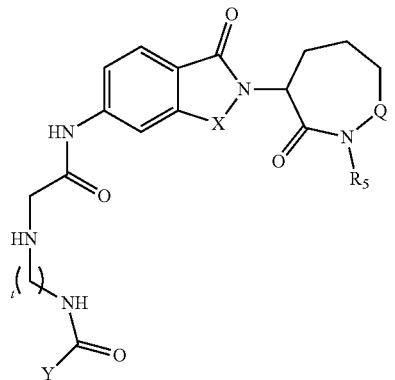
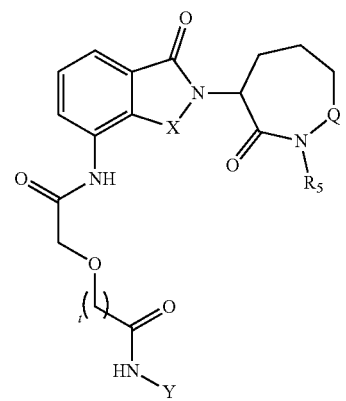
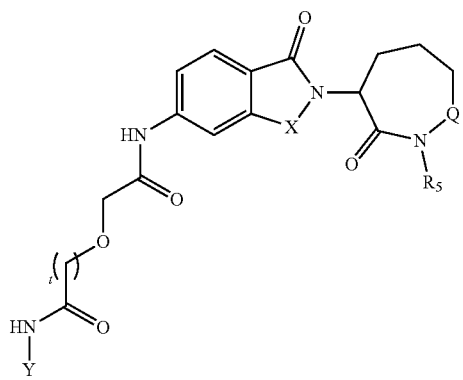

67
-continued
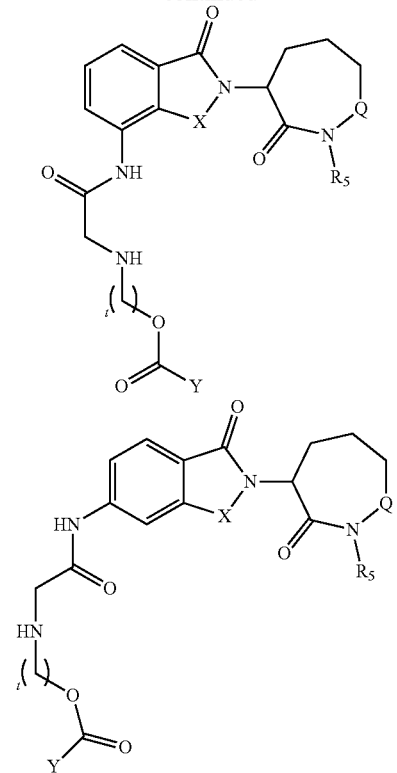
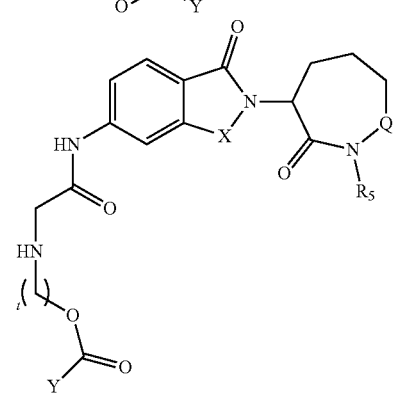
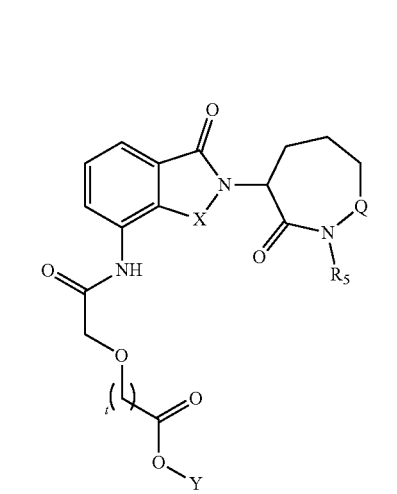
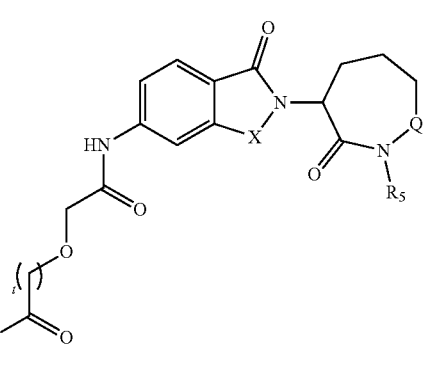
68
-continued
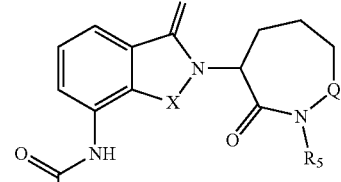
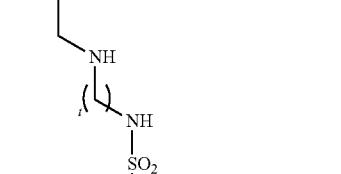
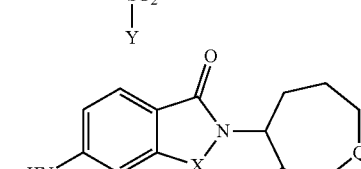
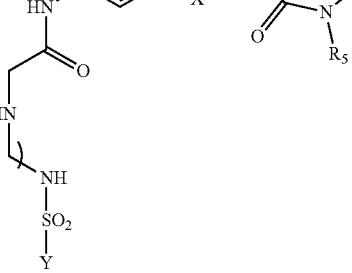
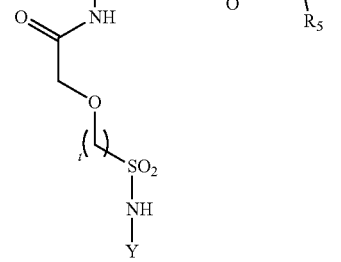
In some embodiments of this paragraph, each $R_5$ is independently an optionally substituted $C_1$ to $C_6$ alkyl or an optionally substituted $C_3$ to $C_6$ cycloalkyl. In some embodiments of this paragraph, each $R_5$ is independently an unsubstituted $C_1$ to $C_6$ alkyl or an unsubstituted $C_3$ to $C_6$ cycloalkyl. In some embodiments of this paragraph, one $R_5$ is an optionally substituted $C_1$ to $C_6$ alkyl and the other $R_5$ is an optionally substituted $C_3$ to $C_6$ cycloalkyl. In some embodiments of this paragraph, one $R_5$ is an unsubstituted $C_1$ to $C_6$ alkyl and the other $R_5$ is an unsubstituted $C_3$ to $C_6$ cycloalkyl. In some embodiments of this paragraph, t is 2. In some embodiments of this paragraph, t is 3. In some embodiments of this paragraph, t is 4. In some embodiments of this paragraph, Q and X are both C=O. In some embodiments of this paragraph, Q and X are both $CH_2$. In some embodiments of this paragraph, Q is C=O and X is $CH_2$. In some embodiments of this paragraph, X is C=O and Q is $CH_2$. In some embodiments of this paragraph, Y is

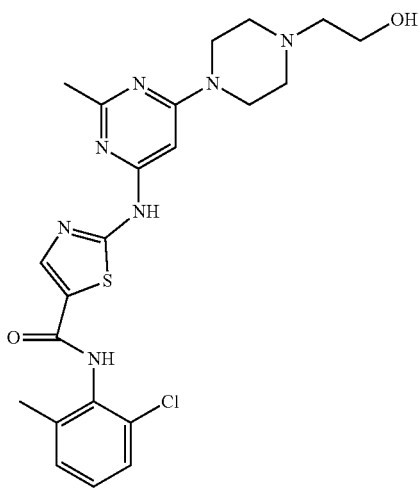 [SMILES: Cc1nc(Nc2ncc(C(=O)Nc3c(C)cccc3Cl)s2)cc(N2CCN(CCO)CC2)n1]

(derivatized through the carboxy group to attach to the rest of the molecule);

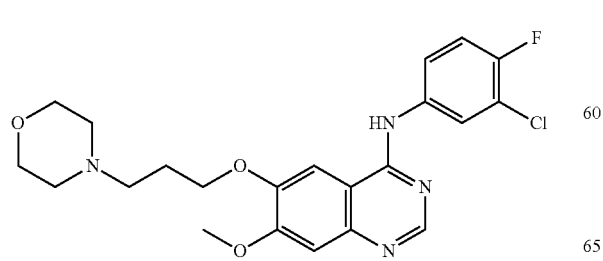

(derivatized through the hydroxyl group exposed upon removal of the N-propylmorpholino group, or after removing the methyl group from the methoxy group, to attach to the rest of the molecule);

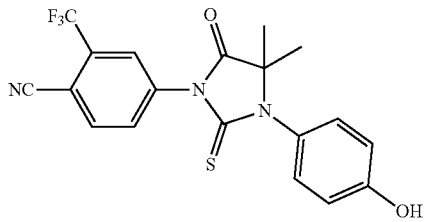 [SMILES: CC1(C)C(=O)N(c2ccc(C#N)c(C(F)(F)F)c2)C(=S)N1c1ccc(O)cc1]

(derivatized through the hydroxyl group to attach to the rest of the molecule);

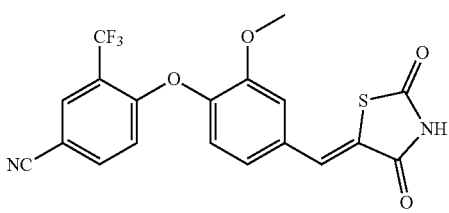 [SMILES: COc1cc(/C=C2\SC(=O)NC2=O)ccc1Oc1ccc(C#N)cc1C(F)(F)F]

(derivatized through hydroxyl group exposed upon removal of the methyl group from the methoxy group, to attach to the rest of the molecule);

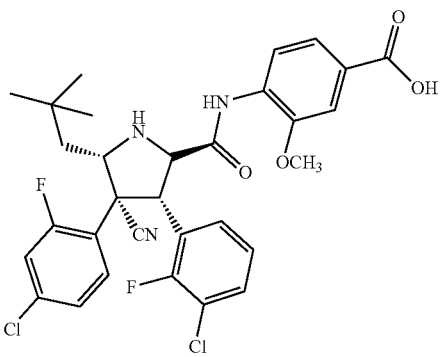

(derivatized through the carboxy group to attach to the rest of the molecule);

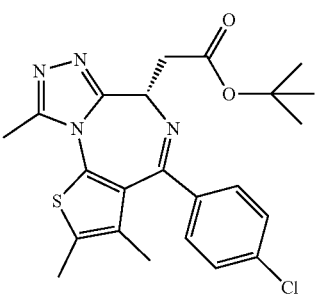 [SMILES: Cc1sc2c(c1C)C(c1ccc(Cl)cc1)=N[C@@H](CC(=O)OC(C)(C)C)c1nnc(C)n1-2]

(derivatized through the carboxy group exposed upon hydrolysis of the t-butyl ester group to attach to the rest of the molecule); (derivatized through the primary amino group to connect to the rest (derivatized through the hydroxyl group exposed upon removal of the N-ethylpyrrolidine, or through the sulfonamide exposed upon removal of the N-tertiary butyl group to attach to the rest of the molecule); or

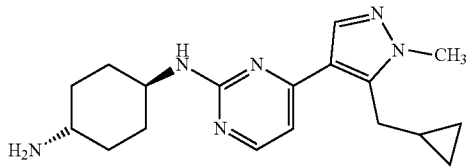

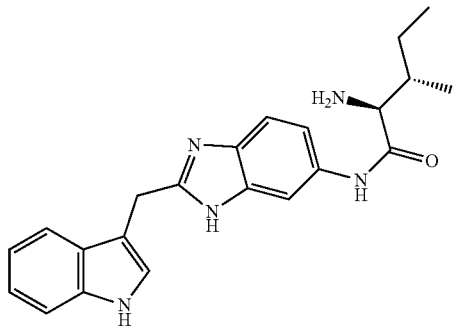 [SMILES: CC[C@H](C)[C@H](N)C(=O)Nc1ccc2nc(Cc3c[nH]c4ccccc34)[nH]c2c1]

(derivatized through the primary amino group to attach to the rest of the molecule).

In some embodiments, Y is compound that targets a particular protein, proteins, and/or protein complex. In some embodiments, Y is an HSP90 inhibitor. In some embodiments, Y is a kinase inhibitor. In some embodiments, Y is a phosphatase inhibitor. In some embodiments, Y is a compound targeting the estrogen receptor. In some embodiments, Y is a compound targeting the androgen receptor. In some embodiments, Y is an inhibitor of HDM2/MDM2. In some embodiments, Y is an HDAC inhibitor. In some embodiments, Y is an inhibitor of lysine methyltransferase. In some embodiments, Y is an inhibitor of one or more core-binding factor(s).

(derivatized through the primary amino group to attach to the rest of the molecule);

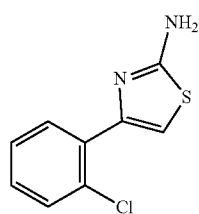 [SMILES: Nc1nc(-c2ccccc2Cl)cs1]

(derivatized through to primary amino group to attach to the rest of the molecule);

In some embodiments, Y is a compound targeting the BET bromodomain. In some embodiments, Y is a compound targeting FKBP. In some embodiments, Y is a compound targeting the RAF receptor. In some embodiments, Y is a compound targeting the aryl hydrocarbon receptor. In some embodiments, Y is an immunosuppressive compound. In some embodiments, Y is an angiogenesis inhibitor. In some embodiments, Y is a compound targeting HIV protease. In some embodiments, Y is a compound targeting the thyroid hormone receptor. In some embodiments, Y is a compound targeting one or more ligase(s).

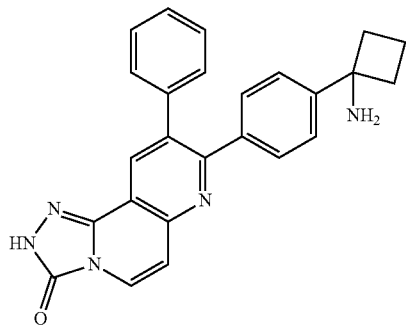 [SMILES: NC1(c2ccc(-c3nc4ccn5c(=O)[nH]nc5c4cc3-c3ccccc3)cc2)CCC1]

In some embodiments, Y is a compound targeting HIV integrase. In some embodiments, Y is a compound targeting HCV protease. In some embodiments, Y is a compound targeting acyl-protein thioesterase 1. In some embodiments, Y is a compound targeting acyl-protein thioesterase 2. In some embodiments, Y is a compound that is derivatized where L is attached.

(derivatized through the primary amino group to attach to the rest of the molecule);

In some embodiments, Y is a compound disclosed in Vallee, et al., *J. Med. Chem.* 54: 7206 (2011), including, but not limited to (N-[4-(3H-imidazo[4,5-C]Pyridin-2-yl)-9H-Fluoren-9-yl]-succinamide):

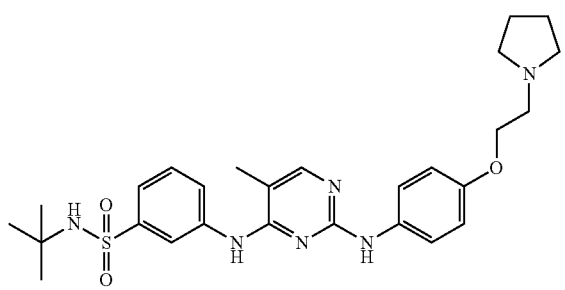 [SMILES: Cc1cnc(Nc2ccc(OCCN3CCCC3)cc2)nc1Nc1cccc(S(=O)(=O)NC(C)(C)C)c1]

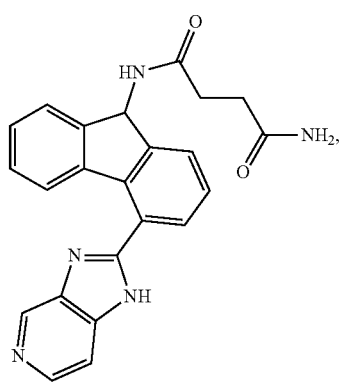 [SMILES: NC(=O)CCC(=O)NC1c2ccccc2-c2c(-c3nc4cnccc4[nH]3)cccc21]

derivatized where a linker group L is attached, for example, via the terminal amide group.

In some embodiments, Y is (8-[(2,4-dimethylphenyl)sulfanyl]-3]pent-4-yn-1-yl-3H-purin-6-amine):

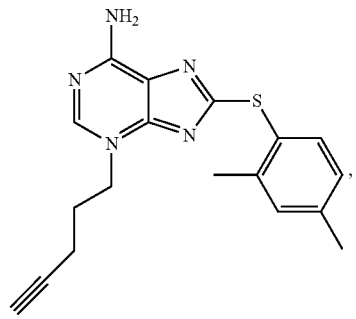

where a linker group L is attached, for example, via the terminal acetylene group.

In some embodiments, Y is a compound disclosed in Brough, et al., "*J. Med. Chem.* vol: 51, page 196 (2008), including (5[-2,-4-dihydroxy-5-(1-methylethyl)phenyl]n-ethyl-4-[4-(morpholin-4-ylme-thyl)phenyl[isoxazole-3-carboxamide) having the structure:

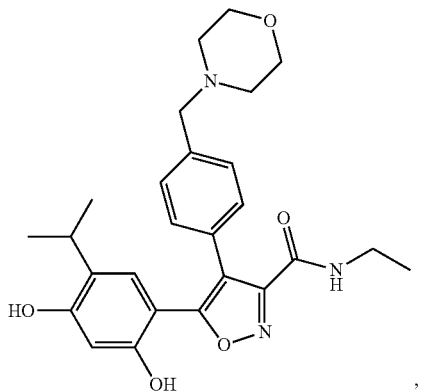 [SMILES: CCNC(=O)c1noc(-c2cc(C(C)C)c(O)cc2O)c1-c1ccc(CN2CCOCC2)cc1]

derivatized, where a linker group L is attached, for example, via the amide group.

In some embodiments, Y is a compound disclosed in Wright, et al., *Chem Biol.*,11(6):775-85 (2004), including:

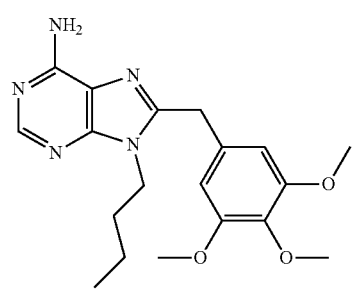 [SMILES: CCCCn1c(Cc2cc(OC)c(OC)c(OC)c2)nc2c(N)ncnc21]

where a linker group L or is attached, for example, via the butyl group.

In some embodiments, Y is geldanamycin ((4E,6Z,8S,9S, 10E,12S,13R,14S,16R)-13-hydroxy-8,14,19-trimethoxy-4, 10,12,-16-tetramethyl-3,20,22-trioxo-2-azabicyclo[16.3.1], or a derivative thereof (e.g. 17-alkylamino-17-desmethoxygeldanamycin ("17-AAG") or 17-(2-dimethylaminoethyl)amino-17-desmethoxygeldanamycin ("17-DMAG")) (derivatized where a linker group L is attached, for example, via the amide group).

In some embodiments, Y is

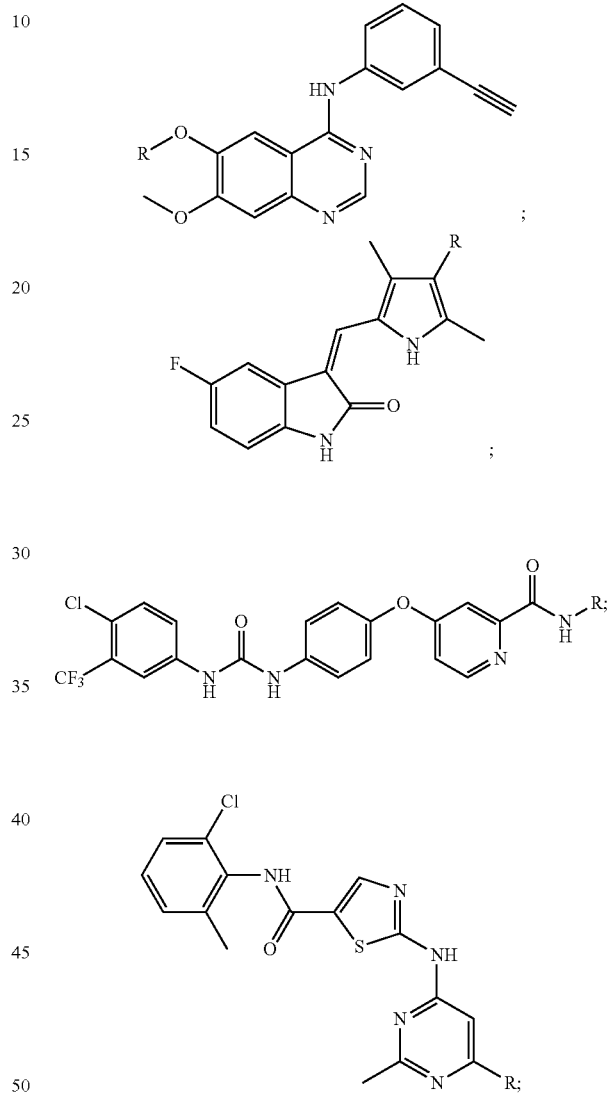

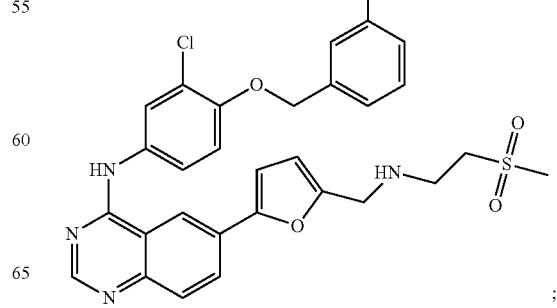

; or

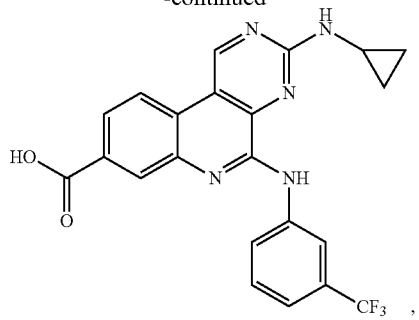

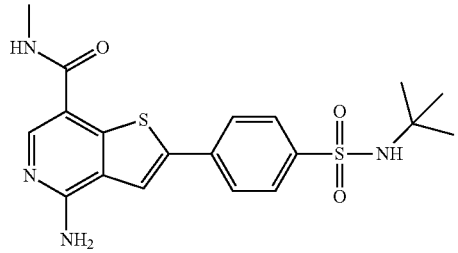

4-amino-2-[4-(tert-butylsulfamoyl)phenyl]-N-methylthieno[3,2-c]pyridine-7-carboxamide and each derivatized either through R (representing a linker group, L), or through another point of attachment.

In some embodiments, Y is a compound disclosed in Millan, et al., *J. Med. Chem.*, vol:54, pag:7797(2011), including:

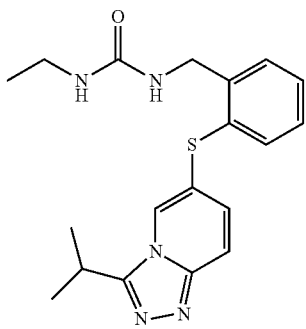 [SMILES: CCNC(=O)NCc1ccccc1Sc1ccc2nnc(C(C)C)n2c1]

(1-ethyl-3-(2-{[3-(1-methylethyl)[1,2,4]triazolo[4,3-a]pyridine-6-yl]sulfanyl}benzyl)urea derivatized where a linker group L is attached, for example, via the isopropyl group;

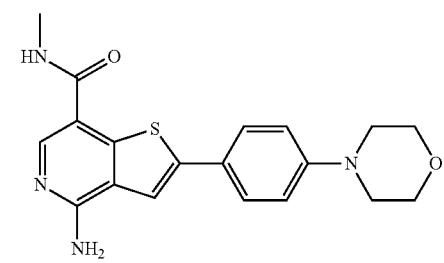

4-amino-N-methyl-2-[4-(morpholin-4-yl)phenyl[thieno[3,2-c]pyridine-7-carboxamide, derivatized where a linker group L is attached, for example, via the terminal amide moiety.

In some embodiments, Y is a compound disclosed in Van Eis, et al., *Biorg. Med. Chem. Lett.* 21(24):7367-72 (2011), including:

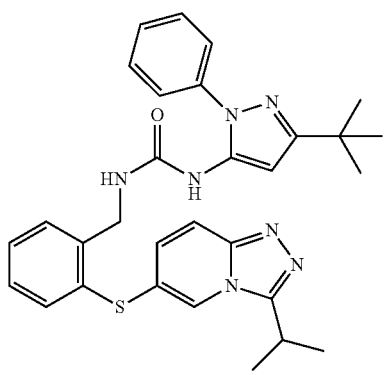 [SMILES: CC(C)c1nnc2ccc(Sc3ccccc3CNC(=O)Nc3cc(C(C)(C)C)nn3-c3ccccc3)cn12]

1-(3-tert-butyl-1-phenyl-1H-pyrazol-5-yl)-3-(2-{[3-(1-methylethyl)[1,2,4]-triazolo [4,3-a]pyridin-6-yl sulfanyl } benzyl) urea derivatized where a linker group L is attached, for example, via the tert-butyl group.

In some embodiments, Y is a compound disclosed in Schenkel, et al., *J. Med. Chem.*,54(24), pp 8440-8450 (2011) including:

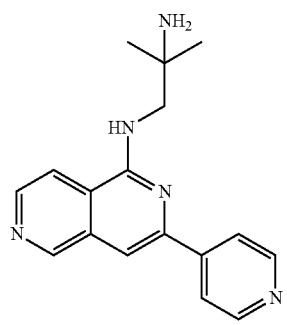 [SMILES: CC(C)(N)CNc1nc(-c2ccncc2)cc2cnccc12]

2-methyl-N-1-[3-(pyridin-4-yl)-2,6-naphthyridin-1-yl]propane-1,2-diamine derivatized where a linker group L is attached, for example, via the terminal amino group.

In some embodiments, Y is a compound disclosed in Lountos, et al., "*J. Struct. Biol.*, vol. 176, page 292 (2011), including:

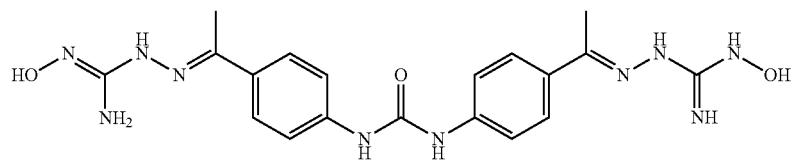 [SMILES: C/C(=N\NC(=N)NO)c1ccc(NC(=O)Nc2ccc(/C(C)=N/N/C(N)=N/O)cc2)cc1]

derivatized where a linker group L is attached, for example, via either of the terminal hydroxyl groups.

In some embodiments, Y is

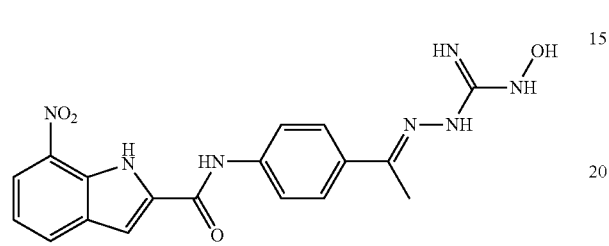

N-{4-[(1 E)-N-(N-hydroxycarbamimidoyl)ethanehydrazonoyl]phenyl}-7-nitro-1H-indole-2-carboxamide or

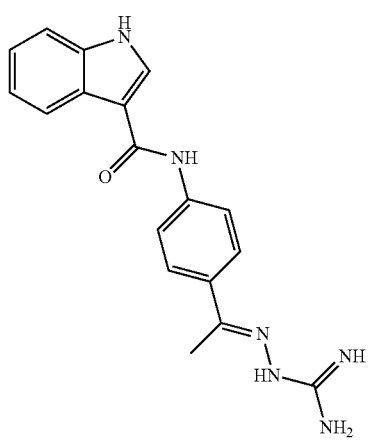 [SMILES: C/C(=N\NC(=N)N)c1ccc(NC(=O)c2c[nH]c3ccccc23)cc1]

N-55 4-[(1E)-N-carbamidoylethanehydrazonoyl]phenyl}-1H-indole-3-carboxamide derivatized where a linker group L is attached, for example, via the terminal hydroxyl group or the hydrazone.

In some embodiments, Y is afatinib (derivatized where a linker group L is attached, for example, via the aliphatic amine group); fostamatinib (derivatized where a linker group L is attached, for example, via a methoxy group); gefitinib (derivatized where a linker group L is attached, for example, via a methoxy or ether group); lenvatinib (derivatized where a linker group L is attached, for example, via the cyclopropyl group); vandetanib (derivatized where a linker group L is attached, for example, via the methoxy or hydroxyl group); vemurafenib ((derivatized where a linker group L is attached, for example, via the sulfonyl propyl group); Gleevec (derivatized where R as a linker group L is attached, for example, via the amide group or via the aniline amine group); pazopanib (derivatized where R is a linker group L attached, for example, to the phenyl moiety or via the aniline amine group); AT-9283

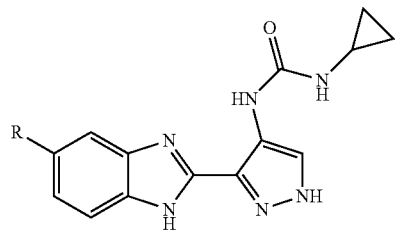

(derivatized where R is a linker group L attached, for example, to the phenyl moiety); TAE684

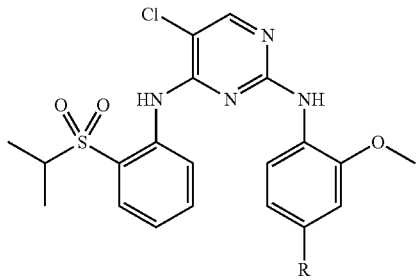

(derivatized where R is a linker group L attached, for example, to the phenyl moiety);

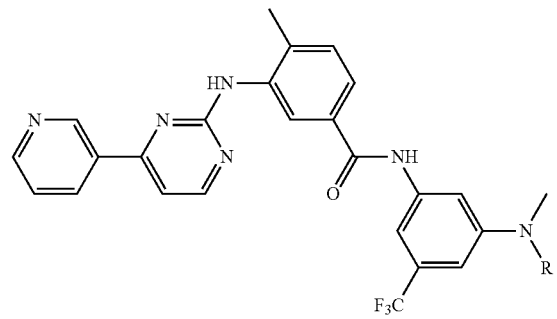

(derivatized where R is a linker group L attached, for example, to the phenyl moiety or the aniline amine group);

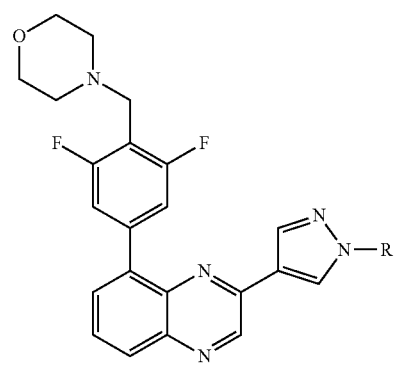

(derivatized where R is a linker group L attached, for example, to the phenyl moiety or the diazole group);

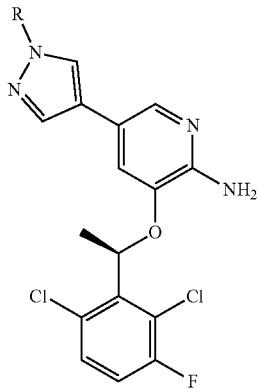

(derivatized where R is a linker group L attached, for example, to the phenyl moiety or the diazole group);

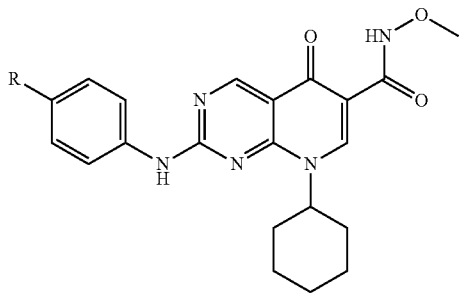

(derivatized where R is a linker group L attached, for example, to the phenyl moiety);

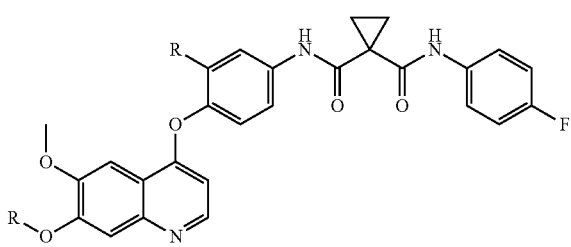

(derivatized where R is a linker group L attached, for example, to the phenyl moiety or a hydroxyl or ether group on the quinoline moiety);

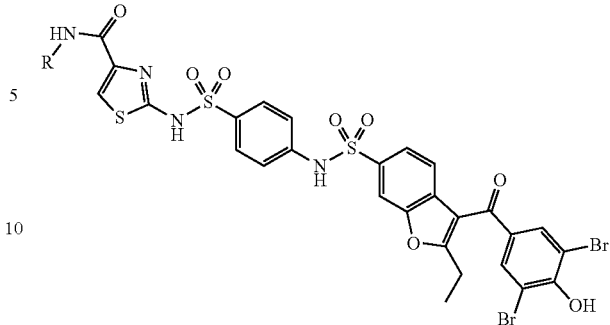

(derivatized where a linker group L is attached, for example, at R);

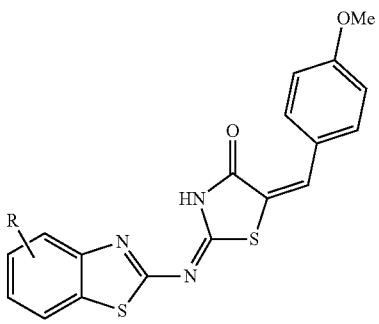

(derivatized where a linker group L is attached, for example, at R);

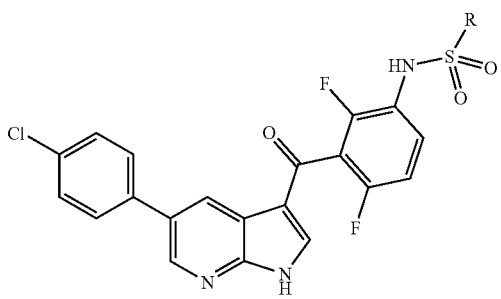

(derivatized where a linker group L is attached, for example, at R);

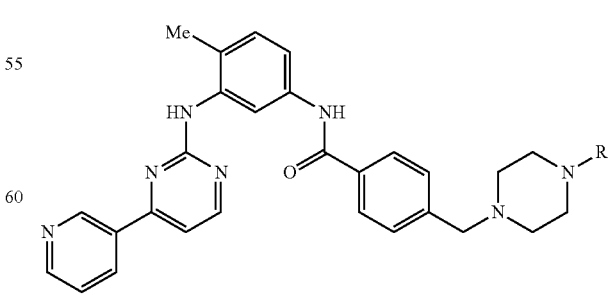

(derivatized where a linker group L is attached, for example, at R);

81

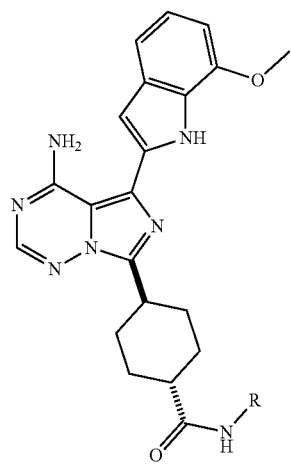

(derivatized where a linker group L is attached, for example, at R);

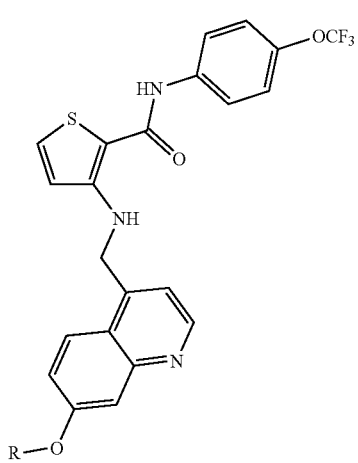

(derivatized where a linker group L is attached, for example, at R); or

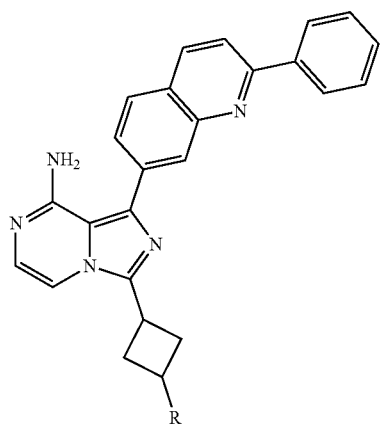

(derivatized where a linker group L is attached, for example, at R). In some embodiments, Y is a compound disclosed in Vassilev, et al., Science, vol. 303, pages 844-848 (2004), and

82

Schneekloth, et al., Bioorg. Med. Chem. Lett., vol. 18, pages 5904-5908(2008), including nutlin-3, nutlin-2, and nutlin-1 (shown below):

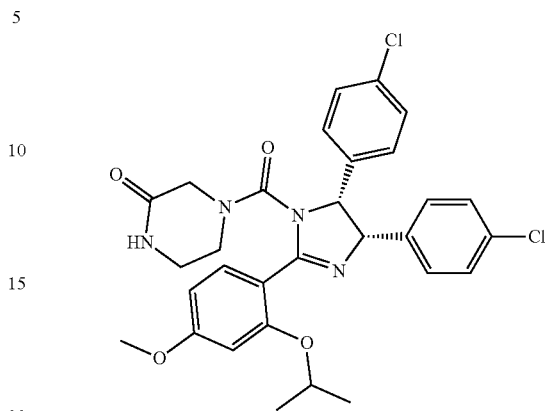

(derivatized where a linker group L is attached, for example, at the methoxy group or as a hydroxyl group);

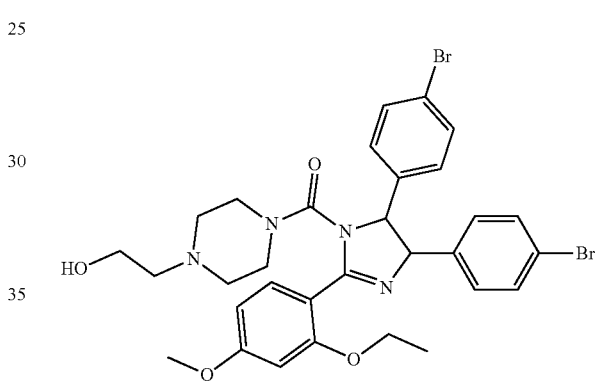

(derivatized where a linker group L is attached, for example, at the methoxy group or hydroxyl group);

(derivatized where a linker group L is attached, for example, via the methoxy group or as a hydroxyl group); and trans-4-Iodo-4'-Boranyl-Chalcone

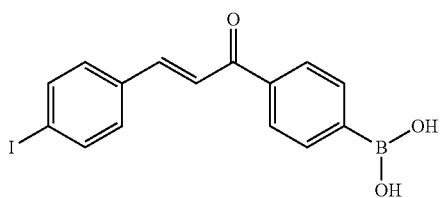 [SMILES: O=C(/C=C/c1ccc(I)cc1)c1ccc(B(O)O)cc1]
(derivatized where a linker group L or a linker group L is attached, for example, via a hydroxy group).
In some embodiments, Y is one of the compounds shown below, derivatized by the attachment of a linker group L (in some instances denoted by "R," below).
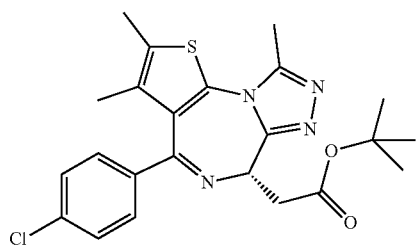
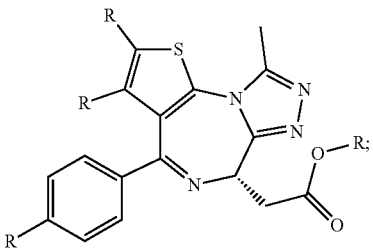
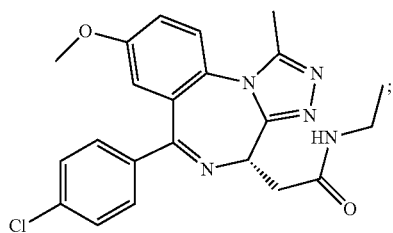
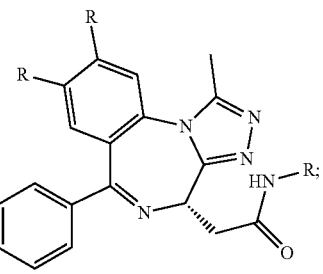
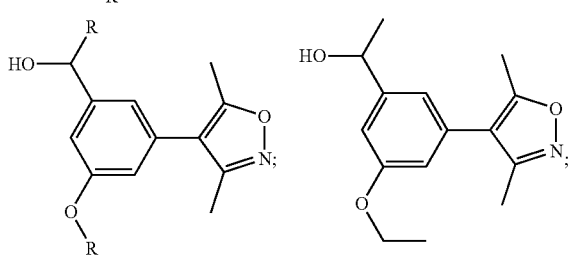
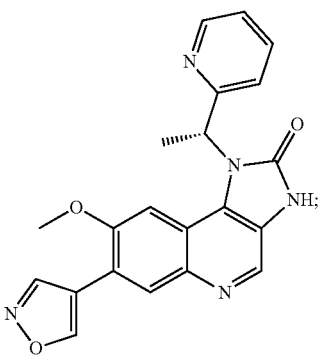
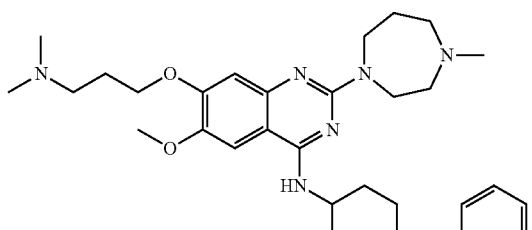
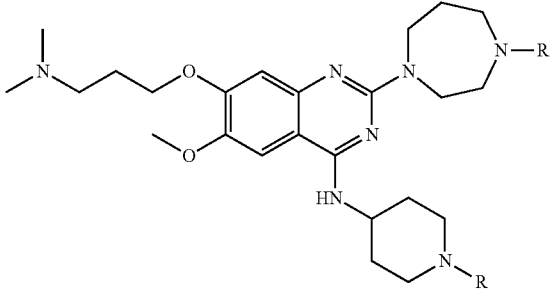
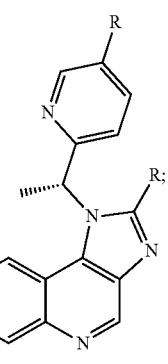
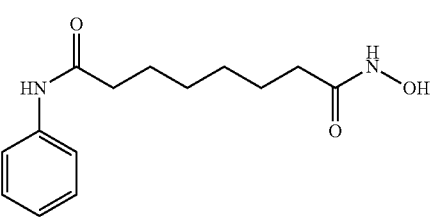

-continued

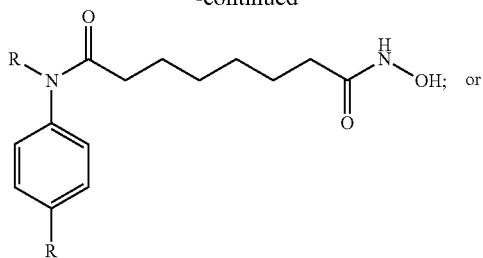

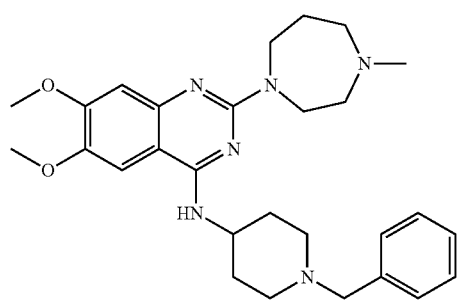

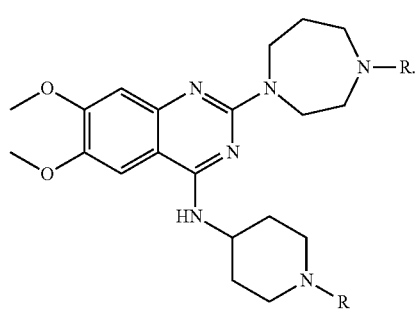

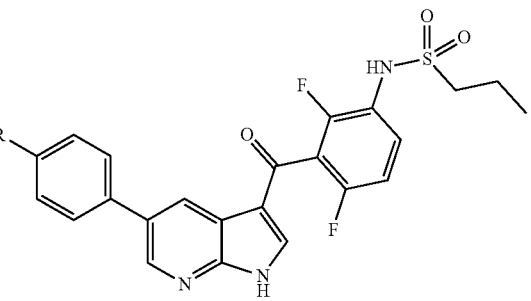

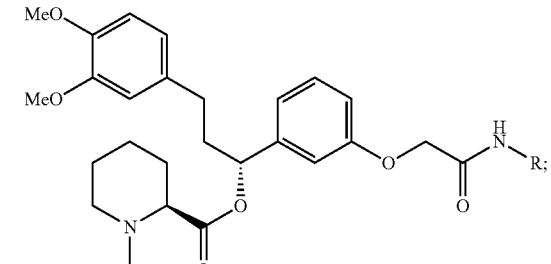

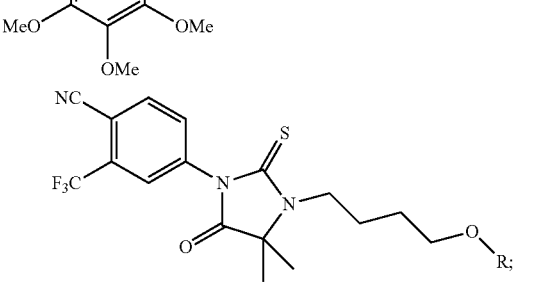

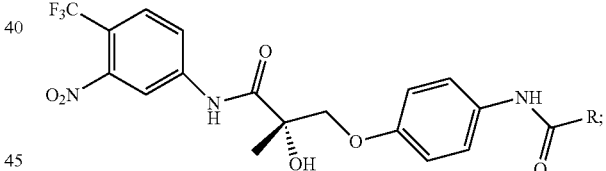

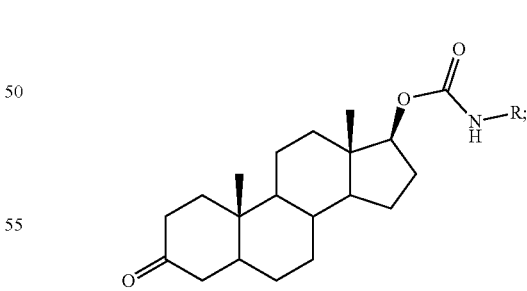

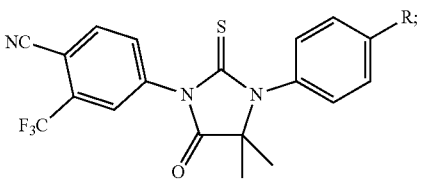

In some embodiments, Y is azacitidine ((derivatized where a linker group L is attached, for example, via the hydroxy or amino groups). In some embodiments, Y is decitabine (derivatized) (4-amino-1-(2-deoxy-b-D-erythro-pentofuranosyl)-1,3,5-triazin-2(1H)-one) (Derivatized where a linker group L is attached, for example, via either of the hydroxy groups or at the amino group).

In some embodiments, Y is GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics*, 2(12): 1350-58 (2003).

In some embodiments, Y is estradiol or testosterone, and related derivatives (including, but not limited to, DHT) which may be bound to a linker group L as is generally described in Rodriguez-Gonzalez, et al., *Oncogene*, 27, 7201-7211 (2008) and/or Sakamoto, et al., *Mol Cell Proteomics*, 2(12):1350-58 (2003).

In some embodiments, Y is ovalicin, fumagillin, a glucocorticoid (including, but not limited to hydrocortisone, prednisone, prednisolone, and methylprednisolone), methotrexate, cyclosporine, tacrolimus (FK-506), rapamycin, apigenin, or an actinomycin, each derivatized where a linker group L is bound. In some embodiments, Y is 87
-continued
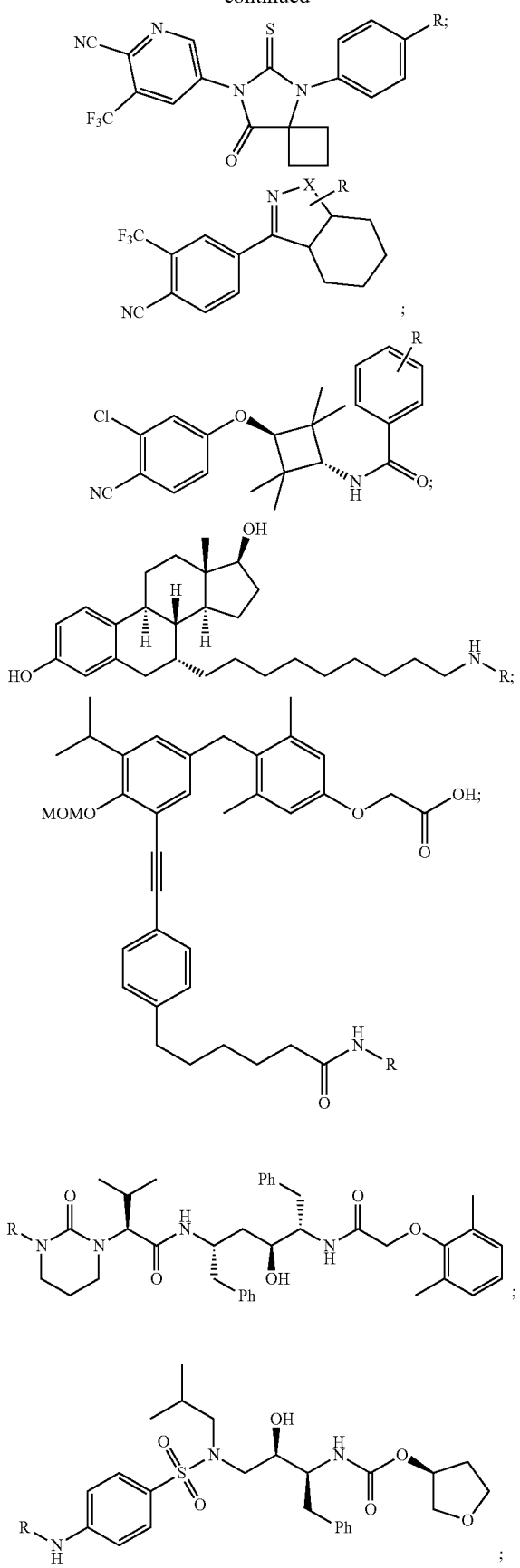
88
-continued
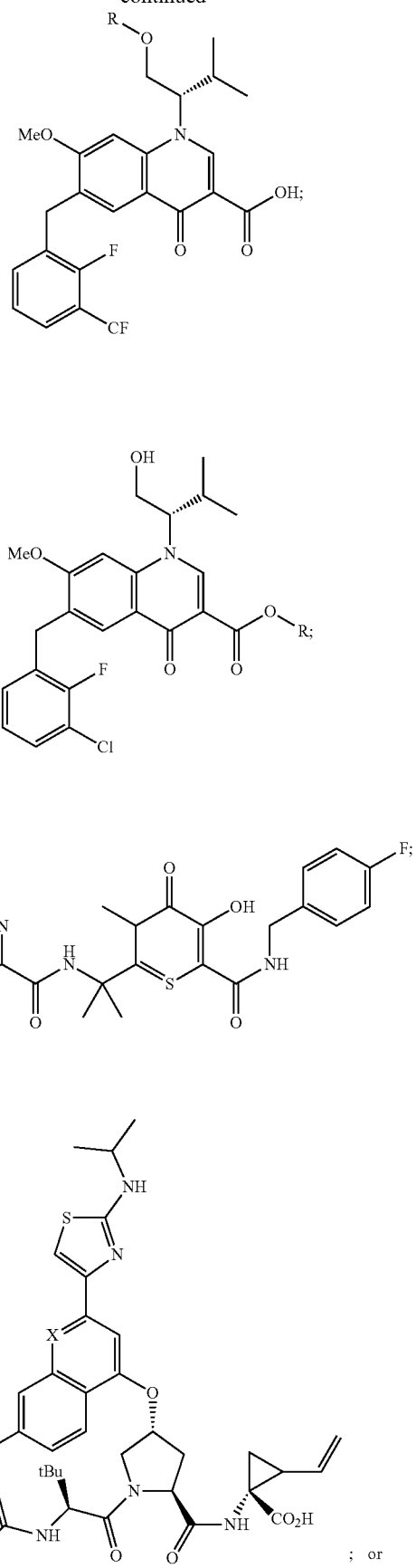

-continued

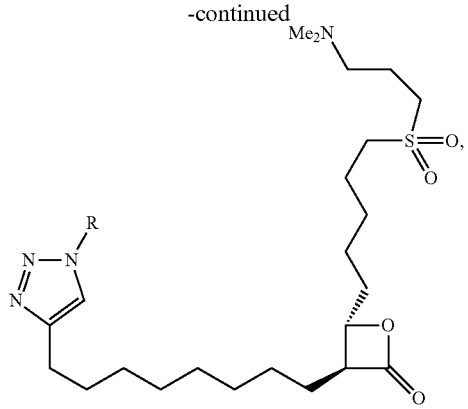

each derivatized where "R" designates a site for linker group L or group attachment, for example.

In some embodiments, Y is a compound disclosed in Cancer Research (2006), 66(11), 5790-5797, including but not limited to the Bcr-Abl tyrosine-kinase inhibitor dasatinib, derivatized where R is a linker group L attached, for example, via an ether or other functional group.

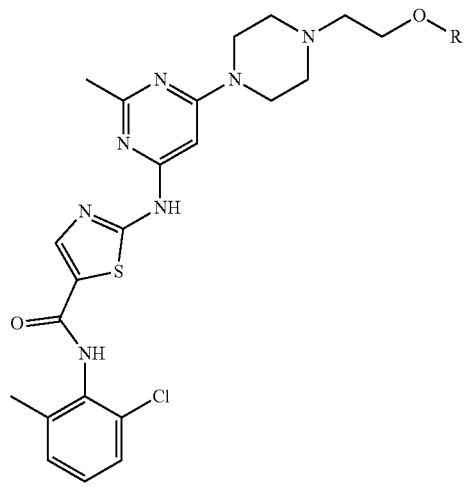

In some embodiments, Y is a compound disclosed in Cancer Cell (2007), 11(3), 209-11, including but not limited to the epidermal growth factor receptor (EGFR) tyrosine kinase inhibitor shown below, derivatized where R is a linker group L attached, for example, via an ether or other functional group.

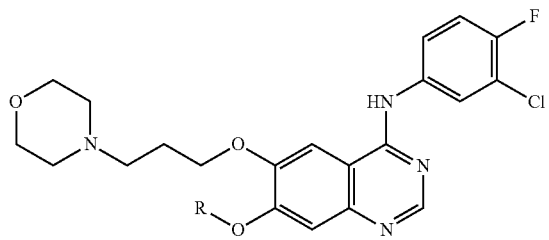

This compound below is replacing [0419] In some embodiments, Y is a compound disclosed in PLoS One (2014), 9(10), e109705/1-e109705/12, including but not limited to the AKT kinase inhibitor shown below, derivatized where R is a linker group L attached, for example, via an amide or other functional group.

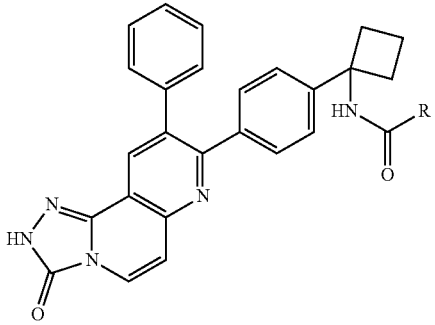

In some embodiments, Y is a compound disclosed in Scientific Reports (2015), 5, 14538, including but not limited to the Janus kinase 2 (JAK2) kinase inhibitor shown below, derivatized where R is a linker group L attached, for example, via an ether or other functional group.

In some embodiments, Y is a casein kinase 1 alpha (CK1α) kinase inhibitor including but not limited to the compound shown below, derivatized where R is a linker group L attached, for example, via an amide or other functional group.

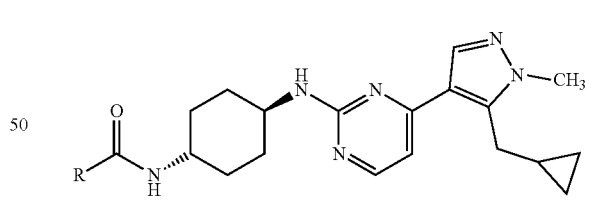

In some embodiments, Y is a compound disclosed in *Journal of Medicinal Chemistry* (2013), 56(14), 5979-5983, including but not limited to the MDM2 inhibitor shown below, derivatized where R is a linker group L attached, for example, via an amide or other functional group.

In some embodiments, Y is a compound disclosed in *Proceedings of the National Academy of Sciences of the United States of America* (2015), 112(51), 15713-15718, including but not limited to the bromodomain-containing protein 4 (BRD4) inhibitor shown below, derivatized where R is a linker group L attached, for example, via an amide or other functional group.

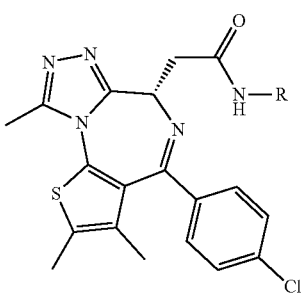

In some embodiments, Y is a compound disclosed in *Journal of Medicinal Chemistry* (2010), 53(7), 2779-2796, including but not limited to the androgen receptor (AR) modulator shown below, derivatized where R is a linker group L attached, for example, via an ether or other functional group.

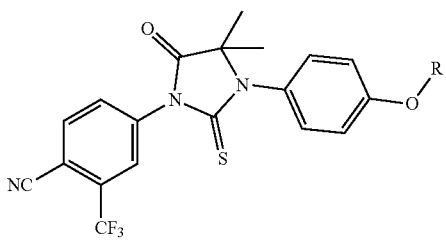

In some embodiments, Y is a compound disclosed in *Journal of Medicinal Chemistry* (2011), 54(3), 788-808, including but not limited to the estrogen receptor alpha (ERα) modulator shown below, derivatized where R is a linker group L attached, for example, to the nitrogen of the thiazolidinedione.

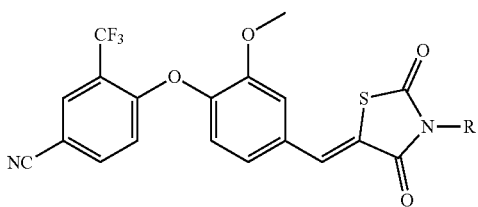

In some embodiments, Y is a compound disclosed in *Chemistry & Biology* (Cambridge, Mass., United States) (2007), 14(10), 1186-1197, including but not limited to the core-binding factor beta (CBFβ) inhibitor shown below, derivatized where R is a linker group L attached, for example, via an amide or other functional group.

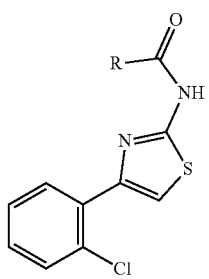

Some embodiments provide a pharmaceutical composition comprising a compound of Formula (I), Formula (II), Formula (III), or a pharmaceutically acceptable salt of any of the foregoing, and at least one pharmaceutically acceptable carrier. Some embodiments provide a pharmaceutical composition comprising a pharmaceutically acceptable salt or a solvate of a compound of Formula (I), Formula (II), Formula (III), or a pharmaceutically acceptable salt of any of the foregoing, and at least one pharmaceutically acceptable carrier. The definitions for compounds of Formula (I), Formula (II), and Formula (III) are the same as those set forth above.

Some embodiments provide methods of treating, ameliorating, or preventing a disease, disorder, or condition associated with protein misregulation, comprising administering a therapeutically effective amount of a compound of Formula (I), Formula (II), Formula (III), or a pharmaceutically acceptable salt of any of the foregoing, wherein the protein is the target of Y. For example, if Y targets the fibroblast growth factor receptor (FGFR), then the embodiments provides methods of treating, ameliorating, or preventing a disease, disorder, or condition associated with FGFR misregulation, comprising administering a therapeutically effective amount of a compound of Formula (I), Formula (II), Formula (III), or a pharmaceutically acceptable salt of any of the foregoing. Likewise, if Y targets JAK (janus kinase, e.g., JAK2), then the embodiments provides methods of treating, ameliorating, or preventing a disease, disorder, or condition associated with JAK misregulation, comprising administering a therapeutically effective amount of a compound of Formula (I), Formula (II), Formula (III), or a pharmaceutically acceptable salt of any of the foregoing. The definitions for compounds of Formula (I), Formula (II), and Formula (III) are the same as those set forth above.

Some embodiments provide methods of inhibiting protein activity, comprising contacting a cell with a compound of Formula (I), Formula (II), Formula (III), or a pharmaceutically acceptable salt of any of the foregoing, wherein the protein is the target of Y. For example, if Y targets the fibroblast growth factor receptor (FGFR), then the embodiments provides methods of inhibiting FGFR activity, comprising contacting a cell with a compound of Formula (I), Formula (II), Formula (III), or a pharmaceutically acceptable salt of any of the foregoing. Likewise, if Y targets JAK, then the embodiments provides methods of inhibiting JAK activity, comprising contacting a cell with a compound of Formula (I), Formula (II), Formula (III), or a pharmaceutically acceptable salt of any of the foregoing. The definitions for compounds of Formula (I), Formula (II), and Formula (III) are the same as those set forth above.

Some embodiments provide methods of treating, ameliorating, or preventing a disease, disorder, or condition associated with cytokines, comprising administering a therapeutically effective amount of a compound of Formula (I), Formula (II), Formula (III), or a pharmaceutically acceptable salt of any of the foregoing. The definitions for compounds of Formula (I), Formula (II), and Formula (III) are the same as those set forth above. In some embodiments, the cytokine is IL-1-alpha, IL-1-beta, IL-2, IL-4, IL-6, IL-10, or a combination thereof.

Some embodiments provide methods of treating, ameliorating, or preventing a disease, disorder, or condition associated with TNF-alpha, comprising administering a therapeutically effective amount of a compound of Formula (I), Formula (II), Formula (III), or a pharmaceutically acceptable salt of any of the foregoing. The definitions for compounds of Formula (I), Formula (II), and Formula (III) are the same as those set forth above.

Some embodiments provide methods of treating, ameliorating, or preventing a disease, disorder, or condition associated with aiolos or ikaros, comprising administering a therapeutically effective amount of a compound of Formula (I), Formula (II), Formula (III), or a pharmaceutically acceptable salt of any of the foregoing. The definitions for compounds of Formula (I), Formula (II), and Formula (III) are the same as those set forth above.

Some embodiments provide methods of treating, ameliorating, or preventing a disease, disorder, or condition associated with CK1-alpha, comprising administering a therapeutically effective amount of a compound of Formula (I), Formula (II), Formula (III), or a pharmaceutically acceptable salt of any of the foregoing. The definitions for compounds of Formula (I), Formula (II), and Formula (III) are the same as those set forth above.

In some embodiments, the disease, disorder, or condition selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, organ transplant rejection, and cancer. In some embodiments, the compound of Formula (I), Formula (II), Formula (III), or a pharmaceutically acceptable salt of any of the foregoing, is administered in combination with a second therapeutic agent.

Some embodiments provide methods of inhibiting cytokine activity, comprising contacting a cell with a compound of Formula (I), Formula (II), Formula (III), or a pharmaceutically acceptable salt of any of the foregoing. The definitions for compounds of Formula (I), Formula (II), and Formula (III) are the same as those set forth above. In some embodiments, the compound of Formula (I), Formula (II), Formula (III), or a pharmaceutically acceptable salt of any of the foregoing is administered in combination with a second therapeutic agent. In some embodiments, the cytokine is IL-1-alpha, IL-1-beta, IL-2, IL-4, IL-6, IL-10, or a combination thereof.

Some embodiments provide methods of inhibiting TNF-alpha activity, comprising contacting a cell with a compound of Formula (I), Formula (II), Formula (III), or a pharmaceutically acceptable salt of any of the foregoing. The definitions for compounds of Formula (I), Formula (II), and Formula (III) are the same as those set forth above. In some embodiments, the compound of Formula (I), Formula (II), Formula (III), or a pharmaceutically acceptable salt of any of the foregoing is administered in combination with a second therapeutic agent.

Some embodiments provide methods of inhibiting aiolos activity, ikaros activity, or aiolos and ikaros activity, comprising contacting a cell with a compound of Formula (I), Formula (II), Formula (III), or a pharmaceutically acceptable salt of any of the foregoing. The definitions for compounds of Formula (I), Formula (II), and Formula (III) are the same as those set forth above. In some embodiments, the compound of Formula (I), Formula (II), Formula (III), or a pharmaceutically acceptable salt of any of the foregoing is administered in combination with a second therapeutic agent.

Some embodiments provide methods of inhibiting CK1-alpha activity, comprising contacting a cell with a compound of Formula (I), Formula (II), Formula (III), or a pharmaceutically acceptable salt of any of the foregoing. The definitions for compounds of Formula (I), Formula (II), and Formula (III) are the same as those set forth above. In some embodiments, the compound of Formula (I), Formula (II), Formula (III), or a pharmaceutically acceptable salt of any of the foregoing is administered in combination with a second therapeutic agent.

One or more of the compounds of preferred embodiments can be provided in the form of pharmaceutically acceptable salts, solvates, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The pharmaceutical compositions of preferred embodiments can further comprise one or more additional therapeutically active agents other than a compound of the preferred embodiments. Such agents can include, but are not limited to, anti-inflammatory agents, anti-cancer agents, immunostimulatory agents, and immunosuppressive agents.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description Definitions Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

| ACN | Acetonitrile |
| AIBN | 2,2'-Azobis(2-methylpropionitrile) |
| AcOH | Acetic acid |
| ° C. | Temperature in degrees Centigrade |
| DCM | Dichloromethane |
| DIEA | Diisopropylethylamine |
| DMF | N,N-dimethylformamide |
| DMSO | Dimethylsulfoxide |
| EA | Ethyl acetate |
| g | Gram(s) |
| HCl | Hydrochloric acid |
| hr or hrs | Hour(s) |
| IL | Interleukin |
| LPS | Lipopolysaccharide |
| M-CSF | Macrophage colony-stimulating factor |
| MeOH | Methanol |
| MS | Mass spectrometry |
| mg | Milligram(s) |
| mL | Milliliter(s) |
| NaCl | Sodium chloride |
| NBS | N-bromosuccinimide |
| PBMC | Peripheral blood mononuclear cell |
| PG | Protecting group |
| ppt | Precipitate |
| psi | Pounds per square inch |
| RPMI | Roswell Park Memorial Institute medium |
| rt | Room temperature |
| TEA | Triethylamine |
| TFA | Trifluoroacetic acid |
| THF | Tetrahydrofuran |
| TNF | Tumor necrosis factor |
| μL | Microliter(s) |
| μM | Micromolar |
| wt. | weight |

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R_2$, $R_3$, $R_4$, $R_5$, $R_6$, $R_9$, and $R_{10}$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R_2$ and $R_3$, or $R_2$, $R_3$, or $R_4$, and the atom to which it is attached, are indicated to be "taken together" or "joined together" it means that they are covalently bonded to one another to form a ring:

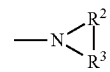

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group, as defined herein, that contains in the straight or branched hydrocarbon chain one or more double bonds. An alkenyl group may be unsubstituted or substituted.

As used herein, "alkynyl" refers to an alkyl group as defined herein, that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "carbocyclyl" or "cyclic hydrocarbyl" refers to all carbon ring systems. Such systems can be unsaturated, can include some unsaturation, or can contain some aromatic portion, or be all aromatic. Carbocyclyl group can contain from 3 to 30 carbon atoms. A carbocyclyl group may be unsubstituted or substituted.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to mono- or polycyclic ring systems including at least one heteroatom (e.g., O, N, S). Such systems can be unsaturated, can include some unsaturation, or can contain some aromatic portion, or be all aromatic. A heterocyclyl group can contain from 3 to 30 atoms. A heterocyclyl group may be unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidone, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

"Lower alkylene groups" are straight-chained —$CH_2$— tethering groups, forming bonds to connect molecular fragments via their terminal carbon atoms. Lower alkylene groups contain from 1 to 6 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "aralkyl" and "aryl(alkyl)" refer to an aryl group, as defined above, connected, as a substituent, via a lower alkylene group, as described above. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via a lower alkylene group, as defined above. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" is a heterocyclic or a heteroalicyclic group, as defined above, connected, as a substituent, via a lower alkylene group, as defined above. The lower alkylene and heterocyclic or a heterocyclyl of a (heteroalicyclyl)alkyl may be substituted or unsubstituted. Examples include but are not limited to tetrahydro-2H-pyran-4-yl) methyl, (piperidin-4-yl)ethyl, (piperidin-4-yl)propyl, (tetrahydro-2H-thiopyran-4-yl)methyl, and (1,3-thiazinan-4-yl) methyl.

As used herein, "alkoxy" refers to the formula —OR wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "acyl" refers to a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-sulfonamido may be substituted or unsubstituted.

An "O-carbamyl" group refers to a "—OC(═O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An O-carbamyl may be substituted or unsubstituted.

An "N-carbamyl" group refers to an "ROC(═O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-carbamyl may be substituted or unsubstituted.

An "O-thiocarbamyl" group refers to a "—OC(═S)—N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An O-thiocarbamyl may be substituted or unsubstituted.

An "N-thiocarbamyl" group refers to an "ROC(═S)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-thiocarbamyl may be substituted or unsubstituted.

A "C-amido" group refers to a "—C(═O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A C-amido may be substituted or unsubstituted.

An "N-amido" group refers to a "RC(═O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-amido may be substituted or unsubstituted.

A "urea" group refers to a "—N(R$_A$R$_B$)—C(═O)—N(R$_A$R$_B$)—" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A urea group may be substituted or unsubstituted.

A "thiourea" group refers to a "—N(R$_A$R$_B$)—C(═S)—N(R$_A$R$_B$)—" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A thiourea group may be substituted or unsubstituted.

The term "halogen atom" or "halogen" as used herein, means any one of the radio-stable atoms of column 7 of the Periodic Table of the Elements, such as, fluorine, chlorine, bromine, and iodine.

In all of the definitions described herein, the terms used to define a new term are as previously defined herein.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4''-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity and properties of the compound.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

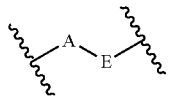

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, prodrugs, crystalline forms, amorphous form, solvated forms, enantiomeric forms, tautomeric forms, and the like).

Additional Therapeutic Agents

Some embodiments provide pharmaceutical compositions comprising a compound of Formula (I), Formula (II), Formula (III), or a pharmaceutically acceptable salt of any of the foregoing and a pharmaceutically acceptable carrier. Some embodiments provide pharmaceutical compositions comprising a compound of Formula (I), Formula (II), Formula (III), or a pharmaceutically acceptable salt of any of the foregoing, a pharmaceutically acceptable carrier, and a second therapeutic agent. Some embodiments provide methods of inhibiting cytokine activity, comprising contacting a cell with a compound of Formula (I), Formula (II), Formula (III), or a pharmaceutically acceptable salt of any of the foregoing. Some embodiments provide methods of inhibiting cytokine activity, comprising contacting a cell with a compound of Formula (I), Formula (II), Formula (III), or a pharmaceutically acceptable salt of any of the foregoing in combination with a second therapeutic agent. Some embodiments provide methods of treating, ameliorating, or preventing a disease, disorder, or condition associated with cytokines, comprising administering a therapeutically effective amount of a compound of Formula (I), Formula (II), Formula (III), or a pharmaceutically acceptable salt of any of the foregoing. Some embodiments provide methods of treating, ameliorating, or preventing a disease, disorder, or condition associated with cytokines, comprising administering a therapeutically effective amount of a compound of Formula (I), Formula (II), Formula (III), or a pharmaceutically acceptable salt of any of the foregoing in combination with a second therapeutic agent.

In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone.

In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; and oxaliplatin.

In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide.

In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; and procarbazine.

In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine.

In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine.

In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin.

In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab.

In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; and rilonacept.

Dosing Regimes

In some embodiments, about 1 mg to about 5 grams of a compound of Formula (I), Formula (II), Formula (III), or a pharmaceutically acceptable salt of any of the foregoing is administered each day. In some embodiments, about 2 mg to about 2 grams of a compound of Formula (I), Formula (II), Formula (III), or a pharmaceutically acceptable salt of any of the foregoing is administered each day. In some embodiments, about 5 mg to about 1 gram of a compound of Formula (I), Formula (II), Formula (III), or a pharmaceutically acceptable salt of any of the foregoing is administered each day. In some embodiments, about 10 mg to about 800 milligrams of a compound of Formula (I), Formula (II), Formula (III), or a pharmaceutically acceptable salt of any of the foregoing is administered each day. In some embodiments, about 20 mg to about 600 milligrams of a compound of Formula (I), Formula (II), Formula (III), or a pharmaceutically acceptable salt of any of the foregoing is administered each day. In some embodiments, about 30 mg to about 400 milligrams of a compound of Formula (I), Formula (II), Formula (III), or a pharmaceutically acceptable salt of any of the foregoing is administered each day. In some embodiments, about 40 mg to about 200 milligrams of a compound of Formula (I), Formula (II), Formula (III), or a pharmaceutically acceptable salt of any of the foregoing is administered each day. In some embodiments, about 50 mg to about 100 milligrams of a compound of Formula (I), Formula (II), Formula (III), or a pharmaceutically acceptable salt of any of the foregoing is administered each day.

In some embodiments, about 1 mg to about 5 grams of a compound of Formula (I), Formula (II), Formula (III), or a pharmaceutically acceptable salt of any of the foregoing is administered each week. In some embodiments, about 2 mg to about 2 grams of a compound of Formula (I), Formula (II), Formula (III), or a pharmaceutically acceptable salt of any of the foregoing is administered each week. In some embodiments, about 5 mg to about 1 gram of a compound of Formula (I), Formula (II), Formula (III), or a pharmaceutically acceptable salt of any of the foregoing is administered each week. In some embodiments, about 10 mg to about 800 milligrams of a compound of Formula (I), Formula (II), Formula (III), or a pharmaceutically acceptable salt of any of the foregoing is administered each week. In some embodiments, about 20 mg to about 600 milligrams of a compound of Formula (I), Formula (II), Formula (III), or a pharmaceutically acceptable salt of any of the foregoing is administered each week. In some embodiments, about 30 mg to about 400 milligrams of a compound of Formula (I), Formula (II), Formula (III), or a pharmaceutically acceptable salt of any of the foregoing is administered each week. In some embodiments, about 40 mg to about 200 milligrams of a compound of Formula (I), Formula (II), Formula (III), or a pharmaceutically acceptable salt of any of the foregoing is administered each week. In some embodiments, about 50 mg to about 100 milligrams of a compound of Formula (I), Formula (II), Formula (III), or a pharmaceutically acceptable salt of any of the foregoing is administered each week.

In some embodiments, about 1 mg to about 5 grams of a compound of Formula (I), Formula (II), Formula (III), or a pharmaceutically acceptable salt of any of the foregoing is administered each cycle of treatment. In some embodiments, about 2 mg to about 2 grams of a compound of Formula (I), Formula (II), Formula (III), or a pharmaceutically acceptable salt of any of the foregoing is administered each cycle of treatment. In some embodiments, about 5 mg to about 1 gram of a compound of Formula (I), Formula (II), Formula (III), or a pharmaceutically acceptable salt of any of the foregoing is administered each cycle of treatment. In some embodiments, about 10 mg to about 800 milligrams of a compound of Formula (I), Formula (II), Formula (III), or a pharmaceutically acceptable salt of any of the foregoing is administered each cycle of treatment. In some embodiments, about 20 mg to about 600 milligrams of a compound of Formula (I), Formula (II), Formula (III), or a pharmaceutically acceptable salt of any of the foregoing is administered each cycle of treatment. In some embodiments, about 30 mg to about 400 milligrams of a compound of Formula (I), Formula (II), Formula (III), or a pharmaceutically acceptable salt of any of the foregoing is administered each cycle of treatment. In some embodiments, about 40 mg to about 200 milligrams of a compound of Formula (I), Formula (II), Formula (III), or a pharmaceutically acceptable salt of any of the foregoing is administered each cycle of treatment. In some embodiments, about 50 mg to about 100 milligrams of a compound of Formula (I), Formula (II), Formula (III), or a pharmaceutically acceptable salt of any of the foregoing is administered each cycle of treatment.

In some embodiments, a compound of Formula (I), Formula (II), Formula (III), or a pharmaceutically acceptable salt of any of the foregoing is administered at least once per day. In some embodiments, a compound of Formula (I), Formula (II), Formula (III), or a pharmaceutically acceptable salt of any of the foregoing is administered at least twice per day. In some embodiments, a compound of Formula (I), Formula (II), Formula (III), or a pharmaceutically acceptable salt of any of the foregoing is administered at least three times per day. In some embodiments, a compound of Formula (I), Formula (II), Formula (III), or a pharmaceutically acceptable salt of any of the foregoing is administered at least four times per day.

In some embodiments, a compound of Formula (I), Formula (II), Formula (III), or a pharmaceutically acceptable salt of any of the foregoing is administered at least once per week. In some embodiments, a compound of Formula (I), Formula (II), Formula (III), or a pharmaceutically acceptable salt of any of the foregoing is administered at least twice per week. In some embodiments, a compound of Formula (I), Formula (II), Formula (III), or a pharmaceutically acceptable salt of any of the foregoing is administered at least three times per week. In some embodiments, a compound of Formula (I), Formula (II), Formula (III), or a pharmaceutically acceptable salt of any of the foregoing is administered at least four times per week.

In some embodiments, each cycle of treatment lasts 1 day.
In some embodiments, each cycle of treatment lasts 2 days.
In some embodiments, each cycle of treatment lasts 3 days.
In some embodiments, each cycle of treatment lasts 4 days.
In some embodiments, each cycle of treatment lasts 5 days.
In some embodiments, each cycle of treatment lasts 6 days.
In some embodiments, each cycle of treatment lasts 7 days.
In some embodiments, each cycle of treatment lasts 8 days.
In some embodiments, each cycle of treatment lasts 9 days.
In some embodiments, each cycle of treatment lasts 10 days.
In some embodiments, each cycle of treatment lasts 11 days.
In some embodiments, each cycle of treatment lasts 12 days.
In some embodiments, each cycle of treatment lasts 13 days.
In some embodiments, each cycle of treatment lasts 14 days.

In some embodiments, each cycle of treatment has at least one day between administrations of a compound of Formula (I), Formula (II), Formula (III), or a pharmaceutically acceptable salt of any of the foregoing. In some embodiments, each cycle of treatment has at least two days between administrations of a compound of Formula (I), Formula (II), Formula (III), or a pharmaceutically acceptable salt of any of the foregoing. In some embodiments, each cycle of treatment has at least three days between administrations of a compound of Formula (I), Formula (II), Formula (III), or a pharmaceutically acceptable salt of any of the foregoing. In some embodiments, each cycle of treatment has at least four days between administrations of a compound of Formula (I), Formula (II), Formula (III), or a pharmaceutically acceptable salt of any of the foregoing. In some embodiments, each cycle of treatment has at least five days between administrations of a compound of Formula (I), Formula (II), Formula (III), or a pharmaceutically acceptable salt of any of the foregoing. In some embodiments, each cycle of treatment has at least six days between administrations of a compound of Formula (I), Formula (II), Formula (III), or a pharmaceutically acceptable salt of any of the foregoing. In some embodiments, each cycle of treatment has at least seven days between administrations of a compound of Formula (I), Formula (II), Formula (III), or a pharmaceutically acceptable salt of any of the foregoing.

In some embodiments, a compound of Formula (I), Formula (II), Formula (III), or a pharmaceutically acceptable salt of any of the foregoing is provided intravenously over about 10 minutes. In some embodiments, a compound of Formula (I), Formula (II), Formula (III), or a pharmaceutically acceptable salt of any of the foregoing is provided intravenously over about 20 minutes. In some embodiments, a compound of Formula (I), Formula (II), Formula (III), or a pharmaceutically acceptable salt of any of the foregoing is provided intravenously over about 30 minutes. In some embodiments, a compound of Formula (I), Formula (II), Formula (III), or a pharmaceutically acceptable salt of any of the foregoing is provided intravenously over about 1 hour. In some embodiments, a compound of Formula (I), Formula (II), Formula (III), or a pharmaceutically acceptable salt of any of the foregoing is provided intravenously over about 1.5 hours. In some embodiments, a compound of Formula (I), Formula (II), Formula (III), or a pharmaceutically acceptable salt of any of the foregoing is provided intravenously over about 2 hours. In some embodiments, a compound of Formula (I), Formula (II), Formula (III), or a pharmaceutically acceptable salt of any of the foregoing is provided intravenously over about 2.5 hours. In some embodiments, a compound of Formula (I), Formula (II), Formula (III), or a pharmaceutically acceptable salt of any of the foregoing is provided intravenously over about 3 hours. In some embodiments, a compound of Formula (I), Formula (II), Formula (III), or a pharmaceutically acceptable salt of any of the foregoing is provided intravenously over about 3.5 hours. In some embodiments, a compound of Formula (I), Formula (II), Formula (III), or a pharmaceutically acceptable salt of any of the foregoing is provided intravenously over about 4 hours.

EXAMPLES

Additional embodiments are disclosed in further detail in the following examples, which are not in any way intended to limit the scope of the claims.

Characterization of the compounds disclosed herein was performed with Bruker AV-500 and Bruker DRX-500 NMR spectrometers and a Perkin Elmer PE-SCIEX API-150 mass spectrometer.

Synthesis

5-Nitro-2-[(3S)-2-oxoazepan-3-yl]isoindoline-1,3-dione (Compound 12)

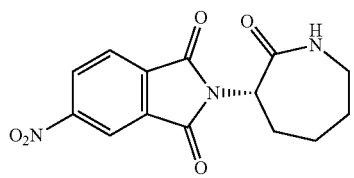 [SMILES: O=C1NCCCC[C@@H]1N1C(=O)c2ccc([N+](=O)[O-])cc2C1=O]

(S)-3-Aminoazepan-2-one (0.398 g, 3.11 mmol) was added to a mixture of 5-nitroisobenzofuran-1,3-dione (0.600 g, 3.11 mmol) and AcOH (2 mL) in ACN (20 mL). The reaction mixture was stirred at 70° C. overnight. Sodium acetate (0.382 g, 4.66 mmol) and additional AcOH (4 mL) was then added to the reaction mixture. After continued heating for 1 day at 70° C., the solution was cooled to rt and evaporated under vacuum. The residue was dissolved in EA (150 mL) and washed with saturated sodium bicarbonate (2×100 mL). The solution was dried over magnesium sulfate, filtered, and concentrated under vacuum to afford the title compound as an off-white solid (0.466 g, 49% yield). MS (M+1) 304. $^1$H NMR (DMSO-d$_6$) δ 8.65 (d, 1H, J=0.017), 8.51 (s, 1H), 8.15 (d, 1H, J=0.017), 4.90 (dd, 1H, J=0.021), 3.24 (m, 1H), 3.14 (m, 1H), 2.37 (m, 1H), 2.04 (m, 2H), 1.81 (m, 1H), 1.69 (m, 1H), 1.32 (m, 1H).

2-[(3S)-2,7-Dioxoazepan-3-yl]-5-nitro-isoindoline-1,3-dione (Compound 13)

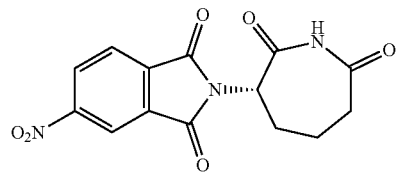 [SMILES: O=C1CCC[C@H](N2C(=O)c3ccc([N+](=O)[O-])cc3C2=O)C(=O)N1]

Potassium permanganate (0.261 g, 1.65 mmol) was added to a mixture of 5-nitro-2-(2-oxoazepan-3-yl)isoindoline-1,3-dione (0.100 g, 0.330 mmol) in sulfuric acid (0.5 mL), water (1 mL), and AcOH (1 mL). The resulting mixture was stirred for 1 day atambient temperature. EA (100 mL) was added, and the organic layer was washed with water (3×50 mL) then saturated sodium bicarbonate (2×50 mL). The solution was dried over magnesium sulfate, filtered, and concentrated under vacuum to afford the title compound as a white solid (0.049 g, 47% yield). MS (M+1) 318. $^1$H NMR (DMSO-d6) δ 10.87 (s, 1H), 8.67 (d, J=0.17), 8.56 (s, 1H), 8.19 (d, 1H, J=0.16), 5.30 (dd, 1H, J=0.24), 3.15 (m, 1H), 2.67 (m, 1H), 2.51 (m, 1H), 2.17 (m, 1H), 1.97 (m, 1H), 1.89 (m, 1H).

5-Amino-2-[(3S)-2-oxoazepan-3-yl]isoindoline-1,3-dione (Compound 14)

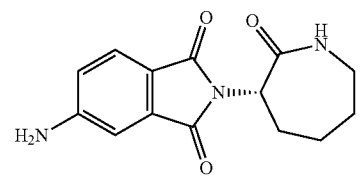

5-Nitro-2-(2-oxoazepan-3-yl)isoindoline-1,3-dione (0.030 g, 0.106 mmol) was dissolved in ethanol (6 mL) then hydrogen gas was bubbled through the solution for 10 seconds. To the solution was added 10 wt. % palladium on carbon (0.020 g) and the mixture was hydrogenated under 20-40 psi of hydrogen for 3 hrs. The mixture was filtered through celite, and the filtrate was concentrated under vacuum to afford the title compound as a light yellow solid (0.024 g, 89% yield). MS (M+1) 274.

5-Nitro-2-[(3S)-2-oxoazepan-3-yl]isoindolin-1-one (Compound 6)

A solution of methyl 2-(bromomethyl)-4-nitro-benzoate (1.00 g, 3.65 mmol), (S)-3-aminoazepan-2-one (0.468 g, 3.65 mmol) and triethyl amine (1 mL, 7 mmol) in dimethyl formamide (10 mL) was stirred for 1 day at 50° C. The solution was then cooled to rt, water (50 mL) was added, and the mixture cooled in an ice water bath for 10 minutes. The resulting precipitate was filtered and dried to afford the title compound as an off-white solid (0.864 g, 82% yield). MS (M+Na) 312. $^1$H NMR (DMSO-d6) δ 8.52 (s, 1H), 8.34 (d, 1H, J=0.016), 7.93 (d, 1H, J=0.016), 7.86 (bs, 1H), 4.94 (d, 1H, J=0.022), 4.82 (d, 1H, J=0.036), 4.61 (d, 1H, J=0.036), 3.26 (m, 2H), 3.12 (m, 1H), 2.02 (m, 2H), 1.82 (m, 1H), 1.71 (m, 1H), 1.30 (m, 1H).

2-[(3S)-2-Oxoazepan-3-yl]isoindoline-1,3-dione (Compound 15)

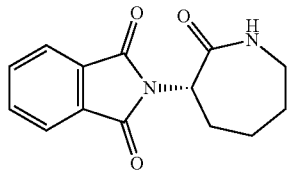 [SMILES: O=C1NCCCC[C@@H]1N1C(=O)c2ccccc2C1=O]

The title compound was afforded as a white solid (0.219 g, 63% yield) using the methods described above. MS (M+1) 259. $^1$H NMR (DMSO-d6) δ 7.85 (dd, 2H, J=0.011), 7.70 (dd, 2H, J=0.011), 5.97 (bs, 1H), 4.94 (dd, 1H, J=0.024). 3.31 (m, 1H), 3.28 (m, 1H), 2.71 (m, 1H), 2.17 (m, 1H), 2.04 (m, 1H), 1.91 (m, 1H), 1.71 (m, 1H), 1.69 (m, 1H).

2-[(3S)-2,7-Dioxoazepan-3-yl]isoindoline-1,3-dione (Compound 1)

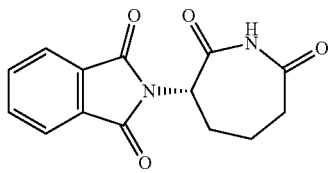 [SMILES: O=C1CCC[C@H](N2C(=O)c3ccccc3C2=O)C(=O)N1]

The title compound was afforded using the methods described above. The crude product was purified by silica gel column chromatography (hexanes/EA, 4:1) to afford the title compound as a white solid (0.068 g, 65% yield). MS (M+1) 273. $_1$H NMR (DMSO-d6) δ 10.82 (s, 1H), 7.93 (m, 2H), 7.90 (m, 2H), 5.23 (dd, 1H), 3.12 (m, 2H), 2.67 (m, 1H), 2.53 (m, 1H), 2.12 (m, 1H), 1.98 (m, 1H), 1.95 (m, 1H).

5-Amino-2-[(3S)-2,7-dioxoazepan-3-yl]isoindoline-1,3-dione (Compound 2)

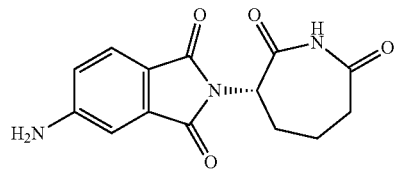 [SMILES: Nc1ccc2c(c1)C(=O)N([C@H]1CCCC(=O)NC1=O)C2=O]

The title compound was afforded as a yellow solid (0.009 g, 33% yield) using the methods described above. MS (M+1) 288.

4-Nitro-2-[(3S)-2-oxoazepan-3-yl]isoindolin-1-one (Compound 3)

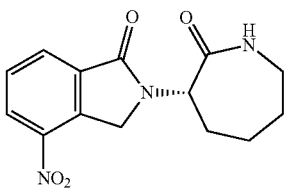

The title compound was afforded as an off-white solid (326 g, 56% yield) using the methods described above. MS (M+Na) 312. $^1$H NMR (DMSO-d6) δ 8.45 (d, 1H, J=0.016), 8.15 (d, 1H, J=0.015), 7.88 (bs, 1H), 7.82 (dd, 1H, J=0.016), 5.12 (d, 1H, J=0.038), 4.96 (d, 1H, J=0.023), 4.92 (d, 1H, J=0.038), 3.26 (m, 2H), 3.12 (m, 1H), 2.02 (m, 2H), 1.92 (m, 1H), 1.84 (m, 1H), 1.73 (m, 1H), 1.31 (m, 1H).

4-Amino-2-[(3S)-2-oxoazepan-3-yl]isoindolin-1-one (Compound 4)

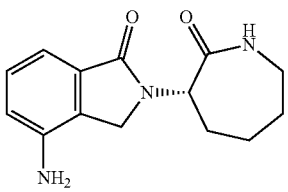 [SMILES: O=C1NCCCC[C@@H]1N1Cc2c(cccc2[N+](=O)[O-])C1=O]

The title compound was afforded as a pale yellow solid (0.013 g, 73% yield) using the methods described above. MS (M+1) 260. $^1$H NMR (DMSO-d6) δ 7.78 (bs, 1H), 7.14 (dd, 1H, J=0.016), 6.86 (d, 1H, J=0.015), 6.75 (d, 1H, J=0.015), 5.39 (bs, 2H), 4.88 (d, 1H, J=0.021), 4.50 (d, 1H, J=0.034), 4.20 (d, 1H, J=0.034), 3.23 (m, 1H), 3.12 (m, 1H), 1.99 (m, 2H), 1.83 (m, 1H), 1.77 (m, 1H), 1.31 (m, 1H).

4-Nitro-2-[(3S)-2-oxoazepan-3-yl]isoindoline-1,3-dione (Compound 5)

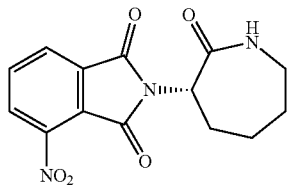 [SMILES: O=C1NCCCC[C@@H]1N1C(=O)c2cccc([N+](=O)[O-])c2C1=O]

The title compound was afforded as a pale yellow solid (0.460 g, 49% yield) using the methods described above. MS (M+Na) 326. $^1$H NMR (DMSO-d6) δ 8.32 (d, 1H, J=0.16), 8.31 (d, 1H, J=0.016), 8.19 (dd, 1H, J=0.015), 7.95 (bs, 1H), 4.86 (dd, 1H, J=0.023), 3.23 (m, 1H), 3.12 (m, 1H), 2.36 (m, 1H), 2.03 (m, 1H), 1.81 (m, 1H), 1.66 (m, 1H), 1.34 (m, 1H).

5-Amino-2-[(3S)-2-oxoazepan-3-yl]isoindolin-1-one (Compound 7)

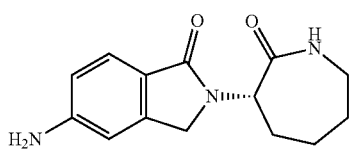 [SMILES: Nc1ccc2c(c1)CN([C@H]1CCCCNC1=O)C2=O]

The title compound was afforded as a light beige solid (0.065 g, 87% yield) using the methods described above. MS (M+1) 260.

4-Amino-2-[(3S)-2-oxoazepan-3-yl]isoindoline-1,3-dione (Compound 8)

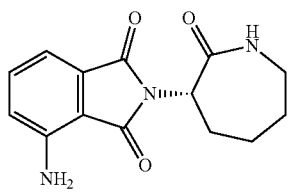

The title compound was afforded as a yellow solid (0.037 g, 61% yield) using the methods described above. MS (M+Na) 296.

2-[(3S)-2,7-Dioxoazepan-3-yl]-4-nitro-isoindoline-1,3-dione (Compound 9)

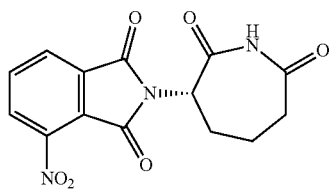

The title compound was afforded using the methods described above. The crude product was obtained, then purified by silica gel column chromatography (DCM/MeOH, 10:1) to afford the title compound as a white solid (0.025 g, 28% yield). MS (M+Na) 341.

4-Amino-2-[(3S)-2,7-dioxoazepan-3-yl]isoindoline-1,3-dione (Compound 10)

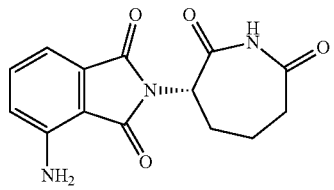 [SMILES: Nc1cccc2c1C(=O)N([C@H]1CCCC(=O)NC1=O)C2=O]

The title compound was afforded as a light yellow solid (0.018 g, 94% yield) using the methods described above. MS (M+Na) 310.

2-(2-Oxoazepan-3-yl)isoindolin-1-one (Compound 11)

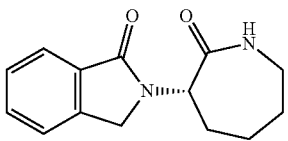 [SMILES: O=C1NCCCC[C@@H]1N1Cc2ccccc2C1=O]

The title compound was afforded as a white solid (0.143 g, 25% yield) using the methods described above. MS (M+Na) 245. $^1$H NMR (DMSO-d6) δ 7.80 (bs, 1H), 7.69 (d, 1H, J=0.15), 7.60 (d, 2H, J=0.008), 7.49 (dd, 1H, J=0.015, 0.008).

4-Nitro-2-[(3R)-2-oxoazepan-3-yl]isoindoline-1,3-dione (Compound 17)

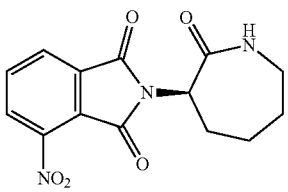 [SMILES: Nc1cccc2c1C(=O)N([C@@H]1CCCCNC1=O)C2=O]

The title compound was afforded as an off-white solid (0.286 g, 54% yield) using the methods described herein. MS (M+Na) 326.

2-[(3R)-2,7-Dioxoazepan-3-yl]-4-nitro-isoindoline-1,3-dione (Compound 18)

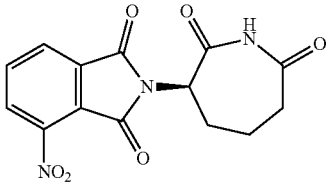 [SMILES: Nc1cccc2c1C(=O)N([C@@H]1CCCC(=O)NC1=O)C2=O]

The title compound was afforded as an off-white solid (0.025 g, 24% yield) using the methods described above. MS (M+Na) 342.

4-Amino-2-[(3R)-2-oxoazepan-3-yl]isoindoline-1,3-dione (Compound 19)

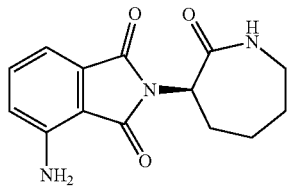

The title compound was afforded as a yellow solid (0.022 g, 96% yield) using the methods described above. MS (M+1) 274.

4-Amino-2-[(3R)-2,7-dioxoazepan-3-yl]isoindoline-1,3-dione (Compound 20)

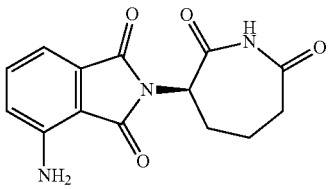

The title compound was afforded as a yellow solid (0.019 g, 91% yield) using the methods described above. MS (M+Na) 310. $^1$H NMR (DMSO-d6) δ 10.76 (bs, 1H), 7.57 (dd, 1H, J=0.014), 7.01 (d, H, J=0.014), 6.99 (d, H, J=0.014), 6.48 (bs, 2H), 5.12 (dd, 1H, J=0.024), 3.10 (m, 1H), 2.68 (m, 1H), 2.53 (m, 1H), 2.07 (m, 1H), 2.05 (m, 1H), 1.98 (m, 1H).

(2S)-2-[(3S)-2,7-Dioxo-3-azepinyl]-2,4-diaza-2H-indene-1,3-dione (Compound 16)

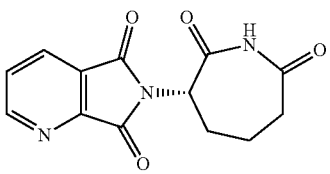 [SMILES: O=C1CCC[C@H](N2C(=O)c3cccnc3C2=O)C(=O)N1]

The title compound was afforded as a white solid (0.229 g, 9% yield) using the methods described above. MS (M+Na) 282.

(2S)-2-[(3S)-2-Oxo-3-azepinyl]-4-methyl-2H-isoindole-1,3-dione (Compound 21)

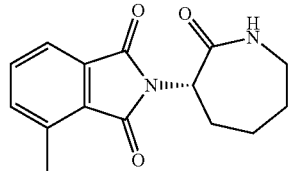 [SMILES: Cc1cccc2c1C(=O)N([C@H]1CCCCNC1=O)C2=O]

The title compound was afforded as an off white solid (0.527 g, 78% yield) using the methods described above. MS (M+1) 273.

(3S)-3-[(2S)-4-Methyl-3-oxo-2H-isoindol-2-oyl]-2,7-azepinedione (Compound 23)

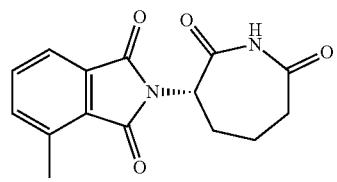 [SMILES: Cc1cccc2c1C(=O)N([C@H]1CCCC(=O)NC1=O)C2=O]

The title compound was afforded as a white solid (0.062 g, 17% yield) using the methods described above. MS (M+Na) 309. $^1$H NMR (DMSO-d6) δ 10.82 (s, 1H), 7.73 (m, 2H), 7.66 (d, 1H), 5.20 (dd, 1H), 3.32 (s, 3H), 3.14 (m, 1H), 2.63 (m, 2H), 2.12 (m, 1H), 1.98 (m, 1H), 1.89 (m, 1H).

(3S)-3-[(2S)-4-Nitro-2-isoindolinoyl]-2,7-azepinedione (Compound 29)

(3S)-3-[(2S)-4-Nitro-2-isoindolinoyl]-2-azepinone (1.81 g, 6.26 mmol) was slurried in fluorobenzene (60 mL) with 200 drops of wet DMSO (prepared by adding 2 drops water to 10 mL DMSO). Dess-martin periodinane (4.00 g, 9.39 mmol) was added and the reaction mixture was stirred at 80° C. for 2.5 hrs. Once cooled to rt, saturated sodium thiosulfate solution (50 mL) was added. After stirring for 5 minutes, the mixture was poured into DCM and washed with a 1:1 mixture of 10% aq. sodium thiosulfate and aq. sodium bicarbonate (saturated solution) then washed with a saturated solution of sodium chloride. The solution was dried over magnesium sulfate, filtered, and concentrated under vacuum. The resulting crude product was purified by silica gel chromatography [EA/hexanes (1:1) to 100% EA]. The unreacted starting material (0.460 g) was recovered and the title compound was isolated as an off white solid (0.650 g, 46% yield). MS (M+Na) 326.2. 1H NMR (DMSO-d6) δ 10.7 (s, 1H), 8.48 (d, 1H, J=0.016), 8.19 (d, 1H, J=0.015), 7.84 (t, 1H), 5.30 (dd, 1H), 4.96 (m, 2H), 3.11 (m, 1H), 2.60 (m, 1H), 2.42 (m, 1H), 2.14 (m, 1H), 2.03 (m, 1H), 1.87 (m, 1H).

(3S)-3-[(2S)-2-Isoindolinoyl]-2,7-azepinedione (Compound 26)

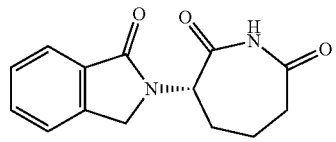 [SMILES: O=C1CCC[C@H](N2Cc3ccccc3C2=O)C(=O)N1]

The title compound was afforded as a white solid (0.015 g, 15% yield) using the methods described above. MS (M+23) 281.3. 1H NMR (DMSO-d6) δ 10.7 (s, 1H), 7.49-7.73 (m, 4H), 5.25 (m, 1H), 4.53 (s, 2H), 3.08 (m, 1H), 2.59 (m, 1H), 2.27 (m, 1H), 2.13 (m, 1H), 2.10 (m, 1H), 1.83 (m, 1H)

(3S)-3-[(2S)-5-Nitro-2-isoindolinoyl]-2,7-azepinedione (Compound 27)

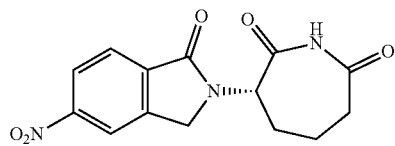

The title compound was afforded as a white solid (0.037 g, 35% yield) using the methods described above. MS (M+23) 326.1. $^1$H NMR (DMSO-d6) δ 10.7 (s, 1H), 7.96-8.54 (m, 3H), 5.25 (m, 1H), 4.66 (s, 2H), 3.10 (m, 1H), 2.55 (m, 1H), 2.27 (m, 1H), 2.13 (m, 1H), 2.10 (m, 1H), 1.83 (m, 1H).

(3S)-3-[(2S)-5-Amino-2-isoindolinoyl]-2,7-azepinedione (Compound 28)

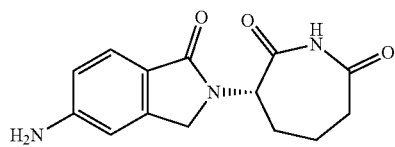 [SMILES: O=C1CCC[C@H](N2Cc3cc([N+](=O)[O-])ccc3C2=O)C(=O)N1]

The title compound was afforded as an off white solid (0.007 g, 50% yield) using the methods described above. MS (M+23) 296.2. $^1$H NMR (DMSO-d6) δ 10.6 (s, 1H), 7.34 (d, 1H), 6.63 (m, 2H), 5.79 (m, 2H), 5.10 (m, 1H), 4.33 (m, 2H), 3.10 (m, 1H), 2.55 (m, 1H), 2.27 (m, 1H), 2.13 (m, 1H), 2.10 (m, 1H), 1.83 (m, 1H).

(3S)-3-[(2S)-4-Amino-2-isoindolinoyl]-2,7-azepinedione (Compound 30)

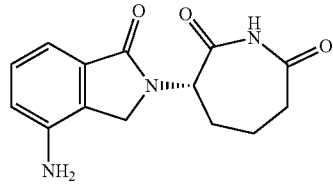 [SMILES: Nc1cccc2c1CN([C@H]1CCCC(=O)NC1=O)C2=O]

The title compound was afforded as an off white solid (0.100 g, 83% yield) using the methods described above. MS (M+23) 296.2. $^1$H NMR (DMSO-d6) δ 10.69 (s, 1H), 7.17 (m, 1H), 6.90 (m, 2H), 6.80 (m, 2H), 5.42 (s, 2H), 5.22 (m, 1H), 4.32 (m, 2H), 3.10 (m, 1H), 2.55 (m, 1H), 2.27 (m, 1H), 2.13 (m, 1H), 2.10 (m, 1H), 1.83 (m, 1H).

(3S)-3-[(2S)-4-Methyl-2-isoindolinoyl]-2,7-azepinedione (Compound 31)

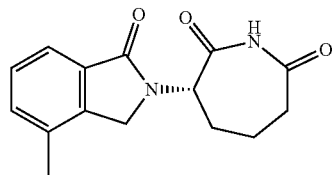 [SMILES: Cc1cccc2c1CN([C@H]1CCCC(=O)NC1=O)C2=O]

The title compound was afforded as a white solid (0.044 g, 15% yield) using the methods described above. MS (M+23) 295.2. $^1$H NMR (DMSO-d6) δ 10.7 (s, 1H), 7.55 (m, 1H), 7.42 (m, 2H), 5.25 (m, 1H), 4.48 (s, 2H), 3.08 (m, 1H), 2.61 (m, 1H), 2.34 (s, 3H), 2.27 (m, 1H), 2.13 (m, 1H), 2.03 (m, 1H), 1.85 (m, 1H).

(3S)-3-[(2S)-4-Methyl-2-isoindolinoyl]-2-azepinone (Compound 32)

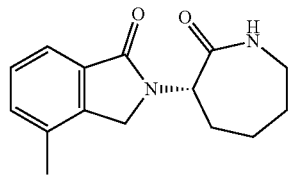 [SMILES: Cc1cccc2c1CN([C@H]1CCCCNC1=O)C2=O]

The title compound was afforded as an off white solid (0.368 g, 30% yield) using the methods described above. MS (M+23) 281.4. $^1$H NMR (DMSO-d6) δ 7.80 (t, 1H), 7.51 (m, 1H), 7.39 (m, 2H), 4.92 (d, 1H), 4.50 (q, 2H), 3.23 (m, 1H), 3.08 (m, 1H), 2.33 (s, 3H), 2.00 (m, 2H), 1.85 (m, 2H), 1.75 (m, 1H), 1.30 (m, 1H).

(3S)-3-[(2S)-4-Chloro-2-isoindolinoyl]-2,7-azepinedione (Compound 33)

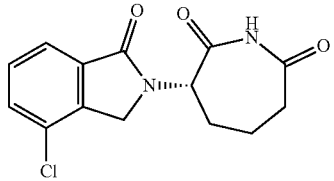 [SMILES: O=C1CCC[C@H](N2Cc3c(Cl)cccc3C2=O)C(=O)N1]

The title compound was afforded as a white solid (0.020 g, 12% yield) using the methods described above. MS (M+23) 315.6. $^1$H NMR (DMSO-d6) δ 10.7 (s, 1H), 7.74 (m, 2H), 7.57 (t, 1H), 5.27 (m, 1H), 4.53 (d, 2H), 3.08 (m, 1H), 2.60 (m, 1H), 2.35 (m, 1H), 2.14 (m, 1H), 2.03 (m, 1H), 1.84 (m, 1H).

(3S)-3-[(2S)-4-Methoxy-2-isoindolinoyl]-2,7-azepinedione (Compound 34)

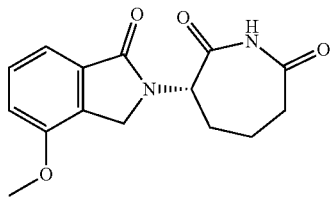 [SMILES: COc1cccc2c1CN([C@H]1CCCC(=O)NC1=O)C2=O]

The title compound was afforded as an off white solid (0.030 g, 18% yield) using the methods described above. MS (M+1) 289.2. $^1$H NMR (DMSO-d6) δ 10.7 (s, 1H), 7.49 (t, 1H), 7.31 (d, 1H), 7.24 (d, 1H), 5.22 (m, 1H), 4.43 (s, 2H), 3.88 (s, 3H), 3.07 (m, 1H), 2.61 (m, 1H), 2.31 (m, 1H), 2.13 (m, 1H), 2.03 (m, 1H), 1.85 (m, 1H).

(3S)-3-[(2S)-5-Methyl-2-isoindolinoyl]-2,7-azepinedione (Compound 35)

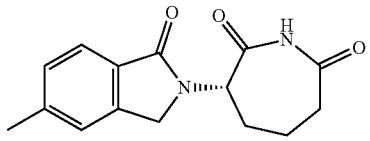 [SMILES: Cc1ccc2c(c1)CN([C@H]1CCCC(=O)NC1=O)C2=O]

The title compound was afforded as an off white solid (0.051 g, 21% yield) using the methods described above. MS (M+1) 295.2. $^1$H NMR (DMSO-d6) δ 10.68 (s, 1H), 7.60 (d, 2H, J=0.015), 7.42 (s, 1H), 7.32 (d, 1H, J=0.014), 5.20 (m, 1H), 4.48 (m, 2H), 3.07 (m, 1H), 2.56 (m, 1H), 2.49 (s, 3H), 2.27 (m, 1H), 2.10 (m, 1H), 2.02 (m, 1H), 1.82 (m, 1H)

(3S)-3-[(2S)-7-Methyl-2-isoindolinoyl]-2,7-azepinedione (Compound 36)

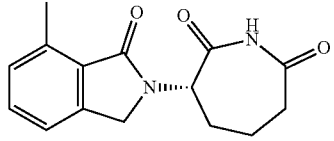 [SMILES: Cc1cccc2c1C(=O)N([C@H]1CCCC(=O)NC1=O)C2]

The title compound was afforded as an off white solid (0.025 g, 12% yield) using the methods described above. MS (M+1) 295.3. $^1$H NMR (DMSO-d6) δ 10.7 (s, 1H), 7.48 (t, 1H), 7.41 (d, 1H), 7.25 (d, 1H), 5.20 (m, 1H), 4.47 (q, 2H), 3.06 (m, 1H), 2.61 (s, 3H), 2.57 (m, 1H), 2.24 (m, 1H), 1.98-2.09 (m, 2H), 1.82 (m, 1H).

(3S)-3-[(2S)-4-Nitro-2-isoindolinoyl]-2-azepinone (Compound 3)

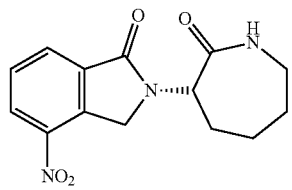

Methyl 2-(bromomethyl)-3-nitrobenzoate (2.00 g, 7.299 mmol) was dissolved in dimethylformamide (15 mL) followed by the addition of (S)-alpha-amino-omega-caprolactam (0.937 g, 7.299 mmol). TEA (1.47 g, 14.6 mmol) was added and the reaction was heated at 50° C. for 18 hrs. The volatiles were then evaporated under vacuum and water (120 mL) was added. After stirring at 0° C. for 30 minutes, the resulting solid was filtered, washed with water and dried providing the title compound as an off-white solid (1.88 grams, 89% yield). MS (M+Na) 312.

(3S)-3-[(2S)-4-Nitro-2-isoindolinoyl]-2,7-azepinedione (Compound 29)

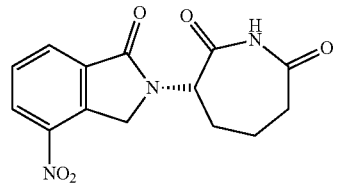

(3S)-3-[(2S)-4-Nitro-2-isoindolinoyl]-2-azepinone (1.81 g, 6.26 mmol) was slurried in fluorobenzene (60 mL) with 200 drops of DMSO. Dess-martin periodinane (4.00 g, 9.39 mmol) was added and the reaction mixture was stirred at 80° C. for 2.5 hrs. Once cooled to rt, saturated sodium thiosulfate solution (50 mL) was added. After stirring for 5 minutes, the mixture was poured into DCM and washed with a 1:1 mixture of 10% aq. sodium thiosulfate and aq. sodium bicarbonate, then washed with brine. The solution was dried, filtered, and concentrated. The resulting crude product was purified by silica gel chromatography [EA/hexanes (1:1) to 100% EA]. The title compound was isolated as a tan solid (0.650 g, 46% yield). MS (M+Na) 326.2. $^1$H NMR (DMSO-d6) δ 10.7 (s, 1H), 8.48 (d, 1H, J=0.016), 8.19 (d, 1H, J=0.015), 7.84 (t, 1H), 5.30 (dd, 1H), 4.96 (m, 2H), 3.11 (m, 1H), 2.60 (m, 1H), 2.42 (m, 1H), 2.14 (m, 1H), 2.03 (m, 1H), 1.87 (m, 1H).

(3S)-3-[(2S)-4-(2-Chloroacetylamino)-2-isoindolinoyl]-2,7-azepinedione

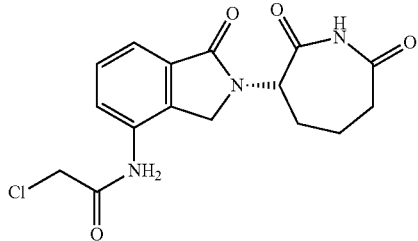

(3S)-3-[(2S)-4-Amino-2-isoindolinoyl]-2,7-azepinedione (50 mg, 0.183 mmol) was stirred in tetrahydrofuran (4 mL) and trimethylamine (25 mg, 0.247 mmol). Chloroacetylchloride (31 mg, 0.274 mmol) was added and the reaction mixture was stirred at 60° C. for 18 hrs. The solvent was evaporated and the residue was purified by silica gel chromatography [EA/hexanes (1:1) to 100% EA] to afford the title compound as a white solid (0.025 grams, 37% yield). MS (M+Na) 372.7.

5-[(2-Chlorotoluidino)carbonyl]-2-[2-methyl-6-(4-{2-[3-(tert-butoxycarbonylamino)propoxy]ethyl}-1-piperazinyl)-4-pyrimidinylamino]-1,3-thiazole

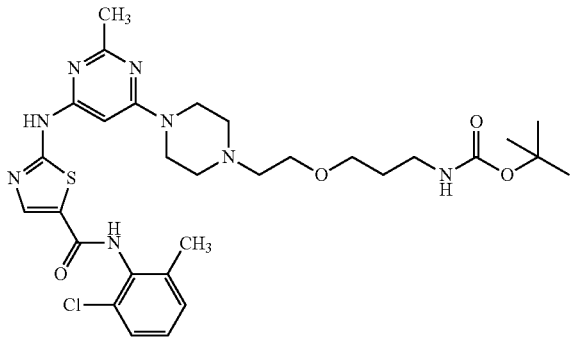 [SMILES: Cc1nc(Nc2ncc(C(=O)Nc3c(C)cccc3Cl)s2)cc(N2CCN(CCOCCCNC(=O)OC(C)(C)C)CC2)n1]

To a solution of Dasatinib (0.70 g, 1.44 mmol) in dimethylformamide (15 mL) was added potassium carbonate (1.55 g, 11.4 mmol). A solution of 3-bromopropylamino 2,2-dimethylpropionate (0.608 g, 2.52 mmol) in dimethylformamide (3 mL) was added and the mixture was stirred overnight. The solvent was then removed under vacuum and the resulting oil was dissolved in DCM. The solution was then washed with saturated sodium bicarbonate, followed by 0.1 N hydrochloride solution, and brine. The organic solution was then dried, filtered, and concentrated under vacuum. The resulting oil was purified by silica gel chromatography (5-10% MeOH in DCM) to afford the title compound as an off-white solid (0.601 g, 65% yield). MS (M+1) 645.

(3S)-3-[(2S)-4-[2-(3-{2-[4-(6-{5-[(2-Chlorotoluidino)carbonyl]-1,3-thiazol-2-ylamino}-2-methyl-4-pyrimidinyl)-1-piperazinyl]ethoxy}propylamino)acetylamino]-2-isoindolinoyl]-2,7-azepinedione

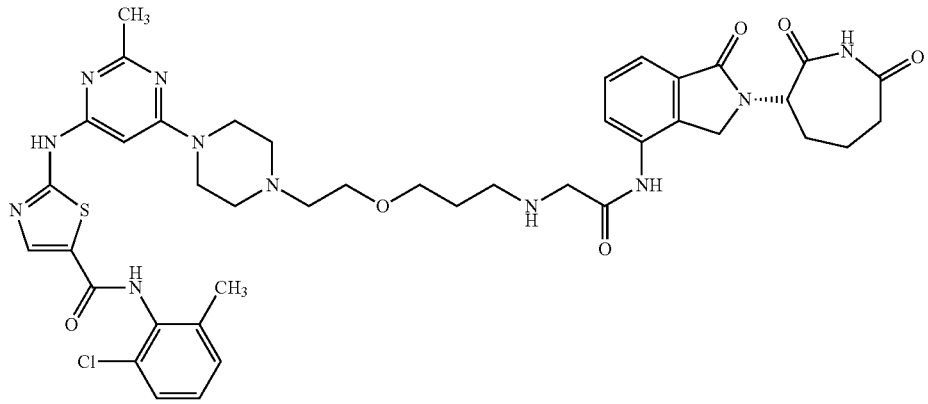

5-[(2-Chlorotoluidino)carbonyl]-2-[2-methyl-6-(4-{2-[3-(tert-butoxycarbonylamino)propoxy]ethyl}-1-piperazinyl)-4-pyrimidinylamino]-1,3-thiazole (0.125 g, 0.194 mmol) was stirred in a solution of TFA (2 mL) and DCM (2 mL) for 2 hrs. The volatiles were removed under vacuum to afford [2-(6-{4-[2-(3-aminopropoxy)ethyl]-1-piperazinyl}-2-methyl-4-pyrimidinylamino)-1,3-thiazol-5-yl](2-chlorotoluidino)formaldehyde as the TFA salt. (3S)-3-[(2S)-4-(2-Chloroacetylamino)-2-isoindolinoyl]-2,7-azepinedione (0.025 g, 0.072 mmol) was dissolved in dimethylformamide (1.5 mL) followed by the addition of [2-(6-{4-[2-(3-aminopropoxy)ethyl]-1-piperazinyl}-2-methyl-4-pyrimidinylamino)-1,3-thiazol-5-yl](2-chlorotoluidino)formaldehyde TFA salt (0.047 g, 0.072 mmol) and potassium carbonate (0.043 g, 0.316 mmol). The reaction mixture was stirred at 70° C. for 4 hrs. The solvent was evaporated under vacuum and the crude residue was triturated with EA and hexanes. The resulting solid was filtered and dried to afford the title compound as a yellow solid (0.030 g, 49% yield). MS (M+1) 860.2. $^1$H NMR (DMSO-d6) δ 9.89 (m, 2H), 8.27 (s, 1H), 7.88 (m, 1H), 7.62 (m, 3H), 7.46 (m, 2H), 7.26 (m, 3H), 6.08 (m, 1H), 4.72 (m, 2H), 4.42 (m, 3H), 4.12 (m, 3H), 3.91 (m, 1H), 3.63 (m, 2H), 3.52 (s, 3H), 3.16 (m, 2H), 2.43 (m, 8H), 2.42 (m, 1H), 2.12 (m, 4H), 1.97 (m, 2H), 1.87 (m, 2H), 1.43 (m, 2H).

(S)-3-(1-Oxo-4-(trifluoromethyl)isodolindoln-2-yl)azepane-2,7-dione (Compound 37)

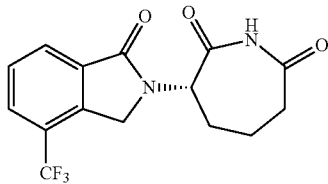 [SMILES: O=C1CCC[C@H](N2Cc3c(cccc3C(F)(F)F)C2=O)C(=O)N1]

To a solution of methyl 2-methyl-3-(trifluoromethyl)benzoate (0.985 grams, 4.52 mmol) in CCl$_4$ (50 mL) at rt was added NBS (0.884 grams, 7.3 mmol) and AIBN) (350 mg, 2.13 mmol). The suspension was stirred at 80° C. for 3 hrs. The reaction was cooled to rt and filtered. The filtrate was concentrated under vacuum to afford methyl 2-(bromomethyl)-3-(trifluoromethyl)benzoate (1.17 g, 86% yield) as a yellow oil. The oil (0.463 g, 1.55 mmol) was dissolved in DMF (3 mL) at rt and Et$_3$N (472 mg, 4.67 mmol) and (S)-3-aminoazepan-2-one (218 mg, 1.70 mmol) were added. The mixture was stirred at 60° C. for 3 hrs, cooled to rt and concentrated under vacuum to afford the crude product, which was triturated with EA and hexanes to afford (S)-2-(2-oxoazepan-3-yl)-4-(trifluoromethyl)isoindolin-1-one (323 mg, 66% yield) as a white solid. MS (ESI) m/z 313.2 [M+H]$^+$.

(S)-2-(2-oxoazepan-3-yl)-4-(trifluoromethyl)isoindolin-1-one (315 mg, 1.00 mmol) was dissolved in fluorobenzene/DMSO (6 mL/0.6 mL) at rt and Dess-Martin reagent (899 mg, 2.12 mmol) was added. The mixture was stirred at 80° C. for 16 hrs, cooled to rt, and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated providing the crude product, which was purified by silica gel to afford the title compound (82 mg, 24% yield) as a white solid. MS (ESI) m/z 327.3 [M+H]$^+$. $^1$H NMR (400 MHz, DMSO-d6) δ 10.7 (s, 1 H), 8.05 (d, 2 H), 7.77 (m, 1H), 5.29 (m, 1H), 4.71 (s, 2 H), 3.08 (m, 1H), 2.59 (m, 1H), 2.38 (m, 1H), 2.319-2.26 (s, 1H), 2.15-2.01 (m, 2 H), 1.84 (m, 1H).

(S)-3-(4-Ethyl-1-oxoisoindolin-2-yl)azepane-2,7-dione (Compound 38)

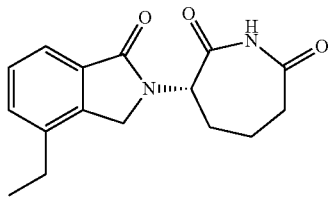 [SMILES: CCc1cccc2c1CN([C@H]1CCCC(=O)NC1=O)C2=O]

To a solution of methyl 3-bromo-2-(bromomethyl)benzoate (2.5 g, 8.11 mmol) in DMF (16 mL) at rt was added TEA (2.8 grams, 27.7 mmol) and (S)-3-aminoazepan-2-one HCl (1.34 grams, 8.16 mmol). The mixture was stirred at 70° C. for 4 hrs. The reaction was cooled to rt and the resulting solid was filtered from the DMF. The solid was washed with EA and hexanes then water. The white solid was then dried providing (S)-4-bromo-2-(2-oxoazepan-3-yl)isoindolin-1-one (2.08 grams, 80% yield). MS (ESI) m/z 324.2 [M+H]$^+$.

(S)-4-bromo-2-(2-oxoazepan-3-yl)isoindolin-1-one (0.600 grams, 1.85 mmol) was taken up in toluene (8 mL) and water (1.8 mL). Ethyl boronic acid (0.275 grams, 2 eq.) was added followed by the addition of [1,1'-bis(diphenylphosphino)ferrocene]dichloropalladium(II), complex with DCM (0.230 grams, 0.15 eq.) and potassium carbonate (0.770 grams, 5.57 mmol). The reaction mixture was heated at 95° C. for 3 hrs. The reaction was filtered through celite then worked up with EA and water. Purified on silica gel providing (S)-4-ethyl-2-(2-oxoazepan-3-yl)isoindolin-1-one (0.230 grams, 45% yield) as a tan solid. MS (ESI) m/z 273.3 [M+H]$^+$.

To a solution of (S)-4-ethyl-2-(2-oxoazepan-3-yl)isoindolin-1-one (225 mg, 0.827 mmol) in fluorobenzene/DMSO (6 mL/0.6 mL) at rt was added Dess-Martin reagent (736 mg, 1.73 mmol). The mixture was stirred at 80° C. for 16 hrs. The reaction mixture was cooled to rt and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated providing the crude product, which was purified by silica gel to afford the title compound (20 mg, 8% yield) as a white solid. MS (ESI) m/z 287.3 [M+H]$^+$. $^1$H NMR (400 MHz, DMSO-d6) δ 10.7 (s, 1 H), 7.55 (d, 1 H), 7.45 (m, 2 H), 5.26 (m, 1H), 4.52 (s, 2 H), 3.08 (m, 1H), 2.66 (q, 2H), 2.34 (m, 1H), 2.15-2.01 (m, 2 H), 1.83 (m, 1H), 1.23 (t, 3H).

(S)-3-(4-Cyclopropyl-1-oxoisoindolin-2-yl)azepane-2,7-dione (Compound 39)

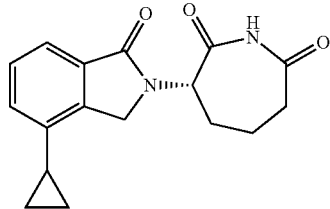 [SMILES: O=C1CCC[C@H](N2Cc3c(cccc3C3CC3)C2=O)C(=O)N1]

(S)-4-bromo-2-(2-oxoazepan-3-yl)isoindolin-1-one (0.900 grams, 2.78 mmol) was taken up in toluene (12 mL) and water (3 mL). Cyclopropyl boronic acid (0.480 grams, 2 eq.) was added followed by of [1,1'-bis(diphenylphosphino)ferrocene]dichloropalladium(II), complex with DCM (0.345 grams, 0.15 eq.) and K$_2$CO$_3$ (1.15 grams, 8.32 mmol). The reaction mixture was heated at 95° C. for 3 hrs, filtered through celite, and extracted with EA and water. Purification on silica gel afforded (S)-4-cyclopropyl-2-(2-oxoazepan-3-yl)isoindolin-1-one (0.567 grams, 72% yield) as a tan solid. MS (ESI) m/z 285.3 [M+H]$^+$.

To a solution of (S)-4-cyclopropyl-2-(2-oxoazepan-3-yl)isoindolin-1-one (290 mg, 1.02 mmol) in fluorobenzene/DMSO (8 mL/0.8 mL) at rt was added Dess-Martin reagent (910 mg, 2.14 mmol). The mixture was stirred at 80° C. for 16 hrs, cooled to rt and 10 mL of a saturated sodium thiosulfate solution was added followed by stirring for 5 min. The resulting mixture was extracted with DCM (30 mL×2) and the combined solution was washed with 10% aq.

sodium thiosulfate/aq. sodium bicarbonate (1:1 mixture) (50 mL) and brine (50 mL). The organic layer was dried over sodium sulfate, filtered and concentrated providing the crude product, which was purified by silica gel to afford the title compound (30 mg, 10% yield) as a white solid. $^1$H NMR (400 MHz, DMSO-d6) δ 10.7 (s, 1 H), 7.5 (m, 2 H), 7.15 (s, 1 H), 5.30 (m, 1H), 4.60 (s, 2 H), 3.08 (m, 1H), 2.60 (m, 1H), 2.34 (m, 1H), 2.15-1.80 (m, 4 H), 1.01 (m, 2H), 0.77 (m, 2H). MS (ESI) m/z 299.3 [M+H]$^+$.

(S)-3-(4-bromo-1-oxoisoindolin-2-yl)azepane-2,7-dione (Compound 40)

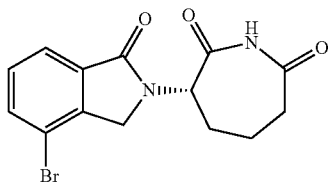 [SMILES: O=C1CCC[C@H](N2Cc3c(Br)cccc3C2=O)C(=O)N1]

To a solution of (S)-4-bromo-2-(2-oxoazepan-3-yl)isoindolin-1-one (300 mg, 0.93 mmol) in fluorobenzene/DMSO (8 mL/0.8 mL) at rt was added Dess-Martin reagent (830 mg, 1.93 mmol). The mixture was stirred at 80° C. for 16 hrs. The reaction mixture was cooled to rt and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated providing the crude product, which was purified by silica gel to afford the title compound (56 mg, 18% yield) as a white solid. MS (ESI) m/z 338.1 [M+H]+. 1H NMR (400 MHz, DMSO-d6) δ 10.7 (s, 1 H), 7.86 (d, 1 H), 7.75 (d, 1 H), 7.49 (t, 1H), 5.27 (m, 1H), 4.46 (d, 2 H), 3.08 (m, 1H), 2.59 (m, 1H), 2.36 (m, 1H), 2.15-1.79 (m, 3 H).

(S)-3-(4-Hydroxy-1-oxoisoindolin-2-yl)azepane-2,7-dione (Compound 41)

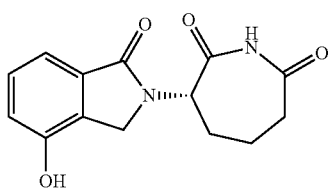

To a solution of (S)-3-(4-methoxy-1-oxoisoindolin-2-yl)azepane-2,7-dione (288 mg, 1.00 mmol) in DCM (10 mL) at 0° C. was added 5 mL of borontribromide (1 M in DCM). The reaction mixture was stirred at rt overnight. The reaction was quenched with saturated sodium bicarbonate then extracted with EA. After the organic layer was concentrated, the crude product was purified on silica gel to afford the title compound (48 mg, 18% yield) as a white solid. MS (ESI) m/z 275.3 [M+H]$^+$. $^1$H NMR (400 MHz, DMSO-d6) δ 10.2 (s, 1 H), 7.30 (d, 1 H), 7.19 (d, 1 H), 7.02 (m, 1H), 5.23 (m, 1H), 4.39 (d, 2 H), 3.05 (m, 1H), 2.59-1.82 (m, 5 H).

(S)-3-(4-(Difluoromethyl)-1-oxoisoindolin-2-yl)azepane-2,7-dione (Compound 42)

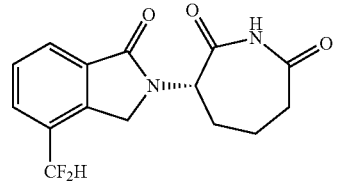 [SMILES: O=C1CCC[C@H](N2Cc3c(cccc3C(F)F)C2=O)C(=O)N1]

To a solution of 3-iodo-2-methylbenzoic acid (2.0 g, 3.82 mmol) in dry MeOH (10 mL) at 0° C. was added thionyl chloride (681 mg, 5.72 mmol). Then the reaction was heated to 80° C. for 16 hrs. TLC showed the starting material was consumed and one main spot was present. The reaction was cooled to rt and the solvent was removed. The residue was diluted with water (20 mL) and extracted with EA (40 mL) twice. The combined organic layers were washed with saturated sodium bicarbonate aqueous (30 mL), brine, dried over sodium sulfate, filtered and concentrated providing crude product, which was purified by column chromatography on silica-gel elution with petroleum ether:EA (from 0% to 8%) providing methyl 3-iodo-2-methylbenzoate (1.7 g, 80.4% yield) as a colorless oil. MS (ESI) m/z 277.0 [M+H]$^+$. $^1$H NMR (400 MHz, CDCl$_3$) δ 7.97 (dd, J=1.2, 8.0 Hz, 1 H), 7.73 (dd, J=0.8, 8.0 Hz, 1 H), 6.92 (t, J=8.0 Hz, 1 H), 3.89 (s, 3 H), 2.66 (s, 3 H).

To a solution of methyl 3-iodo-2-methylbenzoate (15 g, 54.35 mmol) in N,N-dimethylacetamide (200 mL) at rt was added K$_4$[Fe(CN)$_6$].3H$_2$O (5.74 g, 13.59 mmol) and sodium carbonate (5.76 g, 54.35 mmol), followed by palladium acetate (1.5 g) added. The suspension was evacuated and replaced with nitrogen, then heated to 120° C. for 10 hrs. The reaction mixture was cooled to rt, filtered, and the filtrate was diluted with water (100 mL), and extracted with EA (200 mL) twice. The combined organic layers were washed with water, brine, dried over sodium sulfate, filtered and concentrated providing the crude product, which was purified by column chromatography on silica-gel elution with petroleum ether:EA (from 50/1 to 30/1) providing methyl 3-cyano-2-methylbenzoate (4.6 g, 48.4% yield) as a white solid. MS (ESI) m/z 175.9 [M+H]$^+$. $^1$H NMR (400 MHz, CDCl$_3$) δ 8.08 (d, J=7.6 Hz, 1 H), 7.76 (d, J=8.0 Hz, 1 H), 7.36 (t, J=7.6 Hz, 1 H), 3.93 (s, 3 H), 2.80 (s, 3 H).

To a solution of methyl 3-cyano-2-methylbenzoate (1.0 g, 5.71 mmol) in water/Pyridine/AcOH (6 mL/12 mL/6 mL) at 0° C. was added NaH$_2$PO$_2$.2H$_2$O (3.74 g, 45.7 mmol) and Raney Ni (300 mg). The resulting suspension was stirred at rt for 16 hrs, filtered, and the filtrate was concentrated. The residue was diluted with water (20 mL) and extracted with EA (40 mL) twice. The combined organic layers were washed with 1N HCl (20 mL), brine, dried over sodium sulfate, filtered and concentrated providing methyl 3-formyl-2-methylbenzoate (760 mg, 75.24% yield) as a white solid. MS (ESI) m/z 179.1 [M+H]$^+$.

To a solution of methyl 3-formyl-2-methylbenzoate (660 mg, 3.7 mmol) in dry DCM (15 mL) at 0° C. was added diethylaminosulfur trifluoride (DAST) (2.98 g, 18.5 mmol), the resulting solution was stirred at rt for 16 hrs, then water (20 mL) was added and the suspension was separated. The organic layer was washed with saturated sodium bicarbonate aqueous, brine, dried over sodium sulfate, filtered and concentrated providing methyl 3-(difluoromethyl)-2-methylbenzoate (700 mg, 94.6% yield) as a yellow oil.

To a solution of methyl 3-(difluoromethyl)-2-methylbenzoate (700 mg, 3.5 mmol) in Tetrachloromethane (20 mL) was added NBS (685 mg, 3.85 mmol). The suspension was heated to 85° C. for 5 minutes and AIBN (180 mg, 1.05 mmol) was added. The mixture was refluxed for 4 hrs, the solvent was removed, and the residue was purified by silica-gel chromatography with petroleum ether/EA (from 0% to 3%) providing a mixture of methyl 2-(bromomethyl)-3-(difluoromethyl)benzoate and methyl 3-(difluoromethyl)-2-methylbenzoate (682 mg). $^1$H NMR showed the ratio was 2:1. It was used directly for the next step without further purification. 1H NMR (400 MHz, CDCl$_3$) δ 8.03 (d, J=7.6 Hz, 1H), 7.78 (d, J=7.6 Hz, 1H), 7.48 (t, J=8.0 Hz, 1 H), 7.06 (t, J=54.8 Hz, 1H), 5.07 (s, 2H), 3.96 (s, 3 H).

To a solution of methyl 2-(bromomethyl)-3-(difluoromethyl)benzoate (682 mg, 1.59 mmol) in DMF (5 mL) at rt was added (S)-3-aminoazepan-2-one (203 mg, 1.586 mmol) and TEA (321 mg, 3.172 mmol), and the mixture was heated to 50° C. for 16 hrs. The reaction was cooled to rt and the solvent was removed. The residue was diluted with water (5 mL) and stirred at 0° C. for 30 min. The resulting solid was filtered off and washed with water (5 mL). The solid was dried in vacuum providing (S)-4-(difluoromethyl)-2-(2-oxoazepan-3-yl)isoindolin-1-one (350 mg, 81.4% yield) as a yellow solid. $^1$H NMR (400 MHz, CDCl$_3$) δ 7.97 (d, J=7.2 Hz, 1H), 7.61 (d, J=7.2 Hz, 1H), 7.54 (t, J=7.2 Hz, 1 H), 6.77 (t, J=56.0 Hz, 1H), 5.98 (s, 1H), 5.21 (dd, J=3.2, 10.4 Hz, 1H), 4.84 (dd, J=17.6, 206.8 Hz, 2H), 3.51-3.42 (m, 1H), 3.31-3.25 (m, 1H), 2.177-2.12 (m, 1H), 2.05-1.90 (m, 3H), 1.87-1.80 (m, 1H), 1.54-1.47 (m, 1H).

(S)-4-(Difluoromethyl)-2-(2-oxoazepan-3-yl)isoindolin-1-one (350 mg, 1.19 mmol) was slurried in fluorobenzene (12 mL) with 2 mL DMSO and 1 drop of water. Dess-Martin reagent (1.06 g, 2.49 mmol) was added, the reaction mixture was stirred at 80° C. for 16 hrs, and then cooled to rt and 5 mL of a saturated sodium thiosulfate solution was added followed by stirring for 5 min. The resulting mixture was extracted with DCM (15 mL×2) and the combined solution was washed with 10% aq. sodium thiosulfate/aq. sodium bicarbonate (1:1 mixture) (20 mL) and brine. The organic layer was dried over sodium sulfate, filtered and concentrated to afford the crude product, which was purified by preparative TLC (EA) providing the title compound (50 mg, 19.1% yield) as a white solid. MS (ESI) m/z 308.9 [M+H]$^+$. $^1$H NMR (400 MHz, DMSO-d$_6$) δ 10.74 (s, 1H), 7.91 (d, J=7.6 Hz, 1H), 7.82 (d, J=7.6 Hz, 1H), 7.68 (t, J=8.0 Hz, 1 H), 7.27 (t, J=55.2 Hz, 1H), 5.27 (dd, J=4.8, 12.0 Hz, 1H), 4.67 (s, 2H), 3.13-3.04 (m, 1H), 2.60-2.58 (m, 1H), 2.38-2.29 (m, 1H), 2.18-2.09 (m, 1H), 2.06-1.99 (m, 1H), 1.88-1.79 (m, 1H).

(S)-3-(1-Oxo-4-(prop-1-en-2-yl)isoindolin-2-yl)azepane-2,7-dione (Compound 43)

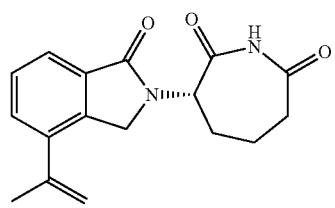 [SMILES: C=C(C)c1cccc2c1CN([C@H]1CCCC(=O)NC1=O)C2=O]

(S)-4-Bromo-2-(2-oxoazepan-3-yl)isoindolin-1-one (1.00 grams, 3.09 mmol) was taken up in toluene (12 mL) and water (3 mL). Isopropenyl boronic acid (1.10 grams, 2 eq.) was added followed by [1,1'-bis(diphenylphosphino)ferrocene]dichloropalladium(II), complex with DCM (0.380 grams, 0.15 eq.) and K$_2$CO$_3$ (1.30 grams, 9.41 mmol). The reaction was heated at 95° C. for 16 hrs, filtered through celite then worked up with EA and water, followed by purification on silica gel providing (S)-2-(2-oxoazepan-3-yl)-4-(prop-1-en-2-yl)isoindolin-1-one (0.532 grams, 60% yield) as a tan solid. MS (ESI) m/z 285.3 [M+H]$^+$.

To a solution of (S)-2-(2-oxoazepan-3-yl)-4-(prop-1-en-2-yl)isoindolin-1-one (250 mg, 0.880 mmol) in fluorobenzene/DMSO (8 mL/0.8 mL) at rt was added Dess-Martin reagent (784 mg, 1.85 mmol). The mixture was stirred at 80° C. for 16 hrs, cooled to rt and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated to afford the crude product, which was purified by silica gel to afford the title compound (22 mg, 10% yield) as a white solid. MS (ESI) m/z 299.3 [M+H]$^+$. $^1$H NMR (400 MHz, DMSO-d6) δ 10.6 (s, 1 H), 7.53-7.65 (m, 3 H), 5.34 (s, 1H), 5.25 (m, 2H), 4.61 (s, 2 H), 3.07 (m, 1H), 2.61 (m, 1H), 2.39 (m, 1H), 2.15-1.82 (m, 6 H).

(S)-3-(4-Isopropyl-1-oxoisoindolin-2-yl)azepane-2,7-dione (Compound 45)

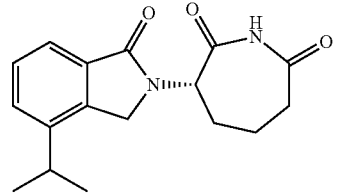 [SMILES: CC(C)c1cccc2c1CN([C@H]1CCCC(=O)NC1=O)C2=O]

To a solution of (S)-2-(2-oxoazepan-3-yl)-4-(prop-1-en-2-yl)isoindolin-1-one (1.10 grams, 3.85 mmol) in MeOH (25 mL) was added a catalytic amount of palladium on carbon and the reaction was stirred for 18 hrs under H$_2$(g). The reaction was filtered through celite and the solvent evaporated providing (S)-4-isopropyl-2-(2-oxoazepan-3-yl)isoindolin-1-one (1.09 grams, 93% yield) as a white solid. MS (ESI) m/z 287.3 [M+H]$^+$.

To a solution of (S)-4-isopropyl-2-(2-oxoazepan-3-yl)isoindolin-1-one (350 mg, 1.22 mmol) in ACN (16 mL) was added 21 drops of wet DMSO. N$_2$(g) was bubbled in for 2 min. followed by the addition of Dess-Martin reagent (1.09 grams, 2.57 mmol). The mixture was stirred at 80° C. for 16 hrs, cooled to rt, and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated to afford the crude product, which was purified on silica gel to afford the title compound (184 mg, yield: 50% yield) as a white solid. MS (ESI) m/z 301.3 [M+H]$^+$. $^1$H NMR (400 MHz, DMSO-d6) δ 10.6 (s, 1 H), 7.53-7.55 (m, 3 H), 5.20 (m, 1H), 4.52 (s, 2 H), 3.08 (m, 1H), 3.01 (m, 1H), 2.60 (m, 1H), 2.34 (m, 1H), 2.14-1.81 (m, 3H), 1.22 (d, 6H).

(S)-3-(4-Fluoro-1-oxoisoindolin-2-yl)azepane-2,7-dione (Compound 46)

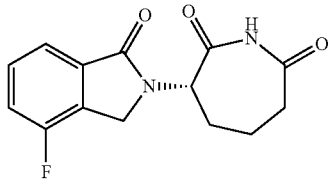 [SMILES: O=C1CCC[C@H](N2Cc3c(F)cccc3C2=O)C(=O)N1]

To a solution of methyl 3-fluoro-2-methylbenzoate (2.07 grams, 12.3 mmol) in $CCl_4$ (75 mL) at rt was added N-bromosuccinimide (NBS) (2.30 grams, 12.9 mmol) and AIBN (700 mg, 4.23 mmol). The suspension was stirred at 80° C. for 4 hrs, cooled to rt, and filtered. The filtrate was concentrated under vacuum to afford methyl 2-(bromomethyl)-3-fluorobenzoate (2.94 grams, 97% yield) as a yellow oil.

To a solution of methyl 2-(bromomethyl)-3-fluorobenzoate (1.00 g, 4.04 mmol) in DMF (8 mL) at rt was added TEA (1.47 g, 14.5 mmol) and (S)-3-aminoazepan-2-one HCl salt (663 mg, 4.04 mmol). The mixture was stirred at 70° C. for 3 hrs, cooled to rt and concentrated under vacuum to afford the crude product, which was extracted with DCM and purified on silica gel to afford (S)-4-fluoro-2-(2-oxoazepan-3-yl)isoindolin-1-one (558 mg, yield: 53% yield) as a white solid. MS (ESI) m/z 263.3 [M+H]$^+$.

To a solution of (S)-4-fluoro-2-(2-oxoazepan-3-yl)isoindolin-1-one (280 mg, 1.07 mmol) in ACN (12 mL) was added 20 drops of wet DMSO. $N_2$(g) was bubbled in for 2 min. followed by the addition of Dess-Martin reagent (0.952 grams, 2.24 mmol). The mixture was stirred at 80° C. for 16 hrs, cooled to rt, and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated to afford the crude product, which was purified by silica gel to afford the title compound (107 mg, 37% yield) as a white solid. MS (ESI) m/z 277.3 [M+H]$^+$.

(S)-3-(5-Fluoro-4-methyl-1-oxoisoindolin-2-yl)azepane-2,7-dione (Compound 47)

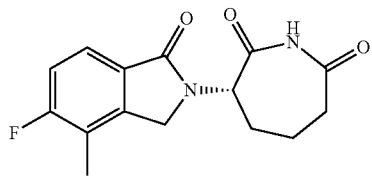

To a solution of 2, 2, 6, 6-tetramethylpiperidine (7.09 g, 50.22 mmol) in THF (100 mL) at −20° C. was added n-butyl lithium (31.4 mL, 50.22 mmol), and the reaction was cooled to −50° C. 3-bromo-4-fluorobenzoic acid (5.0 g, 22.8 mmol) was added in THF (20 mL). The resulting solution was stirred at −50° C. for 1 hr, iodomethane (12.9 g, 91.2 mmol) was added in THF (20 mL), and the reaction mixture was warmed to 15° C. over 30 minutes. The reaction was quenched with water (10 mL), adjusted to pH=3 with 1N HCl, and extracted with EA (100 mL) twice. The combined organic layers were dried over sodium sulfate, filtered and concentrated providing the crude 3-bromo-4-fluoro-2-methylbenzoic acid (5.2 g) which was used directly for the next step without further purification.

To a solution of 3-bromo-4-fluoro-2-methylbenzoic acid (5.2 g, 22.32 mmol) in dry MeOH (100 mL) at 0° C. was added thionyl chloride (5.31 g, 44.64 mmol) and the resulting solution was refluxed for 2 hrs. The solvent was removed under vacuum and the residue was purified by column chromatography on silica-gel with EA/petroleum ether from 0% to 2% providing crude methyl 3-bromo-4-fluoro-2-methylbenzoate (3.86 g) as a yellow oil.

To a solution of methyl 3-bromo-4-fluoro-2-methylbenzoate (3.86 g, 15.69 mmol) in Tetrachloromethane (150 mL) was added NBS (3.35 g, 18.83 mmol). The suspension was heated to 85° C. for 5 min and AIBN (1.35 g, 7.85 mmol) was added. The mixture was refluxed for 4 hrs, then the solvent was removed and the residue was purified by column chromatography on silica-gel with EA/petroleum ether (from 0% to 3% yield) providing methyl 3-bromo-2-(bromomethyl)-4-fluorobenzoate (1.83 g, 36% yield) as a colorless oil. $^1$H NMR (300 MHz, CDCl$_3$) δ 8.05 (dd, J=2.1, 6.1 Hz, 1H), 7.80 (dd, J=5.4, 8.7 Hz, 1H), 5.18 (s, 2 H), 3.96 (s, 3H).

To a solution of methyl 3-bromo-2-(bromomethyl)-4-fluorobenzoate (1.83 g, 5.65 mmol) in DMF (40 mL) at rt was added (S)-3-aminoazepan-2-one (723 mg, 5.65 mmol) and TEA (1.14 g, 11.3 mmol). The mixture was heated to 50° C. for 16 hrs, cooled to rt, and the solvent was removed. The residue was diluted with water (30 mL) and extracted with EA (50 mL) twice. The combined organic layers were dried over sodium sulfate, filtered and concentrated providing crude product, which was triturated with EA providing (S)-4-bromo-5-fluoro-2-(2-oxoazepan-3-yl)isoindolin-1-one (785 mg, 40.9% yield) as a light yellow solid. MS (ESI) m/z 341.0 [M+H]$^+$. $^1$H NMR (400 MHz, DMSO-d$_6$) δ 7.86-7.84 (m, 1H), 7.77-7.74 (dd, J=4.0, 8.0 Hz, 1H), 7.50 (t, J=8.0 Hz, 1H), 4.90 (d, J=11.2 Hz, 1H), 4.60 (dd, J=17.6, 84.0 Hz, 2H), 3.28-3.22 (m, 1H), 3.14-3.11 (m, 1 H), 2.04-1.98 (m, 2H), 1.89-1.71 (m, 3H), 1.30-1.23 (m, 1H).

To a solution of (S)-4-bromo-5-fluoro-2-(2-oxoazepan-3-yl)isoindolin-1-one (400 mg, 1.18 mmol) in dioxane/water (30 mL/3 mL) at rt was added 2,4,6-trimethyl-1,3,5,2,4,6-trioxatriborinane (738 mg, 5.88 mmol) and potassium phosphate (751 mg, 3.54 mmol). The suspension was bubbled with $N_2$(g) for 2 minutes, then Pd(dppf)Cl$_2$ (173 mg, 0.236 mmol) was added and the mixture was heated to 100° C. for 16 hrs. The reaction was cooled to rt and the solvent was removed. The residue was diluted with water (10 mL) and extracted with EA (20 mL) twice. The combined organic layers were dried over sodium sulfate, filtered and concentrated providing crude product, which was purified by silica gel column chromatography with EA/petroleum ether from 40% to 100% providing (S)-5-fluoro-4-methyl-2-(2-oxoazepan-3-yl)isoindolin-1-one (281 mg, 86.3% yield) as a light yellow solid. MS (ESI) m/z 277.1 [M+H]$^+$. $^1$H NMR (400 MHz, DMSO-d$_6$) δ 7.81 (m, 1H), 7.55 (dd, J=4.8, 8.4 Hz, 1H), 7.27 (t, J=8.4 Hz, 1H), 4.88 (dd, J=4.4, 12.0 Hz, 1H), 4.55 (dd, J=17.6, 74.0 Hz, 2H), 3.29-3.24 (m, 1H), 3.14-3.07 (m, 1 H), 2.40 (s, 3H), 2.00-1.97 (m, 2H), 1.87-1.73 (m, 3H), 1.29-1.26 (m, 1H).

(S)-5-Fluoro-4-methyl-2-(2-oxoazepan-3-yl)isoindolin-1-one (310 mg, 1.12 mmol) was slurried in fluorobenzene (30 mL) with 5 mL DMSO and 1 drop of water. Dess-martin reagent (2.38 g, 5.62 mmol) was added and the reaction was stirred at 80° C. for 16 hrs. The reaction was cooled to rt and 15 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (20 mL) and brine. The organic layer was dried over sodium sulfate, filtered and concentrated to afford the crude product, which was purified by preparative HPLC, using a 5 micron C18 column and 0.1% TFA in water and 0.1% TFA in acetonitrile with a gradient of 95% to 5% aqueous TFA, providing the title compound (40.6 mg, 12.5% yield) as a white solid. MS (ESI) m/z 291.0 [M+H]+. 1H NMR (400 MHz, DMSO-d6) δ 7.59 (dd, J=5.2, 8.8 Hz, 1H), 7.30 (t, J=8.8 Hz, 1H), 5.24 (dd, J=5.2, 12.4 Hz, 1H), 4.51 (s, 2H), 3.12-3.04 (m, 1H), 2.61-2.55 (m, 1H), 2.33-2.25 (m, 1H), 2.13-2.00 (m, 2H), 1.85-1.80 (m, 1H).

(3S)-3-[(2S)-4-sec-Butyl-2-isoindolinoyl]-2,7 azepenedione (Compound 48)

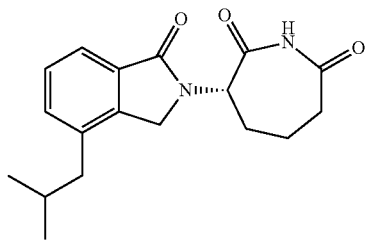 [SMILES: CC(C)Cc1cccc2c1CN([C@H]1CCCC(=O)NC1=O)C2=O]

The title compound was afforded as an off white solid (0.012 g, 15% yield) using the methods described above for Compound 47. MS (M+1), 315. 1H NMR (DMSO-d6) 10.7 (m, 1H), 7.6 (m, 1H), 7.5 (m, 1H), 5.2 (m, 1H), 4.5 (m, 2H), 3.0 (m, 1H), 2.5 (m, 5H), 2.3 (m, 1H), 2.1 (m, 1H), 2.0 (m, 1H) 1,9 (m, 1H), 1.8 (m, 1H), 0.9 (m, 6H).

(S)-3-(4-(Dimethylamino)-1-oxoisoindolin-2-yl) azepane-2,7-dione (Compound 49)

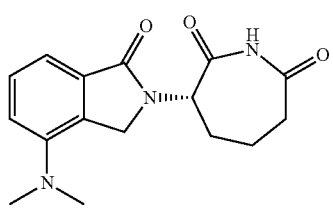 [SMILES: CN(C)c1cccc2c1CN([C@H]1CCCC(=O)NC1=O)C2=O]

To a solution of (S)-3-(4-amino-1-oxoisoindolin-2-yl) azepane-2,7-dione (0.20 g, 0.73 mmol) in DMF (5 mL) at rt was added iodomethane (0.260 g, 1.83 mmol). The mixture was stirred at rt for 16 h, was washed with water, and extracted with EA (15 mL×2) and the combined organic solution was washed brine (50 mL). The organic layer was dried over magnesium sulfate, filtered and the solvent removed under vacuum to afford the crude product, which was purified by re-crystallization in EA to afford the title compound (0.020 g, 9% yield) as an off white solid. MS (ESI) m/z 302.3 [M+H]+. 1H NMR (400 MHz, DMSO-d6) δ 10.7 (s, 1 H), 7.3 (m, 1 H), 7.00 (m, 1 H), 6.7 (m, 1H), 5.7 (m, 1H), 5.3 (m, 1H), 4.3 (m, 1H), 3.1 (m, 1 H), 2.9 (s, 3H), 2.7 (s, 3H), 2.6 (m, 1H), 2.319-2.26 (s, 2H), 2.15-2.01 (m, 1 H), 1.84 (m, 1H).

(S)-(2-(2,7-Dioxoazepan-3-yl)-1-oxoisoindolin-4-yl) methanaminium 2,2,2-trifluoroacetate (Compound 50)

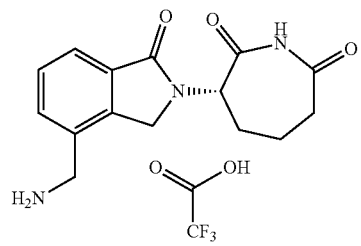

To a solution of methyl 3-iodo-2-methylbenzoate (2.0 g, 7.25 mmol) in CCl4 (50 mL) at rt was added N-bromosuccinimide (NBS) (1.42 g, 7.97 mmol). The reaction was heated to 85° C. for 5 minutes and AIBN (623 mg, 3.63 mmol) was added. The reaction was stirred at 85° C. for 16 hrs. cooled to rt, and the solid was filtered off. The filtrate was concentrated providing the crude product, which was purified by silica gel column chromatography with EA/petroleum ether from 0% to 3% providing methyl 2-(bromomethyl)-3-iodobenzoate (1.22 g, 47.5% yield) as a yellow oil. 1H NMR (400 MHz, CDCl3) δ 8.04 (dd, J=1.6, 8.0 Hz, 1H), 7.89 (dd, J=1.6, 8.0 Hz, 1H), 7.04 (t, J=8.0 Hz, 1H), 5.12 (s, 2H), 3.95 (s, 3H).

To a solution of methyl 2-(bromomethyl)-3-iodobenzoate (1.22 g, 3.45 mmol) in DMF (40 mL) at rt was added (S)-3-aminoazepan-2-one (442 mg, 3.45 mmol). Then TEA (697 mg, 6.9 mmol) was added, and the mixture was heated to 60° C. for 16 hrs. The reaction was cooled to rt and the solvent was removed. The residue was diluted with water (100 mL). The suspension was stirred at rt for 20 minutes. The solid was filtered off and the solid was triturated with EA providing (S)-4-iodo-2-(2-oxoazepan-3-yl)isoindolin-1-one (979 mg, 77.8% yield) as a white solid. MS (ESI) m/z 371.0[M+H]+.

To a solution of (S)-4-iodo-2-(2-oxoazepan-3-yl)isoindolin-1-one (1.7 g, 4.59 mmol) in N,N-dimethylacetamide (70 mL) at rt was added K4[Fe(CN)6].3H2O (1.94 g, 4.59 mmol). The suspension was bubbled with N2(g) for 2 min Pd(dppf)Cl2 (335 mg, 0459 mmol) was added. The reaction was heated at 90° C. for 18 hrs, cooled to rt, and filtered. The filtrate was diluted with water (40 mL), and extracted with EA (50 mL) twice. The combined organic layers were dried over sodium sulfate, filtered and concentrated providing the crude product. It was purified by silica-gel column chromatography with EA/petroleum ether from 40% to 100% providing (S)-1-oxo-2-(2-oxoazepan-3-yl)isoindoline-4-carbonitrile (481 mg, 39.1% yield) as a yellow solid. MS (ESI) m/z 270.1 [M+H]+. 1H NMR (400 MHz, DMSO-d6) δ 8.11 (dd, J=0.8, 7.6 Hz, 1H), 8.04 (dd, J=0.4, 7.6 Hz), 7.88-7.86 (m, 1H), 7.71 (t, J=7.6 Hz, 1H), 4.94-4.91 (m, 1H), 4.85-4.71 (m, 2H), 3.27-3.23 (m, 1H), 3.14-3.08 (m, 1H), 2.03-1.98 (m, 2H), 1.91-1.71 (m, 3H), 1.31-1.23 (m, 1H).

To a solution of (S)-1-oxo-2-(2-oxoazepan-3-yl)isoindoline-4-carbonitrile (430 mg, 1.59 mmol) in fluorobenzene/

DMSO (30 mL/5 mL) at 0° C. was added Dess-Martin reagent (1.69 g, 3.99 mmol). The suspension was heated at 85° C. for 18 hrs, cooled to rt, and additional Dess-Martin reagent (1.69 g, 3.99 mmol) was added and the suspension was heated at 85° C. for 18 hrs. The reaction was cooled to rt, filtered, and the filtrate was added to 30 mL of saturated aqueous sodium thiosulfate. The suspension was stirred at rt for 30 min and extracted with DCM (50 mL) twice. The combined organic layers were washed with 1/1 10% of sodium thiosulfate aqueous/saturated sodium bicarbonate aqueous (30 mL×2), dried over sodium sulfate, filtered and concentrated to afford the crude product, which was purified by silica-gel column chromatography eluting with EA/petroleum ether from 30% to 75% providing (S)-2-(2,7-dioxoazepan-3-yl)-1-oxoisoindoline-4-carbonitrile (252 mg, 56% yield) as a white solid. MS (ESI) m/z 305.9 [M+Na]$^+$. $^1$H NMR (400 MHz, DMSO-d$_6$) δ 10.75 (s, 1H), 8.14 (dd, J=0.8, 7.6 Hz, 1H), 8.07 (dd, J=0.4, 7.6 Hz), 7.74 (t, J=7.6 Hz, 1H), 5.28 (m, 1H), 4.80-4.68 (m, 2H), 3.13-3.05 (m, 1H), 2.60-2.54 (m, 1H), 2.39-2.36 (m, 1H), 2.14-2.11 (m, 1H), 2.04-2.00 (m, 1H), 1.86-1.82 (m, 1H).

To a solution of (S)-2-(2,7-dioxoazepan-3-yl)-1-oxoisoindoline-4-carbonitrile (80 mg, 0.283 mmol) in THF (10 mL) at rt was added Raney Ni (40 mg), the suspension was stirred under H$_2$(g) (1 atm) for 2 hrs. Di-tert-butyl dicarbonate (Boc$_2$O) (73.9 mg, 0.339 mmol) was added, the suspension was stirred for 2 hrs, filtered, and the filtrate was concentrated providing the crude product. Further purification by silica gel chromatography with EA/petroleum ether from 30% to 75% providing (S)-tert-butyl ((2-(2,7-dioxoazepan-3-yl)-1-oxoisoindolin-4-yl)methyl)carbamate (40 mg, 36.6% yield) as a white solid. MS (ESI) m/z 388.2 [M+H]$^+$.

To a solution of (S)-tert-butyl ((2-(2,7-dioxoazepan-3-yl)-1-oxoisoindolin-4-yl)methyl)carbamate (40 mg, 0.103 mmol) in DCM (4 mL) at 0° C. was added TFA (1 mL). The reaction was stirred at rt for 30 min, the solvent was removed, and the residue was diluted with water (3 mL) and extracted with DCM (5 mL). The aqueous phase was lyophilized providing the title compound (18.5 mg, 62.5% yield) as a white solid. MS (ESI) m/z 288.0 [M+H]$^+$. $^1$H NMR (400 MHz, DMSO-d$_6$) δ 10.76 (s, 1 H), 8.27 (s, 3H), 7.74-7.72 (m, 2H), 7.63-7.59 (m, 1H), 5.31-5.27 (m, 1H), 4.67 (s, 2H), 4.14 (s, 2H), 3.14-3.07 (m, 1H), 2.61-2.57 (m, 1H), 2.33-2.27 (m, 1H), 2.13-2.03 (m, 2H), 1.86-1.79 (m, 1H).

(R)-3-(4-Methyl-1-oxoisoindolin-2-yl)azepane-2,7-dione (Compound 51)

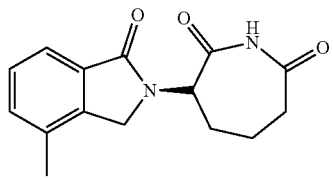

To a solution of methyl 2,3dimethyl benzoate (0.5 g, 3.05 mmol) in carbon tetrachloride (25 mL) at rt was added NBS (0.569 g, 3.2 mmol) and AIBN (0.05 mL of 12% in acetone). The mixture was stirred at 80° C. for 16 hrs, cooled to rt, and filtered. The solvent was removed under vacuum to afford clear oil of 3-bromo-2-(bromomethyl)benzoate, which was taken to the next step without further purification (0.738 g, 98% yield). MS (ESI) m/z 244.2 [M+H]$^+$.

To a solution of methyl 3-bromo-2-(bromomethyl)benzoate (0.730 g, 3.05 mmol) in DMF (10 mL) at rt was added TEA (0.618 g, 6.1 mmol) and (R)-3-aminoazepan-2-one HCl (0.502 g, 3.05 mmol). The mixture was stirred at 60° C. for 16 hrs, cooled to rt, and water was added to the reaction mixture, the product was extracted with EA (20 mL) twice, then washed with brine (50 mL), and dried with magnesium sulfate. The solvent was removed under vacuum, and the crude material was purified through silica gel using 10% MeOH in DCM. The fractions containing product were combined and the solvent removed under vacuum to afford (R)-4-methyl-2-(2-oxoazepan-3-yl)isoindolin-1-one (0.33 g, yield: 42% yield). MS (ESI) m/z 259.3 [M+H]$^+$.

To a solution of (R)-4-methyl-2-(2-oxoazepan-3-yl)isoindolin-1-one (0.130 g, 0.500 mmol) in ACN/DMSO (6 mL/0.6 mL) at rt was bubbled with N$_2$(g) for five minutes followed by the addition of Dess-Martin reagent (0.448 g, 1.06 mmol). The mixture was stirred at 80° C. for 16 hrs, cooled to rt, and the resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over magnesium sulfate, filtered and concentrated to afford the crude product, which was purified by silica gel to afford the title compound (0.3 g, yield: 22% yield) as a white solid. MS (ESI) m/z 273.2 [M+H]$^+$. $^1$H NMR (400 MHz, CDCl3-d6) δ 7.9 (s, 1 H), 7.7 (m, 1 H), 7.4 (m, 1H), 5.6 (m, 1 H), 4.7 (m, 1H), 4.3 (m, 1H), 3.7 (m, 1H), 3.0 (m, 1H), 2.9 (m, 1 H), 2.4 (m, 1H), 2.2 (m, 1H), 2.1 (m, 1H), 1.6 (s, 3H).

(S)—N-(2-(2,7-Dioxoazepan-3-yl)-1-oxoisoindolin-4-yl)acetamide (Compound 52)

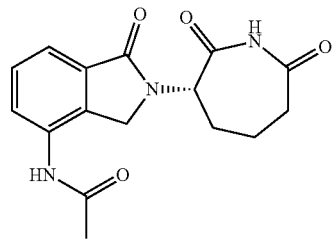 [SMILES: CC(=O)Nc1cccc2c1CN([C@H]1CCCC(=O)NC1=O)C2=O]

To a solution of (S)-3-(4-amino-1-oxoisoindolin-2-yl)azepane-2,7-dione (0.10 g, 0.37 mmol) in DCM (6 mL) at rt was added acetic anhydride (0.410 g, 0.41 mmol). The mixture was stirred at rt for 16 hrs, washed with water, and extracted with EA (15 mL×2) and the combined organic solution was washed brine (50 mL). The organic layer was dried over Magnesium sulfate, filtered and the solvent removed under vacuum to afford the crude product, which was purified by re-crystallization in EA to afford the title compound (0.026 g, yield: 26% yield) as white solid. MS (ESI) m/z 316.3 [M+H]$^+$. $^1$H NMR (400 MHz, DMSO-d6) δ 10.7 (s, 1 H), 7.3 (m, 1 H), 7.00 (m, 1 H), 6.7 (m, 1H), 5.7 (m, 1H), 5.3 (m, 1H), 4.3 (m, 1H), 3.1 (m, 1H), 2.2 (s, 3H), 2.6 (m, 1H), 2.319-2.26 (s, 2H), 2.15-2.01 (m, 1 H), 1.84 (m, 1H).

(S)-3-(1-Oxo-4-propylisoindolin-2-yl)azepane-2,7-dione (Compound 53)

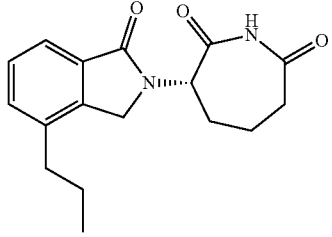 [SMILES: CCCc1cccc2c1CN([C@H]1CCCC(=O)NC1=O)C2=O]

(S)-4-Bromo-2-(2-oxoazepan-3-yl)isoindolin-1-one (1.00 grams, 3.09 mmol) was taken up in toluene (12 mL) and water (3 mL). Isopropyl boronic acid (1.10 grams, 2 eq.) was added followed by the addition of [1,1'-bis(diphenylphosphino) ferrocene]dichloropalladium(II), complex with DCM (0.380 grams, 0.15 eq.) and $K_2CO_3$ (1.30 grams, 9.41 mmol). The reaction mixture was heated at 95° C. for 16 hrs, cooled to rt, filtered through celite, and then extracted with EA and water. Purification on silica gel afforded (S)-2-(2-oxoazepan-3-yl)-4-propylisoindolin-1-one (0.532 grams, 60% yield) as a tan solid (rearrangement occurred providing the straight chain analog). MS (ESI) m/z 287.3 [M+H].

To a solution of (S)-2-(2-oxoazepan-3-yl)-4-propylisoindolin-1-one (300 mg, 1.04 mmol) in ACN (14 mL) was added 18 drops of wet DMSO. $N_2(g)$ was bubbled in for 2 min. followed by the addition of Dess-Martin reagent (0.934 grams, 2.20 mmol). The mixture was stirred at 80° C. for 16 hrs, cooled to rt, and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered and concentrated to afford the crude product, which was purified on silica gel to afford the title compound (207 mg, yield: 66% yield) as a white solid. MS (ESI) m/z 301.3 [M+H]$^+$.

(S)-3-(4-Cyclobutyl-1-oxoisoindolin-2-yl)azepane-2,7-dione (Compound 54)

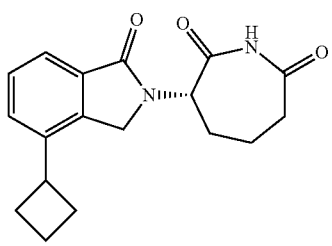 [SMILES: O=C1CCC[C@H](N2Cc3c(cccc3C3CCC3)C2=O)C(=O)N1]

(S)-4-bromo-2-(2-oxoazepan-3-yl)isoindolin-1-one (0.30 g, 0.93 mmol) was taken up in toluene (12 mL) and water (3 mL) and cyclobutyl boronic acid (0.07 g, 1.39 mmol) was added followed by [1,1'-bis(diphenylphosphino)ferrocene] dichloropalladium(II), complex with DCM (0.113 g, 0.14 mmol) and $K_2CO_3$ (0.20 g, 1.86 mmol). The reaction mixture was heated at 100° C. for 16 hrs, filtered through celite, and then worked up with EA and water. Purification on silica gel afforded (S)-2-(2-oxoazepan-3-yl)-4-(cyclobutyl)isoindolin-1-one (0.08 grams, 29% yield) as a tan solid. MS (ESI) m/z 299.2 [M+H]$^+$.

To a solution of (S)-4-cyclobutyl-2-(2-oxoazepan-3-yl) isoindolin-1-one (0.08 g, 0.27 mmol) in ACN/DMSO (5 mL/0.5 mL) at rt was bubbled $N_2(g)$ for five minutes followed by the addition of Dess-Martin reagent (0.285 g, 0.67 mmol). The mixture was stirred at 80° C. for 16 hrs, cooled to rt and 10 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered, and concentrated to afford the crude product, which was purified on silica gel to afford the title compound (10 mg, yield: 11% yield) as a white solid. MS (ESI) m/z 313.3 [M+H]$^+$. $^1$H NMR (400 MHz, DMSO-d6) δ 10.7 (s, 1 H), 7.55-7.65 (m, 2H), 7.45 (m, 1H), 5.25 (m, 1H), 4.51 (m, 2 H), 3.7 (m, 1H), 3.3 (m, 1H), 2.6 (m, 1H), 2.39 (bm, 3H), 2.2-1.82 (m, 5 H), 1.8 (m, 2H).

(3S)-3-(4-(Sec-butyl)-1-oxoisoindolin-2-yl)azepane-2,7-dione (Compound 55)

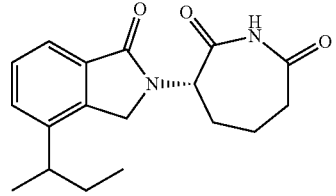 [SMILES: CCC(C)c1cccc2c1CN([C@H]1CCCC(=O)NC1=O)C2=O]

To a solution of methyl 3-bromo-2-methylbenzoate (5.0 g, 21.83 mmol) in $CCl_4$ (50 mL) was added NBS (4.66 g, 26.19 mmol) and the suspension was heated at 80° C. for 5 min. AIBN (1.88 g, 10.92 mmol) was added and the suspension stirred at 80° C. for 16 hrs. The reaction was cooled to rt, filtered, and the filtrate was concentrated providing the crude product, which was purified on silica gel with EA/petroleum ether from 0% to 3% providing methyl 3-bromo-2-(bromomethyl)benzoate (4.94 g, 74.1% yield) as a colorless oil. $^1$H NMR (300 MHz, CDCl$_3$) δ 7.90 (d, J=7.8 Hz, 1H), 7.78 (d, J=7.8 Hz, 1H), 7.24 (t, J=7.8 Hz, 1H), 5.14 (s, 2H), 3.97 (s, 3H).

To a solution of methyl 3-bromo-2-(bromomethyl)benzoate (3.0 g, 9.81 mmol) in DMF (50 mL) at 0° C. was added (S)-3-aminoazepan-2-one (444 mg, 3.47 mmol), followed by TEA (1.98 g, 19.62 mmol). The suspension was stirred at 50° C. for 16 hrs, cooled to rt, and the solvent was removed and the residue was diluted with water (20 mL). The suspension was stirred at rt for 30 min, filtered, and the filter cake was washed with water, dried in vacuum providing (S)-4-bromo-2-(2-oxoazepan-3-yl)isoindolin-1-one (1.93 g, 61.2% yield) as a white solid. MS (ESI) m/z 325.0 [M+H]$^+$. $^1$H NMR (300 MHz, DMSO-d$_6$) δ 7.91-7.82 (m, 2H), 7.73 (d, J=7.2 Hz, 1H), 7.47 (t, J=10.2 Hz, 1H), 4.91 (dd, J=3.3, 14.1 Hz, 1H), 4.50 (q, J=17.4 Hz, 2H), 3.28-3.07 (m, 2H), 2.06-1.71 (m, 5H), 1.30-1.22 (m, 1H).

To a suspension of (S)-4-bromo-2-(2-oxoazepan-3-yl) isoindolin-1-one (700 mg, 2.17 mmol) in toluene/water (50 mL/5 mL) at rt was added (E)-but-2-en-2-ylboronic acid (474 mg, 2.60 mmol), followed by $K_2CO_3$ (749 mg, 5.43 mmol) and Pd(dppf)Cl$_2$ (318 mg, 0.43 mmol). The mixture was heated at 100° C. for 18 hrs, cooled to rt, and the solvent was removed. The residue was purified on silica gel with MeOH/EA from 0% to 6% providing (S,Z)-4-(but-2-en-2-yl)-2-(2-oxoazepan-3-yl)isoindolin-1-one (478 mg, 74.0% yield) as a light yellow solid. MS (ESI) m/z 299.2 [M+H]$^+$.

To a solution of (S,Z)-4-(but-2-en-2-yl)-2-(2-oxoazepan-3-yl)isoindolin-1-one (200 mg, 0.671 mmol) in THF (12 mL) at rt was added Pd/C (200 mg), the suspension was stirred at 25° C. for 48 hrs, diluted with water (10 mL), and extracted with EA (20 mL×2). The suspension was filtered and the filtrate was concentrated providing 4-(sec-butyl)-2-((S)-2-oxoazepan-3-yl)isoindolin-1-one (191 mg, 94.9% yield) as a colorless gum. MS (ESI) m/z 301.2 [M+H]$^+$.

To a solution of 4-(sec-butyl)-2-((S)-2-oxoazepan-3-yl)isoindolin-1-one (191 mg, 0.637 mmol) in fluorobenzene/DMSO (18 mL/3 mL, 1 drop water in DMSO) was added Dess-Martin reagent (675 mg, 1.592 mmol). The suspension was heated at 80° C. for 18 hrs, then added to saturated aqueous sodium thiosulfate (10 mL). The suspension was stirred at 0° C. for 5 min, extracted with DCM (30 mL×2), and the combined organic layers were washed with 10% of sodium thiosulfate aqueous/saturated sodium bicarbonate aqueous (1/1, 20 mL), brine, dried over sodium sulfate, filtered and concentrated providing crude product. Purification on silica gel EA/petroleum ether from 20% to 69% afforded the title compound (84 mg, 42.0% yield) a white solid. MS (ESI) m/z 315.0 [M+H]$^+$. $^1$H NMR (400 MHz, DMSO-d$_6$) δ 10.74 (s, 1H), 7.57-7.46 (m, 3H), 5.25 (dd, J=5.2, 12.4 Hz, 1H), 4.52 (s, 2H), 3.13-3.05 (m, 1H), 2.77-2.74 (m, 1H), 2.57 (d, J=18.0 Hz, 1H), 2.36-2.32 (m, 1H), 2.16-1.99 (m, 2H), 1.84-1.79 (m, 1H), 1.65-1.59 (m, 2H), 1.24 (d, J=6.4 Hz, 3H), 0.80 (t, J=7.2 Hz, 3H).

(S)-3-(5-(Aminomethyl)-1-oxoisoindolin-2-yl)azepane-2,7-dione TFA salt (Compound 56)

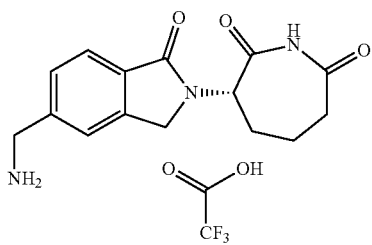

To a solution of methyl 4-cyano-2-methylbenzoate (4.0 g, 22.83 mmol) in CCl$_4$ (150 mL) was added NBS (4.88 g, 27.4 mmol) and the suspension was heated at 80° C. for 5 min. AIBN (1.88 g, 11.42 mmol) was added and the suspension was stirred at 80° C. for 16 hrs, cooled to rt and filtered. The filtrate was concentrated providing the crude product, which was purified on silica gel with EA/petroleum ether from 0% to 5% providing methyl 2-(bromomethyl)-4-cyanobenzoate (3.84 g, 66.9% yield) as a white solid.

To a solution of methyl 2-(bromomethyl)-4-cyanobenzoate (4.28 g, 16.85 mmol) in DMF (80 mL) at rt was added (S)-3-aminoazepan-2-one (2.59 g, 20.22 mmol), followed by TEA (3.40 g, 33.7 mmol). The suspension was stirred at 85° C. for 16 hrs, the solvent was removed and the residue was diluted with water (20 mL). The suspension was stirred at rt for 30 min, filtered, and the filter cake was washed with water, dried in vacuum providing (S)-1-oxo-2-(2-oxoaze-pan-3-yl)isoindoline-5-carbonitrile (2.30 g, 44.2% yield) as a light yellow solid. MS (ESI) m/z 270.1 [M+H]$^+$.

To a solution of (S)-1-oxo-2-(2-oxoazepan-3-yl)isoindoline-5-carbonitrile (500 mg, 1.86 mmol) in fluorobenzene/DMSO (30 mL/5 mL, 1 drop water in DMSO) was added Dess-Martin reagent (1.97 g, 4.65 mmol). The suspension was heated at 80° C. for 18 hrs, then added to saturated aqueous sodium thiosulfate (20 mL). The suspension was stirred at 0° C. for 5 min, extracted with DCM (40 mL×2), and the combined organic layers were washed with 10% of sodium thiosulfate aqueous/saturated sodium bicarbonate aqueous (1/1, 50 mL), brine, dried over sodium sulfate, filtered and concentrated providing crude product. It was triturated with EA (246 mg) as a white solid. The filtrate was concentrated and purified on silica gel with EA/petroleum ether from 20% to 96% providing (S)-2-(2,7-dioxoazepan-3-yl)-1-oxoisoindoline-5-carbonitrile (49 mg, totally 56.0% yield) a white solid. MS (ESI) m/z 284.1 [M+H]$^+$.

To a solution of (S)-2-(2,7-dioxoazepan-3-yl)-1-oxoisoindoline-5-carbonitrile (1.1 g, 3.92 mmol) in THF (70 mL) at rt was added Raney Ni (300 mg), followed by di-tert-butyl dicarbonate (Boc$_2$O) (1.03 g, 4.71 mmol). The suspension was stirred at 25° C. under H$_2$(g) (1 atm) for 14 hrs. The suspension was filtered, the filter cake was washed with EA (10 mL), and the combined filtrate was concentrated providing the crude product. Purification on silica gel with MeOH/DCM from 0% to 4% afforded (S)-tert-butyl ((2-(2,7-dioxoazepan-3-yl)-1-oxoisoindolin-5-yl)methyl)carbamate (870 mg, 57.2% yield) a white solid. MS (ESI) m/z 388.2 [M+H]$^+$.

To a solution of (S)-tert-butyl ((2-(2,7-dioxoazepan-3-yl)-1-oxoisoindolin-5-yl)methyl)carbamate (100 mg, 0.258 mmol) in DCM (10 mL) was added TFA (1.5 mL) at 0° C. and the solution was stirred at rt for 2 hrs. The solvent was removed and the residue was diluted with water (2 mL) and extracted with DCM (3 mL). The aqueous layer was lyophilized providing the title compound (100 mg, TFA salt) as a white solid. MS (ESI) m/z 288.0 [M+H]$^+$. $^1$H NMR (400 MHz, DMSO-d$_6$) δ 10.74 (s, 1H), 8.35 (s, 1H), 7.79 (d, J=7.6 Hz, 1H), 7.70 (s, 1H), 7.59 (d, J=7.6 Hz, 1H), 5.25 (dd, J=5.2, 12.4 Hz, 1H), 4.55 (s, 2H), 4.18 (d, J=5.2 Hz, 2H), 3.14-3.05 (m, 1H), 2.58 (d, J=16.4 Hz, 1H), 2.33-2.26 (m, 1H), 2.15-1.99 (m, 2H), 1.85-1.79 (m, 1H).

(S)-3-(6-Fluoro-4-methyl-1-oxoisoindolin-2-yl)azepane-2,7-dione (Compound 57)

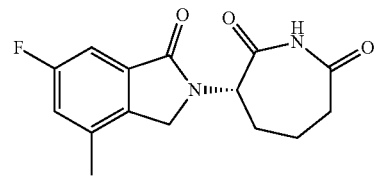 [SMILES: Cc1cc(F)cc2c1CN([C@H]1CCCC(=O)NC1=O)C2=O]

To a solution of 5-fluoro-2-methylbenzoic acid (3.0 g, 19.5 mmol) in sulfuric acid (30 mL) at 0° C. was added NBS (3.4 g, 19.5 mmol) portion wise. The mixture was stirred at 0° C. for 3 hrs, warmed to rt, and stirred for 16 hrs. The mixture was then poured slowly into ice water and extracted with EA (60 mL×3), washed with brine (80 mL), dried by sodium sulfate, filtrated and evaporated providing the crude 3-bromo-5-fluoro-2-methylbenzoic acid (4.2 g crude) as a yellow solid, which was used for next step without further purification.

To a solution of 3-bromo-5-fluoro-2-methylbenzoic acid (4.2 g crude) in MeOH (16 mL) at rt was added thionyl chloride (2.5 mL). The reaction mixture was stirred at 70° C. for 3 hrs, cooled to rt and the solvent was removed under vacuum to afford crude product, which was purified on silica gel with petroleum ether/EA=50/1 to afford methyl 3-bromo-5-fluoro-2-methylbenzoate (2.3 g, yield: 51% yield) as a yellow oil.

To a solution of methyl 3-bromo-5-fluoro-2-methylbenzoate (2.0 g, 8.13 mmol) in CCl$_4$ (20 mL) at rt was added NBS (2.2 g, 12.19 mmol) and AIBN (533 mg, 3.25 mmol). The suspension was stirred at 90° C. for 16 hrs, cooled to rt, and filtered. The filtrate was concentrated under vacuum to afford the crude product, which was purified on silica gel with petroleum ether/EA=50/1 to afford methyl 3-bromo-2-(bromomethyl)-5-fluorobenzoate (2.5 g yield: 96%) as a yellow oil.

To a solution of methyl 3-bromo-2-(bromomethyl)-5-fluorobenzoate (1.0 g, 3.08 mmol) in DMF (14 mL) at rt was added TEA (622 mg, 6.16 mmol) and (S)-3-aminoazepan-2-one (474 mg, 3.70 mmol) (in 2 mL DMF). The mixture was stirred at 50° C. for 4 hrs, cooled to rt, and filtered. The filtrate was concentrated under vacuum to afford the crude product, which was purified on silica gel with petroleum ether/EA=5/1 to 1/3 to afford (S)-4-bromo-6-fluoro-2-(2-oxoazepan-3-yl)isoindolin-1-one (430 mg, yield: 34% yield) as a white solid. MS (ESI) m/z 341.0 [M+H]$^+$.

To a solution of (S)-4-bromo-6-fluoro-2-(2-oxoazepan-3-yl)isoindolin-1-one (200 mg, 0.58 mmol) in dioxane/water (15 mL/1.5 mL) at rt was added methylboronic acid (369 mg, 2.94 mmol), potassium phosphate (374 mg, 1.76 mmol) and Pd(dppf)Cl$_2$ (86 mg, 0.12 mmol). The suspension was degassed under vacuum and purged with nitrogen twice. The mixture was stirred at 100° C. for 4 hrs, cooled to rt, filtered, and concentrated under vacuum to get the crude product, which was purified on silica gel DCM/MeOH=50/1 to 10/1 providing (S)-6-fluoro-4-methyl-2-(2-oxoazepan-3-yl)isoindolin-1-one (130 mg, yield: 80% yield) as a yellow solid. MS (ESI) m/z 277.1 [M+H]$^+$.

To a solution of (S)-6-fluoro-4-methyl-2-(2-oxoazepan-3-yl)isoindolin-1-one (160 mg, 0.58 mmol) in fluorobenzene/DMSO (10 mL/1 mL) at rt was added Dess-Martin reagent (615 mg, 1.45 mmol). The mixture was stirred at 80° C. for 16 hrs, cooled to rt, and 20 mL of a saturated sodium thiosulfate solution was added followed by stirring for 5 min. The resulting mixture was extracted with DCM (30 mL×2) and the combined solution was washed with 10% aq. sodium thiosulfate/aq. sodium bicarbonate (1:1 mixture) (50 mL) and brine (50 mL). The organic layer was dried over sodium sulfate, filtered, and concentrated to afford the crude product, which was purified by preparative HPLC, using a 5 micron C18 column and 0.1% TFA in water and 0.1% TFA in acetonitrile with a gradient of 95% to 5% aqueous TFA, to afford the title compound (42 mg, 25% yield) as a white solid. MS (ESI) m/z 291.0 [M+H]$^+$. $^1$H NMR (400 MHz, DMSO-d6) δ 10.73 (s, 1 H), 7.35 (s, 2 H), 5.28-5.24 (m, 1 H), 4.47 (s, 2 H), 3.10 (t, J=13.2 Hz, 1 H), 2.59 (d, J=17.6 Hz, 1 H), 2.36 (s, 3 H), 2.319-2.26 (s, 1 H), 2.15-2.01 (m, 2 H), 1.84 (s, 1 H).

(S)-2-((3-(4-((4-((3-(N-(tert-Butyl) sulfamoyl)phenyl)amino)pyrimidin-2-yl)amino)phenoxy)propyl)amino)-N-(2-(2,7-dioxoazepan-3-yl)-1,3-dioxoisoindolin-4-yl)acetamide (Compound 58)

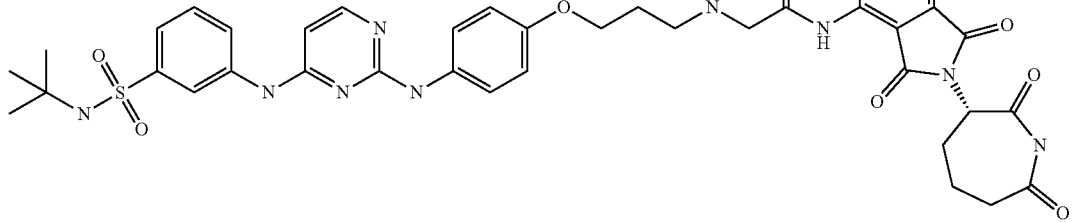

To a solution of 4-aminophenol (2.8 g, 25.9 mmol) and tert-butyl (3-chloropropyl)carbamate (5.0 g, 25.9 mmol) in DMF (120 mL), sodium hydroxide (2.1 g, 51.8 mmol) was added. The reaction mixture was stirred at 75° C. for 2 hrs, cooled to rt, concentrated under vacuum, and the residue was purified on silica gel using 1%-50% EA in petroleum ether to afford tert-butyl (3-(4-aminophenoxy)propyl)carbamate (4.45 g, 16.71 mmol, 65% yield) as brown solid. MS (ESI) m/z 167.0 [M-Boc+H]$^+$.

To a solution of 3-amino-N-(tert-butyl)benzenesulfonamide (6.1 g, 26.8 mmol) and 2,4-dichloro-pyrimidine (2.0 g, 13.4 mmol) in dioxane (120 mL) and DIEA (3.5 g, 26.8 mmol) was added. The reaction mixture was stirred at 100° C. for 72 hrs, cooled to rt, concentrated under vacuum, and the residue was purified on silica gel using 20%-50% EA in petroleum ether to afford N-(tert-butyl)-3-((2-chloropyrimidin-4-yl)amino)benzenesulfonamide (2.4 g, 7.04 mmol, 26% yield) as yellow solid. MS (ESI) m/z 340.9 [M+H]$^+$.

To a solution of tert-butyl (3-(4-aminophenoxy)propyl)carbamate (1.4 g, 4.1 mmol) and N-(tert-butyl)-3-((2-chloropyrimidin-4-yl)amino)benzenesulfonamide (1.1 g, 4.1 mmol) in dioxane (120 mL), Pd(OAc)$_2$ (91.4 mg, 0.41 mmol) and BINAP (510.0 mg, 0.82 mmol) were added. The reaction mixture was stirred at 100° C. 16 hrs, cooled to rt, concentrated under vacuum, and the residue was purified on silica gel with 20%-50% EA in petroleum ether to afford tert-butyl (3-(4-((4-((3-(N-(tert-butyl) sulfamoyl)phenyl)amino)pyrimidin-2-yl)amino)phenoxy)propyl)carbamate (1.65 g, 2.89 mmol, 70% yield) as brown solid. MS (ESI) m/z 571.1 [M+H]$^+$.

To a solution of tert-butyl (3-(4-((4-((3-(N-(tert-butyl) sulfamoyl)phenyl)amino)pyrimidin-2-yl)amino)phenoxy)propyl)carbamate (1.5 g, 2.6 mmol) in MeOH (5 mL), HCl/MeOH (10.0 mL) was added at 0° C. and the reaction mixture was stirred at rt for 2 hrs. The solvent was removed under vacuum, ammonia in THF (10 mL) was added, and the resulting mixture was filtered and dried to afford 3-((2-((4-(3-aminopropoxy)phenyl)amino)pyrimidin-4-yl)amino)-N-

(tert-butyl)benzenesulfonamide (1.2 g, 2.55 mmol, 90% yield) as a brown solid. MS (ESI) m/z 471.0 [M+H]+.

To a solution of (S)-4-amino-2-(2,7-dioxoazepan-3-yl)isoindoline-1,3-dione (400.0 mg, 1.39 mmol) and TEA (351.5 mg, 3.48 mmol) in THF (5.0 mL), 2-chloroacetyl chloride (314.1 mg, 2.78 mmol) was added slowly at 0° C. The reaction mixture was stirred at rt for 2 hrs, concentrated, and the residue was purified on silica gel with 20%-60% EA in petroleum ether) to afford (S)-2-chloro-N-(2-(2,7-dioxoazepan-3-yl)-1,3-dioxoisoindolin-4-yl)acetamide (422.0 mg, 1.16 mmol, 83% yield) as white solid. MS (ESI) m/z 380.9 [M+H$_2$O]+.

To a solution of (S)-2-chloro-N-(2-(2,7-dioxoazepan-3-yl)-1,3-dioxoisoindolin-4-yl)acetamide (125 mg, 0.34 mmol) and 3-((2-((4-(3-aminopropoxy)phenyl)amino)pyrimidin-4-yl)amino)-N-(tert-butyl)benzenesulfonamide (178.0 mg, 0.38 mmol) in DMF (2.0 mL) was added DIEA (87.7 mg, 0.68 mmol). The reaction was stirred at for 16 hrs, cooled to rt, concentrated, and the residue was purified by preparative HPLC (0.5% ammonium/water and 30% ACN in water) to afford the title compound (48.1 mg, 0.06 mmol, 18% yield) as yellow solid. $^1$H NMR (400 MHz, DMSO-d6) δ 10.83 (s, 1 H), 9.60 (s, 1 H), 8.90 (s, 1 H), 8.82-8.80 (m, 1 H), 8.14-8.12 (m, 1 H), 8.03-8.01 (m, 2 H), 7.85-7.81 (m, 1 H), 7.59-7.54 (m, 5 H), 7.47-7.40 (m, 3 H), 6.84-6.82 (m, 2 H), 6.21-6.20 (m, 1 H), 5.19 (dd, J=2.8, 11.6 Hz, 1 H), 4.08-4.05 (m, 2 H), 3.37-3.30 (m, 2 H), 3.13-3.05 (m, 1 H), 2.77-2.74 (m, 2 H), 2.16-2.18 (m, 7 H), 1.12 (s, 9 H). MS (ESI) m/z 797.9 [M+H]+.

was collected. The aqueous layer was extracted with DCM/MeOH (10:1) twice. The combined organic layers were dried over sodium sulfate, filtered, and concentrated providing 4-((3-chloro-4-fluorophenyl)amino)-6-(3-morpholinopropoxy)quinazolin-7-ol (320 mg, 22% yield) as a yellow solid. MS (ESI) m/z 433.1 [M+H]+. $^1$H NMR (400 MHz, CDCl$_3$) δ 8.65 (s, 1 H), 7.89 (dd, J=2.8, 6.4 Hz, 1 H), 7.53-7.49 (m, 1 H), 7.36 (d, J=19.6 Hz, 1 H), 7.18-7.12 (m, 2H), 4.11 (t, J=5.6 Hz, 2 H), 3.85 (t, J=4.4 Hz, 4 H), 3.71 (t, J=4.8 Hz, 1 H), 2.76-2.64 (m, 5 H), 2.50-2.44 (m, 1 H), 2.10-2.04 (m, 2 H).

To a solution of 4-((3-chloro-4-fluorophenyl)amino)-6-(3-morpholinopropoxy)quinazolin-7-ol (300 mg, 0.694 mmol) in DMF (8 mL) at rt was added tert-butyl (3-chloropropyl)carbamate (201 mg, 1.042 mmol), followed by K$_2$CO$_3$ (191 mg, 1.39 mmol). The suspension was heated at 70° C. for 4 hs, cooled to rt, and water (10 mL) was added. The suspension was extracted with DCM (15 mL) twice, the combined organic layers were dried over sodium sulfate, filtered, and concentrated providing the crude product, which was purified by preparative TLC (DCM:MeOH=10:1) providing tert-butyl (3-((4-((3-chloro-4-fluorophenyl)amino)-6-(3-morpholinopropoxy)quinazolin-7-yl)oxy)propyl)carbamate (116 mg, 28.4% yield) as a white solid and recover 4-((3-chloro-4-fluorophenyl)amino)-6-(3-morpholinopropoxy)quinazolin-7-ol (147 mg). $^1$H NMR (400 MHz, DMSO-d$_6$) δ 9.60 (s, 1 H), 8.49 (s, 1 H), 8.14 (dd, J=2.8, 7.2 Hz, 1 H), 7.86 (s, 1 H), 7.82-7.80 (m, 1 H), 7.44 (t, J=9.2 Hz, 1 H), 7.19 (s, 1 H), 6.89 (s, 1 H), 4.24-4.14 (m, 4 H), 3.61 (s, 4 H), 3.17-3.12 (m, 3 H), 2.56-2.44 (m, 5 H), 2.02-2.00 (m, 2 H), 1.93-1.89 (m, 2 H), 1.38 (s, 9 H).

To a solution of tert-butyl (3-((4-((3-chloro-4-fluorophenyl)amino)-6-(3-morpholinopropoxy)quinazolin-7-yl)oxy)propyl)carbamate (96 mg, 0.163 mmol) in DCM (5 mL) was

(S)-2-((3-((4-((3-Chloro-4-fluorophenyl)amino)-6-(3-morpholinopropoxy)quinazolin-7-v)oxy)propyl)amino)-N-(2-(2,7-dioxoazepan-3-yl)-1,3-dioxoisoindolin-4-yl)acetamide (Compound 59)

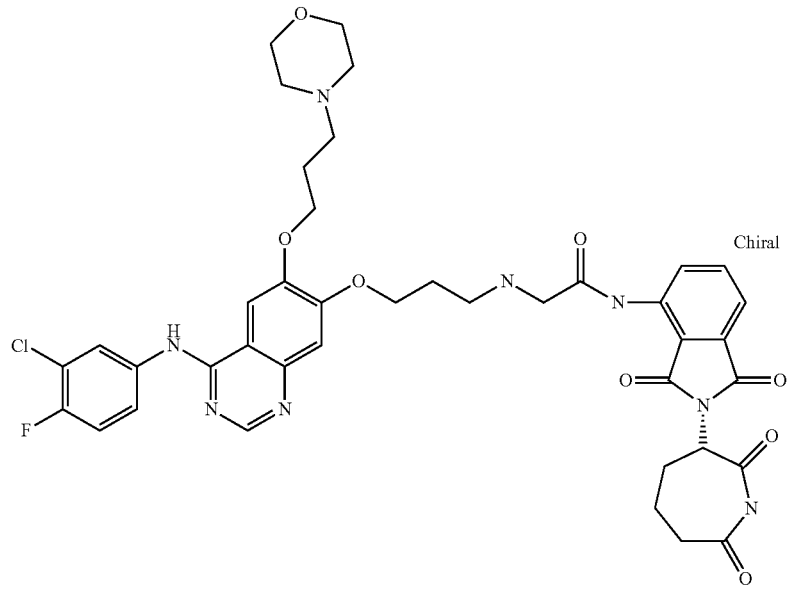

To a solution of N-(3-chloro-4-fluorophenyl)-7-methoxy-6-(3-morpholinopropoxy)quinazolin-4-amine (1.5 g, 3.36 mmol) in dry DCM (200 mL) at 0° C. was added AlCl$_3$ (3.59 g, 26.89 mmol). The reaction was heated at 40° C. for 8 hrs, cooled to 0° C., and saturated sodium bicarbonate was added. The suspension was separated and the organic layer added HCl/MeOH (2 mL) at 0° C., and the resulting solution was stirred at rt for 1 hr. The solvent was removed and the residue was dried under vacuum providing 7-(3-aminopropoxy)-N-(3-chloro-4-fluorophenyl)-6-(3-morpholinopropoxy)quinazolin-4-amine (85 mg, 100% yield) which was used directly for the next step.

To a solution of 7-(3-aminopropoxy)-N-(3-chloro-4-fluorophenyl)-6-(3-morpholinopropoxy)quinazolin-4-amine (80 mg, 0.163 mmol) in DMF (2 mL) at rt was added DIEA (42.6 mg, 0.326 mmol), followed by (S)-2-chloro-N-(2-(2,7-dioxoazepan-3-yl)-1,3-dioxoisoindolin-4-yl)acetamide (65 mg, 0.180 mmol). The resulting solution was heated at 60° C. for 16 hrs, cooled to rt, the solvent was removed, and the residue was purified by preparative HPLC, using a 5 micron C$_{18}$ column and 0.1% TFA in water and 0.1% TFA in acetonitrile with a gradient of 95% to 5% aqueous TFA, to provide the title compound (30 mg, 22.6% yield) as a white solid. MS (ESI) m/z 816.9 [M+H]$^+$. $^1$H NMR (400 MHz, DMSO-d$_6$) δ 10.79 (s, 1 H), 9.42 (s, 1 H), 8.69 (d, J=8.4 Hz, 1 H), 8.42 (s, 1 H), 8.10 (dd, J=2.4, 6.8 Hz, 1 H), 7.79-7.74 (m, 2 H), 7.36 (d, J=7.2 Hz, 1 H), 7.11 (s, 1 H), 5.07 (dd, J=3.2, 12.0 Hz, 1 H), 4.33-4.31 (m, 2 H), 4.02-3.98 (m, 2 H), 3.59-3.50 (m, 5 H), 3.20-3.04 (m, 3 H), 2.86-2.79 (m, 3 H), 2.68-2.58 (m, 3 H), 2.48-2.44 (m, 2 H), 2.38 (s, 4 H), 2.03-1.94 (m, 4 H), 2.76-2.64 (m, 5 H), 2.50-2.44 (m, 1 H), 2.10-2.04 (m, 2 H).

(S)—N1-(4-(2-((4-(2-Chlorophenyl)thiazol-2-yl)amino)acetamido)butyl)-N4-(2-(2,7-dioxoazepan-3-yl)-1-oxoisoindolin-4-yl)succinamide (Compound 60)

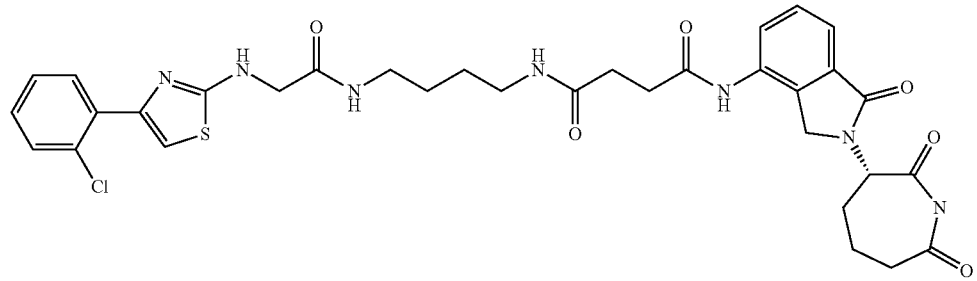 [SMILES: O=C(CCC(=O)Nc1cccc2c1CN([C@H]1CCCC(=O)NC1=O)C2=O)NCCCCNC(=O)CNc1nc(-c2ccccc2Cl)cs1]

To a solution of 4-(2-chlorophenyl)thiazol-2-amine (2.0 g, 9.5 mmol) in DMF (80 mL) at rt was added tert-butyl 2-bromoacetate (2.78 g, 14.24 mmol) and Cs$_2$CO$_3$ (6.20 g, 19 mmol). The mixture was heated at 100° C. for 16 hrs, cooled to rt, and the solvent was removed. The residue was diluted with water (50 mL) and extracted with EA (60 mL×2). The combined organic layers were washed with water, dried over sodium sulfate, filtered and concentrated providing the crude product, which was purified by chromatography on silica-gel eluted with petroleum ether/EA (20/1 to 10/1) providing tert-butyl 2-((4-(2-chlorophenyl)thiazol-2-yl)amino)acetate (0.9 g, 29.2% yield) as a yellow oil. MS (ESI) m/z 325.1 [M+H]$^+$.

To a solution of tert-butyl 2-((4-(2-chlorophenyl)thiazol-2-yl)amino)acetate (0.9 g, 2.78 mmol) in DCM (10 mL) was added TFA (7 mL) at 0° C., and then the resulting solution was stirred at rt for 4 hrs. The solvent was removed and the residue was dried under vacuum providing crude 2-((4-(2-chlorophenyl)thiazol-2-yl)amino)AcOH (0.6 g, 80.2% yield) which was used directly for the next step. MS (ESI) m/z 269.0 [M+H]$^+$.

To a solution of 2-((4-(2-chlorophenyl)thiazol-2-yl)amino)AcOH (300 mg, 1.12 mmol) in DMF (10 mL) at rt was added tert-butyl (4-aminobutyl)carbamate (421 mg, 2.24 mmol), followed by 1-hydrogenbenzotriazole (HOBt) (182 mg, 1.34 mmol), 3-(ethyliminomethylideneamino)-N,N-dimethylpropan-1-amine,hydrochloride (EDCI) (256 mg, 1.34 mmol), and DIEA (289 mg, 2.24 mmol). The resulting mixture was stirred at rt for 16 hrs, and then water (20 mL) was added and the suspension was extracted with EA (30 mL×2). The combined organic layers were washed with water, dried over sodium sulfate, filtered and concentrated providing the crude product, which was purified by chromatography on silica-gel eluted with petroleum ether/EA (1/1 to 1/2) providing tert-butyl (4-(2-((4-(2-chlorophenyl)thiazol-2-yl)amino)acetamido)butyl)carbamate (145 mg, 22.2% yield) as a white solid. MS (ESI) m/z 439.0[M+H]$^+$.

To a solution of tert-butyl (4-(2-((4-(2-chlorophenyl)thiazol-2-yl)amino) acetamido)butyl)carbamate (175 mg, 0.4 mmol) in DCM (5 mL) was added HCl/MeOH (2 mL) at 0° C., and then the resulting solution was stirred at rt for 2 hrs. The solvent was removed and the residue was dried under vacuum providing N-(4-aminobutyl)-2-((4-(2-chlorophenyl)thiazol-2-yl)amino)acetamide (130 mg, 96.2% yield) which was used directly for the next step.

A solution of 4-(benzyloxy)-4-oxobutanoic acid (300 mg, 1.44 mmol) in thionyl chloride (5 mL) was refluxed for 1.5 hrs. The solvent was removed and the residue was dried under vacuum providing benzyl 4-chloro-4-oxobutanoate as yellow oil (320 mg, crude).

(S)-3-(4-amino-1-oxoisoindolin-2-yl)azepane-2,7-dione (200 mg, 0.732 mmol) was dissolved in pyridine (3 mL) and cooled to 0° C., and then the solution of benzyl 4-chloro-4-oxobutanoate in DCM (1 mL) was added slowly. The resulting solution was stirred at rt for 16 hrs, then the solvent was removed and the residue was purified by preparative TLC (EA) providing (S)-benzyl 4-((2-(2,7-dioxoazepan-3-yl)-1-oxoisoindolin-4-yl)amino)-4-oxobutanoate (200 mg, 58.9% yield) as a white solid. MS (ESI) m/z 464.2 [M+H]$^+$.

To a solution of (S)-benzyl 4-((2-(2,7-dioxoazepan-3-yl)-1-oxoisoindolin-4-yl)amino)-4-oxobutanoate (170 mg, 0.367 mmol) in THF (10 mL) at rt was added Pd—C (10% of content, 50 mg). The suspension was degassed under vacuum and purged with hydrogen twice. The mixture was stirred at rt for 2.5 hrs, filtered, and the filtrate was concentrated providing (S)-4-((2-(2,7-dioxoazepan-3-yl)-1-oxoisoindolin-4-yl)amino)-4-oxobutanoic acid (150 mg, crude, ~100% yield) as a yellow solid. MS (ESI) m/z 374.2[M+H]$^+$.

To a solution of (S)-4-((2-(2,7-dioxoazepan-3-yl)-1-oxoisoindolin-4-yl)amino)-4-oxobutanoic acid (70 mg, 0.187 mmol) in DMF (3 mL) at rt was added N-(4-aminobutyl)-2-((4-(2-chlorophenyl)thiazol-2-yl)amino)acetamide (63 mg, 0.187 mmol), then 1-hydrogenbenzotriazole (HOBt) (38 mg, 0.281 mmol), 3-(ethyliminomethylideneamino)-N,N-dimethylpropan-1-amine,hydrochloride (EDCI) (54 mg, 0.281 mmol), and DIEA (72 mg, 0.561 mmol). The resulting mixture was stirred at rt for 16 hrs. Water (5 mL) was added and the suspension was extracted with DCM (10 mL×2). The combined organic layers were washed with water, dried over sodium sulfate, filtered and concentrated providing the crude product, which was purified by preparative HPLC, using a 5 micron C18 column and 0.1% TFA in water and 0.1% TFA in acetonitrile with a gradient of 95% to 5% aqueous TFA, providing the title compound (25.5 mg, 19.8% yield) as a white solid. MS (ESI) m/z 693.9[M+H]$^+$. $^1$H NMR (400 MHz, DMSO-d$_6$) δ 10.73 (s, 1 H), 9.84 (s, 1 H), 7.97-7.95 (m, 1H), 7.88-7.85 (m, 4 H), 7.48-7.44 (m, 3 H), 7.38-7.27 (m, 2 H), 7.13 (s, 1 H), 5.26 (dd, J=5.2, 12.4 Hz, 1 H), 4.48 (q, J=17.6 Hz, 2 H), 3.89 (d, J=5.6 Hz, 2 H), 3.12-3.01 (m, 5 H), 2.73-2.55 (m, 3 H), 2.43-2.39 (m, 2 H), 3.12-3.01 (m, 5 H), 2.73-2.55 (m, 3 H), 2.43-2.39 (m, 2 H), 2.05-1.82 (m, 4 H), 1.38 (s, 4 H).

(S)—N1-(4-(2-((4-(2-Chlorophenyl)thiazol-2-yl)amino)acetamido)butyl)-N4-(2-(2,7-dioxoazepan-3-yl)-1,3-dioxoisoindolin-4-yl)succinamide (Compound 61)

filtered, and the filtrate was concentrated providing the (S)-4-((2-(2,7-dioxoazepan-3-yl)-1,3-dioxoisoindolin-4-yl)amino)-4-oxobutanoic acid (162 mg, crude, ~100% yield) as a yellow solid. MS (ESI) m/z 388.1[M+H]$^+$.

To a solution of (S)-4-((2-(2,7-dioxoazepan-3-yl)-1,3-dioxoisoindolin-4-yl)amino)-4-oxobutanoic acid (92 mg, 0.237 mmol) in DMF (8 mL) at rt was added N-(4-aminobutyl)-2-((4-(2-chlorophenyl)thiazol-2-yl)amino)acetamide (80 mg, 0.237 mmol), 1-hydrogenbenzotriazole (HOBt) (48 mg, 0.356 mmol), 3-(ethyliminomethylideneamino)-N,N-dimethylpropan-1-amine,hydrochloride (EDCI) (68 mg, 0.356 mmol) and DIEA (91 mg, 0.711 mmol) was added. The resulting mixture was stirred at rt for 16 hrs, then water (5 mL) was added and the suspension was extracted with DCM (10 mL×2). The combined organic layers were washed with water, dried over sodium sulfate, filtered and concentrated providing the crude product, which was purified by preparative HPLC as previously described herein, providing the title compound (34.7 mg, 20.4% yield) as a light yellow solid. MS (ESI) m/z 707.9[M+H]$^+$. $^1$H

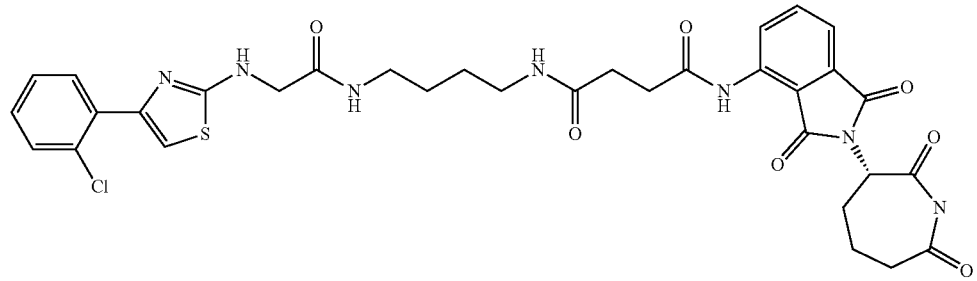 [SMILES: O=C(CCC(=O)Nc1cccc2c1C(=O)N([C@H]1CCCC(=O)NC1=O)C2=O)NCCCCNC(=O)CNc1nc(-c2ccccc2Cl)cs1]

(S)-4-Amino-2-(2,7-dioxoazepan-3-yl)isoindoline-1,3-dione (350 mg, 1.22 mmol) was dissolved in pyridine (5 mL) and cooled to 0° C., and then the solution of benzyl 4-chloro-4-oxobutanoate (500 mg, 2.44 mmol) was added. The resulting solution was stirred at 105° C. cooled to rt, then the solvent was removed and the residue was diluted with water (10 mL), extracted with DCM (20 mL) twice. The combined organic layers were dried over sodium sulfate, filtered and concentrated providing the crude product, which was triturated with EA (5 mL) providing (S)-benzyl 4-((2-(2,7-dioxoazepan-3-yl)-1,3-dioxoisoindolin-4-yl)amino)-4-oxobutanoate (500 mg, 85.9% yield) as a light yellow solid.

To a solution of (S)-benzyl 4-((2-(2,7-dioxoazepan-3-yl)-1,3-dioxoisoindolin-4-yl)amino)-4-oxobutanoate (200 mg, 0.419 mmol) in THF/DCM (10 mL/2 mL) at rt was added Pd—C (10% of content, 50 mg). The suspension was NMR (400 MHz, DMSO-d$_6$) δ 10.86 (s, 1 H), 9.73 (s, 1 H), 8.47 (d, J=8.4 Hz, 1 H), 8.46-7.97 (m, 1 H), 7.88-7.83 (m, 4 H), 7.80 (d, J=8.0 Hz, 1 H), 7.59 (d, J=7.2 Hz, 1 H), 7.48-7.37 (m, 2 H), 7.14 (s, 1 H), 5.21 (dd, J=3.2, 12.0 Hz, 1 H), 3.89 (d, J=5.6 Hz, 2 H), 3.14-3.07 (m, 5 H), 2.68-2.65 (m, 3 H), 2.55-2.52 (m, 1 H), 2.50-2.45 (m, 2 H), 2.43-2.41 (m, 1 H), 2.13-1.96 (m, 2 H), 1.38 (s, 4 H).

(S)-2-((3-(4-((4-(3-(N-(tert-Butyl) sulfamoyl)phenyl)amino)-5-methylpyrimidin-2-yl)amino)phenoxy)propyl)amino)-N-(2-(2,7-dioxoazepan-3-yl)-1-oxoisoindolin-4-yl)acetamide (26.9 mg, 34% yield) as yellow solid. (Compound 62)

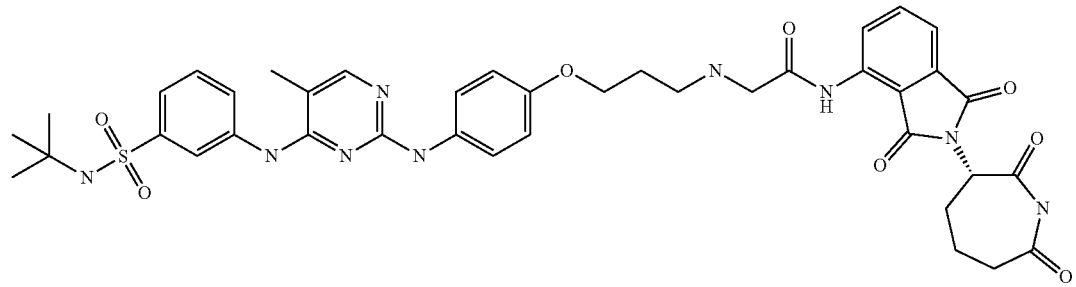 [SMILES: Cc1cnc(Nc2ccc(OCCCNCC(=O)Nc3cccc4c3C(=O)N([C@H]3CCCC(=O)NC3=O)C4=O)cc2)nc1Nc1cccc(S(=O)(=O)NC(C)(C)C)c1]

To a solution of 3-amino-N-(tert-butyl)benzenesulfonamide (3.4 g, 14.9 mmol) and 2,4-dichloro-5-methyl-pyrimidine (608.0 mg, 3.7 mmol) in dioxane (20 mL) was added DIEA (955.0 mg, 7.4 mmol). The reaction mixture was stirred at 120° C. for 72 hrs, cooled to rt, concentration, and the residue was purified on silica gel with 20%-50% EA in petroleum ether to afford N-(tert-butyl)-3-((2-chloro-5-methylpyrimidin-4-yl)amino)benzenesulfonamide (544.0 mg, 41% yield) as yellow solid. MS (ESI) m/z 355.0 [M+H]+.

To a solution of N-(tert-butyl)-3-((2-chloro-5-methylpyrimidin-4-yl)amino)benzenesulfonamide (318.0 mg, 0.896 mmol) and tert-butyl (3-(4-aminophenoxy)propyl)carbamate (239.5 mg, 0.896 mmol) in dioxane (5.0 mL) was added palladium acetate (20.1 mg, 0.090 mmol), followed by BINAP (111.8 mg, 0.180 mmol). The reaction mixture was stirred at 100° C. for 16 hrs. The mixture was concentrated, the residue was purified on silica gel with 20%-50% EA in petroleum ether to afford tert-butyl (3-(4-((4-((3-(N-(tert-butyl) sulfamoyl)phenyl)amino)-5-methylpyrimidin-2-yl)amino)phenoxy)propyl)carbamate (346.3 mg, 66% yield) as yellow solid. MS (ESI) m/z 585.1 [M+H]+.

To a solution of tert-butyl (3-(4-((4-((3-(N-(tert-butyl) sulfamoyl)phenyl)amino)-5-methylpyrimidin-2-yl)amino) phenoxy)propyl)carbamate (219.3 mg, 0.38 mmol) in DCM (6.0 mL) was added HCl/MeOH (2.0 mL) at 0° C. The reaction mixture was stirred at rt for 2 hrs, the solvent was removed under vacuum, and ammonia in THF (5.0 mL) was added. The resulting mixture was filtered and dried leaving 3-((2-((4-(3-aminopropoxy)phenyl)amino)-5-methylpyrimidin-4-yl)amino)-N-(tert-butyl)benzenesulfonamide (161.6 mg, 89% yield) as a brown solid. MS (ESI) m/z 485.1 [M+H]+.

To a solution of (S)-2-chloro-N-(2-(2,7-dioxoazepan-3-yl)-1-oxoisoindolin-4-yl)acetamide (35.0 mg, 0.1 mmol) and 3-((2-((4-(3-aminopropoxy)phenyl)amino)-5-methylpyrimidin-4-yl)amino)-N-(tert-butyl)benzenesulfonamide (48.4 mg, 0.1 mmol) in DMF (1.5 mL) was added DIEA (25.8 mg, 0.2 mmol). The reaction mixture was stirred at 60° C. for 16 hrs, cooled to rt, concentrated, and the residue was purified by preparative HPLC, using a 5 micron C18 column and 0.1% TFA in water and 0.1% TFA in acetonitrile with a gradient of 95% to 5% aqueous TFA, to afford (S)-2-((3-(4-((4-((3-(N-(tert-butyl) sulfamoyl)phenyl)amino)-5-methylpyrimidin-2-yl)amino)phenoxy)propyl)amino)-N-(2-(2,7-dioxoazepan-3-yl)-1-oxoisoindolin-4-yl)acetamide (26.9 mg, 34% yield) as yellow solid. MS (ESI) m/z 798.0 [M+H]+. 1H NMR (400 MHz, DMSO-d6) δ 10.71 (s, 1 H), 8.74 (s, 1 H), 8.52 (s, 1 H), 8.13-8.12 (m, 2 H), 7.90-7.88 (m, 2 H), 7.53-7.47 (m, 7 H), 6.80-6.78 (m, 2 H), 5.24 (dd, J=4.8, 12.0 Hz, 1 H), 4.59-4.44 (m, 2 H), 3.10-3.02 (m, 2 H), 2.76-2.71 (m, 2 H), 2.58-2.57 (m, 2 H), 2.51-2.50 (m, 2 H), 2.23-2.17 (m, 1 H), 2.12 (s, 3 H), 2.03-1.95 (m, 1 H), 1.91-1.85 (m, 3 H), 1.81-1.78 (m, 1 H), 1.28-1.24 (m, 1 H), 1.12 (s, 9 H).

To a solution of (S)-2-chloro-N-(2-(2,7-dioxoazepan-3-yl)-1,3-dioxoisoindolin-4-yl)acetamide (102.0 mg, 0.28 mmol) and 3-((2-((4-(3-aminopropoxy)phenyl)amino)-5-methylpyrimidin-4-yl)amino)-N-(tert-butyl)benzenesulfonamide (163.0 mg, 0.34 mmol) in DMF (2.0 mL) was added DIEA (72.2 mg, 0.56 mmol). The reaction was stirred at 60° C. for 16 hrs, cooled to rt, concentrated, and the residue was purified by preparative HPLC, using a 5 micron C18 column and 0.1% TFA in water and 0.1% TFA in acetonitrile with a gradient of 95% to 5% aqueous TFA, to afford the title compound (26.1 mg, 11% yield) as yellow solid. MS (ESI) m/z 811.9 [M+H]+. 1H NMR (400 MHz, DMSO-d6) δ 10.83 (s, 1 H), 8.82-8.80 (m, 1 H), 8.72 (s, 1 H), 8.53 (s, 2 H), 8.15-8.12 (m, 2 H), 7.90 (s, 1 H), 7.85-7.81 (m, 1H), 7.58-7.55 (m, 2H), 7.50-7.45 (m, 4 H), 6.77-6.75 (m, 2 H), 5.18 (dd, J=4.0, 9.0 Hz, 1 H), 4.05-4.02 (m, 2 H), 3.41-3.36 (m, 3 H), 3.30-3.27 (m, 2 H), 3.12-3.05 (m, 1 H), 2.76-2.62 (m, 4 H), 2.12 (s, 3 H), 1.94-1.83 (m, 4 H), 1.12 (s, 9 H).

(S)—N1-(2-(2,7-Dioxoazepan-3-yl)-1-oxoisoindolin-4-yl)-N4-(4-(2-((1-(4-(3-oxo-9-phenyl-2,3-dihydro-[1,2,4]triazolo[3,4-f][1,6]naphthyridin-8-yl) phenyl)cyclobutyl)amino)acetamido)butyl) succinamide (Compound 63)

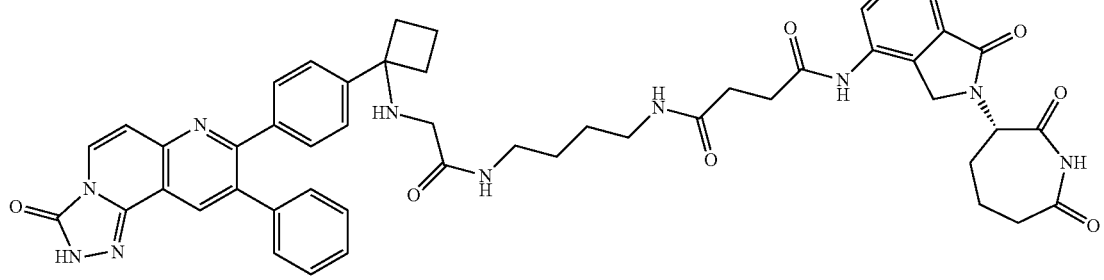

To a solution of tert-butyl (4-aminobutyl)carbamate (500 mg, 2.657 mmol) in DCM (10 mL) at rt was added TEA (537 mg, 5.314 mmol) and the resulting solution was cooled to 0° C. 2-chloroacetyl chloride (327 mg, 2.923 mmol) was added slowly and the resulting solution was warmed to rt and stirred for 2 hrs. The solvent was removed under vacuum and the residue was diluted with water (10 mL) and extracted with DCM (20 mL×2). The combined organic layers were dried over sodium sulfate, filtered and concentrated providing the crude product as a brown solid. It was triturated with EA (5 mL) and filtered, providing tert-butyl (4-(2-chloroacetamido)butyl)carbamate (420 mg, 59.8% yield) as a light yellow solid. 1H NMR (400 MHz, CDCl3) δ 6.72 (s, 1 H), 4, 62 (s, 1 H), 4.05 (s, 2 H), 3.33 (q, 2 H), 3.17-3.08 (m, 4 H), 1.58-1.54 (m, 2H), 1.44 (s, 9H).

To a solution of 8-(4-(1-aminocyclobutyl)phenyl)-9-phenyl-[1,2,4]triazolo[3,4-f][1,6]naphthyridin-3 (2H)-one (400 mg, 0.90 mmol) in DMF (9 mL) at rt was added tert-butyl (4-(2-chloroacetamido)butyl)carbamate (239 mg, 0.90 mmol). Then DIEA (275 mg, 1.806 mmol) was added, and the mixture was heated to 110° C. for 16 hrs, cooled to rt, the solvent was removed under vacuum, and the residue was purified on silica gel eluting with DCM/MeOH (from 0% to 10%) give tert-butyl (4-(2-((1-(4-(3-oxo-9-phenyl-2,3-dihydro-[1,2,4]triazolo[3,4-f][1,6]naphthyridin-8-yl)phenyl)cyclobutyl)amino)acetamido)butyl)carbamate (278 mg, 48.5% yield) as a light yellow solid.

To a solution of tert-butyl (4-(2-((1-(4-(3-oxo-9-phenyl-2,3-dihydro-[1,2,4]triazolo[3,4-f][1,6]naphthyridin-8-yl)phenyl)cyclobutyl)amino)acetamido)butyl)carbamate (278 mg, 0.44 mmol) in DCM (5 mL) was added HCl/MeOH (2 mL) at 0° C., and then the resulting solution was stirred at rt for 1 hr. The solvent was removed and the residue was dried under vacuum providing N-(4-aminobutyl)-2-((1-(4-(3-oxo-9-phenyl-2,3-dihydro-[1,2,4]triazolo[3,4-f][1,6]naphthyridin-8-yl)phenyl)cyclobutyl)amino)acetamide (250 mg, 100% yield) which was used directly for the next step.

To a solution of N-(4-aminobutyl)-2-((1-(4-(3-oxo-9-phenyl-2,3-dihydro-[1,2,4]triazolo[3,4-f][1,6]naphthyridin-8-yl)phenyl)cyclobutyl)amino)acetamide (125 mg, 0.23 mmol) in DMF (6 mL) at rt was added (S)-4-((2-(2,7-dioxoazepan-3-yl)-1-oxoisoindolin-4-yl)amino)-4-oxobutanoic acid (87 mg, 0.23 mmol), then 1-hydrogenbenzotriazole (HOBt) (47 mg, 0.351 mmol), 3-(ethyliminomethylideneamino)-N,N-dimethylpropan-1-amine,hydrochloride (EDCI) (67 mg, 0.351 mmol), and DIEA (91 mg, 0.702 mmol). The resulting mixture was stirred at rt for 16 hrs. The suspension was extracted with EA (15 mL×2), the combined organic layers were washed with water, dried over sodium sulfate, filtered and concentrated providing the crude product, which was purified by preparative HPLC, using a 5 micron $C_{18}$ column and 0.1% TFA in water and 0.1% TFA in acetonitrile with a gradient of 95% to 5% aqueous TFA, providing the title compound (12.2 mg, 5.86% yield) as a white solid. MS (ESI) m/z 891.0 [M+H]$^+$. $^1$H NMR (400 MHz, DMSO-d$_6$) δ 10.78 (s, 1 H), 9.85 (s, 1H), 8.38 (s, 1H), 7.90-7.85 (m, 3H), 7.72 (m, 1H), 7.48 (m, 2 H), 7.34-7.29 (m, 11 H), 6.97 (d, 1H, J=7.6 Hz), 5.26 (dd, J=4.4, 10.8 Hz, 1 H), 4.48 (dd, J=16.8, 39.2 Hz, 2 H), 3.09-3.03 (m, 6 H), 2.68 (s, 2H), 2.65-2.56 (m, 3H), 2.46-2.41 (m, 2 H), 2.26-2.21 (m, 3H), 2.15-2.06 (m, 4H), 2.03-1.96 (m, 2 H), 1.91 (s, 1 H), 1.36 (s, 4H).

(S)—N1-(2-(2,7-Dioxoazepan-3-yl)-1,3-dioxoisoindolin-4-yl)-N4-(4-(2-((1-(4-(3-oxo-9-phenyl-2,3-dihydro-[1,2,4]triazolo[3,4-f][1,6]naphthyridin-8-yl)phenyl)cyclobutyl)amino)acetamido)butyl)succinamide (Compound 64)

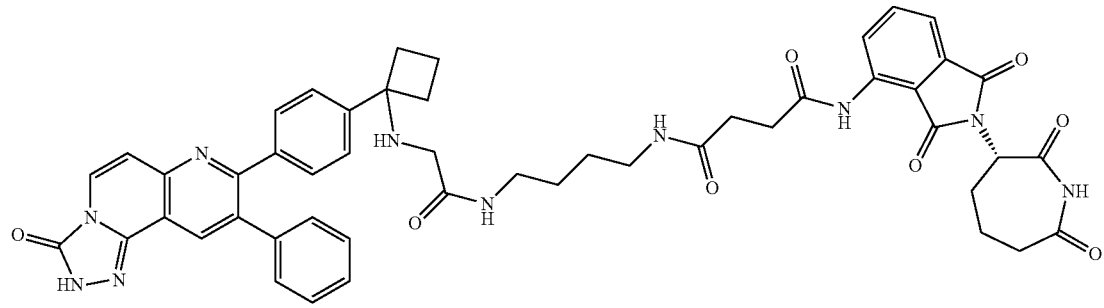 [SMILES: O=C(CCC(=O)Nc1cccc2c1C(=O)N([C@H]1CCCC(=O)NC1=O)C2=O)NCCCCNC(=O)CNC1(c2ccc(-c3nc4ccn5c(=O)[nH]nc5c4cc3-c3ccccc3)cc2)CCC1]

To a solution of N-(4-aminobutyl)-2-((1-(4-(3-oxo-9-phenyl-2,3-dihydro-[1,2,4]triazolo[3,4-f][1,6]naphthyridin-8-yl)phenyl)cyclobutyl)amino)acetamide (125 mg, 0.23 mmol) in DMF (6 mL) at rt was added (S)-4-((2-(2,7-dioxoazepan-3-yl)-1,3-dioxoisoindolin-4-yl)amino)-4-oxobutanoic acid (90 mg, 0.23 mmol), HOBt (47 mg, 0.351 mmol), EDCI (67 mg, 0.351 mmol), and DIEA (91 mg, 0.702 mmol). The resulting mixture was stirred at rt for 16 hrs, then water (10 mL) was added and the suspension was extracted with EA (15 mL×2). The combined organic layers were washed with water, dried over sodium sulfate, filtered and concentrated providing the crude product, which was purified by preparative HPLC as previously described herein, providing the title compound (17.5 mg, 8.3% yield) as a white solid. MS (ESI) m/z 905.0[M+H]$^+$. $^1$H NMR (400 MHz, DMSO-d$_6$) δ 10.57 (s, 1 H), 9.70 (s, 1H), 8.46 (d, J=8.4 Hz, 1H), 8.36 (s, 1 H), 7.87 (m, 2H), 7.79 (t, J=8.4 Hz, 1H), 7.70 (m, 1 H), 7.57 (d, J=7.2 Hz, 1H), 7.34-7.28 (m, 11 H), 6.96 (d, J=7.6 Hz, 1H), 5.19 (dd, J=3.2, 12.0 Hz, 1 H), 3.06-3.01 (m, 6 H), 2.67-2.61 (m, 5H), 2.44-2.40 (m, 2 H), 2.25-2.22 (m, 3H), 2.12-2.09 (m, 4H), 2.01-1.94 (m, 2 H), 1.68-1.63 (m, 1 H), 1.35 (s, 4H).

(S)-2-((3-(4-((4-((3-(N-(tert-Butyl) sulfamoyl)phenyl)amino)pyrimidin-2-yl)amino)phenoxy)propyl)amino)-N-(2-(2,7-dioxoazepan-3-yl)-1-oxoisoindolin-4-yl)acetamide (Compound 65)

To a solution of 3-amino-N-(tert-butyl)benzenesulfonamide (3.4 g, 14.9 mmol) and 2,4-dichloro-5-methyl-pyrimidine (608.0 mg, 3.7 mmol) in dioxane (20 mL) was added DIEA (955.0 mg, 7.4 mmol). The reaction mixture was stirred at 120° C. for 72 hrs, cooled to rt, concentrated, and

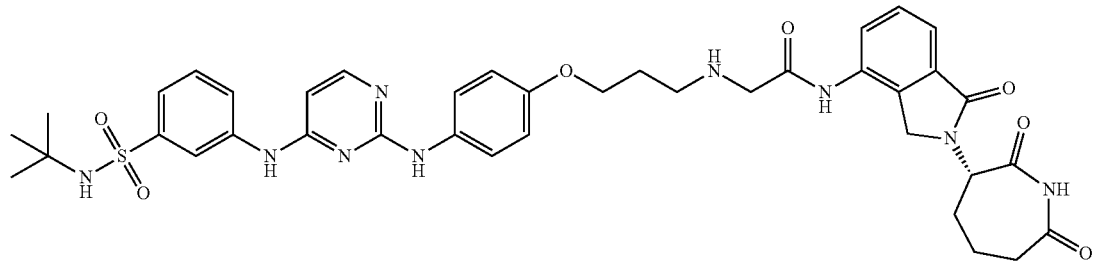 [SMILES: CC(C)(C)NS(=O)(=O)c1cccc(Nc2ccnc(Nc3ccc(OCCCNCC(=O)Nc4cccc5c4CN([C@H]4CCCC(=O)NC4=O)C5=O)cc3)n2)c1]

To a solution of (S)-3-(4-amino-1-oxoisoindolin-2-yl)azepane-2,7-dione (160 mg, 0.586 mmol) in THF/DCM (5 mL/3 mL) at 0° C. was added TEA (147 mg, 1.465 mmol), followed by 2-chloroacetyl chloride (132 mg, 1.17 mmol) added. The reaction mixture was stirred at rt for 2 hrs, the solvent was removed and the residue was purified on silica-gel with DCM/MeOH from 0%-3% providing (S)-2-chloro-N-(2-(2,7-dioxoazepan-3-yl)-1-oxoisoindolin-4-yl)acetamide (170 mg, 83.3% yield) as a light yellow solid. MS (ESI) m/z 350.1 [M+H]$^+$.

To a solution of 3-((2-((4-(3-aminopropoxy)phenyl)amino)pyrimidin-4-yl)amino)-N-(tert-butyl)benzenesulfonamide (125 mg, 0.226 mmol) in DMF (5 mL) at rt was added DIEA (68 mg, 0.532 mmol), followed by (S)-2-chloro-N-(2-(2,7-dioxoazepan-3-yl)-1-oxoisoindolin-4-yl)acetamide (99 mg, 0.266 mmol) added. The reaction mixture was heated at 60° C. for 16 hrs, cooled to rt, then the solvent was removed and the residue was purified by preparative HPLC, using a 5 micron C18 column and 0.1% TFA in water and 0.1% TFA in acetonitrile with a gradient of 95% to 5% aqueous TFA, providing the title compound (20 mg, 9.6% yield) as a white solid. MS (ESI) m/z 784.0 [M+H]$^+$. $^1$H NMR (400 MHz, DMSO-$d_6$) δ 10.71 (s, 1 H), 9.61 (s, 1H), 8.93 (s, 1H), 8.11 (d, J=8.0 Hz, 1H), 8.04 (s, 1H), 8.02 (d, J=6.0 Hz, 1H), 7.59-7.40 (m, 8H), 6.86 (d, J=8.8 Hz, 1H), 6.20 (d, J=5.6 Hz, 1H), 5.24 (dd, J=5.2, 12.8 Hz, 1 H), 4.56 (m, 2H), 4.04 (t, J=6.4 Hz, 2H), 3.10-3.02 (m, 2H), 2.76 (t, J=6.8 Hz, 2H), 2.58-2.56 (m, 1H), 2.33-1.96 (m, 5H), 1.93-1.89 (m, 2H), 1.83-1.74 (m, 1H), 1.12 (s, 9H).

(S)-2-((3-(4-((4-((3-(N-(tert-Butyl) sulfamoyl)phenyl)amino)-5-methylpyrimidin-2-yl)amino)phenoxy)propyl)amino)-N-(2-(2,7-dioxoazepan-3-yl)-1-oxoisoindolin-4-yl)acetamide (Compound 66)

the residue was purified on silica gel with 20%-50% EA/petroleum ether) to afford N-(tert-butyl)-3-((2-chloro-5-methylpyrimidin-4-yl)amino)benzenesulfonamide (544.0 mg, 41% yield) as yellow solid. MS (ESI) m/z 355.0 [M+H]$^+$.

To a solution of N-(tert-butyl)-3-((2-chloro-5-methylpyrimidin-4-yl)amino)benzenesulfonamide (318.0 mg, 0.896 mmol) and tert-butyl (3-(4-aminophenoxy)propyl)carbamate (239.5 mg, 0.896 mmol) in dioxane (5.0 mL) was added palladium acetate (20.1 mg, 0.090 mmol), followed by BINAP (111.8 mg, 0.180 mmol). The reaction mixture was stirred at 100° C. for 16 hrs, cooled to rt, concentrated, and the residue was purified on silica gel with 20%-50% EA/petroleum ether to afford tert-butyl (3-(4-((4-((3-(N-(tert-butyl) sulfamoyl)phenyl)amino)-5-methylpyrimidin-2-yl)amino)phenoxy)propyl)carbamate (346.3 mg, 66% yield) as yellow solid. MS (ESI) m/z 585.1 [M+H]$^+$.

To a solution of tert-butyl (3-(4-((4-((3-(N-(tert-butyl) sulfamoyl)phenyl)amino)-5-methylpyrimidin-2-yl)amino) phenoxy)propyl)carbamate (219.3 mg, 0.38 mmol) in DCM (6.0 mL) was added HCl/MeOH (2.0 mL) at 0° C. and the reaction mixture was stirred at rt for 2 hrs. The solvent was removed under reduced pressure, and ammonia in THF (5.0 mL) was added. The resulting mixture was filtered and dried leaving 3-((2-((4-(3-aminopropoxy)phenyl)amino)-5-methylpyrimidin-4-yl)amino)-N-(tert-butyl)benzenesulfonamide (161.6 mg, 89% yield) as a brown solid. MS (ESI) m/z 485.1 [M+H]$^+$.

To a solution of (S)-2-chloro-N-(2-(2,7-dioxoazepan-3-yl)-1-oxoisoindolin-4-yl)acetamide (35.0 mg, 0.1 mmol) and 3-((2-((4-(3-aminopropoxy)phenyl)amino)-5-methylpyrimidin-4-yl)amino)-N-(tert-butyl)benzenesulfonamide (48.4 mg, 0.1 mmol) in DMF (1.5 mL) was added DIEA (25.8 mg, 0.2 mmol). The reaction mixture was stirred at 60° C. for 16 hrs, cooled to rt, concentrated, and the residue was

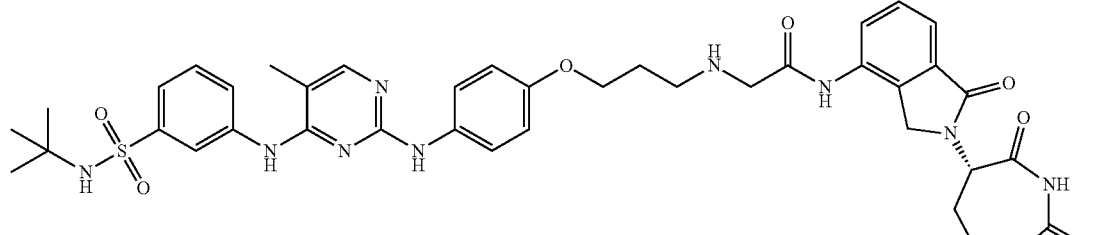

purified by preparative HPLC, using a 5 micron C18 column and 0.1% TFA in water and 0.1% TFA in acetonitrile with a gradient of 95% to 5% aqueous TFA, to afford the title compound (26.9 mg, 34% yield) as yellow solid. MS (ESI) m/z 798.0 [M+H]+. $^1$H NMR (400 MHz, DMSO-d6) δ 10.71 (s, 1 H), 8.74 (s, 1 H), 8.52 (s, 1 H), 8.13-8.12 (m, 2 H), 7.90-7.88 (m, 2 H), 7.53-7.47 (m, 7 H), 6.80-6.78 (m, 2 H), 5.24 (dd, J=4.8, 12.0 Hz, 1 H), 4.59-4.44 (m, 2 H), 3.10-3.02 (m, 2 H), 2.76-2.71 (m, 2 H), 2.58-2.57 (m, 2 H), 2.51-2.50 (m, 2 H), 2.23-2.17 (m, 1 H), 2.12 (s, 3 H), 2.03-1.95 (m, 1 H), 1.91-1.85 (m, 3 H), 1.81-1.78 (m, 1 H), 1.28-1.24 (m, 1 H), 1.12 (s, 9 H).

(2R,3S,4R,5S)-3-(4-Chloro-2-fluorophenyl)-4-(4-chloro-2-fluorophenyl)-4-cyano-N-(4-((4-((2-((2-((S)-2,7-dioxoazepan-3-yl)-1,3-dioxoisoindolin-4-yl)amino)-2-oxoethyl)amino)butyl)carbamoyl)-2-methoxyphenyl)-5-neopentylpyrrolidine-2-carboxamide (Compound 67)

To a solution of (S)-2-chloro-N-(2-(2,7-dioxoazepan-3-yl)-1,3-dioxoisoindolin-4-yl)acetamide (50 mg, 0.138 mmol) in DMF (3 mL) at 0° C. was added DIEA (36 mg, 0.28 mmol), followed by tert-butyl(4-aminobutyl)carbamate (29 mg, 0.15 mmol). The reaction mixture was heated at 50° C. for 16 hrs, cooled to rt, the solvent was removed, and the residue was purified by preparative TLC (petroleum ether: EA=1:2) providing (S)-tert-butyl (4-((2-((2-(2,7-dioxoazepan-3-yl)-1,3-dioxoisoindolin-4-yl)amino)-2-oxoethyl)amino)butyl)carbamate (40 mg, 56.3% yield) as a white solid. MS (ESI) m/z 516.2 [M+H]+.

To a solution of (S)-tert-butyl (4-((2-((2-(2,7-dioxoazepan-3-yl)-1,3-dioxoisoindolin-4-yl)amino)-2-oxoethyl)amino)butyl)carbamate (40 mg, 0.096 mmol) in DCM (4 mL) was added TFA (1 mL) at 0° C., and the resulting solution was stirred at rt for 1 hr. The solvent was removed and the residue was dried under vacuum providing (S)-2-((4-aminobutyl)amino)-N-(2-(2,7-dioxoazepan-3-yl)-1,3-dioxoisoindolin-4-yl)acetamide (30 mg, 93.7% yield) which was used directly for the next step.

To a solution of (S)-2-((4-aminobutyl)amino)-N-(2-(2,7-dioxoazepan-3-yl)-1,3-dioxoisoindolin-4-yl)acetamide (30 mg, 0.072 mmol) in DMF (2 mL) at rt was added 4-((2R,3S,4R,5S)-3-(4-chloro-2-fluorophenyl)-4-(4-chloro-2-fluorophenyl)-4-cyano-5-neopentylpyrrolidine-2-carboxamido)-3-methoxybenzoic acid (30 mg, 0.048 mmol), HOBt (9.8 mg, 0.072 mmol), EDCI (13.8 mg, 0.072 mmol), DIEA (18.5 mg, 0.144 mmol). The resulting mixture was stirred at rt for 16 hrs, extracted with EA (15 mL×2), and the combined organic layers were washed with water, dried over sodium sulfate, filtered and concentrated providing the crude product, which was purified by preparative HPLC as previously described herein providing (2R,3S,4R,5S)-3-(3-

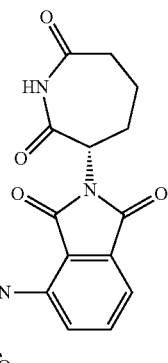

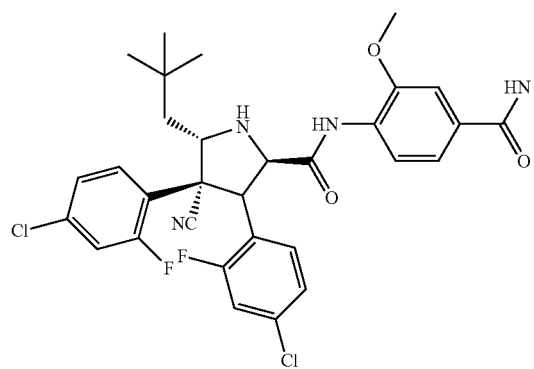

chloro-2-fluorophenyl)-4-(4-chloro-2-fluorophenyl)-4-cyano-N-(4-((4-((2-((2-((S)-2,7-dioxoazepan-3-yl)-1,3-dioxoisoindolin-4-yl)amino)-2-oxoethyl)amino)butyl)carbamoyl)-2-methoxyphenyl)-5-neopentylpyrrolidine-2-carboxamide (8.6 mg, 10.5% yield) as a white solid. MS (ESI) m/z 1012.8[M+H]+. $^1$H NMR (400 MHz, DMSO-d$_6$) δ 10.81 (s, 1 H), 10.38 (s, 1 H), 8.76 (s, 1 H), 8.34 (s, 1 H), 8.27 (dd, J=2.4, 8.8 Hz, 1 H), 7.83 (t, J=8.0 Hz, 1 H), 7.75-7.73 (m, 1 H), 7.59-7.33 (m, 9 H), 5.20-5.16 (m, 1 H), 4.58 (s, 2 H), 4.39-4.33 (m, 1 H), 3.99-3.89 (m, 1 H), 3.87 (s, 4 H), 3.28-3.09 (m, 3 H), 2.67-2.56 (m, 5 H), 2.09-1.83 (m, 5 H), 1.67-1.45 (m, 5 H), 1.30-1.25 (m, 2 H), 0.98 (s, 9 H), 0.87-0.83 (m, 1 H).

2-((S)-4-(4-Chlorophenyl)-2,3,9-trimethyl-6H-thieno[3,2-f][1,2,4]triazolo[4,3-a][1,4]diazepin-6-yl)-N-(4-(2-((2-((S)-2,7-dioxoazepan-3-yl)-1,3-dioxoisoindolin-4-yl)oxy)acetamido)butyl)acetamide (Compound 68)

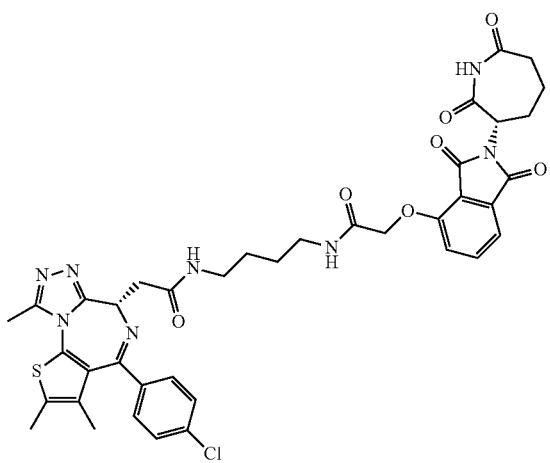 [SMILES: Cc1sc2c(c1C)C(c1ccc(Cl)cc1)=N[C@@H](CC(=O)NCCCCNC(=O)COc1cccc3c1C(=O)N([C@H]1CCCC(=O)NC1=O)C3=O)c1nnc(C)n1-2]

To a solution of tert-butyl (4-aminobutyl)carbamate (500 mg, 2.65 mmol) in dry DCM (10 mL) at 0° C. was added TEA (535 mg, 5.30 mmol) followed by 2-bromoacetyl chloride (460 mg, 2.92 mmol). Then the reaction was stirred at rt for 2 hrs, the solvent was removed and the residue was diluted with water (10 mL). The suspension was extracted with DCM (20 mL) twice, the combined organic layers were dried over sodium sulfate, filtered and concentrated, providing crude product, which was purified on silica gel with petroleum ether:EA from 4:1-1:1, providing tert-butyl (4-(2-bromoacetamido)butyl)carbamate (410 mg, 80.6% yield) as a yellow solid. $^1$H NMR (400 MHz, CDCl$_3$) δ 6.64 (s, 1 H), 4.60 (s, 1 H), 3.87 (s, 2 H), 3.35-3.29 (m, 2 H), 3.17-3.14 (m, 2 H), 1.61-1.51 (m, 4 H), 1.44 (s, 9 H).

A suspension of 4-methoxyisobenzofuran-1,3-dione (2.1 g, 11.8 mmol) and (S)-3-aminoazepan-2-one (1.51 g, 11.8 mmol) in ACN/AcOH (17 mL/23 mL) was heated at 85° C. for 16 hrs. The reaction was cooled to rt and AcOH (10 mL) and NaOAc (2.6 g, 29.5 mmol) were added. The suspension was heated to 8° C. for 24 hrs, cooled to rt, and the solvent was removed. The residue was diluted with water (20 mL), stirred for 20 min, filtered, and the filter cake was dried under vacuum providing (S)-4-methoxy-2-(2-oxoazepan-3-yl)isoindoline-1,3-dione (2.13 g, 67.8% yield) as a light yellow solid. $^1$H NMR (400 MHz, CDCl$_3$) δ 7.64 (t, J=8.0 Hz, 1 H), 7.44 (d, J=7.2 Hz, 1 H), 7.44 (d, J=8.4 Hz, 1 H), 5.99 (s, 1 H), 4.91 (d, J=11.2 Hz, 1H), 4.00 (s, 3H), 3.37-3.26 (m, 2H), 2.75-2.65 (m, 1H), 2.17-2.14 (m, 1 H), 2.04-2.00 (m, 1 H), 1.92-1.88 (m, 1H), 1.74-1.58 (m, 2 H). MS (ESI) m/z 289.1 [M+H]$^+$.

To a solution of (S)-4-methoxy-2-(2-oxoazepan-3-yl)isoindoline-1,3-dione (2.13 g, 7.4 mmol) in DCM/DMSO (100 mL/10 mL) was added Dess-Martin (8.31 g, 19.6 mmol). The suspension was heated to 80° C. for 16 hrs, cooled to rt, and 30 mL of a saturated sodium thiosulfate solution was added followed by stirring for 5 min. The resulting mixture was extracted with DCM (50 mL×2) and the combined solution was washed with 10% aq. sodium thiosulfate/aq. sodium bicarbonate (1:1 mixture) (250 mL) and brine. The organic layer was dried over sodium sulfate, filtered and concentrated to afford the crude product. The resulting compound was triturated with MeOH (20 mL) twice, providing (S)-2-(2,7-dioxoazepan-3-yl)-4-methoxyisoindoline-1,3-dione as a white solid (1.3 g, 58.3% yield). $^1$H NMR (400 MHz, DMSO-d$_6$) δ 10.79 (s, 1H), 7.83 (t, J=7.2 Hz, 1H) 7.51 (d, J=8.8 Hz, 1 H), 7.45 (d, J=6.8 Hz, 1H), 5.15 (dd, J=2.8, 11.6 Hz, 1H), 3.97 (s, 3H), 3.17-3.06 (m, 1 H), 2.68-2.61 (m, 1H), 2.54-2.51 (m, 1H), 2.10-2.04 (m, 1H), 1.98-1.85 (m, 2H). MS (ESI) m/z 303.1 [M+H]$^+$.

To a solution of (S)-2-(2,7-dioxoazepan-3-yl)-4-methoxyisoindoline-1,3-dione (200 mg, 0.66 mmol) in DCM (10 mL) at 0° C. was added BBr$_3$ (1.65 g, 6.6 mmol) in DCM (3 mL). The reaction was stirred at rt for 1 hr, quenched with ice-water, and the organic layer was separated and aqueous phase was extracted with DCM. The combined organic layers were dried over sodium sulfate, filtered, and concentrated providing (S)-2-(2,7-dioxoazepan-3-yl)-4-hydroxyisoindoline-1,3-dione (170 mg, 89.5% yield) as a white solid. MS (ESI) m/z 289.0 [M+H]$^+$. $^1$H NMR (400 MHz, DMSO-d$_6$) δ 11.11 (s, 1 H), 10.79 (s, 1 H), 7.70-7.62 (m, 1 H), 7.31 (d, J=6.8 Hz, 1 H), 7.24 (d, J=8.0 Hz, 1 H), 5.14 (dd, J=3.2, 12.0 Hz, 1 H), 3.15-3.06 (m, 1 H), 2.69-2.60 (m, 1 H), 2.53-2.50 (m, 1 H), 2.10-2.03 (m, 1 H), 1.98-1.85 (m, 2 H).

To a solution of (S)-2-(2,7-dioxoazepan-3-yl)-4-hydroxyisoindoline-1,3-dione (379 mg, 1.32 mmol) in ACN (30 mL) at rt was added tert-butyl(4-(2-bromoacetamido)butyl)carbamate (447 mg, 1.45 mmol) and DIEA (510 mg, 3.96 mmol). The suspension was heated to 80° C. for 16 hrs, cooled to rt, and the solvent was removed. Water (30 mL) was added and the suspension was extracted with EA (40 mL) twice. The combined organic layers were dried over sodium sulfate, filtered and concentrated providing the crude product, which was purified on silica-gel eluting with petroleum ether:EA (20%-90%) providing (S)-tert-butyl(4-(2-((2-(2,7-dioxoazepan-3-yl)-1,3-dioxoisoindolin-4-yl)oxy)acetamido)butyl)carbamate (320 mg, 47% yield) as a yellow solid. MS (ESI) m/z 517.2 [M+H]$^+$.

To a solution of (S)-tert-butyl (4-(2-((2-(2,7-dioxoazepan-3-yl)-1,3-dioxoisoindolin-4-yl)oxy)acetamido)butyl)carbamate (100 mg, 0.194 mmol) in DCM (4 mL) was added TFA (1 mL) at 0° C., and the resulting solution was stirred at rt for 2 hrs. The solvent was removed and the residue was dried under vacuum providing (S)—N-(4-aminobutyl)-2-((2-(2,7-dioxoazepan-3-yl)-1,3-dioxoisoindolin-4-yl)oxy)acetamide (81 mg, 100% yield) which was used directly for the next step. MS (ESI) m/z 417.1 [M+H]$^+$.

To a solution of (S)—N-(4-aminobutyl)-2-((2-(2,7-dioxoazepan-3-yl)-1,3-dioxoisoindolin-4-yl)oxy)acetamide (81 mg, 0.195 mmol) in DMF (5 mL) at rt were added (S)-2-(4-(4-chlorophenyl)-2,3,9-trimethyl-6H-thieno[3,2-f][1,2,4]triazolo[4,3-a][1,4]diazepin-6-yl)acetic acid (79 mg, 0.195 mmol), 2-(7-Aza-1H-benzotriazole-1-yl)-1,1,3,3-tetramethyluronium hexafluorophosphate (HATU) (112 mg, 0.293 mmol), and DIEA (76 mg, 0.585 mmol). The resulting mixture was stirred at rt for 16 hrs, extracted with EA (20 mL×2), and the combined organic layers were washed with water, dried over sodium sulfate, filtered and concentrated providing the crude product, which was purified by preparative HPLC, using a 5 micron C18 column and 0.1% TFA in water and 0.1% TFA in acetonitrile with a gradient of 95% to 5% aqueous TFA, to afford the title compound (49.4 mg, 32.3% yield) as a white solid. MS (ESI) m/z 798.9[M+H]$^+$. $^1$H NMR (400 MHz, DMSO-d$_6$) δ 10.62 (s, 1 H), 8.17 (t, J=5.6 Hz, 1 H), 7.94 (t, J=6.0 Hz, 1 H), 7.82-7.78 (m, 1 H), 7.49-7.38 (m, 6 H), 5.18 (dd, J=2.8, 12 Hz, 1 H), 4.77 (s, 2 H), 4.52-4.48 (m, 1 H), 3.27-3.08 (m, 7 H), 2.69-2.66 (m, 1 H), 2.58 (s, 3 H), 2.40 (s, 3 H), 2.11-2.04 (m, 1 H), 2.00-1.83 (m, 3 H), 1.62 (s, 3 H), 1.47 (s, 4 H).

(S)—(R)-3-(3,4-Dimethoxyphenyl)-1-(3-(4-((4-(2-((2-((S)-2,7-dioxoazepan-3-yl)-1,3-dioxoisoindolin-4-yl)oxy)acetamido)butyl)amino)-4-oxobutanoyl)phenyl)propyl 1-(3,3-dimethyl-2-oxopentanoyl)piperidine-2-carboxylate (Compound 69)

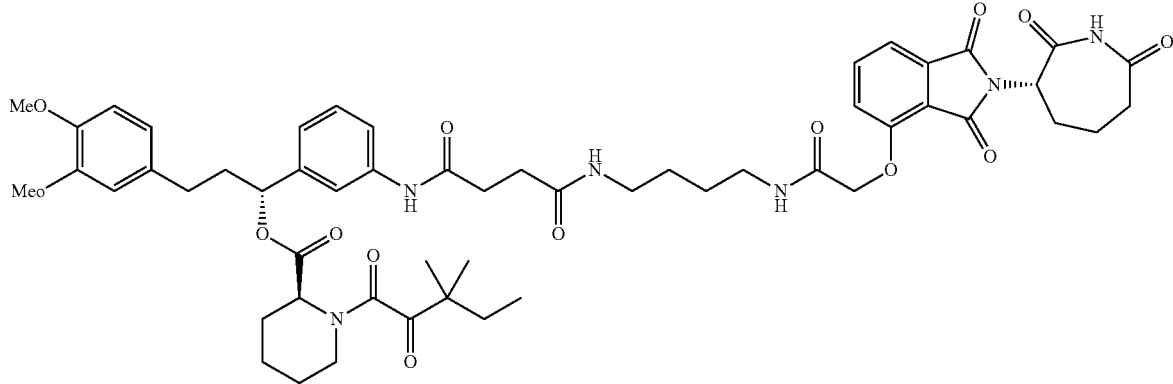

To a solution of (S)—(R)-1-(3-aminophenyl)-3-(3,4-dimethoxyphenyl)propyl 1-(3,3-dimethyl-2-oxopentanoyl)piperidine-2-carboxylate (90 mg, 0.172 mmol) in DMF (4 mL) at rt were added dihydrofuran-2,5-dione (103 mg, 1.03 mmol) and 4-dimethylaminopyridine (21 mg, 0.172 mmol), and the reaction was stirred at rt for 16 hrs. The reaction was diluted with water (10 mL) and extracted with DCM (20 mL) twice. The combined organic layers were dried over sodium sulfate, filtered and concentrated providing 4-((3-((R)-3-(3,4-dimethoxyphenyl)-1-(((S)-1-(3,3-dimethyl-2-oxopentanoyl)piperidine-2-carbonyl)oxy)propyl)phenyl)amino)-4-oxobutanoic acid (110 mg, 100% yield) as a yellow gum. MS (ESI) m/z 625.0 [M+H]$^+$.

To a solution of (S)—N-(4-aminobutyl)-2-((2-(2,7-dioxoazepan-3-yl)-1,3-dioxoisoindolin-4-yl)oxy)acetamide (56 mg, 0.13 mmol) in DMF (5 mL) at rt were added 4-((3-((R)-3-(3,4-dimethoxyphenyl)-1-(((S)-1-(3,3-dimethyl-2-oxopentanoyl)piperidine-2-carbonyl)oxy)propyl)phenyl)amino)-4-oxobutanoic acid (63 mg, 0.10 mmol), HOBt (21 mg, 0.15 mmol), EDCI (29 mg, 0.15 mmol), and DIEA (50 mg, 0.39 mmol). The resulting mixture was stirred at rt for 16 hrs, then water (10 mL) was added and the suspension was extracted with EA (20 mL×2). The combined organic layers were washed with water, dried over sodium sulfate, filtered and concentrated providing the crude product, which was purified by preparative HPLC, using a 5 micron C18 column and 0.1% TFA in water and 0.1% TFA in acetonitrile with a gradient of 95% to 5% aqueous TFA, to afford the title compound (18.3 mg, 17.9% yield) as a white solid. MS (ESI) m/z 1023.0 [M+H]$^+$. $^1$H NMR (400 MHz, DMSO-d$_6$)

δ 10.81 (s, 1 H), 9.97 (s, 1 H), 7.93 (t, J=4.8 Hz, 1 H), 7.84-7.28 (m, 2 H), 7.68 (s, 1 H), 7.49-7.44 (m, 2 H), 7.38 (d, J=8.8 Hz, 1 H), 7.30-7.26 (m, 1 H), 7.00 (d, J=7.6 Hz, 1 H), 6.84 (d, J=8.4 Hz, 1 H), 6.76-6.74 (m, 1 H), 6.68 (d, J=7.6 Hz, 1 H), 5.62 (dd, J=4.4, 7.6 Hz, 1 H), 5.20-5.12 (m, 2 H), 4.76 (s, 2 H), 3.72 (s, 3 H), 3.71 (s, 3 H), 3.29-3.25 (m, 2 H), 3.24-3.22 (m, 4 H), 3.08-3.02 (m, 3 H), 2.67-2.63 (m, 1 H), 2.39-2.36 (m, 2 H), 2.22-2.20 (m, 1 H), 2.13-1.97 (m, 5 H), 1.90-1.88 (m, 1 H), 1.67-1.57 (m, 5 H), 1.42-1.39 (m, 4 H), 1.33-1.29 (m, 3 H), 1.16 (s, 3 H), 1.14 (s, 3 H), 1.04 (d, J=4.0 Hz, 1 H), 0.79 (t, J=7.2 Hz, 3 H).

(S)—(R)-3-(3,4-Dimethoxyphenyl)-1-(3-(1-((2-((S)-2,7-dioxoazepan-3-yl)-1,3-dioxoisoindolin-4-yl)oxy)-2,18-dioxo-7,10,13-trioxa-3,17-diazahenicosanamido)phenyl)propyl 1-(3,3-dimethyl-2-oxopentanoyl)piperidine-2-carboxylate (Compound 70)

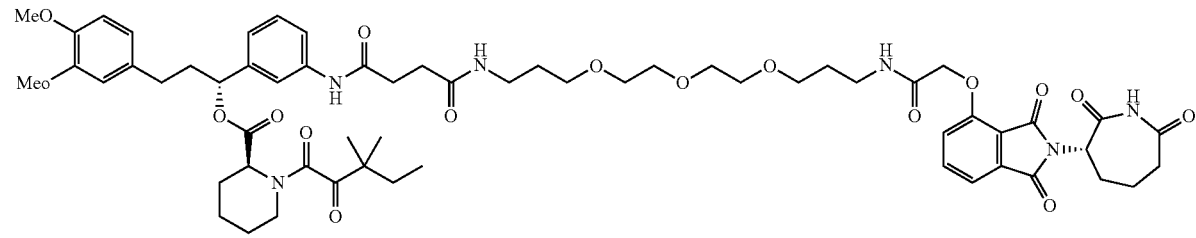

To a solution of tert-butyl (1-bromo-2-oxo-7,10,13-trioxa-3-azahexadecan-16-yl)carbamate (184 mg, 0.416 mmol) and (S)-2-(2,7-dioxoazepan-3-yl)-4-hydroxyisoindoline-1,3-dione (100 mg, 0.347 mmol) in ACN (10 mL) was added DIEA (134 mg, 1.04 mmol) at rt. The reaction mixture was heated to 80° C. and stirred for 16 hrs, the solvent was removed and the residue purified on silica gel with petroleum ether/EA from 30%-100% providing (S)-tert-butyl (1-((2-(2,7-dioxoazepan-3-yl)-1,3-dioxoisoindolin-4-yl)oxy)-2-oxo-7,10,13-trioxa-3-azahexadecan-16-yl)carbamate (100 mg, 44.6% yield) as the white oil. MS (ESI) m/z=649 [M+H]$^+$. $^1$H NMR (DMSO-d$_6$, 400 MHz) δ: 10.82 (s, 1 H), 7.93 (t, J=5.6 Hz, 1 H), 7.81 (t, J=7.6 Hz, 1 H), 7.49 (d, J=7.2 Hz, 1 H), 7.40 (d, J=8.4 Hz, 1 H), 6.73 (t, J=5.2 Hz, 1 H), 5.18 (dd, J=2.8 Hz, 1 H), 4.76 (s, 2 H), 3.51-3.40 (m, 12H), 3.21 (q, J=6.8 Hz, 2 H), 3.16-3.08 (m, 1 H), 2.95 (q, J=6.8 Hz, 2 H), 2.70-2.61 (m, 1 H), 2.12-2.06 (m, 1 H), 2.03-1.95 (m, 2 H), 1.92-1.85 (m, 1 H), 1.67 (t, J=6.8 Hz, 2 H), 1.58 (t, J=6.4 Hz, 2 H), 1.36 (s, 9 H).

To a solution of (S)-tert-butyl (1-((2-(2,7-dioxoazepan-3-yl)-1,3-dioxoisoindolin-4-yl)oxy)-2-oxo-7,10,13-trioxa-3-azahexadecan-16-yl)carbamate (100 mg, 0.1538 mmol) in DCM (6 mL) was added TFA (1 mL) at 0° C. and the mixture was warmed to rt and stirred for 2 hrs. The desired mass value [m/z=549, M+H$^+$] was detected by LC-MS, and the residue was directly used in the next step after solvent removal.

To a solution of (S)—N-(3-(2-(2-(3-aminopropoxy) ethoxy)ethoxy)propyl)-2-((2-(2,7-dioxoazepan-3-yl)-1,3-dioxoisoindolin-4-yl)oxy)acetamide (84 mg, 0.1488 mmol) and 4-((3-((R)-3-(3,4-dimethoxyphenyl)-1-(((S)-1-(3,3-dimethyl-2-oxopentanoyl)piperidine-2-carbonyl)oxy)propyl) phenyl)amino)-4-oxobutanoic acid (70 mg, 0.112 mmol) in DMF (5 mL) was added DIEA (43.29 mg, 0.336 mmol), HOBt (22.66 mg, 0.168 mmol), and EDCI (32.21 mg, 0.168 mmol) at rt. The mixture was stirred at rt for 16 hrs, diluted with water and extracted with EA twice. The combined organic layers were dried over sodium sulfate, filtered, and concentrated providing the crude product, which was purified by preparative HPLC, using a 5 micron C18 column and 0.1% TFA in water and 0.1% TFA in acetonitrile with a gradient of 95% to 5% aqueous TFA, to afford the title compound (16 mg, 12.4% yield) as a white solid. MS (ESI) m/z=1155 [M+H]$^+$. $^1$H NMR (DMSO-d$_6$, 400 MHz) δ: 10.81 (s, 1 H), 9.98 (s, 1 H), 7.93 (t, J=5.2 Hz, 1 H), 7.81 (t, J=6.8 Hz, 2 H), 7.67 (s, 1 H), 7.51-7.39 (m, 3 H), 7.29 (t, J=8.4 Hz, 1 H), 7.01 (d, J=6.8 Hz, 1 H), 6.85 (d, J=8.4 Hz, 1 H), 6.77 (s, 1 H), 6.69 (d, J=8.4 Hz, 1 H), 5.64 (t, J=4.4 Hz, 1 H), 5.20-5.14 (m, 2 H), 4.77 (s, 2 H), 3.73 (d, J=4.8 Hz, 6 H), 3.48 (t, J=5.2 Hz, 9 H), 3.24-3.16 (m, 6 H), 3.10-3.06 (m, 4 H), 2.71-2.66 (m, 3 H), 2.38 (t, J=6.8 Hz, 3 H), 2.23 (d, J=12.8 Hz, 1 H), 2.12 (d, J=6.4 Hz, 2 H), 2.00 (t, J=9.2 Hz, 3 H), 1.69-1.59 (m, 10 H), 1.24 (s, 2 H), 1.16 (d, J=9.2 Hz, 6 H), 1.04 (d, J=3.6 Hz, 1 H), 0.81 (t, J=6.8 Hz, 3 H).

2-((S)-4-(4-Chlorophenyl)-2,3,9-trimethyl-6H-thieno [3,2-f][1,2,4]triazolo[4,3-a][1,4]diazepin-6-yl)-N-(2-(2-((S)-2,7-dioxoazepan-3-yl)-1,3-dioxoisoindolin-4-yl)amino)ethoxy)ethyl)acetamide (Compound 71)

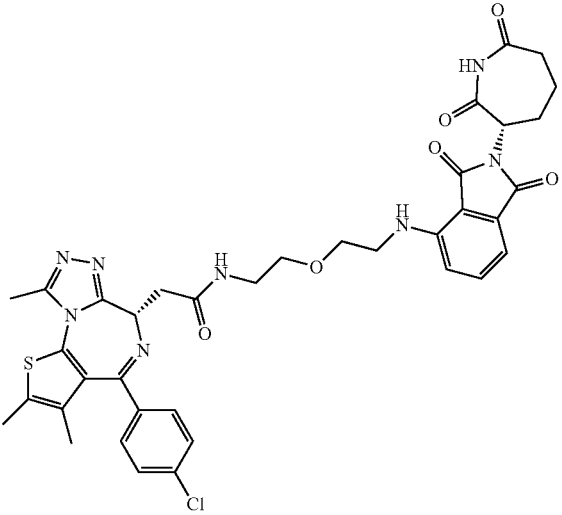 [SMILES: Cc1sc2c(c1C)C(c1ccc(Cl)cc1)=N[C@@H](CC(=O)NCCOCCNc1cccc3c1C(=O)N([C@H]1CCCC(=O)NC1=O)C3=O)c1nnc(C)n1-2]

To a solution of (S)-4-amino-2-(2,7-dioxoazepan-3-yl) isoindoline-1,3-dione (105 mg, 0.366 mmol) in ACN (10 mL) at rt was added tert-butyl (2-(2-bromoethoxy)ethyl) carbamate (117 mg, 0.439 mmol), followed by K$_2$CO$_3$ (101 mg, 0.732 mmol) added. The mixture was heated at 80° C. for 18 hrs, diluted with water (10 mL), and extracted with EA (20 mL×2). The combined organic layers were concentrated providing the crude product, which was purified on silica gel with EA/petroleum ether from 20%-60% providing (S)-tert-butyl (2-(2-((2-(2,7-dioxoazepan-3-yl)-1,3-dioxoisoindolin-4-yl)amino)ethoxy)ethyl)carbamate (85 mg, 49.1% yield) as a yellow gum. MS (ESI) m/z 475.2 [M+1]$^+$.

To a solution of (S)-tert-butyl (2-(2-((2-(2,7-dioxoazepan-3-yl)-1,3-dioxoisoindolin-4-yl)amino)ethoxy)ethyl)carbamate (85 mg, 0.179 mmol) in DCM (6 mL) at 0° C. was added TFA (1.5 mL). The mixture was stirred at rt for 1 hr, the solvent was removed, and the residue was dried under vacuum providing (S)-4-((2-(2-aminoethoxy)ethyl)amino)-2-(2,7-dioxoazepan-3-yl)isoindoline-1,3-dione (67 mg, 100% yield) as a yellow gum. MS (ESI) m/z 375.2 [M+H]$^+$.

To a solution of (S)-4-((2-(2-aminoethoxy)ethyl)amino)-2-(2,7-dioxoazepan-3-yl)isoindoline-1,3-dione (67 mg, 0.179 mmol) in DMF (10 mL) at rt was added (S)-2-(4-(4-chlorophenyl)-2,3,9-trimethyl-6H-thieno[3,2-f][1,2,4]triazolo[4,3-a][1,4]diazepin-6-yl)acetic acid (71.5 mg, 0.179 mmol), followed by HATU (102 mg, 0.268 mmol) and DIEA (69 mg, 0.536 mmol). The mixture was stirred at rt for 16 hrs, the solvent was removed and the residue was purified by preparative TLC (DCM/MeOH=10:1) to afford the title compound (38.1 mg, 28.1% yield) as a yellow solid. MS (ESI) m/z 756.9 [M+H]$^+$. $^1$H NMR (400 MHz, DMSO-d$_6$) δ 8.24 (s, 1H), 7.49-7.41 (m, 5H), 7.01 (t, J=8.4 Hz, 2H), 6.51 (s, 2H), 5.17 (d, J=10.8 Hz, 1H), 4.52 (t, J=6.4 Hz, 1H), 3.95-3.90 (m, 1H), 3.83-3.80 (m, 1H), 3.46-3.43 (m, 4H), 3.32-3.22 (m, 5H), 2.71-2.64 (m, 2H), 2.59 (s, 3H), 2.40 (s, 3H), 2.04-1.86 (m, 3H), 1.62 (s, 3H).

2-((S)-4-(4-chlorophenyl)-2,3,9-trimethyl-6H-thieno
[3,2-f][1,2,4]triazolo[4,3-a][1,4]diazepin-6-yl)-N-(2-
(2-(2-(2-((2-((S)-2,7-dioxoazepan-3-yl)-1,3-diox-
oisoindolin-4-yl)amino)ethoxy)ethoxy)ethoxy)ethyl)
acetamide (Compound 72)

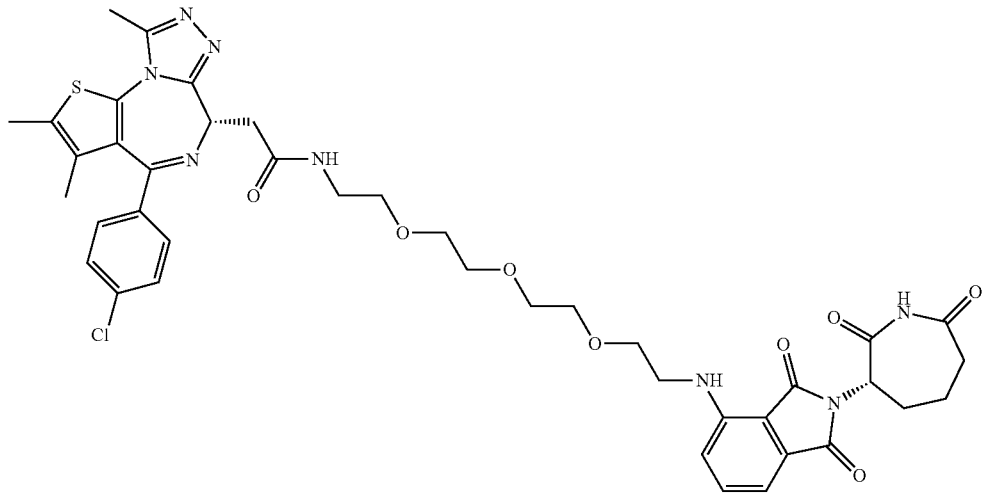 [SMILES: Cc1sc2c(c1C)C(c1ccc(Cl)cc1)=N[C@@H](CC(=O)NCCOCCOCCOCCNc1cccc3c1C(=O)N([C@H]1CCCC(=O)NC1=O)C3=O)c1nnc(C)n1-2]

To a solution of 4-nitroisobenzofuran-1,3-dione (3.0 g, 15.54 mmol) in AcOH (70 mL) and ACN (50 mL) was added (S)-3-aminoazepan-2-one (1.99 g, 15.54 mmol). The mixture stirred at 85° C. for 16 hrs, then NaOAc (3.82 g, 46.62 mmol) was added and the mixture was stirred at 85° C. for 24 hrs, then cooled to rt, and the solvent was removed under vacuum. The residue was diluted with water and stirred for 30 minutes. The resulting solid was filtered and dried providing (S)-4-nitro-2-(2-oxoazepan-3-yl)isoindoline-1,3-dione (1.6 g, 34% yield) as white solid. MS (ESI) m/z=304 [M+H]+.

To a solution of (S)-4-nitro-2-(2-oxoazepan-3-yl)isoindoline-1,3-dione (1.6 g, 5.28 mmol) in 1,2-dichloroethane (50 mL), DMSO (5 mL) and 1 drop water was added Dess-Martin (5.6 g, 13.2 mmol) at 0° C. The reaction mixture was heated to 80° C. for 16 hrs, Dess-Martin (2.24 g, 5.28 mmol) was added, and the mixture was stirred at 80° C. for 16 hrs. The suspension was cooled to rt, filtered, and the filtrate was treated with saturated aqueous sodium thiosulfate and stirred at 0° C. for 30 min. The resulting mixture was extracted with DCM twice and the combined organic layers were washed with 1/1 sodium bicarbonate (sat.)/sodium thiosulfate (10%), and brine, dried, filtered, and concentrated providing (S)-2-(2,7-dioxoazepan-3-yl)-4-nitroisoindoline-1,3-dione (1.66 g, 99.4% yield). MS (ESI) m/z=318 [M+H]+.

To a solution of (S)-2-(2,7-dioxoazepan-3-yl)-4-nitroisoindoline-1,3-dione (1.46 g, 4.6 mmol) in MeOH (300 mL) and DMF (80 mL) was added Pd/C (440 mg) at rt. The reaction vessel was purged twice with H2 and stirred at rt for 2 hrs, filtered through Celite, and concentrated under reduce pressure. The residue was triturated with MeOH providing (S)-4-amino-2-(2,7-dioxoazepan-3-yl)isoindoline-1,3-dione (640 mg, 48.5% yield) as a green solid. MS (ESI) m/z=288 [M+H]+.

To a solution of (S)-4-amino-2-(2,7-dioxoazepan-3-yl) isoindoline-1,3-dione (100 mg, 0.35 mmol) and tert-butyl (2-(2-(2-(2-bromoethoxy)ethoxy)ethoxy)ethyl) carbamate (149 mg, 0.420 mmol) in DMF (10 mL) was added potassium carbonate (96.3 mg, 0.700 mmol) at rt. The reaction mixture was heated to 80° C. for 16 hrs, cooled to rt and quenched with water and extracted with EA twice. The combined organic layers were dried, filtered, and concentrated providing the crude product which was purified on silica gel with petroleum/EA from 10%-100% providing (S)-tert-butyl (2-(2-(2-(2-((2-(2,7-dioxoazepan-3-yl)-1,3-dioxoisoindolin-4-yl)amino)ethoxy)ethoxy)ethoxy)ethyl)carbamate (130 mg, 66.4% yield). MS (ESI) m/z=563 [M+H]+.

To a solution of (S)-tert-butyl (2-(2-(2-(2-((2-(2,7-dioxoazepan-3-yl)-1,3-dioxoisoindolin-4-yl)amino)ethoxy) ethoxy)ethoxy)ethyl)carbamate (130 mg, 0.231 mmol) in DCM (6 mL) was added TFA (1.5 mL) at 0° C. and the mixture was warmed to rt and stirred for 1 hr. The solvent was removed and the residue was directly used in the next step without further purification. MS (ESI) m/z=463 [M+H]+.

To a solution of (S)-4-((2-(2-(2-(2-aminoethoxy)ethoxy) ethoxy)ethyl)amino)-2-(2,7-dioxoazepan-3-yl)isoindoline-1,3-dione (100 mg, 0.216 mmol) and (S)-2-(4-(4-chlorophenyl)-2,3,9-trimethyl-6H-thieno[3,2-f][1,2,4]triazolo[4,3-a] [1,4]diazepin-6-yl)acetic acid (86.4 mg, 0.216 mmol) in DMF (6 mL) at 0° C. was added DIEA (70 mg, 0.54 mmol) and HATU (98.4 mg, 0.259 mmol) and the mixture was warmed to rt and stirred for 16 hrs. The reaction was quenched with water and extracted with EA twice. The combined organic layers were concentrated providing crude product which was purified by preparative TLC with DCM/MeOH=10:1 to afford the title compound (63.7 mg, 35% yield) as a yellow solid. MS (ESI) m/z=845 [M+H]+. 1H NMR (DMSO-$d_6$, 400 MHz) δ: 8.27 (s, 1 H), 7.49-7.41 (m, 5 H), 7.00 (t, J=8.8 Hz, 2 H), 6.50 (s, 2 H), 5.15 (d, J=10.4 Hz, 1 H), 4.51 (t, J=6.4 Hz, 1 H), 3.89-3.76 (m, 2 H), 3.52-3.42 (m, 13 H), 3.29-3.10 (m, 3 H), 2.69-2.59 (m, 5 H), 2.40 (s, 3 H), 2.08-1.82 (m, 4 H), 1.62 (s, 3 H).

(S)-2-((2-(2,7-Dioxoazepan-3-yl)-1,3-dioxoisoindolin-4-yl)oxy)-N-(6-(2-((1-(4-(3-oxo-9-phenyl-2,3-dihydro-[1,2,4]triazolo[3,4-f][1,6]naphthyridin-8-yl)phenyl)cyclobutyl)amino)acetamido)hexyl)acetamide (Compound 73)

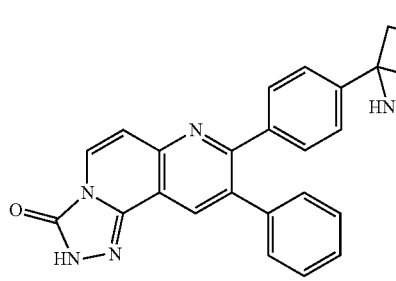
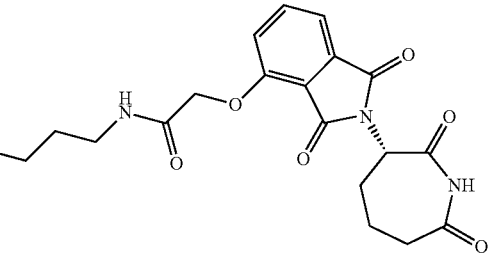

To a solution of 3-methoxyphthalic acid (3.0 g, 15.3 mmol) in THF (30 mL) at rt was added acetic anhydride (10 mL) and the reaction was heated at 80° C. for 4 hrs. The solvent was removed and the residue was dried under vacuum providing 4-methoxyisobenzofuran-1,3-dione (2.66 g, 97.8% yield) as a white solid. $^1$H NMR (400 MHz, DMSO-$d_6$) δ 7.98-7.94 (m, 1H), 7.63-7.59 (m, 2H), 4.01 (s, 3H).

To a solution of (S)-3-aminoazepan-2-one (1.92 g, 14.94 mmol) in AcOH/ACN (28 mL/21 mL) was added 4-methoxyisobenzofuran-1,3-dione (2.66 g, 14.94 mmol). The suspension was heated at 85° C. for 18 hrs, cooled to rt and NaOAc (3.25 g, 37.35 mmol) was added, followed by AcOH (12 mL). The suspension was heated at 85° C. for 24 hrs, cooled to rt, the solvent was removed, and the residue was diluted with water (30 mL). The suspension was stirred at rt for 30 min, filtered, and the filter cake was triturated with EA providing (S)-4-methoxy-2-(2-oxoazepan-3-yl)isoindoline-1,3-dione (2.54 g, 59.3% yield) as a white solid. MS (ESI) m/z 289.1 [M+H]$^+$.

To a solution of (S)-4-methoxy-2-(2-oxoazepan-3-yl)isoindoline-1,3-dione (2.54 g, 8.82 mmol) in 1,2-dichloroethane/DMSO (120 mL/12 mL, 2 drops water) at 0° C. was added Dess-martin reagent (10 g, 23.8 mmol). The suspension was heated at 80° C. for 16 hrs, Dess-martin reagent (5.0 g) was added and the suspension was continued to stir at 80° C. for 24 hrs. The reaction was cooled to rt and 100 mL of a saturated sodium thiosulfate solution was added followed by stirring for 5 min. The resulting mixture was extracted with DCM (50 mL×2) and the combined solution was washed with 10% aq. sodium thiosulfate/aq. sodium bicarbonate (1:1 mixture) (50 mL) and brine. The organic layer was dried over sodium sulfate, filtered and concentrated to afford the crude product, which was triturated with MeOH providing (S)-2-(2,7-dioxoazepan-3-yl)-4-methoxyisoindoline-1,3-dione (1.56 g, 58.6% yield) as a white solid. MS (ESI) m/z 303.1 [M+H]$^+$.

To a solution of (S)-2-(2,7-dioxoazepan-3-yl)-4-methoxyisoindoline-1,3-dione (500 mg, 1.66 mmol) in DCM (20 mL) at 0° C. was added BBr$_3$ (0.77 mL) in DCM (4 mL), warmed to rt and stirred for 5 hrs. The reaction was then quenched with ice-water, extracted with DCM (40 mL×2) and the combined organic layers were washed with brine, dried over sodium sulfate, filtered, and concentrated providing the crude product. The crude product was triturated with EA providing (S)-2-(2,7-dioxoazepan-3-yl)-4-hydroxyisoindoline-1,3-dione (240 mg, 50.2% yield) as a light yellow solid. $^1$H NMR (400 MHz, DMSO-$d_6$) δ 11.12 (s, 1H), 10.79 (s, 1H), 7.67-7.63 (dd, J=7.2 Hz, 8.4 Hz, 1H), 7.31 (d, J=6.8 Hz, 1H), 7.24 (d, J=8.0 Hz, 1H), 5.16-5.12 (m, 1H), 3.14-3.06 (m, 1H), 2.71-2.64 (m, 1H), 2.53-2.51 (m, 1H), 2.10-2.03 (m, 1H), 1.98-1.84 (m, 2H).

To a solution of (S)-2-(2,7-dioxoazepan-3-yl)-4-hydroxyisoindoline-1,3-dione (240 mg, 0.833 mmol) in ACN (15 mL) at rt was added tert-butyl (6-(2-bromoacetamido)hexyl)carbamate (336 mg, 0.999 mmol) and DIEA (215 mg, 1.66 mmol). The mixture was heated at 80° C. for 16 hrs, cooled to rt, the solvent was removed, and the residue was purified on silica gel with EA/petroleum ether from 20% to 80% providing (S)-tert-butyl (6-(2-((2-(2,7-dioxoazepan-3-yl)-1,3-dioxoisoindolin-4-yl)oxy)acetamido)hexyl)carbamate (289 mg, 63.8% yield) as a white solid. MS (ESI) m/z 545.3 [M+H]$^+$.

To a solution of (S)-tert-butyl (6-(2-((2-(2,7-dioxoazepan-3-yl)-1,3-dioxoisoindolin-4-yl)oxy)acetamido)hexyl)carbamate (100 mg, 0.184 mmol) in DCM (4 mL) at 0° C. was added TFA (1 mL) and the mixture was stirred at rt for 1 hr. The solvent was removed and the residue was dried under vacuum providing (S)—N-(6-aminohexyl)-2-((2-(2,7-dioxoazepan-3-yl)-1,3-dioxoisoindolin-4-yl)oxy)acetamide (80 mg, 100% yield) as a colorless oil. MS (ESI) m/z 445.2 [M+H]$^+$.

To a solution of (S)—N-(6-aminohexyl)-2-((2-(2,7-dioxoazepan-3-yl)-1,3-dioxoisoindolin-4-yl)oxy)acetamide (86 mg, 0.193 mmol) in DMF (5 mL) at rt was added DIEA (50 mg, 0.386 mmol), 2-((1-(4-(3-oxo-9-phenyl-2,3-dihydro-[1,2,4]triazolo[3,4-f][1,6]naphthyridin-8-yl)phenyl)cyclobutyl)amino)acetic acid (90 mg, 0.193 mmol) and HATU (110 mg, 0.290 mmol). The mixture was stirred at rt for 16 hrs, diluted with water (10 mL), and extracted with DCM (15 mL×2). The combined organic layers were dried over sodium sulfate, filtered, and concentrated providing crude product, which was purified by preparative TLC (DCM:MeOH=10:1) providing the title compound (23 mg, 13.4% yield) as a white solid. MS (ESI) m/z 892.5 [M+H]$^+$. $^1$H NMR (400 MHz, DMSO-$d_6$) δ 8.18 (s, 1H), 7.95 (m, 1H), 7.80 (d, J=7.2 Hz, 1H), 7.76-7.73 (m, 1H), 7.79 (t, J=7.6 Hz, 1H), 7.30 (d, J=6.8 Hz, 1H), 7.23-7.15 (m, 11 H), 6.84 (d, J=7.6 Hz, 1H), 5.00 (m, 1H), 4.58 (s, 2H), 4.41 (s, 2H), 3.01-2.92 (m, 5H), 2.50-2.42 (m, 1H), 2.26-2.24 (m, 2H), 2.07-2.02 (m, 1H), 1.91-1.68 (m, 5 H), 1.56-1.47 (m, 1H), 1.23 (s, 4H), 1.09-1.06 (d, 6H).

(S)—N1-(2-(2,7-Dioxoazepan-3-yl)-1,3-dioxoisoindolin-4-yl)-N4-(2-oxo-1-((1-(4-(3-oxo-9-phenyl-2,3-dihydro-[1,2,4]triazolo[3,4-f][1,6]naphthyridin-8-yl)phenyl)cyclobutyl)amino)-6,9,12,15-tetraoxa-3-azaheptadecan-17-yl)succinamide (Compound 74)

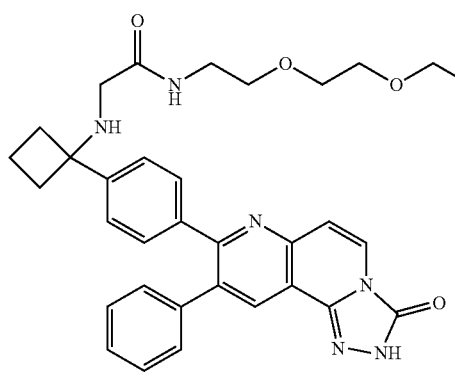

To a solution of tert-butyl (2-oxo-1-((1-(4-(3-oxo-9-phenyl-2,3-dihydro-[1,2,4]triazolo[3,4-f][1,6]naphthyridin-8-yl)phenyl)cyclobutyl)amino)-6,9,12,15-tetraoxa-3-azaheptadecan-17-yl)carbamate (86 mg, 0.113 mmol) in DCM (6 mL) at 0° C. was added TFA (1.5 mL). The mixture was stirred at rt for 1 hr, then the solvent was removed and the residue was dried under vacuum providing N-(14-amino-3,6,9,12-tetraoxatetradecyl)-2-((1-(4-(3-oxo-9-phenyl-2,3-dihydro-[1,2,4]triazolo[3,4-f][1,6]naphthyridin-8-yl)phenyl)cyclobutyl)amino)acetamide (77 mg, 100% yield) as a light yellow oil. MS (ESI) m/z 685.4[M+H]$^+$ To a solution of N-(14-amino-3,6,9,12-tetraoxatetradecyl)-2-((1-(4-(3-oxo-9-phenyl-2,3-dihydro-[1,2,4]triazolo[3,4-f][1,6]naphthyridin-8-yl)phenyl)cyclobutyl)amino)acetamide (65.4 mg, 0.096 mmol) in DMF (5 mL) at 0° C. was added DIEA (25 mg, 0.192 mmol), (S)-4-((2-(2,7-dioxoazepan-3-yl)-1,3-dioxoisoindolin-4-yl)amino)-4-oxobutanoic acid (40.9 mg, 0.106 mmol), and HATU (60 mg, 0.159 mmol). The resulting solution was stirred at rt for 16 hrs, the solvent was removed and the residue was purified by preparative TLC (DCM:MeOH=10:1) to afford the title compound (55 mg, 54.5% yield) as a light yellow solid. MS (ESI) m/z 1053.7[M+H]$^+$. $^1$H NMR (400 MHz, DMSO-d$_6$) δ 9.73 (s, 1H), 8.46 (d, J=8.4 Hz, 1H), 8.36 (s, 1H), 8.31-8.23 (m, 2H), 8.02-7.96 (m, 2H), 7.80 (t, J=8.0 Hz, 1H), 7.58 (d, J=7.2 Hz, 1H), 7.47 (s, 4H), 5.00 (m, 1H), 7.37-7.31 (m, 6H), 7.02 (d, J=7.6 Hz, 1H), 5.20 (dd, J=3.2, 11.6 Hz, 1H), 4.62 (s, 2H), 3.53-3.37 (m, 16H), 3.27-3.24 (m, 2H), 3.21-3.17 (m, 4H), 2.68-2.65 (m, 3H), 2.56-2.51 (m, 3H), 2.49-2.45 (m, 2H), 2.18-2.09 (m, 2H), 1.98-1.92 (m, 1H), 1.81-1.74 (m, 1H), 1.26-1.23 (m, 3H).

N-(4-(2-((S)-4-(4-chlorophenyl)-2,3,9-trimethyl-6H-thieno[3,2-f][1,2,4]triazolo[4,3-a][1,4]diazepin-6-yl)acetamido)butyl)-3-(2-((S)-2,7-dioxoazepan-3-yl)-1,3-dioxoisoindolin-4-yl)propanamide (Compound 75)

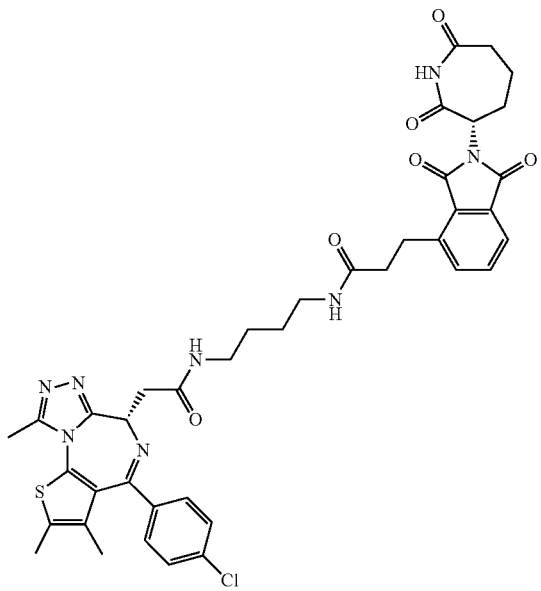 [SMILES: Cc1sc2c(c1C)C(c1ccc(Cl)cc1)=N[C@@H](CC(=O)NCCCCNC(=O)CCc1cccc3c1C(=O)N([C@H]1CCCC(=O)NC1=O)C3=O)c1nnc(C)n1-2]

To a solution of 3-iodophthalic acid (5.0 g, 17.1 mmol) in THF (75 mL) was added acetic anhydride (25 mL) at rt. The mixture was heated to 85° C. and stirred for 6 hrs. The reaction was cooled to rt and concentrated, providing 4-iodoisobenzofuran-1,3-dione (4.59 g, 98% yield) as a yellow solid. MS (ESI) m/z=275 [M+H]$^+$. $^1$H NMR (DMSO-d$_{6, 400}$ MHz) δ: 8.39 (d, J=8.0 Hz, 1 H), 8.06 (d, J=7.2 Hz, 1 H), 7.66 (t, J=7.6 Hz, 1 H).

To a solution of 4-iodoisobenzofuran-1,3-dione (2.97 g, 10.84 mmol) and (S)-3-aminoazepan-2-one (1.39 g, 10.84 mmol) in ACN (15 mL) and AcOH (21 mL) at rt. The suspension was heated to 80° C. and stirred overnight. Cooled to rt, sodium acetate (2.22 g, 27.1 mmol) and AcOH (10 mL) were added. The reaction mixture was heated to 80° C. and stirred overnight. TLC showed the starting material was consumed and a new spot was present. Upon removal of the solvent, the residue was diluted with water (8 mL) and stirred 30 minutes. The mixture was extracted with EA and concentrated providing (S)-4-iodo-2-(2-oxoazepan-3-yl) isoindoline-1,3-dione (2.4 g, 57.7% yield) as a white solid. MS (ESI) m/z=385 [M+H]$^+$.

To a solution of (S)-4-iodo-2-(2-oxoazepan-3-yl)isoindoline-1,3-dione (2.1 g, 5.469 mmol) and benzyl acrylate (1.33 g, 8.204 mmol) in DMF (60 mL) at 0° C. was added K$_2$CO$_3$ (1.51 g, 10.94 mmol). The reaction vessel was purged and exchanged with nitrogen twice and Pd(OAc)$_2$ (245.6 mg, 1.094 mmol) was added. The mixture was heated to 120° C. for 16 hrs, cooled to rt, quenched with water, and extracted with EA twice. The combined organic layers were dried, filtered, and concentrated providing the crude product which was purified on silica gel with EA/petroleum ether (10%-100%) providing (S,E)-benzyl 3-(1,3-dioxo-2-(2-oxoazepan-3-yl)isoindolin-4-yl)acrylate (1.01 g, 44.3% yield) as a white solid. MS (ESI) m/z=419 [M+H]$^+$.

To a solution of (S,E)-benzyl 3-(1,3-dioxo-2-(2-oxoazepan-3-yl) isoindolin-4-yl)acrylate (1.01 g, 2.416 mmol) in 1,2-dichloroethane (80 mL), DMSO (8 mL), and 2 drops water was added Dess-Martin reagent (2.05 g, 4.832 mmol) at 0° C. The mixture was heated to 80° C. for 16 hrs, cooled rt and Dess-Martin reagent (1.03 g, 2.416 mmol) was added, followed by heating at 80° C. for 16 hrs. The reaction was cooled to rt, filtered, and the filtrate was treated with saturated aqueous sodium thiosulfate and stirred at 0° C. for 30 min. The resulting mixture was extracted with DCM twice and the combined organic layers were washed with 1/1 sodium bicarbonate (sat.)/sodium thiosulfate (10%), brine, dried, filtered, and concentrated providing (S,E)-benzyl 3-(2-(2,7-dioxoazepan-3-yl)-1,3-dioxoisoindolin-4-yl)acrylate (651 mg, 62.6% yield) as a white solid. MS (ESI) m/z=433 [M+H]$^+$.

To a solution of (S,E)-benzyl 3-(2-(2,7-dioxoazepan-3-yl)-1,3-dioxoisoindolin-4-yl)acrylate (651 mg, 1.057 mmol) in THF (140 mL) at rt was added Pd/C (300 mg). The mixture was reacted under H$_2$(g) overnight, filtered, and concentrated providing (S)-3-(2-(2,7-dioxoazepan-3-yl)-1,3-dioxoisoindolin-4-yl)propanoic acid (500 mg, 96.4% yield) as a white solid. MS (ESI) m/z=345 [M+H]$^+$.

To a solution of (S)-3-(2-(2,7-dioxoazepan-3-yl)-1,3-dioxoisoindolin-4-yl)propanoic acid (100 mg, 0.29 mmol) and tert-butyl (4-aminobutyl)carbamate (54.65 mg, 0.29 mmol) in DMF (8 mL) was added DIEA (75 mg, 0.5814 mmol) and HATU (132.6 mg, 0.3488 mmol) at rt. The mixture was stirred at rt for 16 hrs, quenched with water, and extracted with EA (×2). The combined organic layers were dried, filtered, and concentrated providing the crude product which was purified by preparative TLC with EA providing (S)-tert-butyl (4-(3-(2-(2,7-dioxoazepan-3-yl)-1,3-dioxoisoindolin-4-yl)propanamido)butyl)carbamate (100 mg, 66.9% yield) as a white solid. MS (ESI) m/z=515 [M+H]$^+$.

To a solution of (S)-tert-butyl (4-(3-(2-(2,7-dioxoazepan-3-yl)-1,3-dioxoisoindolin-4-yl)propanamido)butyl)carbamate (80 mg, 0.1556 mmol) in DCM (6 mL) was added TFA (1.5 mL) at 0° C. The mixture was warmed to rt and stirred for 1 hr. The starting material was consumed completely and the desired mass value was detected from LC-MS. The solvent was removed and the residue was directly used in the next step.

To a solution of (S)—N-(4-aminobutyl)-3-(2-(2,7-dioxoazepan-3-yl)-1,3-dioxoisoindolin-4-yl)propanamide (64.42 mg, 0.1556 mmol) and (S)-2-(4-(4-chlorophenyl)-2,3,9-trimethyl-6H-thieno[3,2-f][1,2,4]triazolo[4,3-a][1,4]diazepin-6-yl)AcOH (62 mg, 0.16 mmol) in DMF (6 mL) at rt was added diethylisopropylamine (DIEA) (40 mg, 0.31 mmol) and HATU) (71 mg, 0.19 mmol). The mixture was warmed to 20° C., stirred for 16 hrs, quenched with water, and extracted with EA (×2). The combined organic layers were dried, filtered, and concentrated to afford the crude product, which was purified by preparative TLC with EA providing the title compound (23.5 mg, 15.2% yield) as a white solid. MS (ESI) m/z=797 [M+H]$^+$. $^1$H NMR (DMSO-d$_6$, 400 MHz) δ: 10.85 (s, 1 H), 8.20 (t, J=5.2 Hz, 1 H), 7.84 (t, J=3.6 Hz, 1 H), 7.74 (s, 2 H), 7.66 (s, 1 H), 7.49 (d, J=8.4 Hz, 2 H), 7.41 (d, J=8.4 Hz, 2 H), 5.21 (d, J=7.6 Hz, 1 H), 4.51 (t, J=5.2 Hz, 1 H), 3.27-3.05 (m, 10 H), 2.69-2.59 (m, 1 H), 2.50 (s, 3 H), 2.45 (d, J=7.6 Hz, 2 H), 2.41 (s, 3 H), 2.12-2.08 (m, 1 H), 2.01-1.85 (m, 2 H), 1.61 (s, 3 H), 1.39 (s, 4 H).

Pharmaceutical Compositions

Parenteral Pharmaceutical Composition

To prepare a parenteral pharmaceutical composition suitable for administration by injection (subcutaneous, intravenous, or the like), 0.1 mg to 100 mg of a water-soluble salt/soluble material itself/solubilized complex of a compound of a preferred embodiment is dissolved in sterile water and then mixed with 10 mL of 0.9% sterile saline. The mixture is incorporated into a dosage unit form suitable for administration by injection.

Injectable Pharmaceutical Composition

To prepare an injectable formulation, 0.1 mg to 100 mg of a compound of Formula I, 2.0 mL of sodium acetate buffer solution (0.4 M), HCl (1 N) or NaOH (1 M) (q.s. to suitable pH), water (distilled, sterile) (q.s. to 20 mL) are mixed. All of the above ingredients, except water, are combined and stirred and if necessary, with slight heating if necessary. A sufficient quantity of water is then added.

Oral Pharmaceutical Composition

To prepare a pharmaceutical composition for oral delivery, 0.1 mg to 100 mg of a compound of a preferred embodiment is mixed with 750 mg of starch. The mixture is incorporated into an oral dosage unit, such as a hard gelatin capsule, or 0.1 mg to 100 mg of compound is granulated with binder solution such as starch solution along with suitable diluents such as microcrystalline cellulose or like, disintegrants such as croscarmellose sodium, dry the resultant mixture and add lubricant and compress into tablet which is suitable for oral administration.

Sublingual (Hard Lozenge) Pharmaceutical Composition

To prepare a pharmaceutical composition for buccal delivery, such as a hard lozenge, 0.1 mg to 100 mg of a compound of a preferred embodiment is mixed with 420 mg of powdered sugar/mannitol/xylitol or such sugars that provide negative heat of solution to the system, 1.6 mL of light corn syrup, 2.4 mL distilled water, and 0.42 mL mint extract or other flavorants. The mixture is blended and poured into a mold to form a lozenge suitable for buccal administration.

Fast-Disintegrating Sublingual Tablet

A fast-disintegrating sublingual tablet is prepared by mixing 48.5% by weigh of a compound of a preferred embodiment, 20% by weight of microcrystalline cellulose (KG-802), 24.5% by weight of either mannitol or modified dextrose or combination that help dissolve the compressed tablet faster in the mouth, 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of the compound of a preferred embodiment with the total quantity of microcrystalline cellulose (MCC) and mannitol/modified dextrose or combination, and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Pharmaceutical Composition

To prepare a pharmaceutical composition for inhalation delivery, 0.1 mg to 100 mg of a compound of a preferred embodiment is mixed with 50 mg of anhydrous citric acid and 100 mL of 0.9% sodium chloride solution. The mixture is incorporated into an inhalation delivery unit, such as a nebulizer, which is suitable for inhalation administration.

Nebulizer Suspension Pharmaceutical Composition

In another embodiment, a compound of a preferred embodiment (0.1 mg to 100 mg) is suspended in sterile water (100 mL); Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Transdermal Patch Pharmaceutical Composition

To prepare a pharmaceutical composition for transdermal delivery, 0.1 mg to 100 mg of a compound of a preferred embodiment is embedded in, or deposited on, a patch with a single adhesive face. The resulting patch is then attached to the skin via the adhesive face for transdermal administration.

Topical Gel Pharmaceutical Composition

To prepare a pharmaceutical topical gel composition, 0.1 mg to 100 mg of a compound of a preferred embodiment is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution

To prepare a pharmaceutical ophthalmic solution composition, 0.1 mg to 100 mg of a compound of a preferred embodiment is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 0.1 mg to 100 mg of a compound of a preferred embodiment is mixed with 30 mL of a 0.05M phosphate buffer solution (pH 4.4). The solution is placed in a nasal administrator designed to deliver 100 µl of spray for each application.

Cell-Based Assays

Western Blot Protocol: K562, U266, and Jurkat cell lines were grown in RPMI 1640 supplemented with streptomycin, penicillin and 10% fetal bovine serum.

Cells were cultured at approximately $10^6$ cells per ml, DMSO or the indicated compound was added to the cells and allowed to incubate for the indicated period. Whole cell extract was prepared with either M-Per Reagent or IP Lysis Buffer according to manufacturer's protocol (Pierce). Briefly, ~$5 \times 10^6$ cells were washed once in PBS, the cell pellet was resuspended in M-PER solution or IP Lysis Buffer and allowed to incubate for 10 min at rt. Cell debris was removed by centrifugation and the cleared whole cell lysate was transferred to a new tube for further analysis.

For western blot analysis, whole cell extracts were separated on 4-12% SDS-polyacrylamide gels, transferred to nitrocellulose and probed with the indicated primary antibodies. Membranes were subsequently washed and probed with the appropriate horseradish peroxidase (HRP)-conjugated secondary antibody. The signal was detected using the WesternBright Sirius Reagent (Advansta).

The following antibodies were used in these studies:

Cereblon rabbit polyclonal antibody: App. Biol. Materials, # Y055422

I2PP2A mouse monoclonal antibody: S.C. Biotech. sc-133138.

Casein kinase 1-alpha goat polyclonal antibody: S.C. Biotech., sc-6477.

Casein kinase 1-epsilon goat polyclonal antibody: S.C. Biotech., sc-6471

Ikaros rabbit monoclonal antibody: Cell Signaling, #9034, D10E5

Aiolos rabbit polyclonal antibody: Cell Signaling, #12720

Donkey anti-goat IgG-HRP: S.C. Biotech., sc-2056

Goat anti-rabbit IgG-HRP: Cell Signaling, #7074

Goat anti-mouse IgG-HRP: Sigma, A4416

PBMCs induced with LPS: Frozen primary blood mononuclear cells (PBMCs) were purchased from AllCells. Cells were quick thawed, washed 1-time with RPMI-1640/10% FBS/1% Penicillin/1% Streptomycin and plated in 96 well plates at 200,000 cells per well. Cells were pretreated with DMSO only, Pomalidomide (Pom), lenalidomide (Len) or the indicated compounds for 1 hr and then induced with 100 ng/ml lipopolysaccharide (LPS) or 250 ng/ml LPS as indicated for 18-24 hrs. The supernatant was analyzed for IL-1 beta, IL-6 and TNF alpha using Meso Scale assay according to manufacturer's protocol. The negative control wells were treated with DMSO. Compound activity is measured as a percentage of the DMSO control.

PBMCs: AllCells PB003F, Normal Peripheral Blood MNC

Media: RPMI 1640/10% FBS/1% Pen-Strep

Assay kit: Meso Scale Discovery 4-Plex ProInflam II (IL-1b, IL-6, IL-8, TNFα), K15053D-2

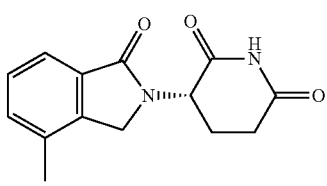

Compound A

PBMCs induced with Anti-CD3 Antibody: 96-well plates were precoated with anti-CD3 (OKT-3) antibody by overnight incubation with anti-CD3 antibody at 1 ug per ml in PBS. PBMCs were prepared as described above and subsequently plated into the anti-CD3 coated 96-well plates at 300,000 to 750,000 cells per well, followed by the addition of DMSO only, pomalidomide, lenalidomide or the indicated Compounds. After 24 or 72 hrs, supernatant was analyzed using the IL-2 Meso Scale assay according to manufacturer's protocol. The negative control wells were treated with DMSO. Compound activity is measured as a percentage of the DMSO control. (compound activity measured as fold change of DMSO, aCD3 treated cells.

PBMCs: AllCells PB003F, Normal Peripheral Blood MNC

Media: RPMI 1640/10% FBS/1% Pen-Strep
Anti-CD3 antibody: eBioscience 16-0037-85, 1 mg/ml
Assay kit: Meso Scale Discovery I12 Single Plex—K151QQD-2

For examples using primary blood mononuclear cells (PBMCs), frozen PBMCs were purchased from AllCells. Cells were thawed in RPMI overnight and plated in 96 well plates at 100,000-200,000 cells per well. Cells were pretreated with compounds for 1 hr and then induced with 200 uM lipopolysaccharide (LPS) for 18-24 hrs. Cytokines in the media were measured according to MesoScale protocol. Pom-10 is 10 uM pomalidomide; Thal-30 is 30 μM thalidomide. The negative control wells were treated with DMSO. Compound activity is measured as a percentage of LPS-induced activity.

Figure 2:
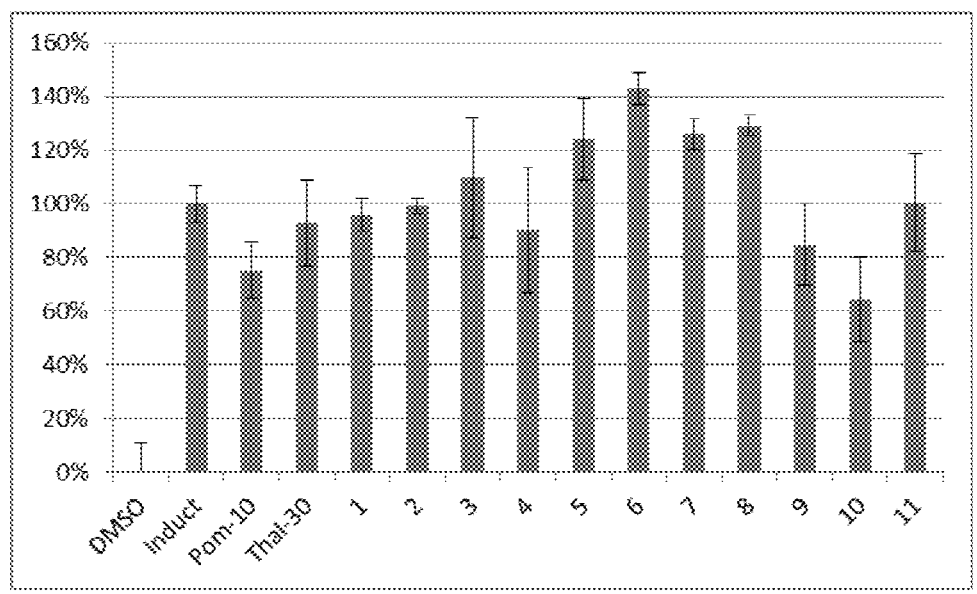
FIG. 2 represents the activity against IL-6 in CD14 macrophages, plated in 96 well plates and treated with 100 ng/mL macrophage colony-stimulating factor (M-CSF) for up to 1 week to differentiate cells into macrophages. Cells were pretreated with compounds for 1 hr and then induced with either 200 ng/ml LPS or 20 ng/ml of TNF-alpha for 18-24 hrs. Cytokines in the media were measured according to MesoScale protocol. Pom-10 is 10 uM pomalidomide; Thal-30 is 30 uM thalidomide. The negative control wells were treated with DMSO. Cells were treated with the indicated Compound (20 uM). Compound activity is measured as a percentage of LPS-induced activity.
Figure 3:
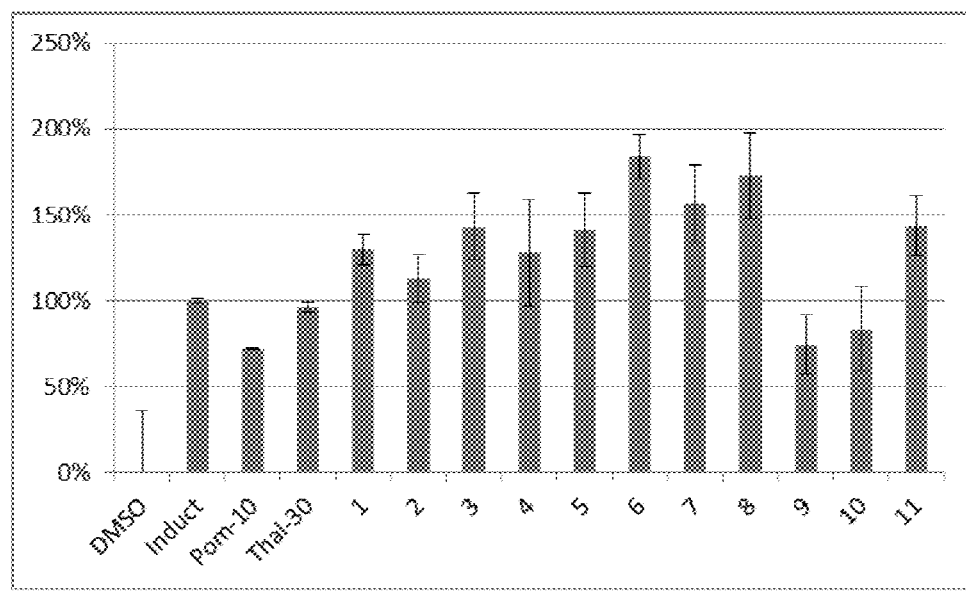
FIG. 3 represents the activity against TNF-alpha in CD14 macrophages, plated in 96 well plates and treated with 100 ng/mL macrophage colony-stimulating factor (M-CSF) for up to 1 week to differentiate cells into macrophages. Cells were pretreated with compounds for 1 hr and then induced with either 200 ng/ml LPS for 18-24 hrs. Cytokines in the media were measured according to MesoScale protocol. Pom-10 is 10 uM pomalidomide; Thal-30 is 30 uM thalidomide. The negative control wells were treated with DMSO. Cells were treated with the indicated compound (20 uM). Compound activity is measured as a percentage of LPS-induced activity.
Figure 4:
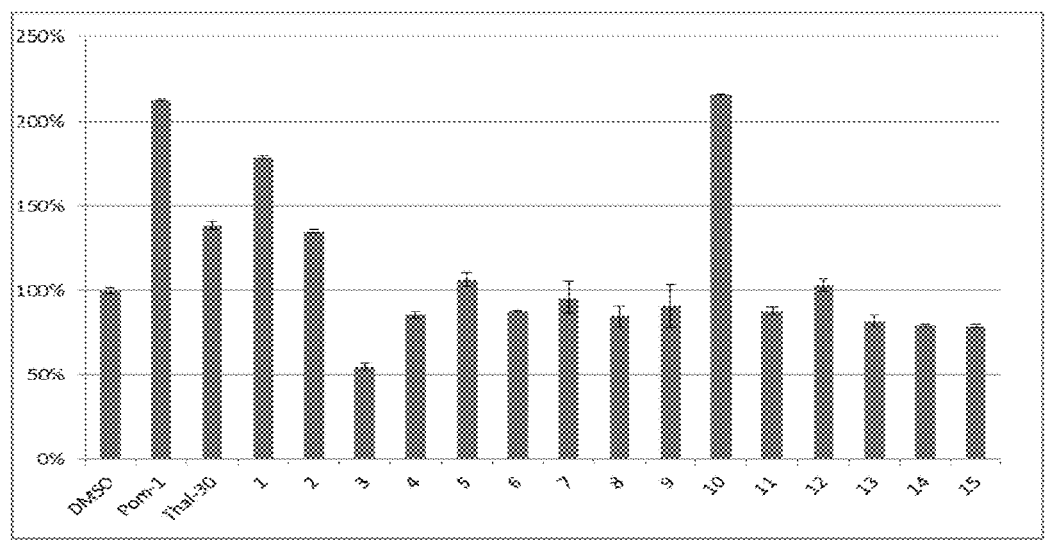
FIG. 4 represents Anti-CD3-induced IL-2 secretion in PBMCs. 1 ug/ml anti-CD3 (OKT-3) antibody in PBS coated onto 96-well plates overnight at 4° C. 150,000 PBMCs were added to each well, followed by addition of DMSO only, pomalidomide (1 uM), thalidomide (30 uM), or Compounds 1-15 (20 uM). Induction was measured after 48 hrs.

For examples using CD14 macrophages, frozen CD14+ mobilized peripheral blood monocytes were purchased from AllCells. Cells were plated in 96 well plates and treated with 100 μM macrophage colony-stimulating factor (M-CSF) for up to 1 week to differentiate cells into macrophages. Cells were pretreated with compounds for 1 hr and then induced with either 200 μM LPS or 20 uM of TNF-alpha for 18-24 hrs. Cytokines in the media were measured according to MesoScale protocol. Pom-10 is 10 μM pomalidomide; Thal-30 is 30 μM thalidomide. The negative control wells were treated with DMSO. Compound activity is measured as a percentage of LPS-induced activity. IL-1-beta activity is shown in FIGS. 1 and 16; IL-6 activity is shown in FIGS. 2 and 16; and TNF-alpha activity is shown in FIGS. 3 and 16.

Figure 5:
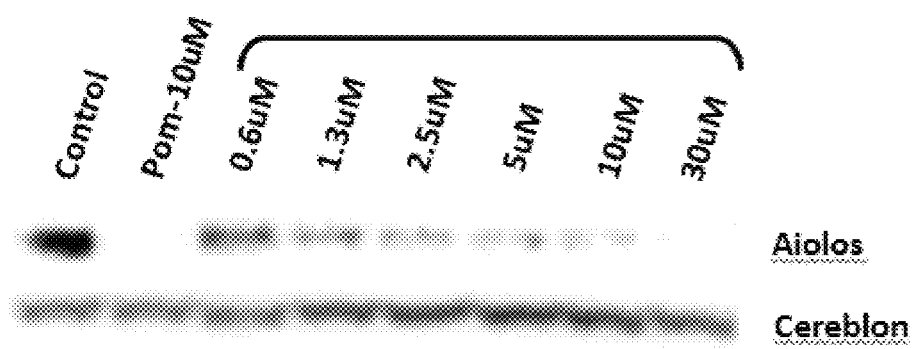
FIG. 5 represents a Western Blot from U266 cells treated with Control (DMSO only), pomalidomide, or Compound 10 at the indicated concentration for 4 hrs. Cells were lysed using MPER (Pierce) and a Western Blot was performed using anti-aiolos and anti-cereblon antibodies.
Figure 6:
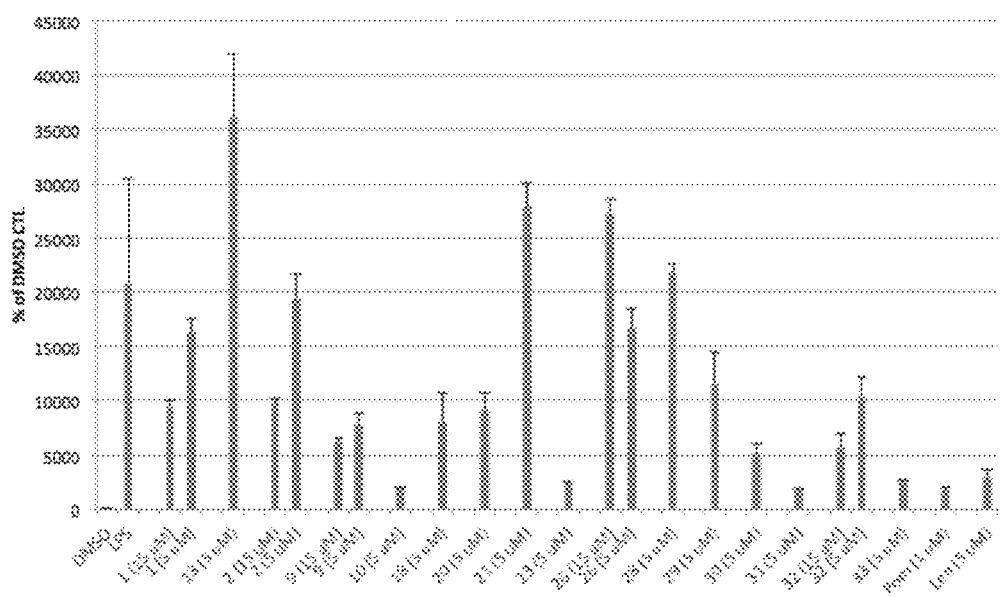
FIG. 6 represents IL-1-beta activity in human PBMCs stimulated with LPS (100 ng/mL), 18 hrs after dosing with Controls (DMSO or LPS only), Compound A, pomalidomide, lenalidomide, or one of Compounds 1, 2, 9, 10, 13, 18, 20, 21, 23, 26, 28, 29, 30, 31, 32, or 33.
Figure 7:
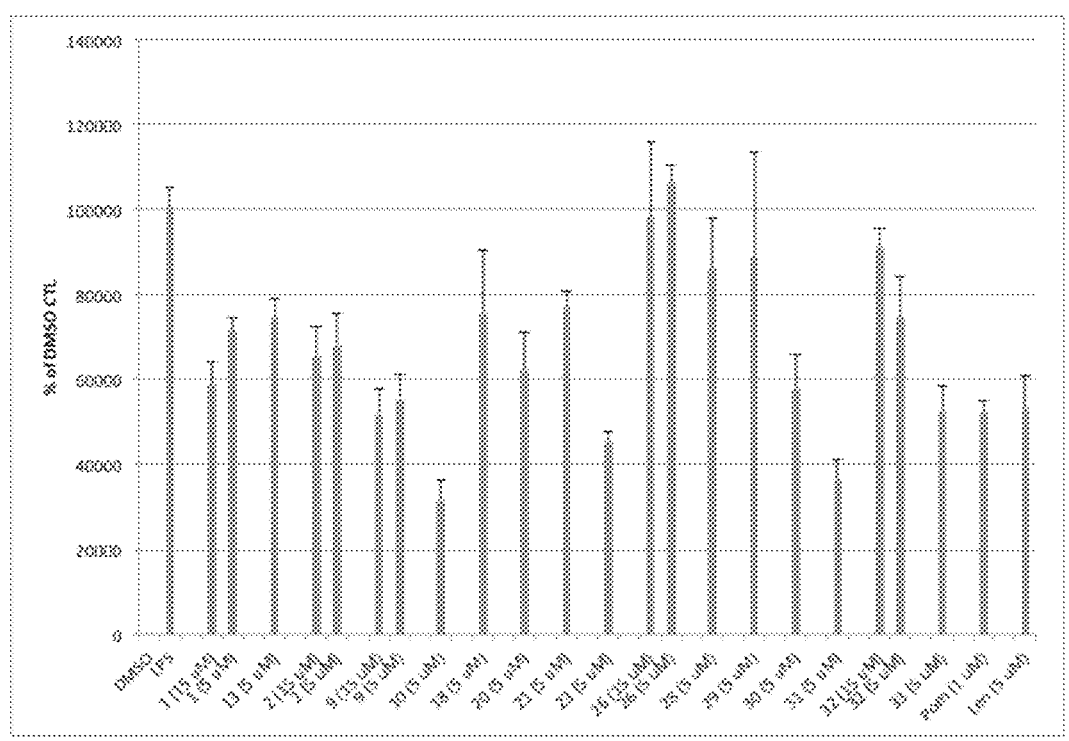
FIG. 7 represents IL-6 activity in human PBMCs stimulated with LPS (100 ng/mL), 18 hrs after dosing with Controls (DMSO or LPS only), Compound A, pomalidomide, lenalidomide, or one of Compounds 1, 2, 9, 10, 13, 18, 20, 21, 23, 26, 28, 29, 30, 31, 32, or 33.
Figure 8:
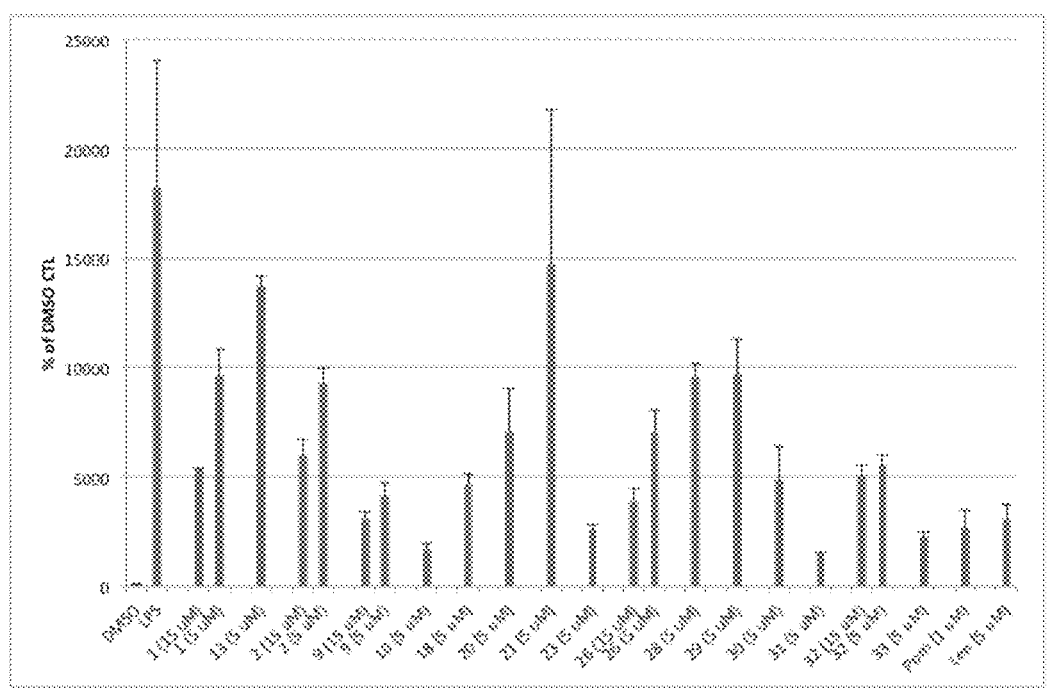
FIG. 8 represents TNF-alpha activity in human PBMCs stimulated with LPS (100 ng/mL), 18 hrs after dosing with Controls (DMSO or LPS only), Compound A, lenalidomide, or one of Compounds 1, 2, 9, 10, 13, 18, 20, 21, 23, 26, 28, 29, 30, 31, 32, or 33.
Figure 9:
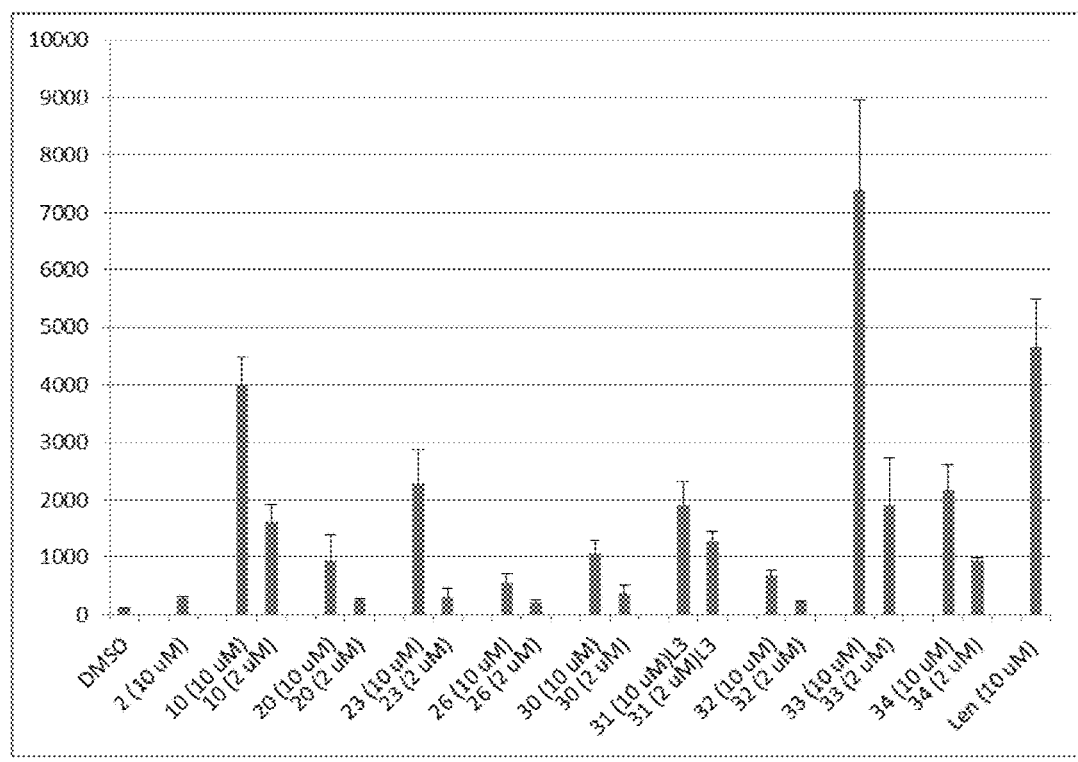
FIG. 9 represents IL-2 expression from anti-CD3-stimulated human PBMCs after treatment (72 hrs post-induction) with Control (DMSO only), pomalidomide, lenalidomide, or one of Compounds 2, 10, 20, 23, 26, 30, 31, 32, 33, or 34.
Figure 10:
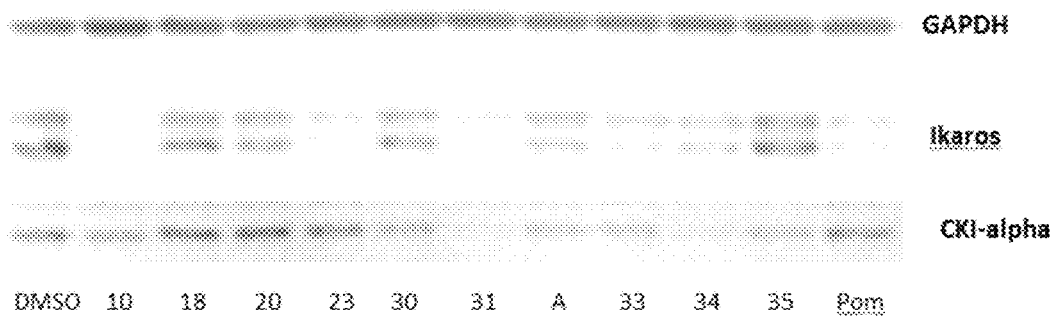
FIG. 10 represents a Western Blot from Jurkat cells treated with Control (DMSO only), Compound A, pomalidomide, or one of Compounds 10, 18, 20, 23, 30, 31, 33, 34, or 35. Cells were lysed using MPER (Pierce) and a Western Blot was performed using anti-ikaros, anti-caseine kinase 1-alpha, and anti-GAPDH antibodies.
Figure 11:
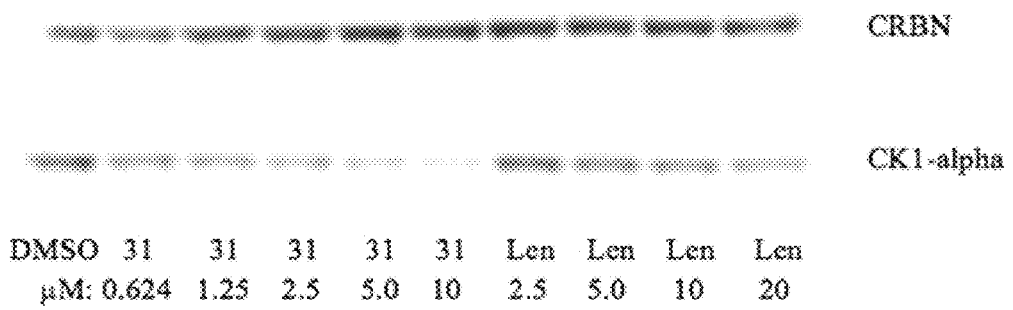
FIG. 11 represents a Western Blot of a dose-response from K562 cells treated with Control (DMSO only), lenalidomide, or Compound 31. Cells were lysed using MPER (Pierce) and a Western Blot was performed using anti-caseine kinase 1-alpha and anti-cereblon antibodies.
Figure 12:
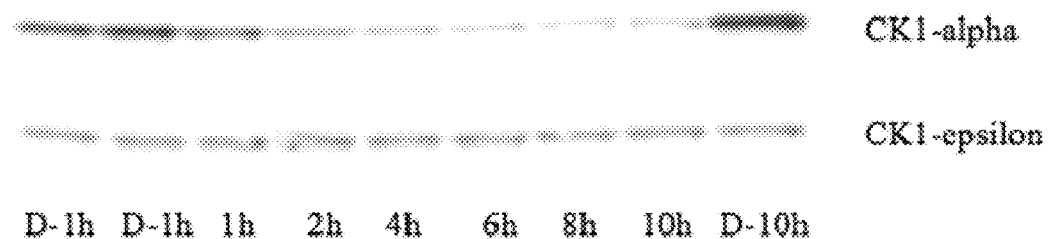
FIG. 12 represents a Western Blot of a time-course from K562 cells treated with Compound 31. Cells were lysed using MPER (Pierce) and a Western Blot was performed using anti-caseine kinase 1-alpha and anti-caseine kinase 1-epsilon.
Figure 13A:
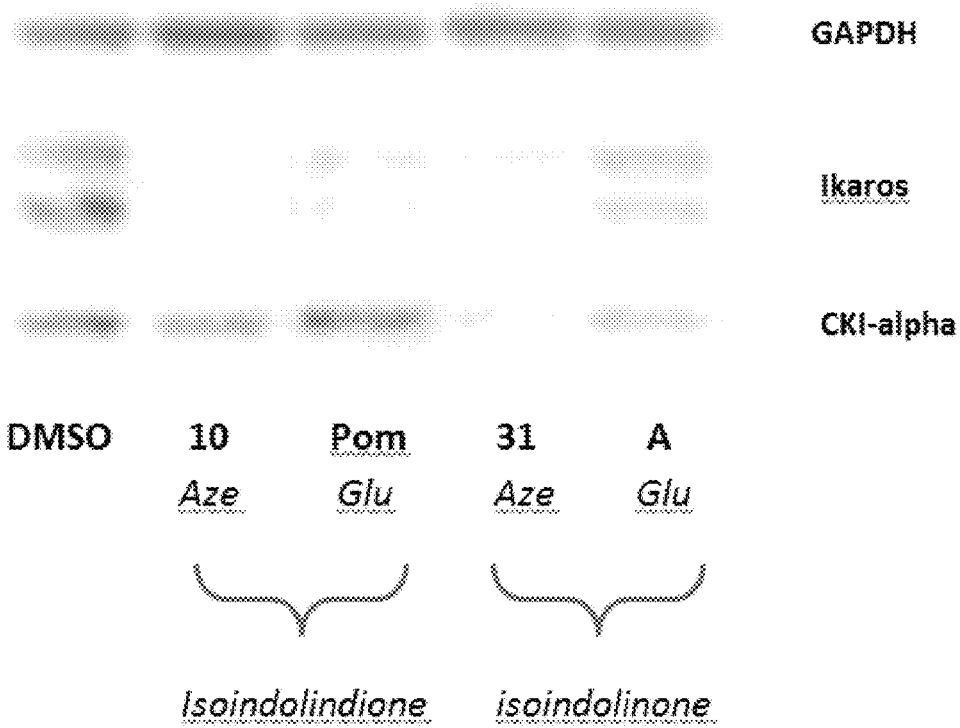
FIG. 13A represents a Western Blot from Jurkat cells treated for 5 hrs with Control (DMSO only), Compound A (10 uM), pomalidomide (10 uM), or Compounds 10 and 31 (10 uM). Cells were lysed using M-PER (Pierce) and a Western Blot was performed using anti-Ikaros, anti-casein kinase 1-alpha, and anti-GAPDH antibodies.
Figure 13B:
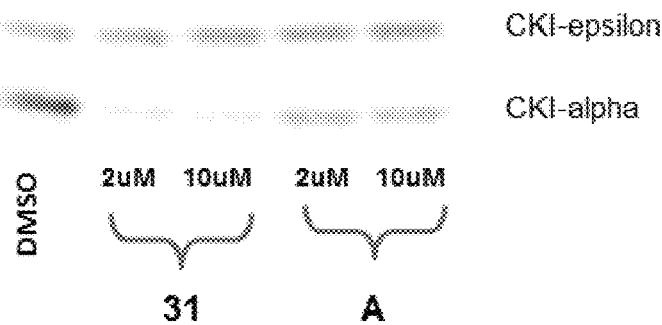
FIG. 13B represents a Western Blot from Jurkat cells treated with Control (DMSO only), Compound A, or Compound 31 for 5 hrs at the indicated concentration. Cells were then lysed using M-PER (Pierce) and a Western Blot was performed using anti-casein kinase 1-alpha, and anti-casein kinase 1-epsilon.
Figure 13C:
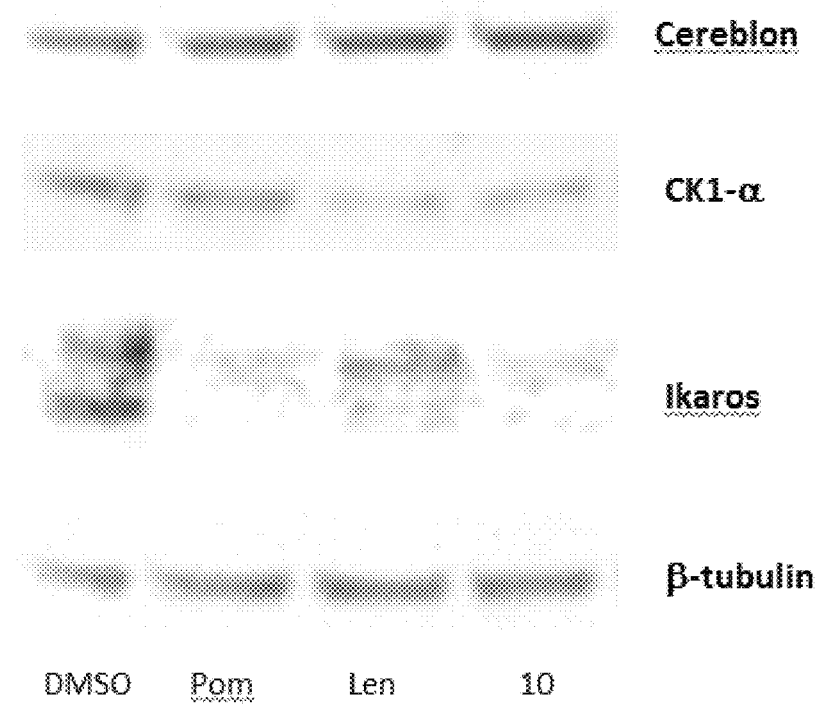
FIG. 13C represents a Western Blot from MM1S cells treated with Control (DMSO only), pomalidomide (Pom), lenalidomide (Len) or Compound 10 at 10 uM for 8 hrs. Cells were then lysed using M-PER (Pierce) and a Western Blot was performed using anti-casein kinase 1, anti-Ikaros, anti-cereblon, and anti-beta-tubulin antibodies.
Figure 14A:
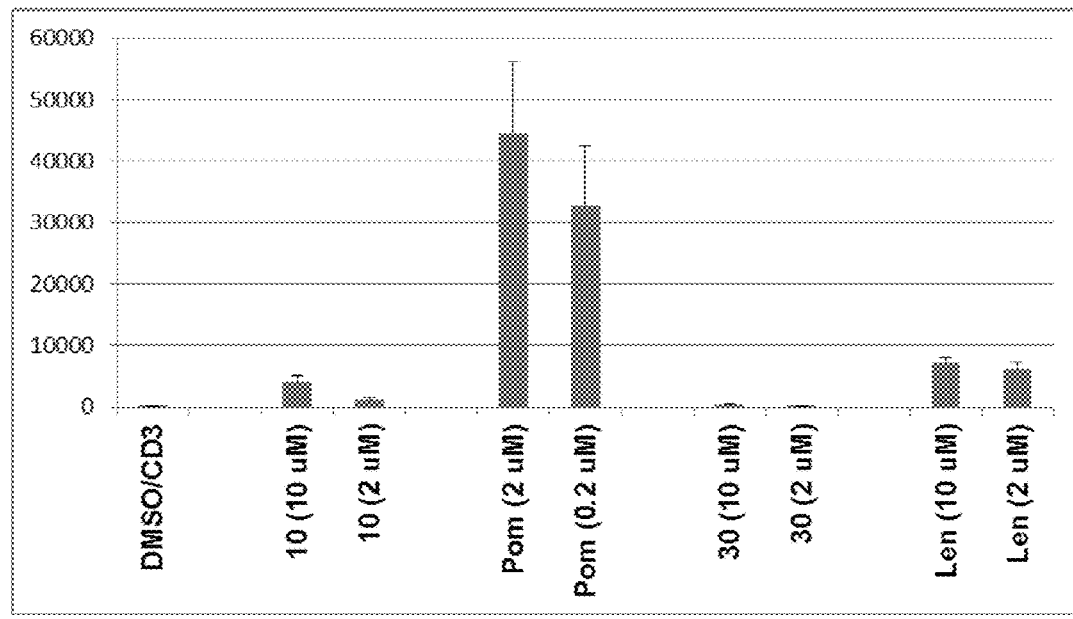
FIG. 14A represents anti-CD3-induced IL-2 secretion in PBMCs. A 96-well plate was coated with anti-CD3 (OKT-3) antibody by overnight incubation with anti-CD3 antibody at 1 ug per ml in PBS. PBMCs (donor 1) were prepared as described above and subsequently plated into the anti-CD3 antibody coated 96-well plate at 300,000 to 750,000 cells per well, followed by the addition of DMSO only, pomalidomide (Pom), lenalidomide (len), Compounds 10 or Compound 30 at the indicated concentration. After 72 hrs, supernatant was analyzed using the IL-2 Meso Scale assay according to manufacturer's protocol. The negative control wells were treated with DMSO. Compound activity is measured as a percentage of the DMSO control.
Figure 14B:
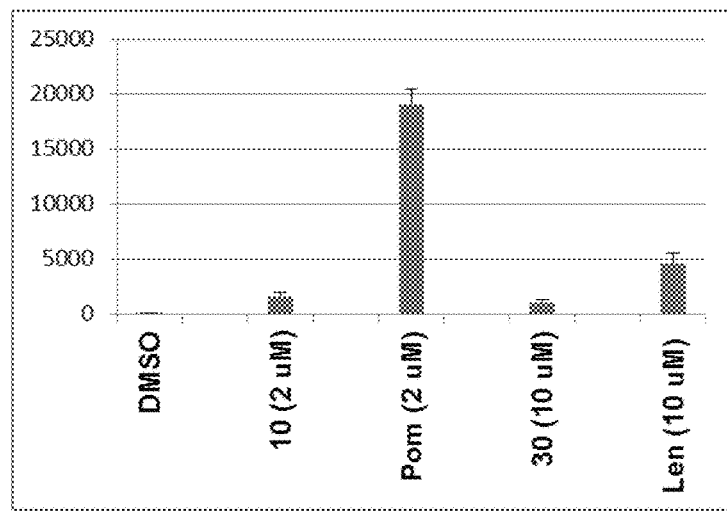
FIG. 14B represents anti-CD3-induced IL-2 secretion in PBMCs. A 96-well plate was coated with anti-CD3 (OKT-3) antibody by overnight incubation with anti-CD3 antibody at 1 ug per ml in PBS. PBMCs (donor 2) were prepared as described above and subsequently plated into the anti-CD3 antibody coated 96-well plate at 300,000 to 750,000 cells per well, followed by the addition of DMSO only, pomalidomide (Pom), lenalidomide (len), Compounds 10 or Compound 30 at the indicated concentration. After 72 hrs, supernatant was analyzed using the IL-2 Meso Scale assay according to manufacturer's protocol. The negative control wells were treated with DMSO. Compound activity is measured as a percentage of the DMSO control.
Figure 14C:
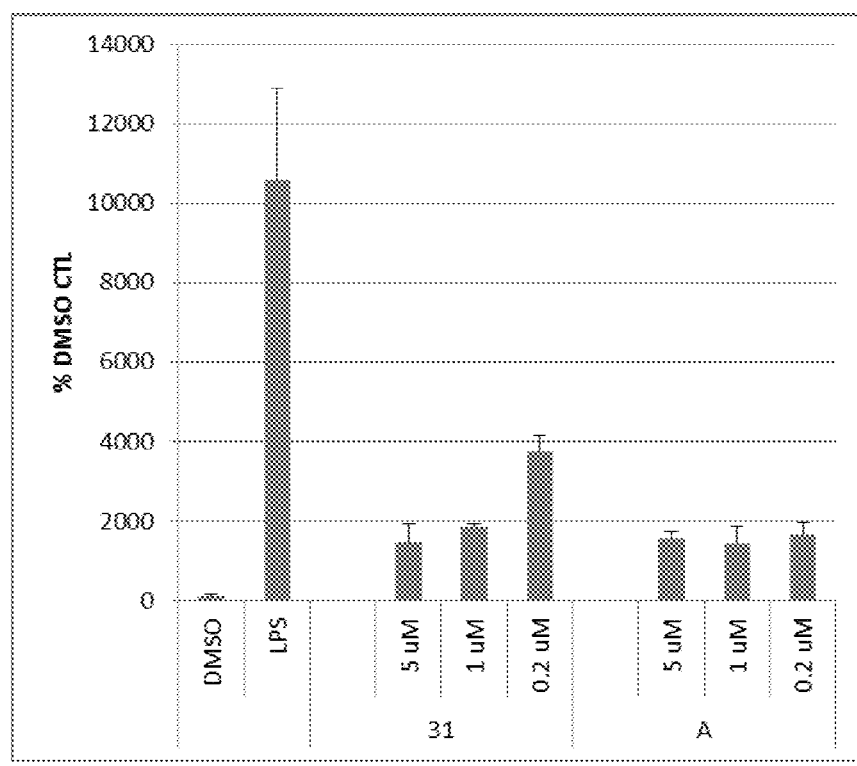
FIG. 14C represents TNF alpha activity in human PBMCs stimulated with LPS (100 ng/mL), 18 hrs after dosing with Controls (DMSO or LPS only), Compound A or Compound 31 at the indicated concentration.
Figure 14D:
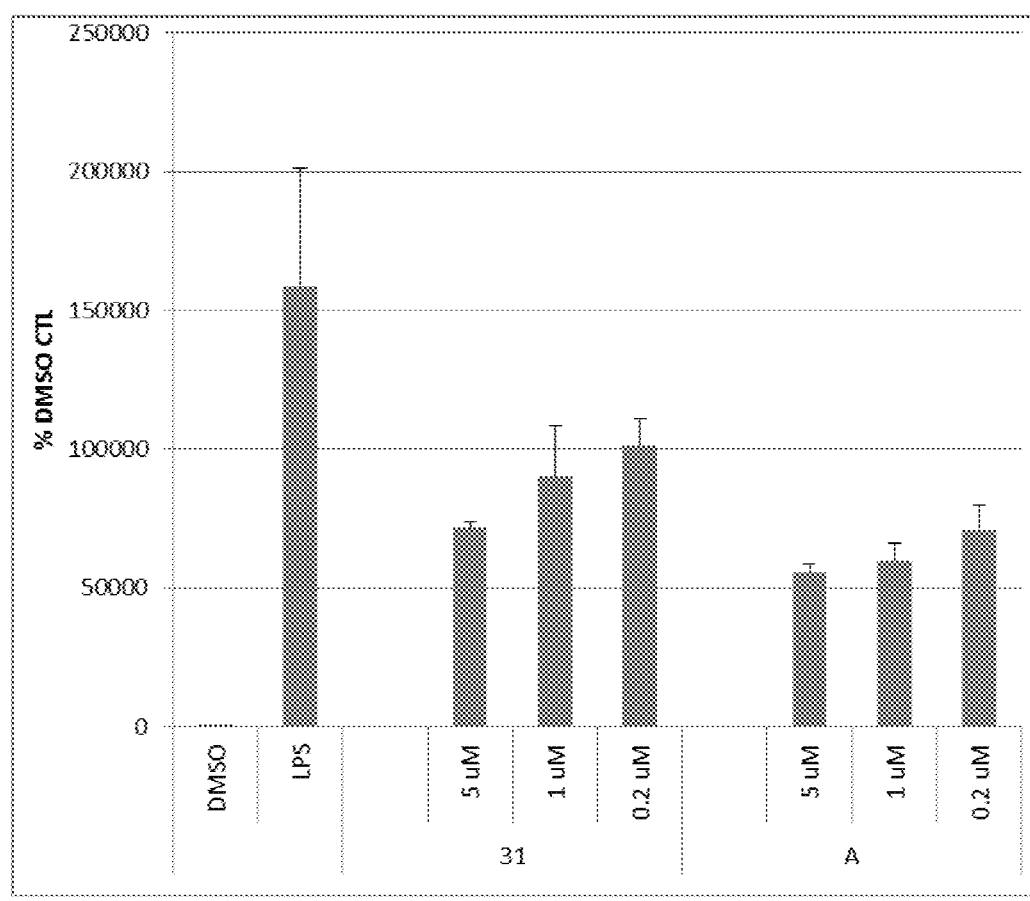
FIG. 14D represents IL-6 activity in human PBMCs stimulated with LPS (100 ng/mL), 18 hrs after dosing with Controls (DMSO or LPS only), Compound A or Compound 31 at the indicated concentration.
Figure 14E:
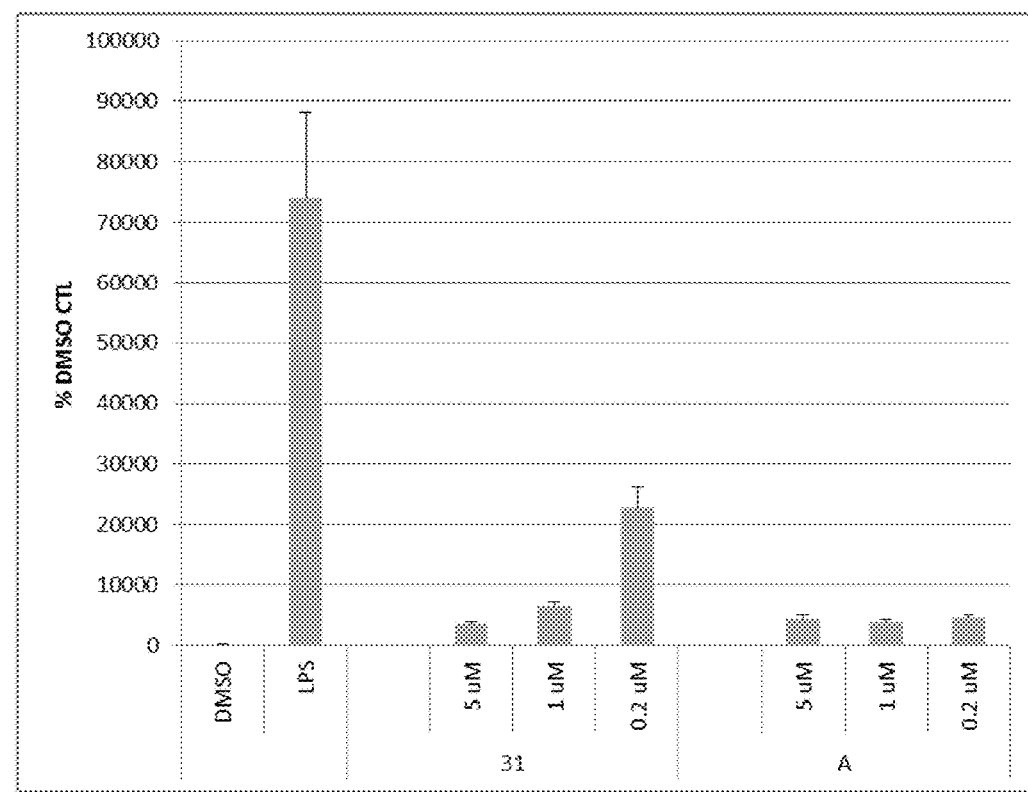
FIG. 14E represents IL-1-beta activity in human PBMCs stimulated with LPS (100 ng/mL), 18 hrs after dosing with Controls (DMSO or LPS only), Compound A or Compound 31 at the indicated concentration.
Figure 15A:
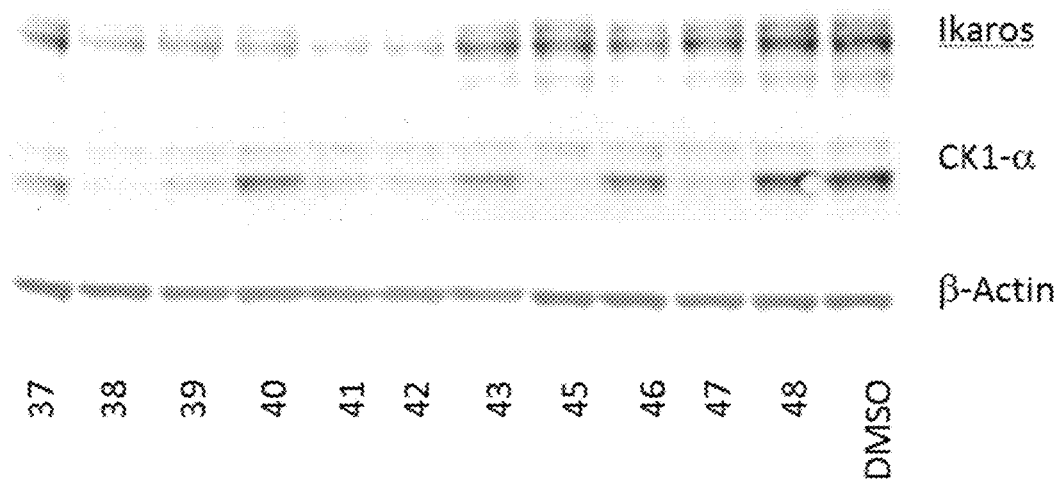
FIGS. 15A and 15B represent Western Blots from Jurkat cells treated with Control (DMSO only) or one of Compounds 37-43 or 45-57 (10 uM) for 5 hours. Cells were lysed using IP Lysis buffer (Pierce) and a Western Blot was performed using anti-ikaros, anti-caseine kinase 1-α, and anti-β-actin antibodies.
Figure 15B:
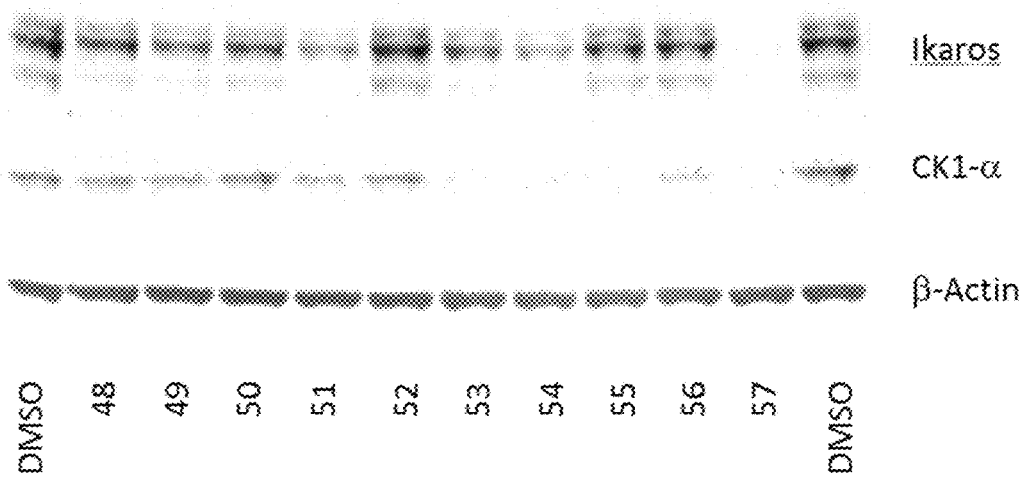

Anti-CD3-IL-2 Induction 1 ug/ml anti-CD3 (OKT-3) antibody in PBS coated onto 96-well plates overnight at 4° C. 150,000 PBMCs were added to each well, following by addition of DMSO only, pomalidomide (Pom), thalidomide (Thal), or Compounds 1-15, 37-43 or 45-57 (as described above). After 48 hrs, supernatant was analyzed using the IL-2 mesoscale assay according to manufacturer's protocol. Anti-CD3-IL-2 activity is shown in FIGS. 5 and 16.

Aiolos Western Blot

U266 cells were treated with Control (DMSO only), pomalidomide, or Compound 10 for 4 hrs. Cells were lysed using MPER (Pierce) and a Western blot was performed using anti-aiolos and anti-cereblon antibodies in standard Western Blot protocols (See FIG. 5).

Daudi Cell Proliferation

Daudi cells, a Burkitt lymphoma cell line, was treated for 4 days with the indicated compound (10 nM, 100 nM, 1 μM, 10 μM, and 100 μM) or vehicle (DMSO), and cell viability was determined using the WST-1 tetrazolium reagent (Roche), and results were expressed as the percentage viability relative to the vehicle control, which was set at 100%. Based on resulting data, an $IC_{50}$ was calculated for each compound.

$IC_{50}$ values less than or equal to 2 μM are represented by "A;" IC50 values greater than 2 μM and less than or equal to 30 μM are represented by "B;" and IC50 values greater than 30 μM are represented by "C."

| Compound | $IC_{50}$ (μM) |
| --- | --- |
| Lenalidomide | C |
| 43 | A |

| Compound | $IC_{50}$ (μM) |
| --- | --- |
| 42 | B |
| 45 | C |

Kinase Inhibition Assay

Kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding.

Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 mL. The assay plates were incubated at room temperature with shaking for 1 hour and the affinity beads were washed with wash buffer (lx PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. Compounds were tested at 500 nM.

| Compound | FES (Percent Control) | FGFR(G697C) (Percent Control) |
| --- | --- | --- |
| 66 | 15 | 4.8 |
| Fedratinib | 89 | 57 |

FGFR: Fibroblast growth factor receptor
Fedratinib:

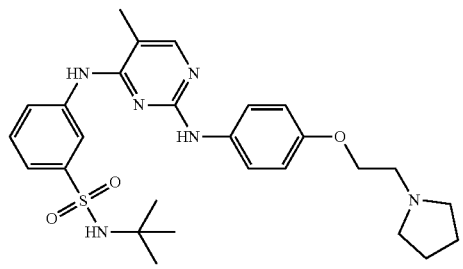 [SMILES: Cc1cnc(Nc2ccc(OCCN3CCCC3)cc2)nc1Nc1cccc(S(=O)(=O)NC(C)(C)C)c1]

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A pharmaceutical composition comprising a compound of Formula (II):

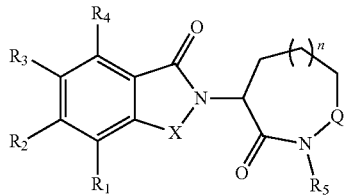
(I)

or a pharmaceutically acceptable salt or solvate thereof, wherein:

$R_1$ is hydroxyl, halogen, nitro, optionally substituted amino, optionally substituted $C_1$ to $C_6$ alkoxy, optionally substituted $C_1$ to $C_6$ alkyl, optionally substituted $C_2$ to $C_6$ alkenyl, optionally substituted $C_3$ to $C_8$ carbocyclyl, or optionally substituted $C_3$ to $C_8$ heterocyclyl;

$R_2$, $R_3$, and $R_4$, are each independently H, deuterium, hydroxyl, halogen, nitro, optionally substituted amino, optionally substituted $C_1$ to $C_6$ alkoxy, optionally substituted $C_1$ to $C_6$ alkyl, optionally substituted $C_2$ to $C_6$ alkenyl, optionally substituted $C_3$ to $C_8$ carbocyclyl, or optionally substituted $C_3$ to $C_8$ heterocyclyl; or, $R_1$ is H and $R_2$ is hydroxyl, halogen, nitro, optionally substituted amino, optionally substituted $C_1$ to $C_6$ alkoxy, optionally substituted $C_1$ to $C_6$ alkyl, optionally substituted $C_2$ to $C_6$ alkenyl, optionally substituted $C_3$ to $C_8$ carbocyclyl, or optionally substituted $C_3$ to $C_8$ heterocyclyl;

$R_5$ is H;

X is $CH_2$ or C=O;

Q is C=O;

n is 1; and at least one pharmaceutically acceptable carrier.

2. The pharmaceutical composition of claim 1, wherein X is C=O.

3. The pharmaceutical composition of claim 1, wherein X is $CH_2$.

4. The pharmaceutical composition of claim 1, wherein $R_2$, $R_3$, and $R_4$, are each independently H, hydroxyl, halogen, unsubstituted $C_1$ to $C_6$ alkoxy, optionally substituted amino, optionally substituted $C_3$ to $C_8$ heterocyclyl, unsubstituted $C_1$ to $C_6$ alkyl, unsubstituted $C_3$ to $C_6$ cycloalkyl, or —$CF_3$; or $R_1$ is H and $R_2$, $R_3$, and $R_4$, are each independently hydroxyl, halogen, unsubstituted $C_1$ to $C_6$ alkoxy, optionally substituted amino, optionally substituted $C_3$ to $C_8$ heterocyclyl, unsubstituted $C_1$ to $C_6$ alkyl, unsubstituted $C_3$ to $C_6$ cycloalkyl, or —$CF_3$.

5. The pharmaceutical composition of claim 4, wherein $R_2$, $R_3$, and $R_4$, are each independently H, hydroxyl, halogen, unsubstituted $C_1$ to $C_6$ alkoxy, unsubstituted $C_1$ to $C_6$ alkyl, optionally substituted $C_3$ to $C_8$ heterocyclyl, or —$CF_3$.

6. The pharmaceutical composition of claim 1, wherein $R_3$ and $R_4$ are each H.

7. The pharmaceutical composition of claim 5, wherein $R_1$ is hydroxyl, halogen, unsubstituted $C_1$ to $C_6$ alkoxy, optionally substituted amino, optionally substituted $C_3$ to $C_8$ heterocyclyl, unsubstituted $C_1$ to $C_6$ alkyl, unsubstituted $C_3$ to $C_6$ cycloalkyl, or —$CF_3$.

8. The pharmaceutical composition of claim 6, wherein $R_1$ is hydroxyl, halogen, unsubstituted $C_1$ to $C_6$ alkoxy, unsubstituted $C_1$ to $C_6$ alkyl, optionally substituted $C_3$ to $C_8$ heterocyclyl, or —$CF_3$; and $R_2$ is H, hydroxyl, halogen, unsubstituted $C_1$ to $C_6$ alkoxy, unsubstituted $C_1$ to $C_6$ alkyl, optionally substituted $C_3$ to $C_8$ heterocyclyl, or —$CF_3$.

9. The pharmaceutical composition of claim 1, wherein the compound of Formula (I) is selected from the group consisting of:

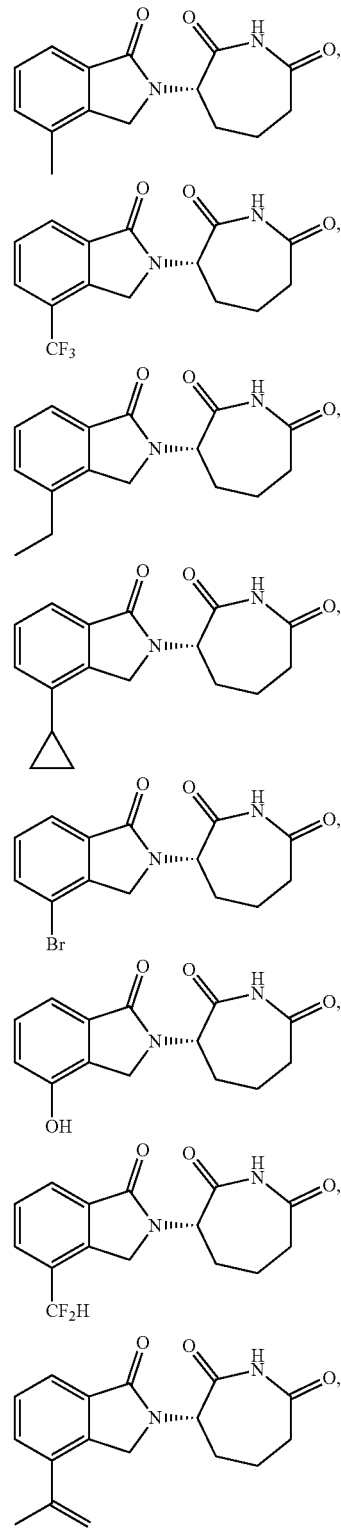

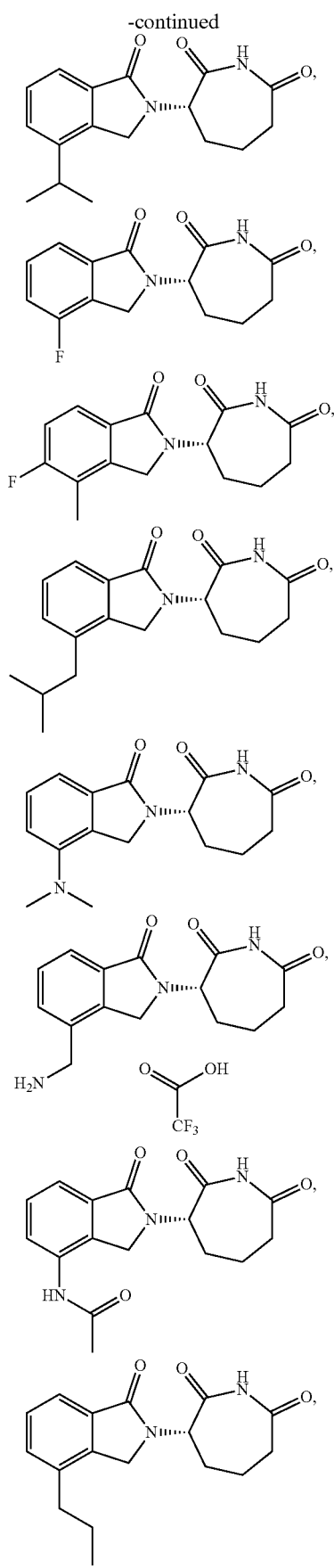

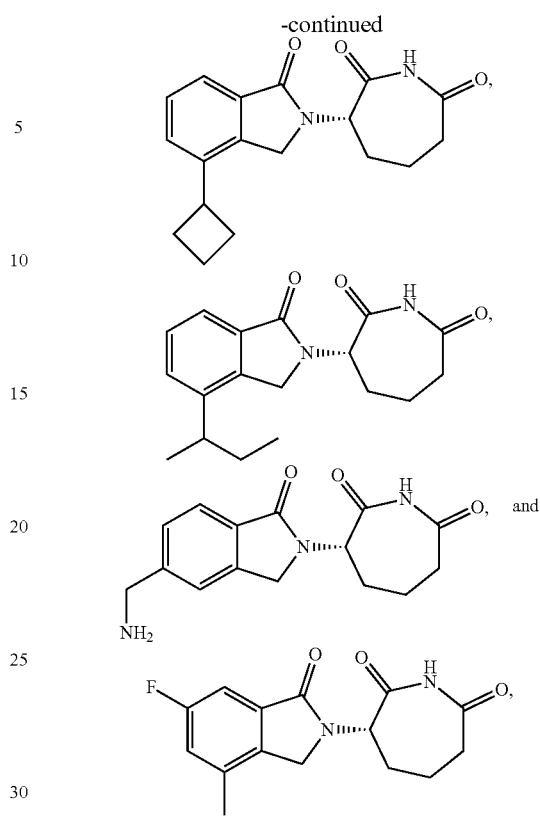

or a pharmaceutically acceptable salt of any of the foregoing.

10. A pharmaceutical composition of Formula (II):

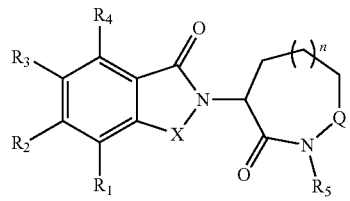

(II)

or a pharmaceutically acceptable salt or solvate thereof, wherein:

one of $R_1$ and $R_2$ is L-Y and the other of $R_1$ and $R_2$ is H, deuterium, hydroxyl, halogen, cyano, nitro, optionally substituted amino, optionally substituted $C_1$ to $C_6$ alkoxy, optionally substituted $C_1$ to $C_6$ alkyl, optionally substituted $C_2$ to $C_6$ alkenyl, or optionally substituted $C_3$ to $C_6$ cycloalkyl;

$R_3$ and $R_4$ are each independently H, deuterium, hydroxyl, halogen, cyano, nitro, optionally substituted amino, optionally substituted $C_1$ to $C_6$ alkoxy, optionally substituted $C_1$ to $C_6$ alkyl, optionally substituted $C_2$ to $C_6$ alkenyl, or optionally substituted $C_3$ to $C_6$ cycloalkyl;

each $R_5$ is independently H, deuterium, or optionally substituted $C_1$ to $C_6$ alkyl;

X is $CH_2$ or C=O;

Q is C=O;

n is 1;

L is —$Z_1$-($R_6$-O-$R_6$)$_t$-$Z_2$; —$Z_1$($R_6$-NH-$R_6$)$_t$-$Z_2$—; —$Z_1$-($R_6$-(NHCO)-$R_6$)$_t$-$Z_2$—; or —$Z_1$—

(R₆-(CONH)-R₆)ₜ-Z₂;
Z₁ is —NH—; —O—; —CH₂—; —NH(C0)—;
Z₂ is —NH—; —O—; —CH₂—; —NH(C0)—; or —(CO)NH—;
each R₆ is independently C₁ to C₆ alkyl;
t is 1; and
Y is

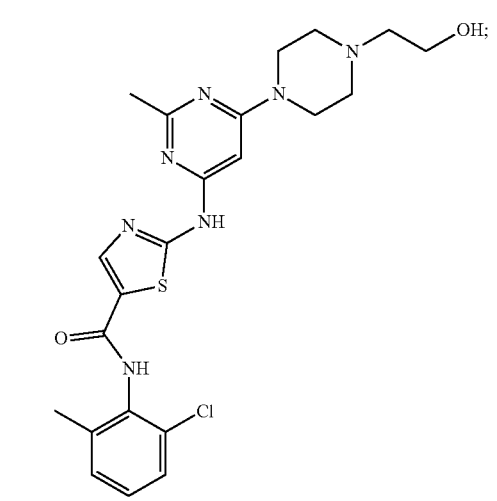

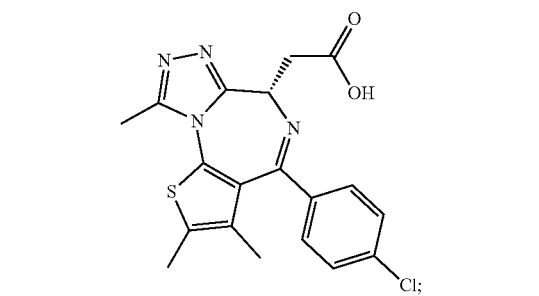

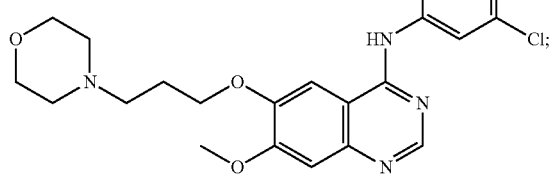

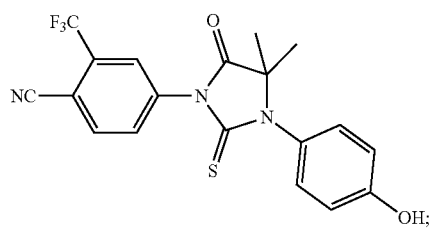

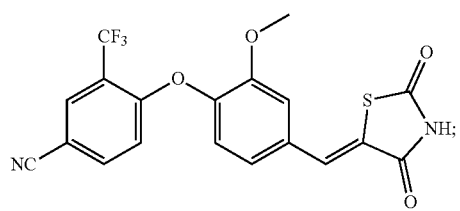

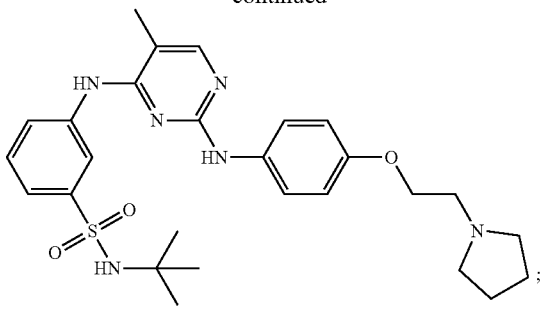

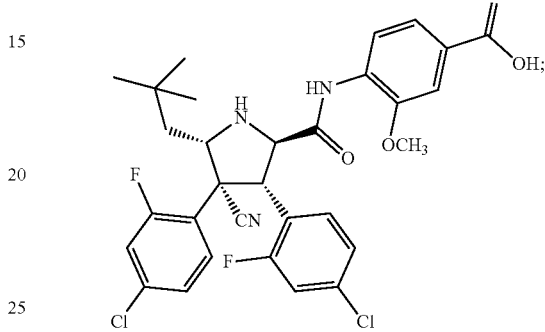

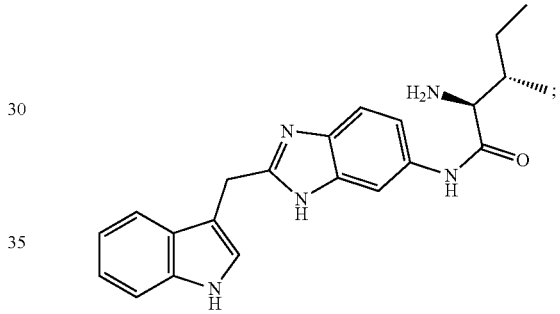

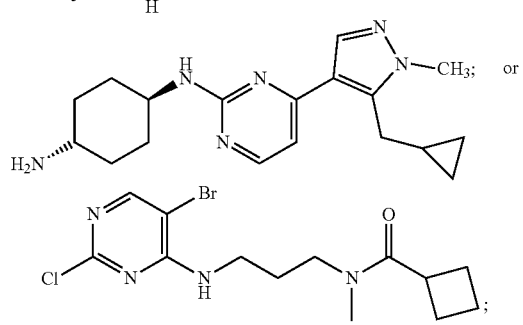

wherein Y is derivatized to attach to L.

11. The pharmaceutical composition of claim 10, wherein X is C=O.
12. The pharmaceutical composition of claim 10, wherein X is CH₂.
13. The pharmaceutical composition of claim 10, wherein R₅ is H.
14. The pharmaceutical composition of claim 10, wherein R₁ is L-Y.
15. The pharmaceutical composition of claim 14, wherein R₂, R₃, and R₄, are each independently H, hydroxyl, halogen, unsubstituted C₁ to C₆ alkoxy, optionally substituted amino, optionally substituted C₃ to C₈ heterocyclyl, unsubstituted C₁ to C₆ alkyl, unsubstituted C₃ to C₆ cycloalkyl, or —CF₃.
16. The pharmaceutical composition of claim 15, wherein R₂, R₃, and R₄, are each independently H, hydroxyl, halogen, unsubstituted $C_1$ to $C_6$ alkoxy, unsubstituted $C_1$ to $C_6$ alkyl, optionally substituted $C_3$ to $C_8$ heterocyclyl, or —$CF_3$.

17. The pharmaceutical composition of claim 10, wherein $R_3$ and $R_4$ are each H.

18. The pharmaceutical composition of claim 17, wherein $R_1$ and $R_2$ are each independently L-Y, H, hydroxyl, halogen, unsubstituted $C_1$ to $C_6$ alkoxy, optionally substituted amino, optionally substituted $C_3$ to $C_8$ heterocyclyl, unsubstituted $C_1$ to $C_6$ alkyl, unsubstituted $C_3$ to $C_6$ cycloalkyl, or —$CF_3$.

19. The pharmaceutical composition of claim 18, wherein $R_1$ and $R_2$ are each independently L-Y, H, hydroxyl, halogen, unsubstituted $C_1$ to $C_6$ alkoxy, unsubstituted $C_1$ to $C_6$ alkyl, optionally substituted $C_3$ to $C_8$ heterocyclyl, or —$CF_3$.

20. The pharmaceutical composition of claim 10, wherein Y is

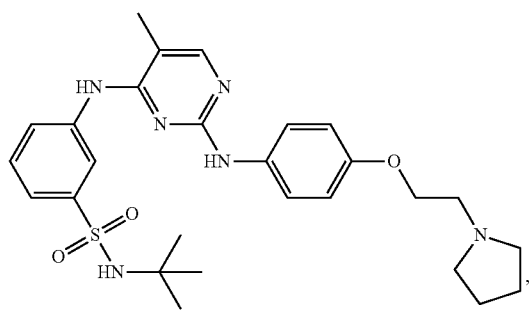

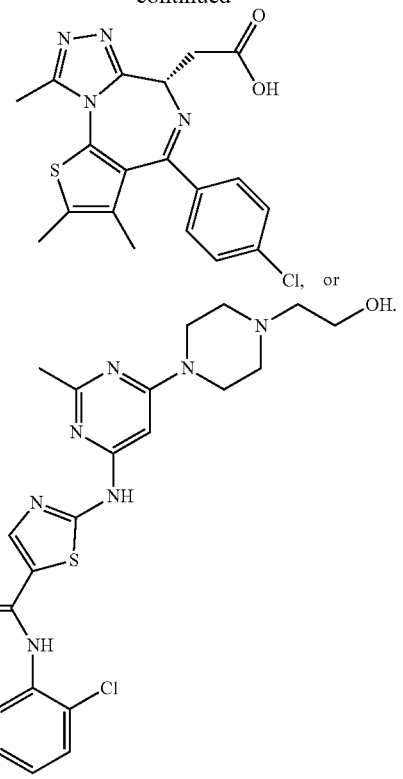

21. The pharmaceutical composition of claim 10, wherein the compound of Formula (II) is selected from the group consisting of:

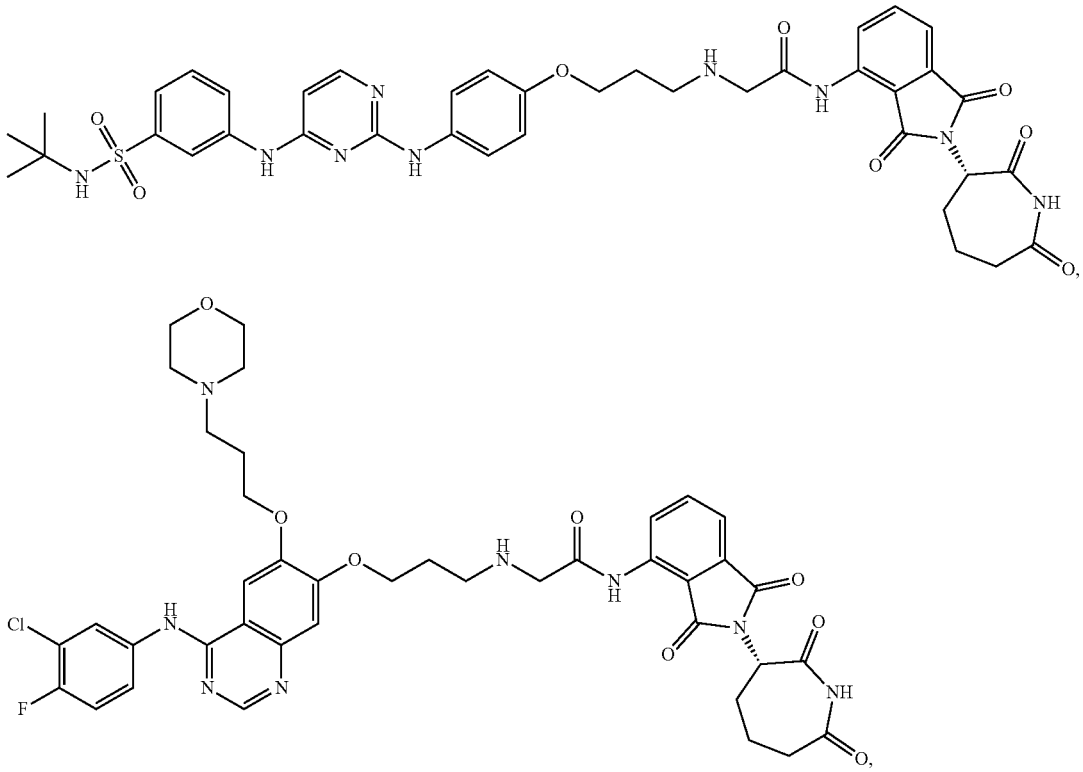

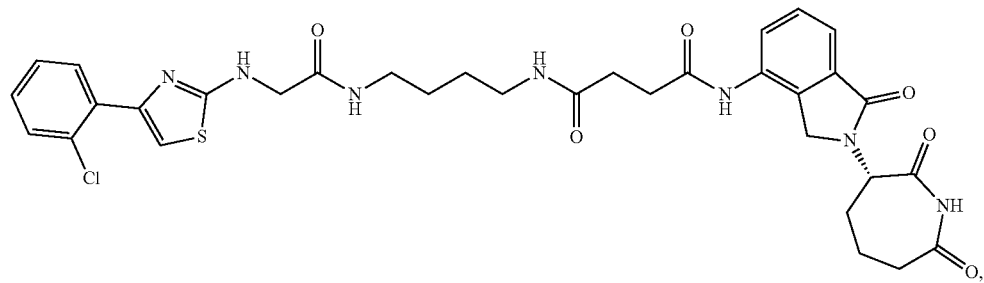
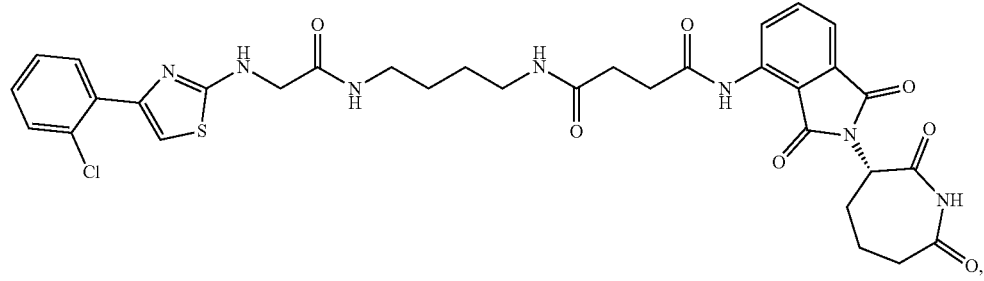
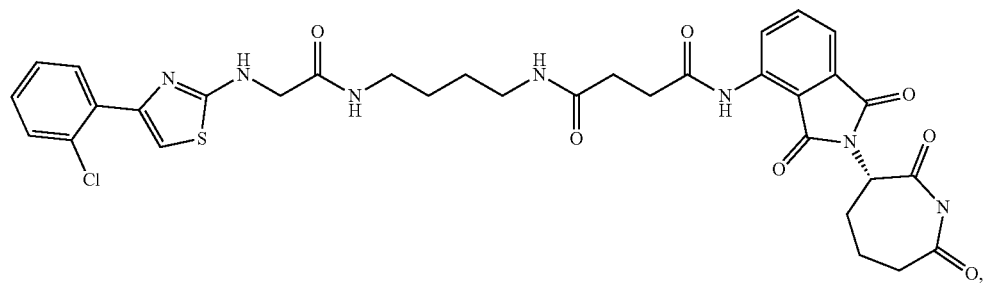
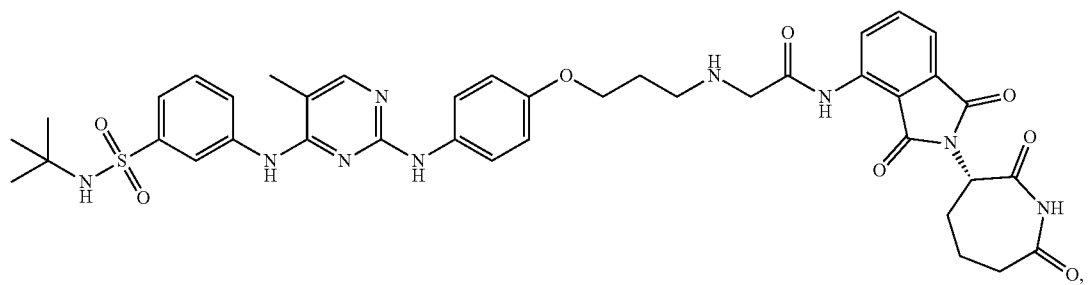
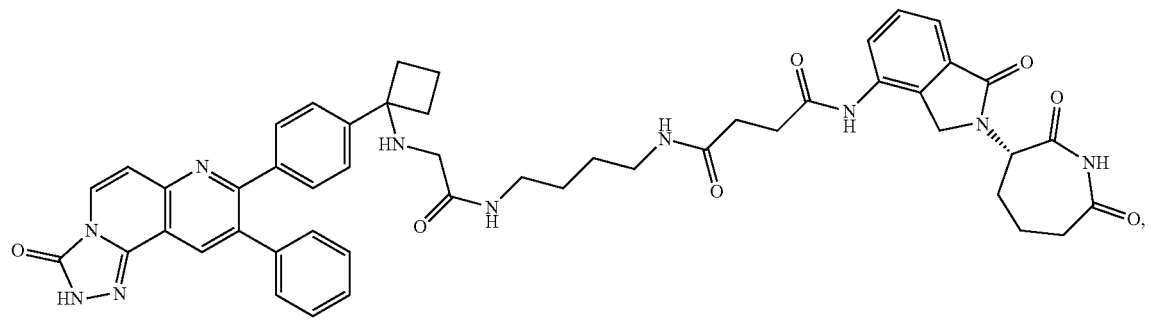

-continued
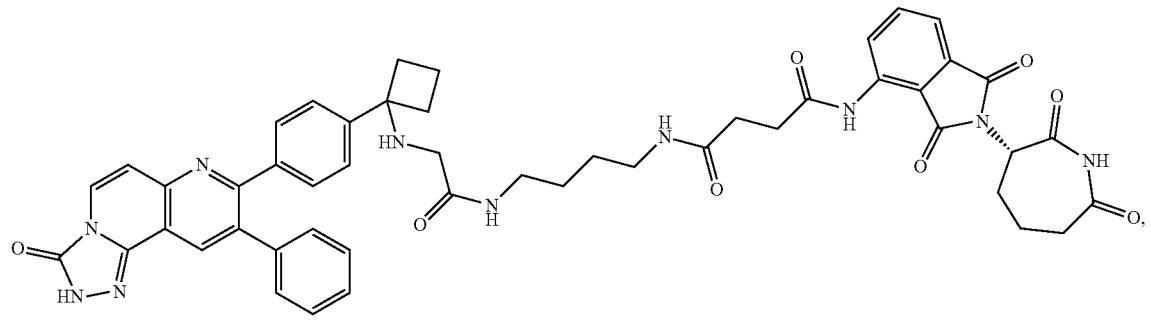
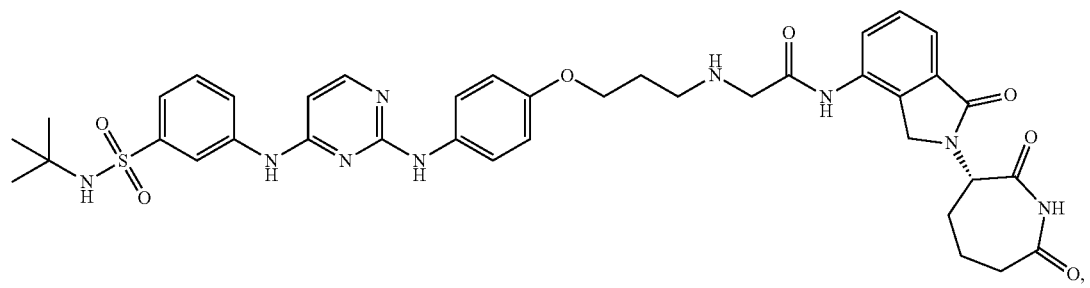
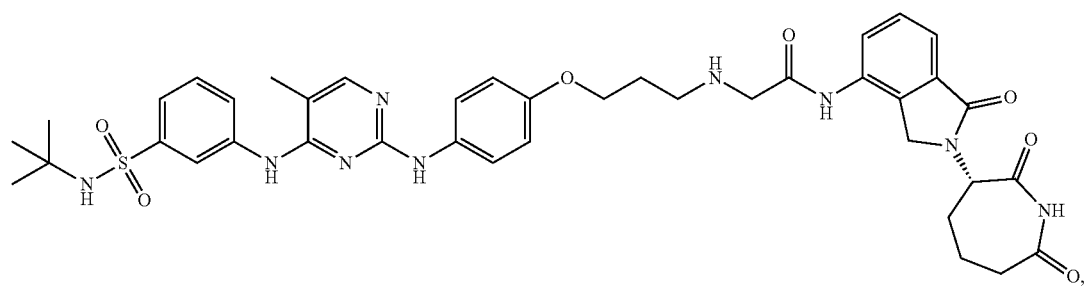
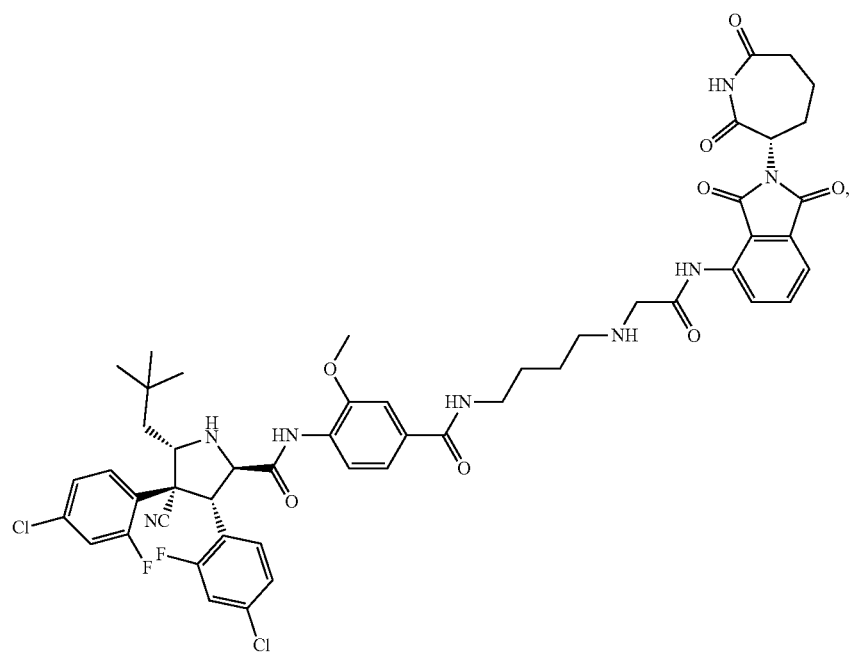

-continued
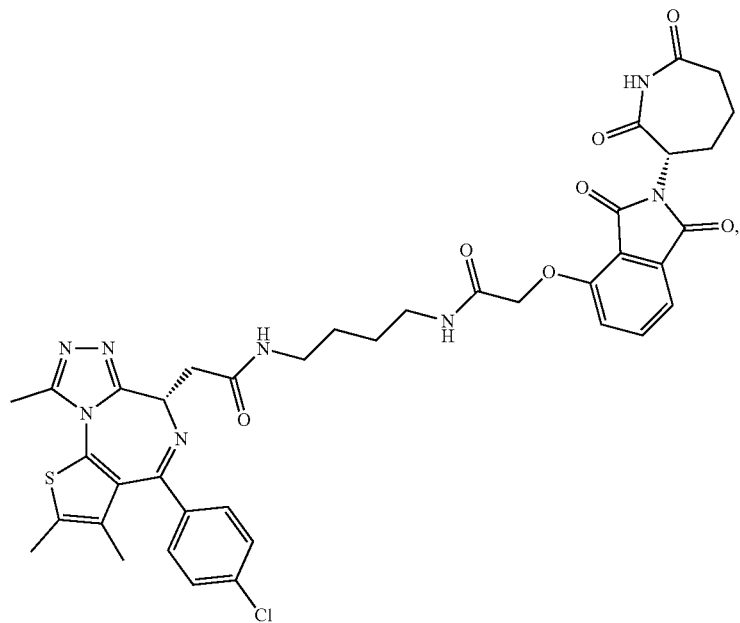
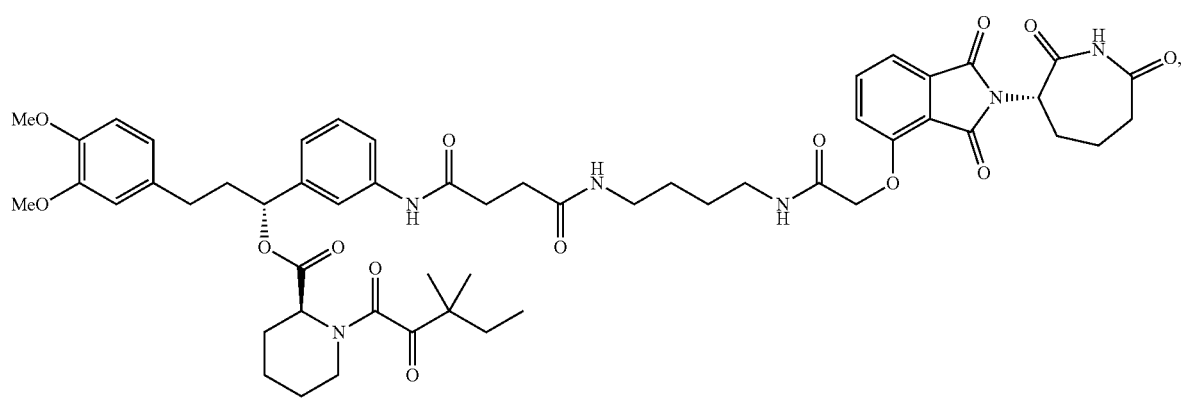
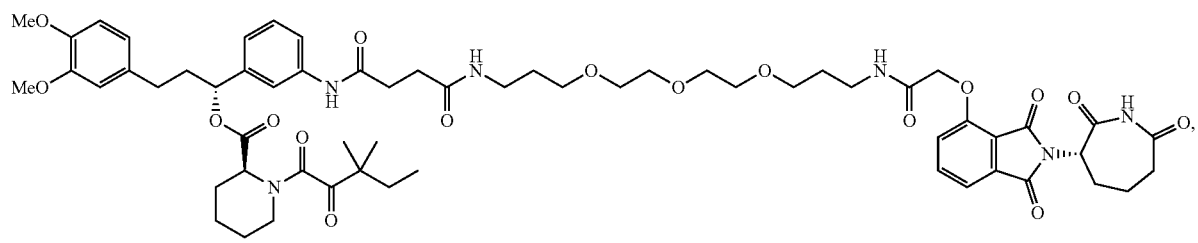

-continued
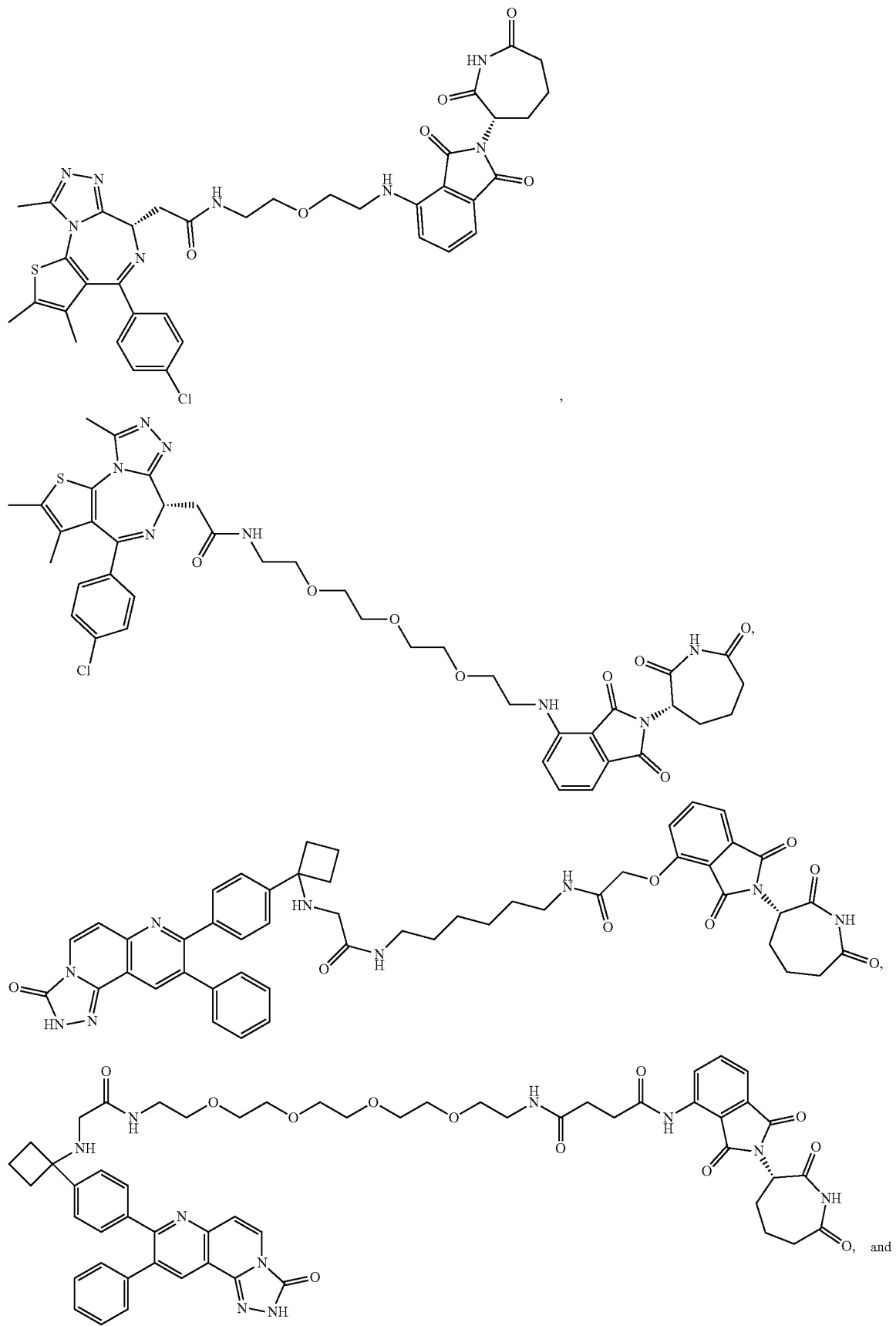

-continued
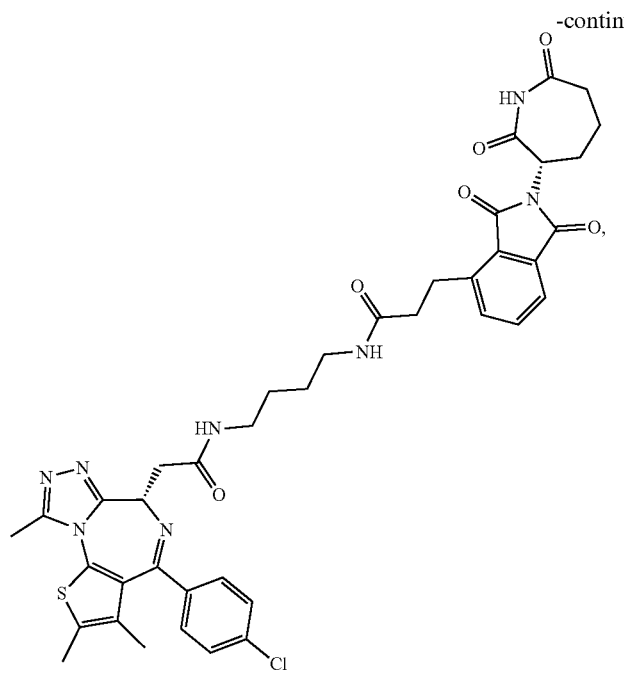
or a pharmaceutically acceptable salt of any of the foregoing.
22. The pharmaceutical composition of claim 7, wherein each $R_2$, $R_3$ and $R_4$ is H.

UNITED STATES PATENT AND TRADEMARK OFFICE
CERTIFICATE OF CORRECTION

Page 1 of 6

PATENT NO. : 10,562,917 B2
APPLICATION NO. : 15/892267
DATED : February 18, 2020
INVENTOR(S) : Kyle W. H. Chan et al.

It is certified that error appears in the above-identified patent and that said Letters Patent is hereby corrected as shown below:

In the Drawings

On Sheet 21 of 21, FIGURE 16, Line 1, delete "Compoud" and insert --Compound--.

In the Specification

In Column 1, Line 47, delete "($R_A$)," and insert --(RA),--.

In Column 3, Line 39, delete "E-3-" and insert --E3- --.

In Column 25, Line 62 (Approx.), delete "derivitization" and insert --derivatization--.

In Column 25, Line 64, delete "derivitization" and insert --derivatization--.

In Column 25, Line 66, delete "derivitization" and insert --derivatization--.

In Column 29, Line 40, delete "caseine" and insert --casein--.

In Column 29, Line 46, delete "caseine" and insert --casein--.

In Column 29, Line 50, delete "caseine" and insert --casein--.

In Column 29, Line 50, delete "caseine" and insert --casein--.

In Column 30, Line 47, delete "caseine" and insert --casein--.

In Column 38, Lines 26-27, delete "$C_1$ to $C_6$" and insert --$C_6$ to $C_{10}$--.

In Column 73, Line 25, delete "ylme-thyl)" and insert --ylmethyl--.

Signed and Sealed this
Twenty-sixth Day of May, 2020

Andrei Iancu
*Director of the United States Patent and Trademark Office*

In Column 74, Lines 53-67, delete " 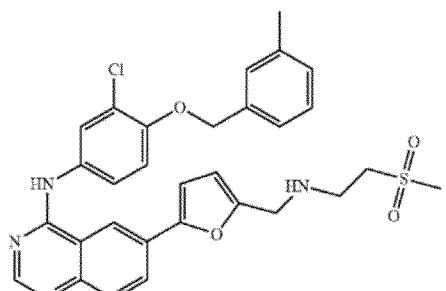 " and insert 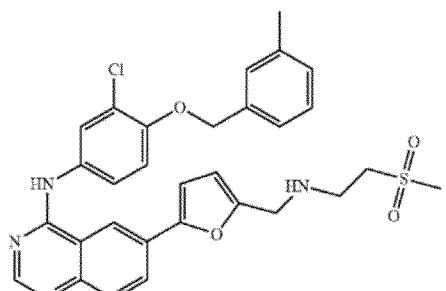
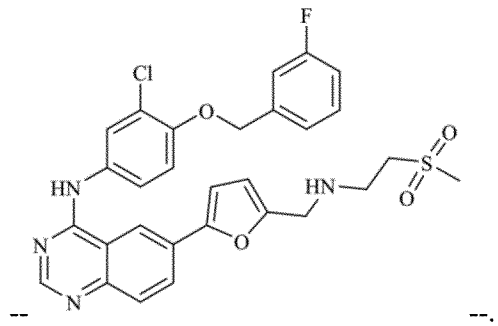
-- --.
In Column 76, Line 35, delete "phenyl[" and insert --phenyl]--.
In Column 77, Line 25, delete "(1 E)" and insert --(1E)--.
In Column 77, Line 47, delete "N-55 4" and insert --N-{4--.
In Column 88, Lines 33-45 (approx.), delete " 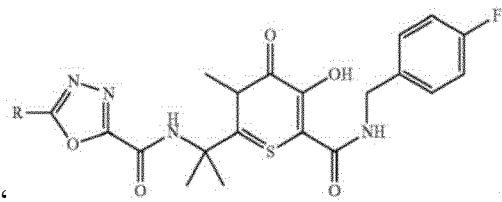 " and insert 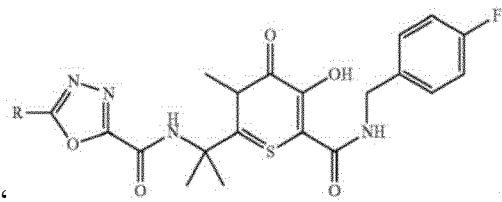
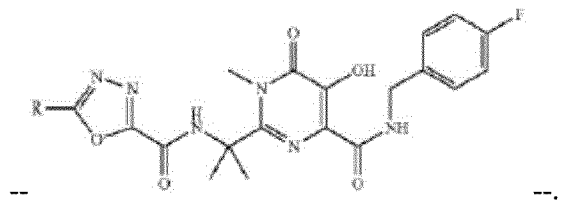
-- --.

CERTIFICATE OF CORRECTION (continued)
U.S. Pat. No. 10,562,917 B2

In Column 88, Lines 47-67 (approx.), delete " 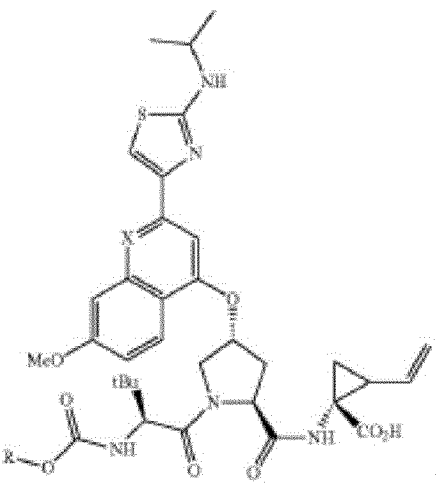 " and insert

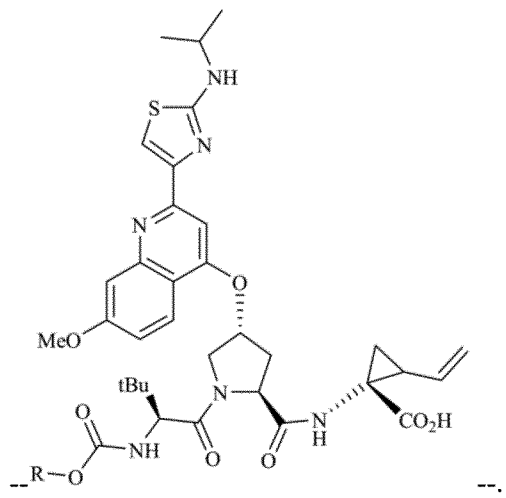

--.

In Column 96, Line 27, delete "$R_2$ and $R_3$, or $R_2$, $R_3$, or $R_4$," and insert --$R^2$ and $R^3$, or $R^2$, $R^3$, or $R^4$,--.

In Column 105, Line 53, delete "mytomycin;" and insert --mitomycin;--.

In Column 106, Line 4, delete "ytarabine;" and insert --cytarabine;--.

In Column 106, Line 25, delete "vorinosta;" and insert --vorinostat;--.

In Column 106, Line 48, delete "zolimoma;" and insert --zolimomab;--.

In Column 110, Line 34, delete "atambient" and insert --at ambient--.

In Column 123, Line 1, delete "isodolindoln" and insert --isoindolin--.

In Column 131, Line 42, delete "1,9" and insert --1.9--.

In Columns 139-140, Lines 15-28, delete
" 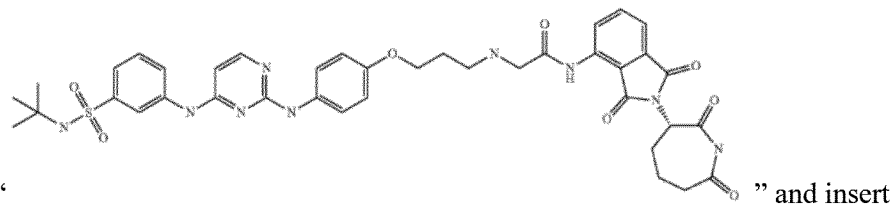 " and insert
-- 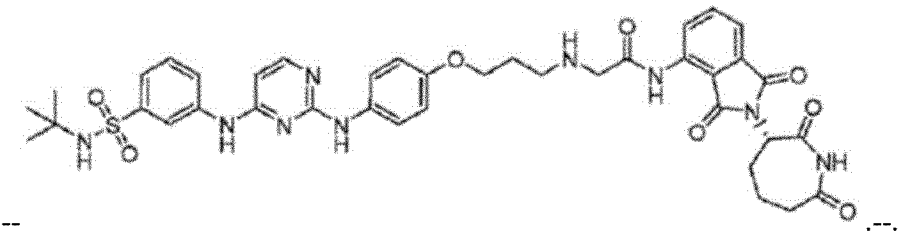 --.
In Column 141, Line 33 (approx.), delete "7-v)" and insert --7-yl)--.
In Columns 141-142, Lines 36-60, delete
" 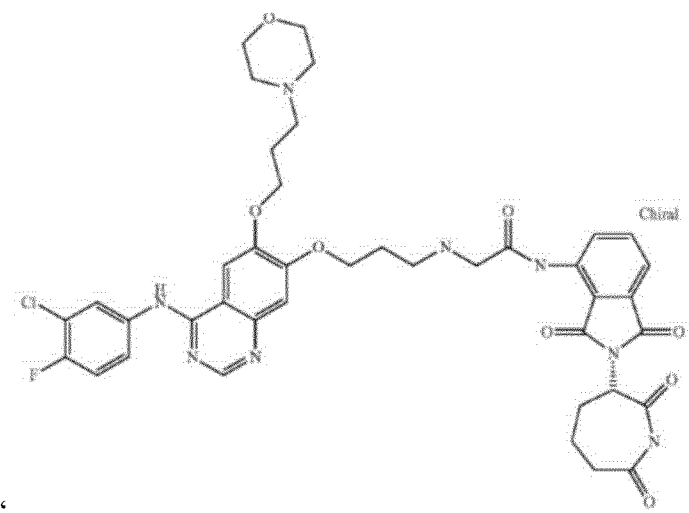 " and insert
-- 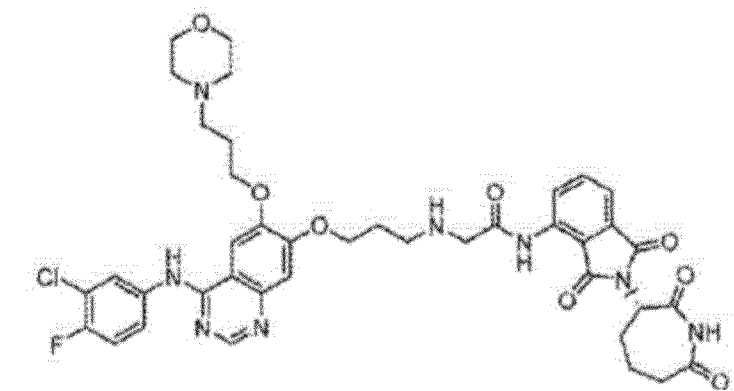 --.

CERTIFICATE OF CORRECTION (continued)
U.S. Pat. No. 10,562,917 B2

In Columns 143-144, Lines 27-40, delete

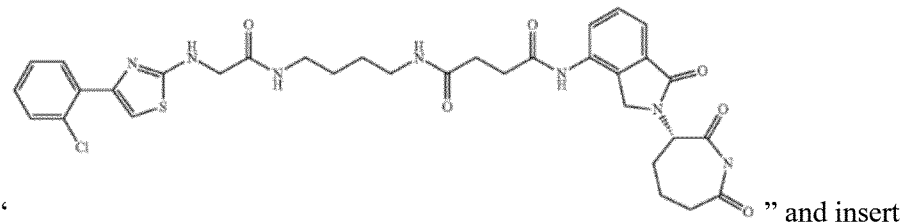

" and insert

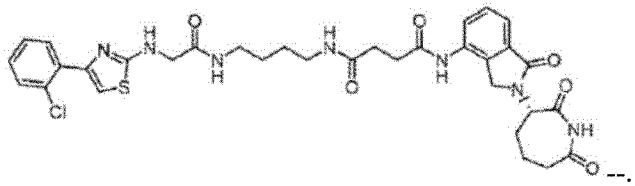

--.

In Columns 145-146, Lines 22-35, delete

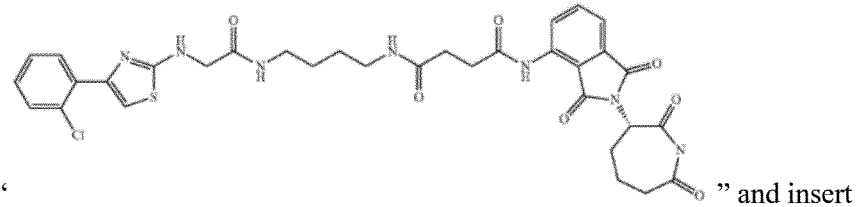

" and insert

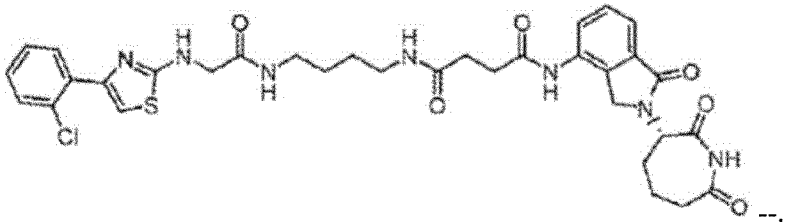

--.

In Columns 145-146, Lines 51-65, delete

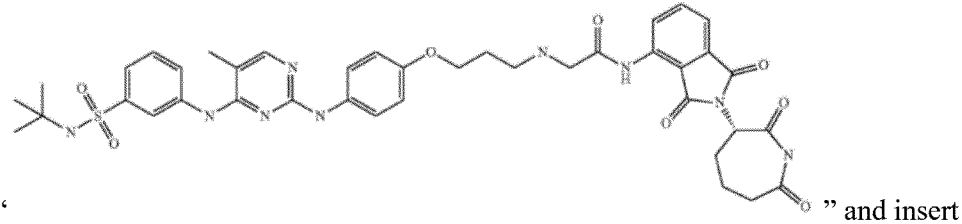

" and insert

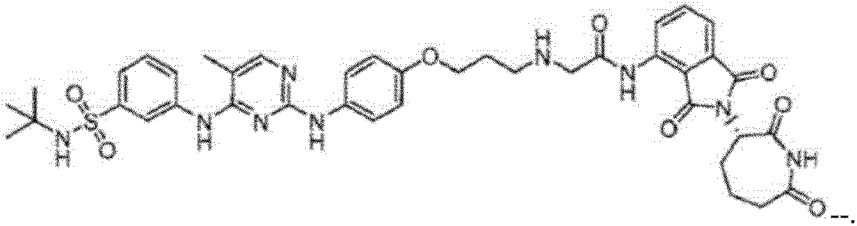

--.

CERTIFICATE OF CORRECTION (continued)
U.S. Pat. No. 10,562,917 B2

In Columns 157-158, Lines 6-24, delete

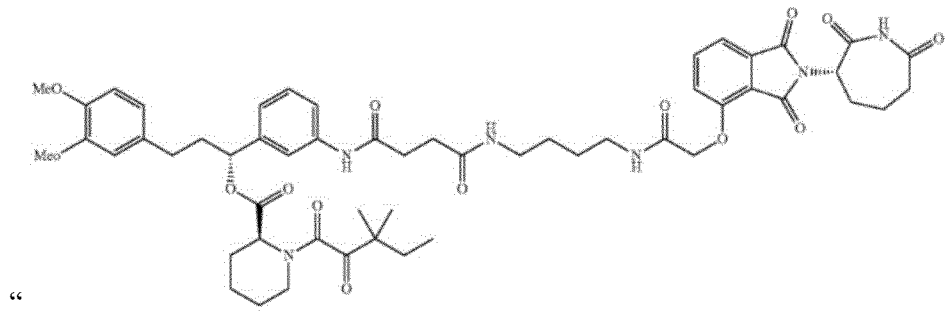

" and insert

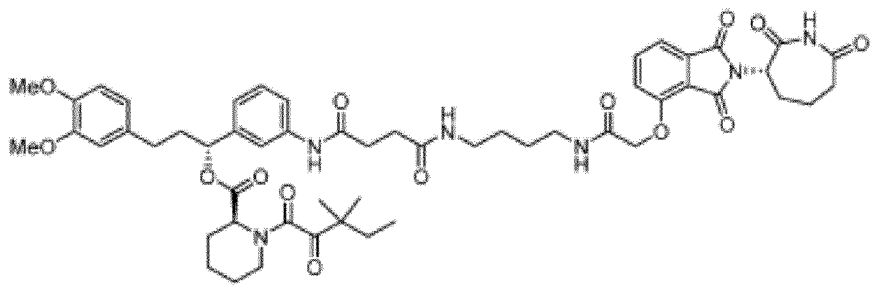

-- --.

In Column 157-158, Lines 46-55, delete

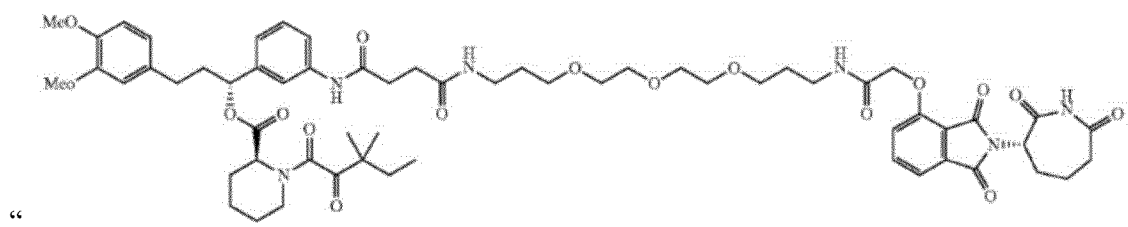

" and

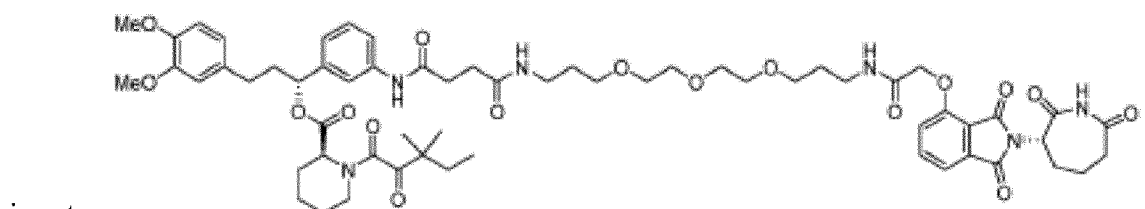

insert -- --.

In the Claims

In Column 178, Line 66, Claim 10, delete "—$Z_1$-($R_6$-O-$R_6$)$_t$-$Z_2$;" and insert
-- —$Z_1$-($R_6$-O-$R_6$)$_t$-$Z_2$—;--.

In Column 179, Line 1, Claim 10, delete "($R_6$-(CONH)-$R_6$)$_t$-$Z_2$;" and insert
--($R_6$-(CONH)-$R_6$)$_t$-$Z_2$—;--.

In Column 179, Line 2, Claim 10, delete "—NH(C0)—" and insert -- —NH(CO)— --.

In Column 179, Line 3, Claim 10, delete "—NH(C0)—" and insert -- —NH(CO)— --.